US010123986B2

(12) United States Patent
Waibel et al.

(10) Patent No.: US 10,123,986 B2
(45) Date of Patent: Nov. 13, 2018

(54) EICOSAPENTAENOIC ACID (EPA) FORMULATIONS

(71) Applicants: Brian J. Waibel, Kennett Square, PA (US); Hans Schonemann, Newburyport, MA (US); Val Krukonis, Lexington, MA (US); Michael Kagan, Jerusalem (IL)

(72) Inventors: Brian J. Waibel, Kennett Square, PA (US); Hans Schonemann, Newburyport, MA (US); Val Krukonis, Lexington, MA (US); Michael Kagan, Jerusalem (IL)

(73) Assignee: Qualitas Health, Ltd., Houston, TX (US)

( * ) Notice: Subject to any disclaimer, the term of this patent is extended or adjusted under 35 U.S.C. 154(b) by 226 days.

(21) Appl. No.: 14/651,665

(22) PCT Filed: Dec. 18, 2013

(86) PCT No.: PCT/US2013/076178
§ 371 (c)(1),
(2) Date: Jun. 12, 2015

(87) PCT Pub. No.: WO2014/105576
PCT Pub. Date: Jul. 3, 2014

(65) Prior Publication Data

US 2017/0035719 A1 Feb. 9, 2017

Related U.S. Application Data

(63) Continuation-in-part of application No. 13/797,802, filed on Mar. 12, 2013, now Pat. No. 9,629,820.

(60) Provisional application No. 61/816,561, filed on Apr. 26, 2013, provisional application No. 61/745,740, filed on Dec. 24, 2012.

(51) Int. Cl.

| | |
|---|---|
| ***A61K 31/202*** | (2006.01) |
| ***A23L 2/52*** | (2006.01) |
| ***A61K 36/02*** | (2006.01) |
| ***A23L 33/12*** | (2016.01) |
| ***C11B 1/10*** | (2006.01) |
| ***A61K 31/122*** | (2006.01) |
| ***A61K 47/48*** | (2006.01) |

(52) U.S. Cl.
CPC .............. *A61K 31/202* (2013.01); *A23L 2/52* (2013.01); *A23L 33/12* (2016.08); *A61K 31/122* (2013.01); *A61K 36/02* (2013.01); *A61K 47/48046* (2013.01); *A61K 47/48053* (2013.01); *C11B 1/10* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 2,729,586 | A | 1/1956 | Peck |
| 4,345,976 | A | 8/1982 | Peter et al. |
| 4,568,495 | A | 2/1986 | Frihart |
| 4,615,839 | A | 10/1986 | Seto et al. |
| 4,675,132 | A | 6/1987 | Stout et al. |
| 4,692,280 | A | 9/1987 | Spinelli et al. |
| 4,906,479 | A | 3/1990 | Kitagawa et al. |
| 4,931,291 | A | 6/1990 | Kojima et al. |
| 5,013,443 | A | 5/1991 | Higashidate et al. |
| 5,059,527 | A | 10/1991 | White et al. |
| 5,073,267 | A | 12/1991 | Adda et al. |
| 5,077,202 | A | 12/1991 | Seto et al. |
| 5,104,587 | A | 4/1992 | Besserman et al. |
| 5,227,403 | A | 7/1993 | Seto et al. |
| 5,362,895 | A | 11/1994 | Engelhardt et al. |
| 5,457,130 | A | 10/1995 | Tisdale et al. |
| 5,539,133 | A | 7/1996 | Kohn et al. |
| 5,620,962 | A | 4/1997 | Winget et al. |
| 5,698,594 | A | 12/1997 | Breivik et al. |
| 5,719,302 | A | 2/1998 | Perrut et al. |
| 5,767,095 | A | 6/1998 | Winget |
| 5,840,944 | A | 11/1998 | Furihata et al. |
| 6,166,230 | A | 12/2000 | Bijl et al. |
| 6,200,624 | B1 | 3/2001 | Mazer et al. |
| 6,204,401 | B1 | 3/2001 | Perrot et al. |
| 6,384,077 | B1 | 5/2002 | Peet et al. |
| 6,479,544 | B1 | 11/2002 | Horrobin |
| 6,689,812 | B2 | 2/2004 | Peet et al. |
| 7,119,118 | B2 | 10/2006 | Peet |
| 7,410,663 | B2 | 8/2008 | Koike et al. |
| 7,560,486 | B2 | 7/2009 | Carpentier et al. |
| 7,842,677 | B2 | 11/2010 | Defrees et al. |
| 7,847,113 | B2 | 12/2010 | Kawashima et al. |

(Continued)

FOREIGN PATENT DOCUMENTS

| | | |
|---|---|---|
| DE | 3937287 | 5/1991 |
| EP | 0404300 | 12/1990 |

(Continued)

OTHER PUBLICATIONS

U.S. Office Action (Requirement for Restriction/Election) dated Jan. 22, 2015 issued in U.S. Appl. No. 13/797,802.

(Continued)

*Primary Examiner* — Brian J Davis

(74) *Attorney, Agent, or Firm* — Weaver Austin Villeneuve & Sampson LLP

(57) ABSTRACT

Provided herein are compositions comprising eicosapentaenoic acid (EPA) and polar lipids (e.g., glycolipids and phospholipids), and which do not contain any docosahexaenoic acid (DHA) or esterified fatty acids.

20 Claims, 25 Drawing Sheets

(56) References Cited

U.S. PATENT DOCUMENTS

| | | | |
|---|---|---|---|
| 7,888,331 | B2 | 2/2011 | Defrees et al. |
| 7,906,666 | B2 | 3/2011 | Marciacq et al. |
| 7,932,236 | B2 | 4/2011 | DeFrees et al. |
| 7,935,365 | B2 | 5/2011 | Dror et al. |
| 7,943,167 | B2 | 5/2011 | Kulkarni et al. |
| 7,968,112 | B2 | 6/2011 | Ben Dror et al. |
| 8,030,348 | B2 | 10/2011 | Sampalis |
| 8,048,462 | B2 | 11/2011 | Brunner et al. |
| 8,052,992 | B2 | 11/2011 | Ben Dror et al. |
| 8,057,825 | B2 | 11/2011 | Sampalis |
| 8,084,038 | B2 | 12/2011 | Kale |
| 8,088,614 | B2 | 1/2012 | Vick et al. |
| 8,115,022 | B2 | 2/2012 | Kale |
| 8,119,859 | B2 | 2/2012 | Vick et al. |
| 8,137,555 | B2 | 3/2012 | Kale |
| 8,137,556 | B2 | 3/2012 | Kale |
| 8,142,659 | B2 | 3/2012 | Kale |
| 8,143,051 | B2 | 3/2012 | Weissman et al. |
| 8,152,870 | B2 | 4/2012 | Kale |
| 8,153,137 | B2 | 4/2012 | Kale |
| 8,157,994 | B2 | 4/2012 | Kale |
| 8,187,463 | B2 | 5/2012 | Kale |
| 8,188,146 | B2 | 5/2012 | Peet |
| 8,202,425 | B2 | 6/2012 | Kale |
| 8,211,308 | B2 | 7/2012 | Kale |
| 8,211,309 | B2 | 7/2012 | Kale |
| 8,212,060 | B2 | 7/2012 | Kale et al. |
| 8,242,296 | B2 | 8/2012 | Kale |
| 8,273,248 | B1 | 9/2012 | Kale |
| 8,278,351 | B2 | 10/2012 | Sampalis |
| 8,293,108 | B1 | 10/2012 | Kale |
| 8,308,949 | B1 | 11/2012 | Kale |
| 8,313,647 | B2 | 11/2012 | Kale |
| 8,314,228 | B2 | 11/2012 | Kilian et al. |
| 8,318,482 | B2 | 11/2012 | Vick et al. |
| 8,404,473 | B2 | 3/2013 | Kilian et al. |
| 8,440,805 | B2 | 5/2013 | Kilian et al. |
| 8,569,530 | B2 | 10/2013 | Hippler et al. |
| 8,685,723 | B2 | 4/2014 | Vick et al. |
| 8,703,818 | B2 | 4/2014 | Green |
| 8,709,765 | B2 | 4/2014 | Bailey et al. |
| 8,722,359 | B2 | 5/2014 | Kilian et al. |
| 8,747,930 | B2 | 6/2014 | Fleischer et al. |
| 8,752,329 | B2 | 6/2014 | Parsheh et al. |
| 8,759,615 | B2 | 6/2014 | Vick et al. |
| 8,765,983 | B2 | 7/2014 | Fleischer et al. |
| 8,769,867 | B2 | 7/2014 | Parsheh et al. |
| 8,785,610 | B2 | 7/2014 | Kilian et al. |
| 8,809,046 | B2 | 8/2014 | Kilian et al. |
| 8,865,452 | B2 | 10/2014 | Radaelli et al. |
| 8,865,468 | B2 | 10/2014 | Kilian et al. |
| 8,926,844 | B2 | 1/2015 | Parsheh et al. |
| 8,940,340 | B2 | 1/2015 | Weissman et al. |
| 9,029,137 | B2 | 5/2015 | Kilian et al. |
| 9,050,308 | B2 | 6/2015 | Maines et al. |
| 9,050,309 | B2 | 6/2015 | Maines et al. |
| 9,629,820 | B2 | 4/2017 | Waibel et al. |
| 2002/0055539 | A1 | 5/2002 | Bockow et al. |
| 2002/0086906 | A1 | 7/2002 | Weidner et al. |
| 2002/0169209 | A1 | 11/2002 | Horrobin |
| 2002/0198177 | A1 | 12/2002 | Horrobin |
| 2003/0157204 | A1 | 8/2003 | Weidner et al. |
| 2004/0234587 | A1 | 11/2004 | Sampalis |
| 2004/0241249 | A1 | 12/2004 | Sampalis |
| 2005/0209329 | A1 | 9/2005 | Horrobin |
| 2006/0110476 | A1 | 5/2006 | Haber et al. |
| 2006/0142390 | A1 | 6/2006 | Manku et al. |
| 2006/0252833 | A1 | 11/2006 | Peet |
| 2007/0098808 | A1 | 5/2007 | Sampalis |
| 2007/0104856 | A1 | 5/2007 | Standal et al. |
| 2007/0105954 | A1 | 5/2007 | Puri |
| 2007/0118916 | A1 | 5/2007 | Puzio et al. |
| 2007/0154498 | A1 | 7/2007 | Bortz et al. |
| 2007/0166413 | A1 | 7/2007 | Haber et al. |
| 2008/0044487 | A1 | 2/2008 | Bruheim et al. |
| 2008/0200547 | A1 | 8/2008 | Peet et al. |
| 2009/0074857 | A1 | 3/2009 | Dror et al. |
| 2009/0093543 | A1 | 4/2009 | Xue et al. |
| 2009/0258081 | A1 | 10/2009 | Minatelli et al. |
| 2010/0069492 | A1 | 3/2010 | Geiringen et al. |
| 2010/0098786 | A1 | 4/2010 | Puri |
| 2010/0197785 | A1 | 8/2010 | Breivik |
| 2010/0215737 | A1 | 8/2010 | Coulter |
| 2010/0233761 | A1 | 9/2010 | Czartoski et al. |
| 2011/0020316 | A1 | 1/2011 | Minatelli et al. |
| 2011/0033595 | A1 | 2/2011 | Krumbholz et al. |
| 2011/0065793 | A1 | 3/2011 | Peet et al. |
| 2011/0086386 | A1 | 4/2011 | Czartoski et al. |
| 2011/0117207 | A1 | 5/2011 | Minatelli et al. |
| 2011/0130458 | A1 | 6/2011 | Breivik et al. |
| 2011/0160161 | A1 | 6/2011 | Sampalis et al. |
| 2011/0195061 | A1 | 8/2011 | Minatelli et al. |
| 2011/0195085 | A1 | 8/2011 | Kale |
| 2011/0218243 | A1 | 9/2011 | Rowe |
| 2011/0236476 | A1 | 9/2011 | Manku |
| 2011/0251278 | A1 | 10/2011 | Weber et al. |
| 2011/0263709 | A1 | 10/2011 | Hutchenson et al. |
| 2011/0268811 | A1 | 11/2011 | Minatelli et al. |
| 2011/0288171 | A1 | 11/2011 | Manku et al. |
| 2011/0293734 | A1 | 12/2011 | Minatelli et al. |
| 2011/0305771 | A1 | 12/2011 | Sampalis |
| 2011/0306666 | A1 | 12/2011 | Minatelli et al. |
| 2012/0016145 | A1 | 1/2012 | D'Addario et al. |
| 2012/0027787 | A1 | 2/2012 | Minatelli et al. |
| 2012/0028922 | A1 | 2/2012 | Sampalis |
| 2012/0035120 | A1 | 2/2012 | DeFrees |
| 2012/0035262 | A1 | 2/2012 | Osterloh et al. |
| 2012/0065172 | A1 | 3/2012 | Sampalis |
| 2012/0079760 | A1 | 4/2012 | Savage |
| 2012/0083616 | A1 | 4/2012 | Harting Glade et al. |
| 2012/0100208 | A1 | 4/2012 | Manku |
| 2012/0108663 | A1 | 5/2012 | Manku et al. |
| 2012/0214771 | A1 | 8/2012 | Sampalis |
| 2012/0277196 | A1 | 11/2012 | Sampalis |
| 2013/0004582 | A1 | 1/2013 | Minatelli et al. |
| 2013/0005828 | A1 | 1/2013 | Minatelli et al. |
| 2013/0046020 | A1 | 2/2013 | Liang et al. |
| 2013/0280341 | A1 | 10/2013 | Minatelli et al. |
| 2013/0287756 | A1 | 10/2013 | Minatelli et al. |
| 2013/0287858 | A1 | 10/2013 | Minatelli et al. |
| 2013/0309316 | A1 | 11/2013 | Minatelli et al. |
| 2013/0310337 | A1 | 11/2013 | Minatelli et al. |
| 2014/0005267 | A1 | 1/2014 | Minatelli et al. |
| 2014/0011888 | A1 | 1/2014 | Minatelli et al. |
| 2014/0023634 | A1 | 1/2014 | Minatelli et al. |
| 2014/0023719 | A1 | 1/2014 | Minatelli et al. |
| 2014/0128341 | A1 | 5/2014 | Minatelli et al. |
| 2014/0148405 | A1 | 5/2014 | Minatelli et al. |
| 2014/0178488 | A1 | 6/2014 | Minatelli et al. |
| 2014/0179781 | A1 | 6/2014 | Waibel et al. |
| 2014/0199342 | A1 | 7/2014 | Minatelli et al. |
| 2014/0205627 | A1 | 7/2014 | Minatelli et al. |
| 2014/0248369 | A1 | 9/2014 | Minatelli et al. |
| 2014/0271706 | A1 | 9/2014 | Astwood et al. |
| 2014/0274922 | A1 | 9/2014 | Van der Meulen et al. |
| 2014/0275483 | A1 | 9/2014 | Hippler et al. |
| 2014/0275596 | A1 | 9/2014 | Astwood et al. |
| 2014/0275613 | A1 | 9/2014 | Hippler et al. |
| 2014/0294987 | A1 | 10/2014 | Minatelli et al. |
| 2014/0328909 | A1 | 11/2014 | Minatelli et al. |
| 2017/0304247 | A1 | 10/2017 | Waibel et al. |

FOREIGN PATENT DOCUMENTS

| | | | |
|---|---|---|---|
| EP | 1 698 685 | A1 | 9/2006 |
| JP | S61-064794 | A | 4/1986 |
| JP | S62-239981 | A | 10/1987 |
| JP | H09-252761 | A | 9/1997 |
| JP | H10-276724 | A | 10/1998 |
| JP | 2005-206789 | A | 8/2005 |
| JP | 2008-540394 | A | 11/2008 |
| JP | 2009-538366 | A | 11/2009 |
| JP | 2009-542205 | A | 12/2009 |
| JP | 2011-525525 | A | 9/2011 |

(56) References Cited

FOREIGN PATENT DOCUMENTS

| | | | |
|---|---|---|---|
| WO | WO 91/18067 | A1 | 11/1991 |
| WO | WO 94/10125 | A1 | 5/1994 |
| WO | WO 2000/62625 | A1 | 10/2000 |
| WO | WO 2001/03696 | A1 | 1/2001 |
| WO | WO 02/092540 | A1 | 11/2002 |
| WO | WO 2004/064716 | A2 | 8/2004 |
| WO | WO 2004/098510 | A2 | 11/2004 |
| WO | WO 2005/027937 | A1 | 3/2005 |
| WO | WO 2006/067498 | A1 | 6/2006 |
| WO | WO 2006/117668 | A1 | 11/2006 |
| WO | WO 2007/136281 | A1 | 11/2007 |
| WO | WO 2008/004900 | A1 | 1/2008 |
| WO | WO 2009/009040 | A2 | 1/2009 |
| WO | WO 2009/156991 | A2 | 12/2009 |
| WO | WO 2010/028067 | A1 | 3/2010 |
| WO | WO 2010/127099 | A2 | 11/2010 |
| WO | WO 2011/080503 | A2 | 7/2011 |
| WO | WO 2011/109586 | A1 | 9/2011 |
| WO | WO 2011/109724 | A1 | 9/2011 |
| WO | WO 2011/127169 | A1 | 10/2011 |
| WO | WO 2011/155852 | A1 | 12/2011 |
| WO | WO 2012/109539 | A1 | 8/2012 |
| WO | WO 2012/156986 | A1 | 11/2012 |
| WO | WO 2014/105576 | A1 | 7/2014 |

OTHER PUBLICATIONS

U.S. Office Action dated Aug. 6, 2015 issued in U.S. Appl. No. 13/797,802.

U.S. Final Office Action dated May 5, 2016 issued in U.S. Appl. No. 13/797,802.

U.S. Notice of Allowance dated Dec. 19, 2016 issued in U.S. Appl. No. 13/797,802.

PCT International Search Report and Written Opinion dated Jun. 10, 2014 issued in PCT/US2013/076178.

PCT International Preliminary Report on Patentability dated Jun. 30, 2015 issued in PCT/US2013/076178.

European Partial Supplementary Search Report dated Jul. 26, 2016 issued in EP 13 86 7433.

European Extended Search Report dated Oct. 27, 2016 issued in EP 13 86 7433.

Adarme-Vega, et al. (2012) "Microalgal biofactories: a promising approach towards sustainable omega-3 fatty acid production," *Microbial Cell Factories*, 11(96):1-10.

Appleton, Katherine M. et al., (2010) "Updated systematic review and meta-analysis of the effects of n-3 long-chain polyunsaturated fatty acids on depressed mood[1-3]," *The American Journal of Clinical Nutrition*, 91:757-770.

Ballantyne, Christie M. et al., (2012) "Efficacy and Safety of Eicosapentaenoic Acid Ethyl Ester (AMR101) Therapy in Statin-Treated Patients With Persistent High Triglycerides (from the ANCHOR study)," *American Journal of Cardiology*, 110:984-992.

Bays, Harold E. et al., (2011) "Eicosapentaenoic Acid Ethyl Ester (AMR101) Therapy in Patients With Very High Triglyceride Levels (from the Multi-center, plAcebo-controlled, Randomized, double-blINd, 12-week study with an open-label Extension [MARINE] trial)," *Preventive Cardiology/AMR101 Therapy for Very High Triglycerides, The American Journal of Cardiology*, pp. 682-690. [doi:10.1016/j.amjcard.2011.04.015].

Bays, Harold E. et al., (2008) "Prescription omega-3 fatty acids and their lipid effects: physiologic mechanisms of action and clinical implications," *Expert Rev. Cardiovasc. Ther.*, 6(3):391-409.

Bays, Harold E. et al., (2012) "Icosapent ethyl, a pure EPA omega-3 fatty acid: effects on lipoprotein particle concentration and size in patients with very high triglyceride levels (the MARINE study)," *Journal of Clinical Lipidology*, 6(6):565-572.

Belarbi, et al., (2000) "A process for high yield and scaleable recovery of high purity eicosapentaenoic acid esters from microalgae and fish oil," *Enzyme and Microbial Technology*, 26:516-529.

Berger, Alvin, (2014) "Polar Lipids—Phospholipids and Glycolipids—An Enhanced Omega-3 structure," almega$^{PL}$ ™ *Qualitas Health*, 11pp.

Burri, Lena et al., (2012) "Marine Omega-3 Phospholipids: Metabolism and Biological Activities," *Int. J. Mol. Sci.*, 13:15401-15419. [doi:10.3390/ijms131115401].

Calder, Philip C., (2006) "n-3 Polyunsaturated fatty acids, inflammation, and inflammatory diseases[1-3]," *The Am J Clin Nutr*, 83(suppl):1505S-1519S.

Calder, Philip C., (2012) "The role of marine omega-3 (n-3) fatty acids in inflammatory processes, atherosclerosis and plaque stability," *Mol. Nutr. Food Res.*, 56:1073-1080.

Cazzola, Roberta et al., (2007) "Age-and dose-dependent effects of an eicosapentaenoic acid-rich oil on cardiovascular risk factors in healthy male subjects," *Atherosclerosis*,193:159-167.

Colhoun, Helen M. et al., (Jul. 21, 2007) "Eicosapentaenoic acid for prevention of major coronary events," *The Lancet Correspondence*, 370:215.

Cottin, S.C. et al., (2011) "The differential effects of EPA and DHA on cardiovascular risk factors," *Proceedings of the Nutrition Society*, 70:215-231.

Coutteau, et al. (1997) "Lipid classes and their content of n-3 highly unsaturated fatty acids (HUFA) in *Artemia franciscana* after hatching, HUFA-enrichment and subsequent starvation," *Marine Biology*, 130:81-91.

Douglas, N., (2011) "Extract characteristics of supercritical carbon dioxide extracted *Nannochloropsis oculata*," Master's Thesis, Colorado State University, Fort Collins, CO 2011; pp. 1-91.

Dunstan, et al., (1993) "Changes in the lipid composition and maximisation of the polyunsaturated fatty acid content of three microalgae grown in mass culture," *J Applied Phycology*, 5(1):71-83.

Dyerberg, J. et al., (2010) "Bioavailability of marine n-3 fatty acid formulations," *Prostaglandins, Leukotrienes and Essential Fatty Acids*, 83:137-141.

Frangou, Sophia et al., (2006) "Efficacy of ethyl-eicosapentaenoic acid in bipolar depression: randomized double-bling placebo-controlled study," *British Journal of Psychiatry*, 188:46-50.

Grierson, et al., (2012) "Assessment of Bio-oil Extraction from *Tetraselmis chui* Microalgae Comparing Supercritical $CO_2$, Solvent Extraction, and Thermal Processing," *Energy Fuels*, 26:248-255.

Halim, et al., (2011) "Oil extraction from microalgae for biodiesel production," *Biosource Technology*, 102:178-185.

Hall, Wendy L. et al., (2008) "A High-Fat Meal Enriched with Eicosapentaenoic Acid Reduces Postprandial Arterial Stiffness Measured by Digital Volume Pulse Analysis in Healthy Men[1,2]," *The Journal of Nutrition, Nutrient Physiology, Metabolism, and Nutrient-Nutrient Interactions, J. Nutr.*, 138:287-291.

Hamazaki-Fujita, Nina et al., (2011) "Polyunsaturated fatty acids and blood circulation in the forebrain during a mental arithmetic task," *Brain Research*, 1397:38-45.

Hodgson, et al., (1991) "Patterns of variation in the lipid class and fatty acid composition of *Nannochloropsis oculata* (Eustigmatophyceae) during batch culture," *J Applied Phycology*, 3(2):169-181.

Horrobin, et al., (2002) "Eicosapentaenoic acid and arachidonic acid: collaboration and not antagonism is the key to biological understanding," *Prostaglandins, Leukotrienes and Essential Fatty Acids*, 66(1):83-90.

Iketani, Tashiro et al., (2013) "Effect of eicosapentaenoic acid on central systolic blood pressure," *Prostaglandins, Leukotrienes and Essential Fatty Acids*, 88:191-195.

Kagan, Michael L. et al., (2013) "Acute appearance of fatty acids in human plasma—a comparative study between polar-lipid rich oil from the microalgae *Nannochloropsis oculata* and krill oil in healthy young males," *Lipids in Health and Disease*,12:102, 10 pages.

Kagan, Michael L. et al., (2015) "Comparative study of tissue deposition of omega-3 fatty acids from polar-lipid rich oil of the microalgae *Nannochloropsis oculata* with hill oil in rats," *Royal Society of Chemistry, Food Funct*, 6:186-192.

Kelley, Darshan S. et al., (2012) "Chronic and degenerative diseases, Similarities and differences between the effects of EPA and DHA on markers of atherosclerosis in human subjects," *5th Inter-*

(56) References Cited

OTHER PUBLICATIONS

*national Immunonutrition Workshop, Mexico on* Apr. 6-8, 2011, *Proceedings of the Nutrition Society*, 71:322-331.
Lawson, Larry D. et al., (Apr. 15, 1988) "Human Absorption of Fish Oil Fatty Acids as Triacylglycerols, Free Acids, or Ethyl Esters," *Biochemical and Biophysical Research Communications*, 152(1):328-335.
Lemaitre-Delaunay, Dominique et al., (1999) "Blood compartmental metabolism of docosahexaenoic acid (DHA) in humans after ingestion of a single dose of [$^{13}$ C]DHA in phosphatidylcholine," *Journal of Lipid Research*, 40:1867-1874.
Lin, Pao-Yen et al., (Dec. 2012) "Are omega-3 fatty acids antidepressants or just mood-improving agents?" *Mol Psychiatry*, 17(12):1161-1163.
Lin, Pao-Yen et al., (Jul. 2007) "A Meta-Analytic Review of Double-Blind, Placebo-Controlled Trials of Antidepressant Efficacy of Omega-3 Fatty Acids," J *Clin Psychiatry*, 68(7):1056-1061.
Maki, Kevin C. et al., (2009) "Krill oil supplementation increases plasma concentrations of eicosapentaenoic and docosahexaenoic acids in overweight and obese men and women," *Nutrition Research*, 29:609-615.
Maki, Kevin C. et al., (2012) "Treatment options for the management of hypertriglyceridemia: Strategies based on the best-available evidence," *Journal of Clinical Lipidology*, 6:413-426.
Manku, et al., (May 30, 2003) "Phospholipid and Fatty Acid Metabolism in Schizophrenia and Depression," Chapter 4 in *Nutrition and Biochemistry of Phospholipids*, Editors Szuhaj and van Nieuwenhuyzen, eds., AOCS Publishing; Second Edition, pp. 40-49.
Martins, Julian G., (2009) "EPA but Not DHA Appears to be Responsible for the Efficacy of Omega-3 Long Chain Polyunsaturated Fatty Acid Supplementation in Depression: Evidence from a Meta-Analysis of Randomized Controlled Trials," *Journal of the American College of Nutrition*, 28(5):525-542.
Mendes, et al., (2003) "Supercritical carbon dioxide extraction of compounds with pharmaceutical importance from microalgae," *Inorganica Chimica Acta*, 356:328-334.
Miller, Andrew H. et al., (May 1, 2009) "Inflammation and Its Discontents: The Role of Cytokines in the Pathophysiology of Major Depression," *Biol Psychiatry*, 65(9):732-741.
Mischoulon, David et al., "(Dec. 2009)" A Double-Blind Randomized Controlled Trial of Ethyl-Eicosapentaenoate (EPA-E) for Major Depressive Disorder, *J Clin Psychiatry*, 70(12):1636-1644.
Mozaffarian, Dariush et al., (2012) "(n-3) Fatty Acids and Cardiovascular Health: Are Effects of EPA and DHA Shared or Complementary?[1-3]" *The Journal of Nutrition*, Supplement: Heart Healthy Omega-3s for Food-Stearidonic Acid (SDA) as a Sustainable Choice, 142:614S-625S.
Nemets, Boris et al., (Mar. 2002) "Addition of Omega-3 Fatty Acid to Maintenance Medication Treatment for Recurrent Unipolar Depressive Disorder," *Am J Psychiatry*, 159(3):477-479.
Nemets, Hanah et al., (2006) "Omega-3 Treatment of Childhood Depression: A Controlled, Eouble-Blind Pilot Study," *Am J. Psychiatry*, 163(6):1098-1100.
Peet, Malcolm et al., (2002) "A Dose-Ranging Study of the Effects of Ethyl-Eicosapentaenoate in Patients With Ongoing Depression Despite Apparently Adequate Treatment With Standard Drugs," *Arch Gen Psychiatry*, 59:913-919.
Pepeu, (May 30, 2003) "Is There Evidence That Phospholipid Administration is Beneficial for Your Brain?" Chapter 3 in *Nutrition and Biochemistry of Phospholipids*, Editors Szuhaj and van Nieuwenhuyzen, eds., AOCS Publishing; Second edition, pp. 30-39.
Ramprasath, Vanu R. et al., (2013) "Enhanced increase of omega-3 index in healthy individuals with response to 4-week n-3 fatty acid supplementation from hill oil versu fish oil," *Lipids in Health and Disease*, 12:178, 11pp.
Ross, Brian M. et al., (2007) "Omega-3 fatty acids as treatments for mental illness: which disorder and which fatty acid?" *Lipids in Health and Disease*, 6:21, 19pp.
Rossmeisl, Martin et al., (Jun. 2012) "Metabolic Effects of n-3 PUFA as Phospholipids Are Superior to Triglycerides in Mice Fed a High-Fat Diet: Possible Role of Endocannabinoids," *PLoS ONE*, 7(6):E38834, 13pp.
Saito, Yasushi et al., (2008) Effects of EPA on coronary artery disease in hypercholesterolemic patients with multiple risk factors: sub-analysis of primary prevention cases from the Japan EPA Lipid Intervention Study (JELIS), *Atherosclerosis*, 200:135-140.
Saravanan, Palaniappan et al., (2010) "Cardiovascular effects of marine omega-3 fatty acids," *Lancet*, 375:540-550.
Sarter, Barbara et al., (Apr. 2015) "Blood docosahexaenoic acid and eicosapentaenoic acid in vegans: Associations with age and gender and effects of an algal-derived omega-3 fatty acid supplement," *Clin Nutr.*,34(2):212-218.
Schuchardt, Jan Philipp et al., (2011) "Incorporation of EPA and DHA into plasma phospholipids in response to different omega-3 fatty acid formulations—a comparative bioavailability study of fish oil vs. krill oil," *Lipids in Health and Disease*, 10:145, 7pp.
Sublette, M. Elizabeth et al., (2011) "Meta-Analysis of the Effects of Eicosapentaenoic Acid (EPA) in Clinical Trials in Depression," *J Clin Psychiatry*, © 2011 Physicians Postgraduate Press, Inc., e1-e8.
Takaki, Akira et al., (2011) "Add-on Therapy of EPA Reduces Oxidative Stress and Inhibits the Progression of Aortic Stiffness in Patients with Coronary Artery Disease and Station Therapy: A Randomized Controlled Study," *Journal of Atherosclerosis and Thrombosis*, 18(10):857-866.
Ulven, Stine M. et al., (2011) "Metabolic Effects of Krill Oil are Essentially Similar to Those of Fish Oil but at Lower Dose of EPA and DHA, in Healthy Volunteers," *Lipids*, 46:37-46.
Von Schacky, Clemens, (2006) "A review of omega-3 ethyl esters for cardiovascular prevention and treatment of increased blood triglyceride levels," *Vascular Health and Risk Management*, 2(3):251-262.
Wen, et al., (2003) "Heterotrophic production of eicosapentaenoic acid by microalgae," *Biotechnology Advances*, 21:273-294.
West, M.L. et al., (Jul. 15, 2013) "Study: Almega PL's EPA Absorption and Bioavailability Better than Krill," almega$^{PL}$ ™ summary from *Lipids Health Dis.*,12:102, 2pp.
Wu, Yong et al., (Apr. 2012) "Activation of the AMP-Activated Protein Kinase by Eicosapentaenoic Acid (EPA, 20:5 n-3) Improves Endothelial Function In Vivo," *PLoS ONE*, 7(4).:e35508, 9pp.
Yamakawa, Ken et al., (2012) "Eicosapentaenoic Acid Supplementation Changes Fatty Acid Composition and Corrects Endothelial Dysfunction in Hyperlipidemic Patients," *Cardiology Research and Practice*, vol. 2012, Article ID 754181, 9 pages.
Yokoyama, Mitsuhiro et al., (2007) "Effects of eicosapentaenoic acid on major coronary events in hypercholesterolaemic patients (JELIS): a randomized open-label, blinded endpoint analysis," *Lancet*, 369:1090-1098.
U.S. Appl. No. 15/493,148, filed Apr. 21, 2017, Waibel et al.
U.S. Office Action dated Sep. 19, 2017 issued in U.S. Appl. No. 15/493,148.
Australian Examination report No. 1 dated Sep. 28, 2017 issued in Application No. AU 2013371074.
Japanese Office Action dated Sep. 20, 2017 issued in Application No. JP 2015-549635.
Singapore Supplementary Examination Report dated Sep. 21, 2017 issued in Application No. SG 11201504641S.

A

MGDG

B

DGDG

EICOSAPENTAENOIC ACID (EPA) FORMULATIONS

CROSS-REFERENCE TO RELATED APPLICATIONS

This application is a U.S. national phase under 35 U.S.C. § 371 of International Application No. PCT/US2013/076178, filed on Dec. 18, 2013, which is a continuation-in-part of U.S. Non-Provisional application Ser. No. 13/797,802, filed on Mar. 12, 2013 and claims the benefit under 35 U.S.C. § 119(e) of U.S. Provisional Application No. 61/745,740, filed on Dec. 24, 2012 and U.S. Provisional Application No. 61/816,561, filed on Apr. 26, 2013, all of which are hereby incorporated herein by reference in their entireties for all purposes.

FIELD

Provided herein are compositions comprising eicosapentaenoic acid (EPA) and polar lipids (e.g., phospholipids and glycolipids), and which do not contain any docosahexaenoic acid (DHA).

BACKGROUND

The main source of EPA formulations to date is either fish oil or krill. In the case of fish oil, there are several problems: depletion of fisheries, a relatively low EPA content, DHA and the other six Omega-3 compounds in the mixture, and a variance in EPA content based on natural variance within and between species. The presence of the five other Omega-3 compounds is problematic as they compete with EPA for access to protein receptors. Due to fisheries depletion, at least one producer of fish oil has had its Atlantic menhaden allocation reduced by 20% (on the internet at nutraingredients-usa.com/Industry/Omega-Protein-s-Atlantic-menhaden-catch-to-be-cut-by-20).

The lower concentration of EPA in the raw fish oil and the presence of other near molecular weight components results in refining loss. Fish oil does not include any glycolipids. Phospholipids (PL) present in the raw fish oil tend to be removed through degumming steps adapted from the oilseed industry that as specifically designed to remove these components. Moreover, the transesterification to ethyl esters, one step along the most common refinement methods, also tends to destroy the phospholipids. Phospholipids in the final product would be less than 0.5 wt %.

With respect to krill oil, some of the same problems apply. Krill (*Euphausia superba*) naturally occur in the Antarctic. Krill is considered by many scientists to be the largest biomass in the world. Antarctic krill is fundamental to the survival of almost every species of animal that lives in the Antarctic or sub-Antarctic waters and island groups. Krill also contain eight Omega-3 fatty acids. Many of the fatty acids in Krill are nearly the same molecular weight as EPA and, therefore difficult to remove via refining. The other Omega-3s compete for receptors and, thus, decrease the EPA that is present. Krill, too, have a broad variation in the Omega-3 content and are very susceptible to breakdown of the PLs into FFA by both thermal and enzymatic action.

If everyone in the US and Europe ingested 2 g per day of EPA, a level that has been demonstrated to be effective in cardiovascular and mental health, there is not enough fish in the sea to provide a sustainable supply.

SUMMARY

Provided are EPA formulations with improved bioavailability by virtue of containing increased concentrations of EPA in its more bioavailable forms (e.g., as free fatty acid, as glycolipid conjugate and as phospholipid conjugate), and reduced or eliminated concentrations of EPA in its least bioavailable forms (e.g., as diglyceride or triglyceride conjugate). The present EPA formulations deliver equivalent or increased levels of EPA to various target organs and tissues (e.g., blood (plasma), brain, liver, adipose, skin) at reduced EPA dosages (e.g., 10%, 15%, 20%, 25% reduced EPA dosages in comparison to krill oil and/or fish oil) and with lower concentrations of polar lipids (e.g., less than 35 wt. % of the total composition in comparison to greater than 35 wt. %, e.g., at least 39 wt. %, in krill oil and/or fish oil).

Accordingly, in varying embodiments, EPA compositions comprising from about 15 wt. % to about 90 wt. % eicosapentaenoic acid (EPA), about 10 wt. % to about 70 wt. % polar lipids, 0 wt. % to about 5 wt. % esterified EPA, wherein the composition does not comprise docosahexaenoic acid (DHA), and wherein the composition is suitable for human consumption. Herein, DHA refers to DHA in any of the lipid forms including free fatty acid, triglyceride, diglyceride, monoglyceride, sphingolipid, phospholipid, and glycolipid. In some embodiments, EPA compositions are provided comprising the following distribution of EPA by lipid class: about 3 wt. % to about 50 wt. % of the EPA is a phospholipid conjugate; about 5 wt. % to about 50 wt. % of the EPA is a glycolipid conjugate; about 0 wt. % to about 10 wt. % of the EPA is a triglyceride conjugate or a diglyceride conjugate; and about 15 wt. % to about 85 wt. % of the EPA is in free fatty acid form, and wherein the composition is suitable for human consumption. In some embodiments, the composition comprises about 15 wt. % to about 75 wt. % EPA, e.g., about 20 wt. % to about 50 wt. % EPA. In some embodiments, the composition does not comprise esterified EPA. In some embodiments, the composition comprises less than about 5 wt. % esterified EPA, e.g., from about 0 wt. % to about 0.5 wt. %, 1.0 wt. %, 1.5 wt. %, 2.0 wt. %, 2.5 wt. %, 3.0 wt. %, 3.5 wt. %, 4.0 wt. %, 4.5 wt. % or 5.0 wt. % esterified EPA. In varying embodiments, the EPA is in one or more forms selected from the group consisting of a free fatty acid a phospholipid conjugate, a glycolipid conjugate, a triglyceride conjugate, and a diglyceride conjugate. In some embodiments, about 0 wt. % to about 10 wt. % of the EPA in the composition is a triglyceride conjugate or a diglyceride conjugate, e.g., less than about 0.2 wt. % of the EPA in the composition is a triglyceride conjugate or a diglyceride conjugate. In some embodiments, about 15 wt. % to about 85 wt. % of the EPA in the composition is in free fatty acid form, e.g., at least about 20 wt. %, 25 wt. %, 30 wt. %, 35 wt. %, 40 wt. %, 50 wt. % to about 85 wt. % of the EPA in the composition is in free fatty acid form. In some embodiments, about 5 wt. % to about 90 wt. % of the EPA in the composition is a polar lipid conjugate, e.g., about 10 wt. % to about 80 wt. % of the EPA in the composition is a polar lipid conjugate. In some embodiments, the composition comprises at least about 13 wt. % polar lipids, e.g., at least about 14 wt. %, 15 wt. %, 16 wt. %, 17 wt. %, 18 wt. %, 19 wt. %, 20 wt. % polar lipids. In some embodiments, the composition comprises from about 10 wt. % to about 35 wt. % polar lipids, e.g., from about 10 wt. % to about 15 wt. %, 20 wt. %, 25 wt. %, 30 wt. %, or 35 wt. % polar lipids. In some embodiments, the polar lipids are comprised of phospholipid conjugates and glycolipid conjugates at a wt. % ratio in the range of about 3:1 to about 1:3. In some embodiments, about 5 wt. % to about 50 wt. % of the EPA in the composition is a glycolipid conjugate. In some embodiments, glycolipid conjugates comprise one or more of digalactosyldiacylglycerol and monogalactosyldiacylglycerol. In some embodiments, about 3 wt. % to about 50 wt. % of the EPA in the composition is a phospholipid conjugate. In some embodiments, the phospholipid conjugates comprise one or more of phosphatidylcholine, lyso-phosphatidylcholine, phosphatidylinositol, phosphatidylethanolamine and phosphatidylglycerol. In some embodiments, the phospholipid conjugates comprise one or more of phosphatidylcholine and phosphatidylglycerol. In some embodiments, the EPA to total omega-3 fatty acids ratio is greater than 90%, e.g., greater than 91%, 92%, 93%, 94%, 95%, 96%, 97%, 98%, 99%, or greater. In some embodiments, the composition comprises at least about 13 wt. % polar lipids, e.g., at least about 14 wt. %, 15 wt. %, 16 wt. %, 17 wt. %, 18 wt. %, 19 wt. %, 20 wt. % polar lipids, less than 0.2 wt. % glyceride conjugates and at least about 30 wt. % free fatty acids. In some embodiments, the composition comprises about 20-50 wt. % EPA, about 10-25 wt. % glycolipids, and about 5-25 wt. % phospholipids. In varying embodiments, the composition comprises chlorophyll a. In varying embodiments, the composition does not comprise chlorophyll c. In some embodiments, the composition comprises less than about 10.0 wt. % arachidonic acid, e.g., less than about 9.5 wt. %, 9.0 wt. %, 8.5 wt. %, 8.0 wt. %, 7.5 wt. %, 7.0 wt. %, 6.5 wt. %, 6.0 wt. %, 5.5 wt. %, 5.0 wt. %, 4.5 wt. %, 4.0 wt. %, 3.5 wt. %, 3.0 wt. %, 2.5 wt. %, 2.0 wt. %, 1.5 wt. % or 1.0% arachidonic acid or does not comprise arachidonic acid. In some embodiments, the EPA composition does not comprise or is substantially free of intact cells, cellular components, polynucleotides, and polypeptides. In some embodiments, the composition comprises coenzyme Q9 (CoQ9) and/or coenzyme Q10 (CoQ10). In some embodiments, the composition comprises less than about 1 wt. % phytosterols. In some embodiments, the composition comprises less than about 2 wt. % carotenoids. In some embodiments, the composition does not comprise fatty acids selected from the group consisting of octadecatetraenoic acid or stearidonic acid (SDA=C18:4ω3), eicosatrienoic acid (ETE=C20:3ω3), eicosatetraenoic acid (ETA=C20:4ω3), heneicosapentaenoic acid or uncosapentaenoic acid (HPA=C21:5ω3), and docapentaenoic acid (DPA=C22:5ω3). In some embodiments, the composition does not comprise one or more, e.g., two or more, e.g., or all of the carotenoids selected from the group consisting of astaxanthin, cis-lutein, trans-lutein, cis-zeaxanthin, trans-alpha-crytoxanthin, trans-alpha-carotene, cis-alpha-carotene, cis-lycopene, and trans-lycopene. In some embodiments, the composition does not comprise one or more phospholipids selected from the group consisting of N-acyl-phosphatidylethanolamine, lyso-phosphatidylcholine, phosphatidylinositol and phosphatidylethanolamine. In some embodiments, the composition does not comprise sphingolipids.

In some embodiments, the composition comprises the following distribution of EPA by lipid class:

- about 3 wt. % to about 50 wt. % of the EPA is a phospholipid conjugate;
- about 5 wt. % to about 50 wt. % of the EPA is a glycolipid conjugate;
- about 0 wt. % to about 10 wt. % of the EPA is a triglyceride conjugate or a diglyceride conjugate; and
- about 15 wt. % to about 85 wt. % of the EPA is in free fatty acid form.

In some embodiments, the composition comprises:

i) 0 to 5 wt. % C:18 fatty acids;
ii) 0 to 20 wt. % C:16 fatty acids;
iii) 0 to 5 wt. % C:14 fatty acids;
iv) 0 to 0.5 wt. % C:12 fatty acids; and/or
v) 0 to 0.5 wt. % C:10 fatty acids.

In varying embodiments, the composition comprises:

| Component | amount |
|---|---|
| Lipid Composition | |
| Total polar lipids | ≥15 wt. % |
| Total phospholipids | ≥6 wt. % |
| Total glycolipids | ≥9 wt. % |
| Fatty Acid Profile | |
| Total omega-3 | ≥25 wt. % |
| C20:5ω3 (EPA) | ≥25 wt. % |
| EPA/Total omega-3 | >98% wt. % |
| C16:1ω7 (omega-7) | ≥8 wt. % |
| Phytonutrients | |
| Chlorophyll | ≥5 wt. % |
| Total Carotenoids | ≥750 mg/kg |

In varying embodiments, the composition comprises:

| Component | wt. % |
|---|---|
| Fatty Acids | |
| Capric (10:0) | 0.1-0.2 |
| Lauric (12:0) | 0.1-0.2 |
| Myristic (14:0) | 1.0 |
| Palmitic (16:0) | 5.3-6.5 |
| Palmitoleic (16:1) | 7.0-8.0 |
| Hexadecadienoic (16:2) | 0.2-0.3 |
| Stearic (18:0) | 0.2-0.3 |
| Oleic (18:1ω9) | 2.0 |
| Oleic (18:1ω7) | 0.3-0.4 |
| Linoleic (18:2ω6) | 1.2-2.0 |
| Alpha-Linolenic (ALA) (18:3ω3) | 0.2 |
| Arachidonic (20:4ω6) | 1.0-8.0 |
| Eicosapentaenoic (EPA) (20:5ω3) | 19-30 |
| Total Fatty Acid | 40-55 |
| Total Omega-3 | 20-30 |
| EPA/Omega-3 | >93 |
| Total Omega-6 | 2-10 |
| Phospholipids | |
| Phosphatidylcholine | 4.7-7.4 |
| Lyso-Phosphatidylcholine | 0.3-0.4 |
| Phosphatidylinositol | 0.8-1.3 |
| Phosphatidylethanolamine | 0.5-0.8 |
| Phosphatidylglycerol | 1.8-2.8 |
| Glycolipids | |
| Digalactosyldiacylglycerol | 10-17 |
| Monogalactosyldiacylglycerol | 3-5 |
| Phytonutrients | |
| Phytosterols | 1.5 |
| Chlorophyll | 4-5 |
| Total Phospholipids (PL) (wt %) | 9-14 |
| Total Glycolipids (GL) (wt %) | 13-21 |
| Total PoL (PL + GL) (wt %) | 22-35 |

In varying embodiments, the composition comprises equivalent or increased bioavailability of EPA to target tissues (e.g., blood (plasma), brain, liver, adipose, skin) in comparison to krill oil or fish oil.

In a further aspect, provided is a capsule, tablet, solution, syrup, or suspension suitable for human consumption comprising an EPA composition as described above and herein. In varying embodiments, the capsule is a gel capsule.

Further provided is a food, beverage, energy bar, or nutritional supplement comprising an EPA composition as described above and herein.

Further provided are methods of preventing, ameliorating, mitigating, delaying progression of and/or treating a disease condition selected from the group consisting of psychiatric disorders, cardiovascular disease, liver disease; chronic hepatitis; steatosis; liver fibrosis; alcoholism; malnutrition; chronic parenteral nutrition; phospholipid deficiency; lipid peroxidation; disarrhythmia of cell regeneration; destabilization of cell membranes; menopausal or post-menopausal conditions; cancer; aging; benign prostatic hyperplasia; kidney disease; edema; skin diseases; gastrointestinal diseases; pregnancy toxemia; arthritis; osteoporosis; inflammatory diseases; and neurodegenerative diseases. In some embodiments, the methods comprise administering to a subject in need thereof an effective amount of a composition, capsule, tablet, solution, syrup, suspension, food, beverage, energy bar, or nutritional supplement as described above and herein. In varying embodiments, administration is orally or transdermally. In some embodiments, the disease condition is a psychiatric disorder selected from the group consisting of depression, unipolar depression, major depression, depressed mood and/or post-partum depression, bipolar disorder, anxiety, panic and social phobic disorders, mood disorders, schizophrenia, Obsessive Compulsive Disorder (OCD), borderline personality disorder, attention deficit hyperactivity disorder and related disorders, and anorexia nervosa. In some embodiments, the disease condition is a cardiovascular disease selected from the group consisting of hypertension, coronary artery disease, hypercholesterolemia, dyslipidaemia, high blood pressure, and peripheral vascular system disease.

Further provided are methods of producing a composition comprising EPA. In some embodiments, the methods comprise:

a) providing an algal paste;
b) extracting lipids from the algal paste with an organic solvent, thereby substantially isolating a crude algae extract (CAE) comprising neutral lipids and polar lipids from the water-soluble components of the paste;
c) substantially removing the remaining water-soluble components from the CAE, thereby yielding a crude algae oil (CAO);
d) contacting the CAO with supercritical CO2, wherein the supercritical CO2 selectively extracts the neutral lipids, thereby splitting the CAO into a neutral lipid fraction comprising free fatty acids and a polar lipid fraction comprising glycolipids and phospholipids;
e) isolating C20 free fatty acids from the neutral lipid fraction, thereby yielding a concentrated EPA free fatty acid fraction; and
f) combining the concentrated EPA free fatty acid fraction produced in step e) and the polar lipid fraction produced in step d).

In some embodiments, the methods comprise:

a) providing an algal paste;
b) extracting lipids from the algal paste with an organic solvent, thereby isolating a crude algae extract (CAE) comprising neutral lipids and polar lipids from the water-soluble components of the paste;
c) substantially removing the remaining water-soluble components from the CAE, thereby yielding a crude algae oil (CAO);
d) hydrolyzing a first portion of the CAO, thereby releasing free fatty acids in the portion of CAO;
e) fractionating the released free fatty acids according to chain length, thereby isolating C20 free fatty acids and yielding a concentrated EPA free fatty acid fraction; and
f) combining the concentrated EPA free fatty acid fraction produced in step e) and a second portion of the CAO produced in step c).

In some embodiments of the methods, the solvent is selected from the group consisting of an ether, a ketone, an alcohol, and mixtures thereof. In some embodiments, the solvent is selected from the group consisting of ethanol, isopropyl alcohol, acetone, dimethyl ether, and mixtures thereof. In some embodiments, the organic solvent is selected from the group consisting of absolute ethanol, 190 proof (95 v/v %) ethanol (EtOH), denatured 190 proof ethanol, special denatured alcohols (SDA), acetone and ethanol, isopropyl alcohol, acetone and methanol, methyl ethyl ketone (MEK) and methanol, MEK and ethanol, dimethyl ether, dimethyl ether and methanol, dimethyl ether and ethanol. In some embodiments, the organic solvent is a mixture of dimethyl ether and ethanol. In varying embodiments, the solvent comprises heptane (Hep), ethyl acetate (EtAc), methanol (MeOH), and water ($H_2O$), e.g., in a volume ratio of 1:1:1:1. In varying embodiments, the solvent comprises propane, EtAC, ethanol (EtOH), and water ($H_2O$), e.g., in a volume ratio of 1:1:1:1. In varying embodiments, the solvent comprises butane, EtAc, EtOH, and water ($H_2O$), e.g., in a volume ratio of 1:1:1:1. In some embodiments, the supercritical CO2 is maintained at a pressure in the range from about 100 bar to about 1000 bar, e.g., in the range from about 340 bar to about 700 bar, e.g., in the range from about 350 bar to about 690 bar and at a temperature in the range from about 35° C. to about 110° C., e.g., in the range from about 40° C. to about 110° C., e.g., in the range from 60° C. and 90° C. In some embodiments, the neutral lipid fraction is subject to hydrolysis, thereby releasing free fatty acids. In some embodiments, a portion of the CAE is subject to hydrolysis, thereby releasing free fatty acids. In some embodiments, a portion of the CAO is subject to hydrolysis, thereby releasing free fatty acids. In some embodiments, the neutral lipid fraction, the CAE or the CAO is exposed to heat, alkali and/or acid to effect hydrolysis. In some embodiments, the C20 free fatty acids are isolated from the released free fatty acids by fractionating the free fatty acids over a pressure gradient of supercritical CO2, e.g., a stepwise or continuous pressure gradient of supercritical CO2. In varying embodiments, the pressure gradient of supercritical CO2 is from about 172 bar to about 345 bar. In varying embodiments, the pressure gradient of supercritical CO2 is isothermal, e.g. i, is maintained at a constant temperature of between about 50° C. and about 70° C.

In a further embodiment, the methods comprise producing a composition comprising EPA and polar lipids, comprising:

a) providing an algal paste;

b) extracting the algal paste with concentrated ethanol, wherein the concentration of the ethanol is at least about 70 vol. %, e.g., at least about 75 vol. %, 80 vol. %, 85 vol. %, 90 vol. % or 95 vol. %;

c) substantially removing the ethanol from the algal paste, thereby yielding a crude algae extract (CAE) comprising neutral lipids and polar lipids;

d) extracting the CAE with a C3-C7 alkane solvent;

e) substantially removing the alkane solvent, thereby yielding a crude algae oil (CAO) enriched in polar lipids and fatty acids;

f) enriching for polar lipids in a first portion of the CAO, comprising:

i) contacting the first portion of CAO with a first silica gel sorbent;

ii) eluting neutral lipids by contacting the first silica gel sorbent with a C3-C7 alkane; and iii) eluting polar lipids by contacting the first silica gel sorbent with a C1-C4 alcohol; thereby yielding concentrated polar lipids (CPL);

g) enriching for free fatty acids in a second portion of the CAO, comprising:

i) subjecting the second portion of the CAO and the neutral lipids eluted in step f) ii) to hydrolysis;

ii) contacting the hydrolyzed CAO with a second silica gel sorbent;

iii) eluting free fatty acids by contacting the second silica gel sorbent with a C3-C7 alkane; and iv) concentrating the EPA from the free fatty acids eluted in step g) iii), thereby yielding concentrated EPA; and h) combining the CPL obtained in step f) iii) and the concentrated EPA obtained in step g) iv), thereby producing a composition comprising EPA and polar lipids. In varying embodiments, the concentration of ethanol used in step b) is less than 96%. In varying embodiments, the methods further comprise the step of extracting the CAE with ethyl acetate in step d). In varying embodiments, the methods further comprise after step f) ii), eluting polar lipids by contacting the first silica gel sorbent with acetone. In some embodiments, the EPA is concentrated from the free fatty acids by urea crystallization. In some embodiments, the EPA is concentrated from the free fatty acids by supercritical carbon dioxide fractionation. In some embodiments, the EPA is concentrated using a pressure gradient of supercritical $CO_2$. In some embodiments, the pressure gradient of supercritical $CO_2$ is from about 172 bar to about 345 bar. In some embodiments, the pressure gradient of supercritical $CO_2$ is isothermal. In some embodiments, the pressure gradient of supercritical $CO_2$ is maintained at a constant temperature of between about 50° C. and about 70° C.

With respect to further embodiments of the methods for production, in some embodiments, the paste is a wet paste. In some embodiments, the algal cells comprise *Nannochloropsis* cells. In some embodiments, the *Nannochloropsis* cells are selected from *N. oculata, N. oceanica*, and mixtures thereof. In some embodiments, the algal cells further comprise *Nannochloris* cells (e.g., less than about 10%, 9%, 8%, 7%, 6%, 5%, 4%, 3%, 2%, or 1% of the total cells), e.g., as a typical by-product of outdoor cultivation. In varying embodiments, the method does not comprise an esterification step. In some embodiments, the algal cells are not subject to mechanical cracking, thermal pretreatment, alkaline treatment and/or acid treatment. In some embodiments, the cell membranes of the algal cells are not disrupted. In some embodiments, the paste has not been subject to drying. In some embodiments, the paste has not been subject to thermal drying, vacuum drying, ambient temperature drying, and/or freeze drying.

In a further aspect, EPA compositions produced by the methods described above and herein are provided.

Definitions

The term "substantially" with respect to isolation, removal or purification refers to at least about 90% isolated, removed and/or purified, e.g., at least about 91%, 92%, 93%, 94%, 95%, 96%, 97%, 98%, 99%, or more, isolated, removed or purified.

As used herein, "administering" refers to local and systemic administration, e.g., including enteral, parenteral, and topical/transdermal administration. Routes of administration for the EPA formulations that find use in the methods described herein include, e.g., oral (per os (P.O.)) administration, administration as a suppository, topical contact, transdermal delivery (e.g., via a transdermal patch), intravenous ("iv") administration, intraperitoneal ("ip") administration, or the implantation of a slow-release device e.g., a mini-osmotic pump, a depot formulation, etc., to a subject. Administration can be by any route including parenteral and transmucosal (e.g., oral, nasal, vaginal, rectal, or transdermal). Parenteral administration includes, e.g., intravenous, intra-arterial, intraventricular. Other modes of delivery include, but are not limited to, the use of liposomal formulations, intravenous infusion, transdermal patches, etc.

The term "co-administering" or "concurrent administration", when used, for example with respect to the EPA formulations described herein and another active agent (e.g., pharmacological agents currently administered to treat or ameliorate depression, hypertension, and/or elevated cholesterol levels, astaxanthin, vitamin E, phospholipids, coenzyme Q9 (CoQ9), coenzyme Q10 (CoQ10)), refers to administration of EPA composition and the active agent such that both can simultaneously achieve a physiological effect. The two agents, however, need not be administered together. In certain embodiments, administration of one agent can precede administration of the other. Simultaneous physiological effect need not necessarily require presence of both agents in the circulation at the same time. However, in certain embodiments, co-administering typically results in both agents being simultaneously present in the body (e.g., in the plasma) at a significant fraction (e.g., 20% or greater, preferably 30% or 40% or greater, more preferably 50% or 60% or greater, most preferably 70% or 80% or 90% or greater) of their maximum serum concentration for any given dose.

The term "effective amount" or "pharmaceutically effective amount" refer to the amount and/or dosage, and/or dosage regime of the EPA compositions described herein necessary to bring about the desired result e.g., an amount sufficient to mitigate in a mammal one or more symptoms associated with a disease condition mitigated by EPA (e.g., depression), or an amount sufficient to lessen the severity or delay the progression of a disease condition mitigated by EPA in a mammal (e.g., therapeutically effective amounts), an amount sufficient to reduce the risk or delaying the onset, and/or reduce the ultimate severity of a disease condition mitigated by EPA in a mammal (e.g., prophylactically effective amounts).

"Sub-therapeutic dose" refers to a dose of a pharmacologically active agent(s), either as an administered dose of pharmacologically active agent, or actual level of pharmacologically active agent in a subject that functionally is insufficient to elicit the intended pharmacological effect in itself (e.g., to obtain analgesic and/or anti-inflammatory effects), or that quantitatively is less than the established therapeutic dose for that particular pharmacological agent (e.g., as published in a reference consulted by a person of skill, for example, doses for a pharmacological agent published in the Physicians' Desk Reference, 67th Ed., 2013, Thomson Healthcare or Brunton, et al., Goodman & Gilman's The Pharmacological Basis of Therapeutics, 12th edition, 2010, McGraw-Hill Professional). A "sub-therapeutic dose" can be defined in relative terms (i.e., as a percentage amount (less than 100%) of the amount of pharmacologically active agent conventionally administered). For example, a sub-therapeutic dose amount can be about 1% to about 75% of the amount of pharmacologically active agent conventionally administered. In some embodiments, a sub-therapeutic dose can be about 75%, 50%, 30%, 25%, 20%, 10% or less, than the amount of pharmacologically active agent conventionally administered.

The phrase "cause to be administered" refers to the actions taken by a medical professional (e.g., a physician), or a person controlling medical care of a subject, that control and/or permit the administration of the EPA compositions described herein to the subject. Causing to be administered can involve diagnosis and/or determination of an appropriate therapeutic or prophylactic regimen, and/or prescribing the EPA compositions described herein for a subject. Such prescribing can include, for example, drafting a prescription form, annotating a medical record, and the like.

The phrase "in conjunction with" when used in reference to the use of the EPA compositions described herein in conjunction with one or more other active agent(s) so that there is at least some chronological overlap in their physiological activity on the organism. When they are not administered in conjunction with each other, there is no chronological overlap in physiological activity on the organism. In certain preferred embodiments, the "other drug(s)" are not administered at all (e.g., not co-administered) to the organism.

As used herein, the terms "treating" and "treatment" refer to delaying the onset of, retarding or reversing the progress of, reducing the severity of, or alleviating or preventing either the disease or condition to which the term applies, or one or more symptoms of such disease or condition.

The term "mitigating" refers to reduction or elimination of one or more symptoms of that pathology or disease, and/or a reduction in the rate or delay of onset or severity of one or more symptoms of that pathology or disease, and/or the prevention of that pathology or disease.

The term "psychiatric condition," including the psychiatric conditions listed herein, are as defined in the Diagnostic and Statistical Manual of Mental Disorders DSM-IV-TR Fourth Edition (Text Revision) by American Psychiatric Association (June 2000).

As used herein, the phrase "consisting essentially of" refers to the genera or species of active pharmaceutical agents recited in a method or composition (e.g., the EPA compositions described herein), and further can include other agents that, on their own do not substantial activity for the recited indication or purpose. In some embodiments, the phrase "consisting essentially of" expressly excludes the inclusion of one or more additional agents that have pharmacological activity other than the EPA compositions and/or the listed components of the EPA compositions described herein.

The terms "subject," "individual," and "patient" interchangeably refer to a mammal, preferably a human or a non-human primate, but also domesticated mammals (e.g., canine or feline), laboratory mammals (e.g., mouse, rat, rabbit, hamster, guinea pig) and agricultural mammals (e.g., equine, bovine, porcine, ovine). In various embodiments, the subject can be a human (e.g., adult male, adult female, adolescent male, adolescent female, male child, female child) under the care of a physician or other healthworker in a hospital, psychiatric care facility, as an outpatient, or other clinical context. In certain embodiments the subject may not be under the care or prescription of a physician or other healthworker.

DETAILED DESCRIPTION

1. Introduction

Figure 1:
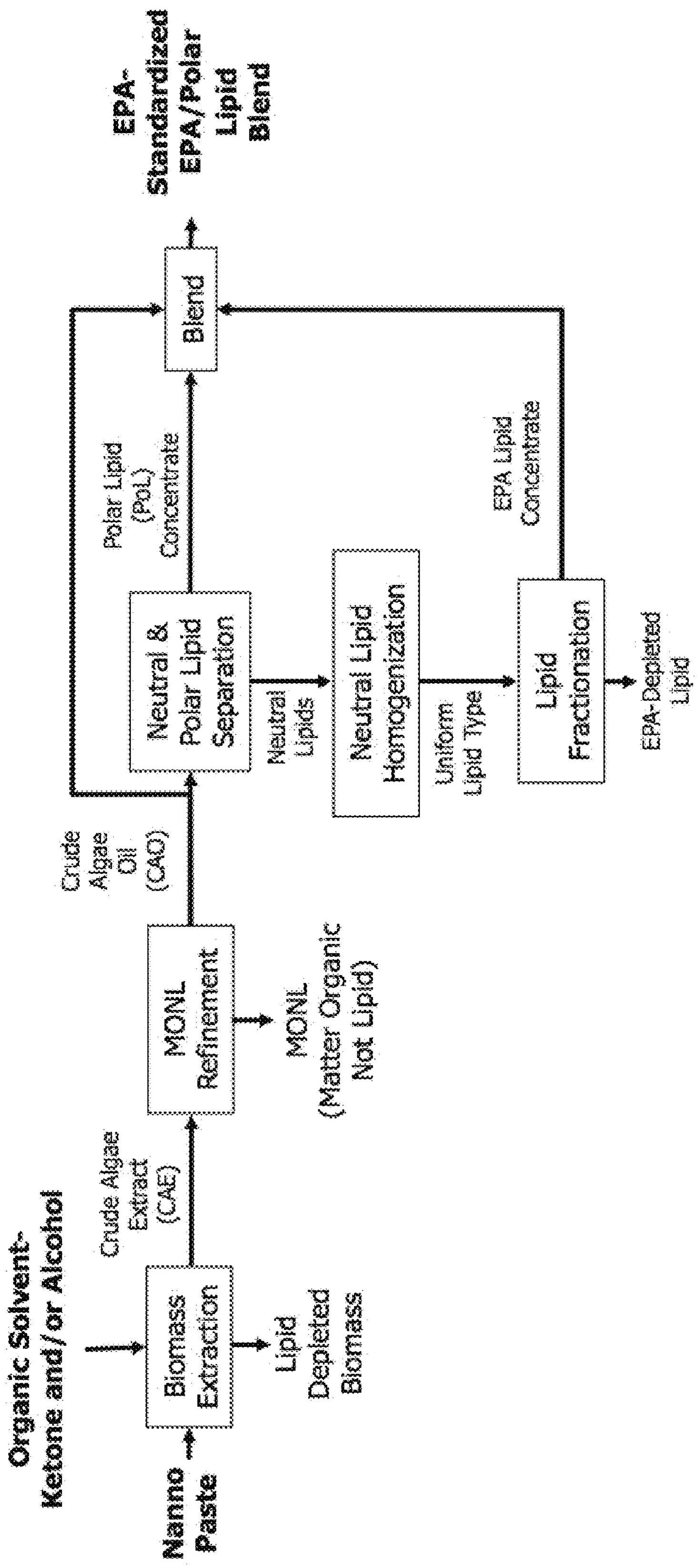
FIG. 1 provides a general overview of an illustrative process from a *Nannochloropsis* paste to a standardized EPA and polar lipid mixture.

Provided herein are compositions of nutritionally and pharmacologically beneficial mixtures comprising eicosapentanoic acid (EPA) Omega 3 fatty acids, polar lipids, and phytonutrients derived from *Nannochloropsis oculata*, an eustigmatophyte. These phytonutrients include Omega-7 fatty acid, chlorophyll, carotenoids, and coenzyme Q9 (CoQ9) and coenzyme Q10 (CoQ10). *N. oculata* is an eukaryotic algae that is unicellular with polysaccharide cells walls and coccoid cells. *Nannochloropsis* contains a yellow-green chloroplast, which contains chlorophyll a, zeaxanthin, and beta-carotene and specifically lacks chlorophyll b and c. The species synthesizes fatty acids in a number of different classes: neutral lipids comprised of free fatty acid, triglycerides, and diglycerides and polar lipids comprised of phospholipids and glycolipids. Over two thirds of the fatty acids produced by *Nannochloropsis* consist of eicosapentaenoic acid (EPA=C20:5ω3), palmitic acid (C16:0), palmitoleic acid (C16:1=C16:1ω7). The species produces only one other Omega-3, alpha-linolenic acid (ALA=C18:3ω3). Decosahexaenoic acid (DHA=C22:6ω3) is not produced by the species at all. Other Omega-3s fatty acids that are notably absent are octadecatetraenoic acid or stearidonic acid (SDA=C18:4ω3), eicosatrienoic acid (ETE=C20:3ω3), eicosatetraenoic acid (ETA=C20:4ω3), heneicosapentaenoic acid or uncosapentaenoic acid (HPA=C21:5ω3), docapentaenoic acid (DPA=C22:5ω3).

Table 1 shows the relative fatty acid profile of fish oil ethyl esters (EPAX 6000 EE and EPAX 4020 EE), highly refined fish oil (Minami Nutrition Plus EPA), krill oil (NOW Neptune Krill Oil (NKO)), S12 and S14 variants of *Nannochloropsis oculata*. While the other sources include at least seven of these eight Omega-3 fatty acids, *Nannochloropsis oculata* oil only contains two-EPA and ALA. In pure algal culture and under the best growth conditions, the ratio of EPA to Total Omega3 is greater than 99%. Under real-world conditions and in the presence of thermal stress, the algae may produce additional ALA. The EPA to Total Omega-3 ratio is greater than 90% and, more typically, greater than 93%, 95%, 96%, 97%, or 98%. Other minor fatty acid components found in excess of 0.5% of the fatty acid profile are myristic (C14:0), Myristoleic (C14:1), Oleic (C18:1ω9), Oleic (C18:1ω7), linoleic (C18:2ω6), and arachidonic (C20:4ω6).

TABLE 1

Fatty Acid Profile From Different Omega-3 Sources

| Fatty Acid | C#: Dbl. Bond | Fish Oil Ethyl Esters EPAX 6000 EE | Fish Oil Ethyl Esters EPAX 4020 EE | Refined EPA Plus EPA | Krill Oil NOW NKO | *Nannochloropsis Oculata* S12 | *Nannochloropsis Oculata* S14 |
|---|---|---|---|---|---|---|---|
| Caprylic | 8:0 | 0.00 | 0.00 | 0.17 | 0.00 | 0.38 | 0.15 |
| Capric | 10:0 | 0.08 | 0.05 | 0.12 | 0.09 | 0.36 | 1.52 |
| Lauric | 12:0 | 0.00 | 0.00 | 0.00 | 0.18 | 0.70 | 0.41 |
| Myristic | 14:0 | 0.12 | 0.23 | 0.00 | 8.55 | 3.58 | 4.54 |
| Myristoleic | 14:1 | 0.00 | 0.00 | 0.00 | 0.36 | 4.26 | 0.09 |
| Pentadecanoic | 15:0 | 0.00 | 0.00 | 0.00 | 0.31 | 0.22 | 0.36 |
| Palmitic | 16:0 | 0.49 | 2.51 | 0.00 | 18.69 | 13.12 | 23.48 |
| Palmitoleic | 16:1 | 0.43 | 0.97 | 0.00 | 5.74 | 16.51 | 24.32 |
| Hexadecadienoic | 16:2 | 0.11 | 0.16 | 0.00 | 0.41 | 0.34 | 0.25 |
| Hexadecatrienoic | 16:3 | 0.16 | 0.21 | 0.00 | 0.00 | 0.00 | 0.00 |
| Hexadecatetraenoic | 16:4 | 0.10 | 0.27 | 0.00 | 0.49 | 0.00 | 0.00 |
| Heptadecanoic | 17:0 | 0.06 | 0.21 | 0.00 | 0.00 | 0.00 | 0.31 |
| Stearic | 18:0 | 2.44 | 3.70 | 0.00 | 0.93 | 0.25 | 1.04 |
| Oleic | 18:1ω9 | 4.43 | 7.10 | 0.00 | 9.29 | 2.77 | 2.99 |
| Oleic | 18:1ω7 | 1.45 | 2.36 | 0.00 | 6.62 | 0.88 | 0.45 |
| Linoleic | 18:2ω6 | 0.37 | 0.83 | 0.00 | 1.92 | 4.04 | 2.40 |

TABLE 1-continued

Fatty Acid Profile From Different Omega-3 Sources

| Fatty Acid | C#: Dbl. Bond | Fish Oil Ethyl Esters EPAX 6000 EE | Fish Oil Ethyl Esters EPAX 4020 EE | Refined EPA Plus EPA | Krill Oil NOW NKO | *Nannochloropsis Oculata* S12 | *Nannochloropsis Oculata* S14 |
|---|---|---|---|---|---|---|---|
| Linoleic | 18:2ω4 | 0.30 | 0.35 | 0.00 | 0.00 | 0.00 | 0.00 |
| Gamma-Linolenic | 18:3ω6 | 0.00 | 0.19 | 0.00 | 0.00 | 0.25 | 0.48 |
| Alpha-Linolenic (ALA) | 18:3ω3 | 0.31 | 0.73 | 0.19 | 1.02 | 0.36 | 0.84 |
| Octadecatetraenoic (SDA) | 18:4ω3 | 0.70 | 1.56 | 0.67 | 2.52 | 0.00 | 0.00 |
| Arachidic | 20:0 | 0.55 | 0.51 | 0.00 | 0.00 | 0.00 | 0.17 |
| Eicosanoic | 20:1ω11 | 0.36 | 0.28 | 0.00 | 0.09 | 0.00 | 0.00 |
| Eicosanoic | 20:1ω9 | 2.07 | 2.08 | 0.00 | 0.77 | 0.00 | 0.00 |
| Eicosanoic | 20:1ω7 | 0.77 | 0.63 | 0.00 | 0.29 | 0.00 | 0.00 |
| Eicosadienoic | 20:2ω6 | 0.28 | 0.43 | 0.11 | 0.00 | 0.00 | 0.00 |
| Eicosatrienoic | 20:3ω6 | 0.40 | 0.32 | 0.32 | 0.00 | 0.13 | 0.31 |
| Eicosatrienoic (ETE) | 20:3ω3 | 0.16 | 0.21 | 0.07 | 0.00 | 0.00 | 0.00 |
| Arachidonic | 20:4ω6 | 2.09 | 1.91 | 3.59 | 0.64 | 3.97 | 4.79 |
| Eicosatetraenoic (ETA) | 20:4ω3 | 1.62 | 1.50 | 2.12 | 0.74 | 0.00 | 0.00 |
| Eicosapentaenoic (EPA) | 20:5ω3 | 41.89 | 33.30 | 88.89 | 18.09 | 35.62 | 19.73 |
| Uncosapentaenoic (HPA) | 21:5ω3 | 2.22 | 1.68 | 1.11 | 0.45 | 0.00 | 0.00 |
| Behenic | 22:0 | 0.26 | 0.24 | 0.00 | 0.00 | 0.00 | 0.00 |
| Erucic | 22:1ω11 | 2.31 | 2.25 | 0.00 | 0.00 | 0.23 | 0.00 |
| Erucic | 22:1ω9 | 0.66 | 0.35 | 0.00 | 0.20 | 0.00 | 0.00 |
| Docosatetraenoic | 22:4ω6 | 0.00 | 0.00 | 0.00 | 0.27 | 0.00 | 0.00 |
| Docosapentaenoic | 22:5ω6 | 0.74 | 0.71 | 0.00 | 0.00 | 0.00 | 0.00 |
| Docasapentaenoic (DPA) | 22:5ω3 | 6.16 | 4.61 | 0.10 | 0.97 | 0.00 | 0.00 |
| Docosahexaenoic (DMA) | 22:6ω3 | 21.02 | 23.44 | 0.21 | 10.81 | 0.00 | 0.00 |
| Lignoceric | 24:0 | 0.07 | 0.00 | 0.00 | 0.00 | 0.00 | 0.00 |
| Nervonic | 24:1 | 0.70 | 0.56 | 0.00 | 0.00 | 0.00 | 0.00 |
| Other | n/a | 4.12 | 3.58 | 2.33 | 9.59 | 12.04 | 11.37 |
| Total Fatty Acid (%) | | 100.0 | 100.0 | 100.0 | 100.0 | 100.0 | 100.0 |
| Total Omega-3 (%) | | 74.1 | 67.0 | 93.4 | 34.6 | 36.0 | 20.6 |
| EPA in Total Omega-3 (%) | | 56.5 | 49.7 | 95.2 | 52.3 | 99.0 | 95.9 |
| Total Omega-6 (%) | | 3.9 | 4.4 | 4.0 | 2.8 | 8.4 | 8.0 |

Provided herein are controlled formulations of total EPA, polar lipids, and phytonutrients. The formulations have the beneficial effects similar to that of krill oil, while including further advantages of glycolipids. Oil derived from krill contains solely phospholipids and no glycolipids. Animals, such as krill, synthesize phospholipids and do not synthesize glycolipids. Plants synthesize phospholipids and glycolipids. Surprisingly, the present formulation is created from oil produced by a single cell plant source that grows upon receiving sunlight and $CO_2$ to provide a combination of high concentration of EPA fatty acids, phospholipids, and glycolipids. Furthermore, because of varying environmental exposure, the chemical constituents with the algae can vary. To accommodate this variance, we have identified a means to create a controlled EPA concentration comprised of desirable amounts of EPA, phospholipids, glycolipids, and phytonutrients.

In varying embodiments, the controlled formulations are derived from two unique *N. oculata* strains, referred to herein as S12 and S14. Both strains originated in the University of Texas at Austin's UTEX The Culture Collection of Algae (on the internet at web.biosci.utexas.edu/utex/). S12 is adapted for lower temperature environmental conditions while S14 is more tolerant of higher temperature conditions. The *N. oculata* can be grown in outdoor culture in a raceway cultivation system, known in the art. The biomass is a marine algae growing in a saltwater solution at dilute concentrations between 1 and 20 g/L. At harvest, the algae is concentrated through a number of techniques known to those in the art, including combinations of cross-flow filtration, flocculation, settling, dissolved air floatation, and centrifugation. Following harvest, the resulting solids concentrate is in the range of 100 g/L (10 wt %) to 300 g/L (30 wt %) solids. When centrifugation is employed, the concentration is more typically in range of 18 to 25 wt % solids. We refer to this material form as algae paste. When the algal biomass is predominantly *Nannochloropsis*, it is called Nanno Paste.

The creation of mixture of EPA and polar lipids requires the execution of a series of extraction and refinement steps. This includes biomass extraction, removal of non-lipid and water-soluble components (MONL Refinement), separation of neutral and polar lipid constituents, concentration of the EPA in the neutral lipid fraction, and blending to achieve a standard EPA concentration in the final product. This generic process is shown in FIG. 1. The EPA fatty acid exists in the standardized product conjugated with glycolipids, phospholipids, triglycerides, and as a non-conjugated free fatty acid (FFA). Biomass extraction involves the isolation of a liquid solution comprised predominantly of lipid with minor components of protein, carbohydrate, mineral, and fiber of the biomass. This process creates a lipid mixture called crude algae extract (CAE), a complex mixture of lipids, phytonutrients, carbohydrates, water-soluble proteins, and water. CAE contains a large fraction of constituents other than lipids and phytonutrients—Matter Organic-Not Lipid (MONL). The next process removes between half and greater than 90% of the MONL component, creating Crude Algae Oil (CAO). This intermediate material is one of the three components of the final blend, and contains neutral lipids, polar lipids, and phytonutrients.

We have found that the *Nannochloropsis* contains between 5 and 50 mg/kg (ppm) CoQ9 and between 20 and 100 ppm CoQ10. In S12, we have measured CoQ9 at 8.5 and 25 ppm. In S14, we have measured CoQ9 at 19 ppm. For S12, we have measured CoQ10 at 31 ppm and 35 ppm. For S14, CoQ10 was measured at 67 ppm. CoQ9 and CoQ10 represent phytonutrients or minor micronutrients present in the *Nannochloropsis* extract.

The next process step separates the neutral and polar lipids. The polar lipid (PoL) concentrate contains virtually all the phospholipid and the glycolipid constituents present in the CAO. The neutral lipid fraction is processed in Neutral Lipid Homogenization. This process converts the fatty acids to a single molecular form that is not conjugated with a glycerol backbone. The homogenized stream now consists of a uniform lipid type with the most common forms being salts and FFAs. The lipid fractionation step concentrates the higher molecular weight and greater double bond of the EPA fatty acids from the other fatty acids in the distribution. One form for blending is FFAs. Thus, if salts are employed in the fractionation, the salts are acidified to form FFAs. The Concentrated EPA FFA (EPA-FFA) is the third components of the blend. The controlled formulation is a blend of CAO, PoL Concentrate, and EPA-FFA Concentrate. The individual constituents are characterized for their fatty acid profile and polar lipid profile. The mass ratio of each constituent is adjusted to meet a target PoL and EPA content.

Figure 2:
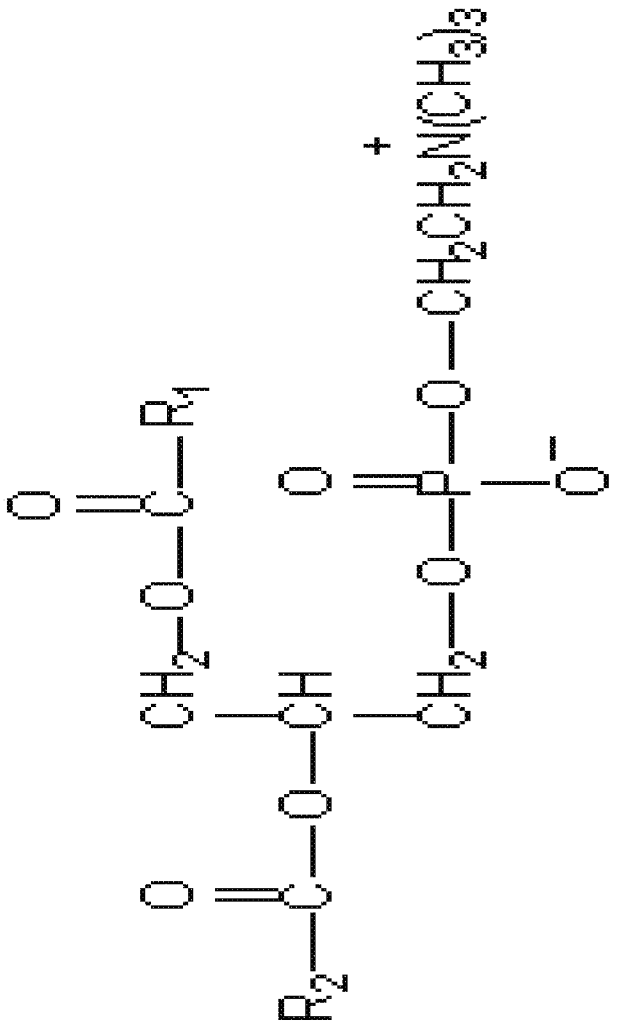
FIG. 2 illustrates the structure of phosphatidylcholine (PC), the most common phospholipid in the Crude Algae Oil (CAO) and concentrated polar lipids (PoL).
Figure 3:
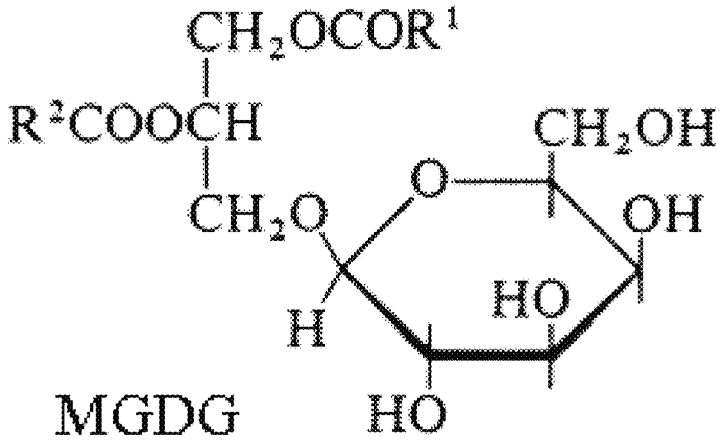
FIGS. 3A-B illustrate the structures of A. MGDG (Monogalactosyldiacylglycerol), a single five carbon sugar ring, and B. DGDG (Digalactosyldiacylglycerol), a double five carbon sugar ring; glycolipids found in the herein described EPA formulations.
Figure 3:
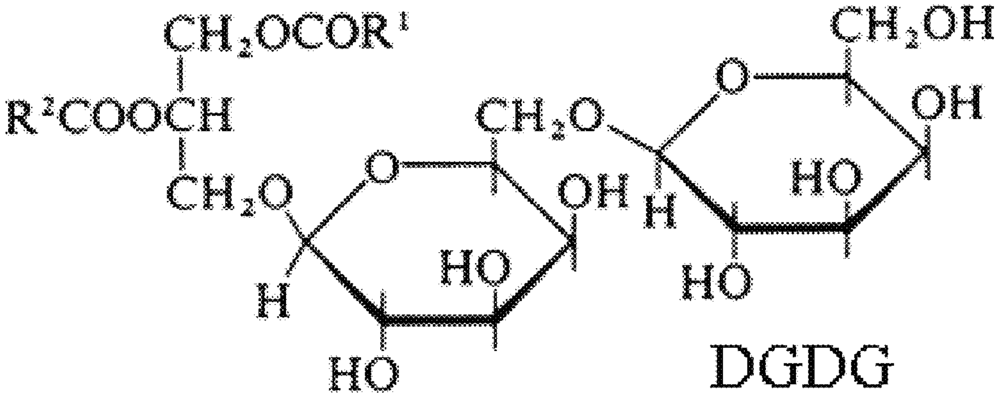

The PoL concentrate is comprised in greater than 30% total polar lipids. The amount of glycolipid is between 1 and 3 times the phospholipid. The phospholipid consistent, typically, of phosphorous and other organic moiety conjugated with the glycerol backbone in the SN3 position and one or two fatty acids in the SN1 and SN2 (middle) position on the glycerol backbone. Phosphatidylcholine (PC), the most common phospholipid in the CAO and concentrated PoL, is shown in FIG. 2. Note that the fatty acid in SN1 position is the $R^1$ group and the carboxylic acid (COO) group. Similarly, the fatty acid in the SN2 position is the $R^2$ group and the COO group. When EPA is associated with the phospholipid class, it is in either the SN1 or SN2 position. The glycolipids are shown in FIG. 3 consist of MGDG (Monogalactosyldiacylglycerol), a single five carbon sugar ring, or DGDG (Digalactosyldiacylglycerol), a double five carbon sugar ring. In a similar fashion, the glycolipid associated fatty acids are in SN1 position as shown by the $OCOR^1$ moiety and SN2 position as shown by the $—OCOR^2$ moiety. The fatty acids conjugated with glycolipids are in these two positions. The EPA fatty acid associated with the Concentrated PoL and CAO is measured. Concentrate EPA-FFA is blended with the other two components to achieve a target EPA amount of at least 25 wt %. EPA concentration in the PoL and the CAO is less than this value. A typical EPA value in the COA and concentrated PoL is 14 wt % and 11 wt %, respectively. The Concentrated EPA-FFA is greater than 40% concentration and, thus, can be blended with lower EPA concentrations to achieve the 25 wt % concentration. The EPA content of the mixture is determined by rule of mixtures, the sum of products of the mass fraction of each blend component and EPA concentration.

The standardized formulation is advantageous due to increased bioavailability as relates to metabolic functions resulting in lipid absorbance into the body (on the internet at vivo.colostate.edu/hbooks/pathphys/digestion/smallgut/absorb_lipids.html). As fats move through the lumen of the small intestine, they must pass through the cell membrane of the enterocytes, the columnar epithelial cells lining the small intestine and colon, to be absorbed into the body. The triglyceride (TG) and, to some extent, the diglyceride (DG) neutral fats are hydrophobic and insoluble in water. When a mixture of TG and DGs is exposed to water, these molecules are attracted to each other and repelled by the water, forming large micelles that disperse in the water. These large micelles are incapable of diffusing across the plasma membrane due to size exclusion. Polar lipids, such as phospholipids (PL) and glycolipids (GL), have a glycerol backbone that links the hydrophobic fatty acid moiety with the hydrophilic phosphorus or carbohydrate moiety. These polar lipids are amphipathic. Along with the bile acids in the intestine, PL and GL aid in emulsifying TG and DG neutral fats. The net effect is to break the TG/DG micelles into multiple smaller micelles, thus preserving mass while increasing the micelle surface area. The presence of TG, PL, and GL is critical, as their presence is the trigger for the release of pancreatic lipase, a water-soluble enzyme. Pancreatic lipase acts on the SN1 and SN3 position of the triglyceride and hydrolyzes the fatty acids in these positions, creating free fatty acids (FFA) and 1-monoglyceride (1-MG), a glycerol backbone with a fatty acid remaining in the SN2 position. FFA are amphipathic like PLs and GLs. The lipases also act on the polar lipids to cleave the fatty acids in SN1 position, forming a 1 lysopholipids (1-PL) such as 1-lysophosphatidylcholine (1-LPC) and 1-lysophosphatidylethanolamine (1-LPE), and 1-lysoPhosphatidylinositol (1-LPI). FFA, 1-MG, and 1-PL can then enter into the enterocytes via diffusion or via a fatty acid transporter protein in the enterocyte membrane. Because the EPA-FFA is a smaller molecule of roughly one third the molecular weight of the TG, PL, or GL and amphipathic, EPA-FFA can be absorbed without enzymatic and/or bile action. EPA is further absorbed via the TG, DG, PL, and GL routes. The formulation contains phytonutrients including chlorophyll, sterols, and carotenoids that are in admixture with the TG and DG, preventing oxidative degradation prior to absorbance. Sterols are noted for inhibiting the uptake of cholesterol in the intestinal tract.

2. EPA Formulations

Generally, the EPA formulations comprise in the range of about 15 wt. % to about 90 wt. % eicosapentaenoic acid (EPA), e.g., from about 20 wt. % to about 75 wt. % EPA, e.g., from about 20 wt. % to about 50 wt. % EPA, in its various chemical forms (e.g., as FFA, diglyceride, triglyceride, phospholipid, glycolipid); in the range of about 10 wt. % to about 70 wt. % polar lipids (glycolipids and phospholipids), e.g., from about 30 wt. % to about 35 wt. % polar lipids, and do not comprise Docosahexaenoic acid (DHA). The present EPA compositions are formulated for human consumption and for improved bioavailability of EPA by increasing the proportion of EPA in its most bioavailable forms (e.g., as a free fatty acid, as a phospholipid conjugate, and/or as a glycolipid conjugate), and reducing or eliminating EPA in its less bioavailable forms (e.g., as a diglyceride conjugate and/or as a triglyceride conjugate). The compositions further do not comprise esterified fatty acids, including esterified EPA.

In varying embodiments, the EPA is in one or more forms (e.g., 2, 3, 4 or all forms) selected from the group consisting of a phospholipid conjugate, a glycolipid conjugate, a triglyceride conjugate, a diglyceride conjugate and/or free fatty acid. In varying embodiments, EPA in the form of a triglyceride conjugate and/or a diglyceride conjugate is reduced to less than about 0.2 wt. % or to non-detectable levels, or completely eliminated.

In varying embodiments, the EPA to total omega-3 fatty acids ratio is greater than 90%, e.g., greater than 91%, 92%, 93%, 94%, 95%, 96%, 97%, 98%, 99% or more. In some embodiments, the composition comprises about 25 wt. % to about 50 wt. % EPA, e.g., about 25 wt. %, 30 wt. %, 35 wt. %, 40 wt. %, 45 wt. % or 50 wt. % EPA.

With respect to the distribution of fatty acids by lipid class in the compositions formulated for human consumption, in varying embodiments, the compositions comprise from about 10 wt. % to about 15 wt. % phospholipids (e.g., about 10 wt. %, 11 wt. %, 12 wt. %, 13 wt. %, 14 wt. %, 15 wt. % phospholipids), from about 15 wt. % to about 25 wt. % glycolipids (e.g., about 15 wt. %, 16 wt. %, 17 wt. %, 18 wt. %, 19 wt. %, 20 wt. %, 21 wt. %, 22 wt. %, 23 wt. %, 24 wt. %, 25 wt. % glycolipids), from about 0 wt. % to about 10 wt. % di- and tri-glycerides (e.g., less than about 10 wt. %, 9 wt. %, 8 wt. %, 7 wt. %, 6 wt. %, 5 wt. %, 4 wt. %, 3 wt. %, 2 wt. %, 1 wt. %, 0.5 wt. % di- and tri-glycerides), and from about 30 wt. % to about 45 wt. % free fatty acids (e.g., about 30 wt. %, 31 wt. %, 32 wt. %, 33 wt. %, 34 wt. %, 35 wt. %, 36 wt. %, 37 wt. %, 38 wt. %, 39 wt. %, 40 wt. %, 41 wt. %, 42 wt. %, 43 wt. %, 44 wt. %, 45 wt. % free fatty acids). In varying embodiments, the compositions comprise about 30-35 wt. % (e.g., about ⅓) polar lipids (i.e., phospholipids and glycolipids combined). In varying embodiments, the compositions do not have detectable levels of, have been isolated from and/or are free of di- and tri-glycerides. In varying embodiments, the compositions comprise less than about 0.2 wt. % of di- and tri-glycerides. Accordingly, in some embodiments, the compositions comprise from about 10 wt. % to about 15 wt. % phospholipids (e.g., about 10 wt. %, 11 wt. %, 12 wt. %, 13 wt. %, 14 wt. %, 15 wt. % phospholipids), from about 15 wt. % to about 25 wt. % glycolipids (e.g., about 15 wt. %, 16 wt. %, 17 wt. %, 18 wt. %, 19 wt. %, 20 wt. %, 21 wt. %, 22 wt. %, 23 wt. %, 24 wt. %, 25 wt. % glycolipids), less than about 0.2 wt. % di- and tri-glycerides, and from about 30 wt. % to about 45 wt. % free fatty acids (e.g., about 30 wt. %, 31 wt. %, 32 wt. %, 33 wt. %, 34 wt. %, 35 wt. %, 36 wt. %, 37 wt. %, 38 wt. %, 39 wt. %, 40 wt. %, 41 wt. %, 42 wt. %, 43 wt. %, 44 wt. %, 45 wt. % free fatty acids).

With respect to the distribution of EPA by lipid class in the compositions formulated for human consumption, in varying embodiments, the compositions comprise from about 3 wt. % to about 30 wt. %, e.g., from about 5 wt. % to about 20 wt. %, as phospholipid conjugate (e.g., about 3 wt. %, 4 wt. %, 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %, 21 wt. %, 22 wt. %, 23 wt. %, 24 wt. %, 25 wt. %, 26 wt. %, 27 wt. %, 28 wt. %, 29 wt. %, 30 wt. % as phospholipid conjugate), from about 8 wt. % to about 50 wt. %, e.g., from about 10 wt. % to about 25 wt. %, as glycolipid conjugate (e.g., about 3 wt. %, 4 wt. %, 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %, 21 wt. %, 22 wt. %, 23 wt. %, 24 wt. %, 25 wt. %, 26 wt. %, 27 wt. %, 28 wt. %, 29 wt. %, 30 wt. %, 31 wt. %, 32 wt. %, 33 wt. %, 34 wt. %, 35 wt. %, 36 wt. %, 37 wt. %, 38 wt. %, 39 wt. %, 40 wt. %, 41 wt. %, 42 wt. %, 43 wt. %, 44 wt. %, 45 wt. %, 46 wt. %, 47 wt. %, 48 wt. %, 49 wt. %, 50 wt. % as glycolipid conjugate), from about 0 wt. % to about 10 wt. % di- and tri-glyceride conjugates (e.g., less than about 10 wt. %, 9 wt. %, 8 wt. %, 7 wt. %, 6 wt. %, 5 wt. %, 4 wt. %, 3 wt. %, 2 wt. %, 1 wt. %, or 0.5 wt. % as di- and tri-glyceride conjugates), and from about 40 wt. % to about 85 wt. %, e.g., from about 50% wt. % to about 80 wt. %, as free fatty acids (e.g., at least about 40 wt. %, 41 wt. %, 42 wt. %, 43 wt. %, 44 wt. %, 45 wt. %, 46 wt. %, 47 wt. %, 48 wt. %, 49 wt. %, 50 wt. %, 51 wt. %, 52 wt. %, 53 wt. %, 54 wt. %, 55 wt. %, 56 wt. %, 57 wt. %, 58 wt. %, 59 wt. %, 60 wt. %, 61 wt. %, 62 wt. %, 63 wt. %, 64 wt. %, 65 wt. %, 66 wt. %, 67 wt. %, 68 wt. %, 69 wt. %, 70 wt. %, 71 wt. %, 72 wt. %, 73 wt. %, 74 wt. %, 75 wt. %, 76 wt. %, 77 wt. %, 78 wt. %, 79 wt. %, 80 wt. %, 81 wt. %, 82 wt. %, 83 wt. %, 84 wt. %, or 85 wt. % as free fatty acids). In varying embodiments, the compositions comprise about from 10 wt. % to about 50 wt. %, e.g., from about 15 wt. % to about 30 wt. % polar lipids (i.e., phospholipids and glycolipids combined). In varying embodiments, the compositions do not have detectable levels of, have been isolated from and/or are free of di- and tri-glycerides. In varying embodiments, the compositions comprise less than about 0.2 wt. % of di- and tri-glycerides. Accordingly, in some embodiments, the compositions comprise EPA distributed by lipid class as from about 3 wt. % to about 30 wt. %, e.g., from about 5 wt. % to about 20 wt. %, phospholipid conjugate (e.g., about 3 wt. %, 4 wt. %, 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %, 21 wt. %, 22 wt. %, 23 wt. %, 24 wt. %, 25 wt. %, 26 wt. %, 27 wt. %, 28 wt. %, 29 wt. %, 30 wt. % phospholipid conjugate), from about 8 wt. % to about 50 wt. %, e.g., from about 10 wt. % to about 25 wt. %, glycolipid conjugate (e.g., about 3 wt. %, 4 wt. %, 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %, 21 wt. %, 22 wt. %, 23 wt. %, 24 wt. %, 25 wt. %, 26 wt. %, 27 wt. %, 28 wt. %, 29 wt. %, 30 wt. %, 31 wt. %, 32 wt. %, 33 wt. %, 34 wt. %, 35 wt. %, 36 wt. %, 37 wt. %, 38 wt. %, 39 wt. %, 40 wt. %, 41 wt. %, 42 wt. %, 43 wt. %, 44 wt. %, 45 wt. %, 46 wt. %, 47 wt. %, 48 wt. %, 49 wt. %, 50 wt. % glycolipid conjugate), less than about 0.2 wt. % di- and tri-glyceride conjugates, and from about 40 wt. % to about 85 wt. %, e.g., from about 50% wt. % to about 80 wt. %, free fatty acids (e.g., about 40 wt. %, 41 wt. %, 42 wt. %, 43 wt. %, 44 wt. %, 45 wt. %, 46 wt. %, 47 wt. %, 48 wt. %, 49 wt. %, 50 wt. %, 51 wt. %, 52 wt. %, 53 wt. %, 54 wt. %, 55 wt. %, 56 wt. %, 57 wt. %, 58 wt. %, 59 wt. %, 60 wt. %, 61 wt. %, 62 wt. %, 63 wt. %, 64 wt. %, 65 wt. %, 66 wt. %, 67 wt. %, 68 wt. %, 69 wt. %, 70 wt. %, 71 wt. %, 72 wt. %, 73 wt. %, 74 wt. %, 75 wt. %, 76 wt. %, 77 wt. %, 78 wt. %, 79 wt. %, 80 wt. %, 81 wt. %, 82 wt. %, 83 wt. %, 84 wt. %, 85 wt. % free fatty acids).

In varying embodiments, the glycolipids comprise one or more of digalactosyldiacylglycerol and monogalactosyldiacylglycerol. In some embodiments, the phospholipids comprise one or more of phosphatidylcholine, lyso-phosphatidylcholine, phosphatidylinositol, phosphatidylethanolamine and phosphatidylglycerol. In some embodiments, the phospholipids comprise one or more of phosphatidylcholine and phosphatidylglycerol.

In some embodiments, the EPA compositions comprise:

i) 0 to 5 wt. % C:18 fatty acids, e.g., 0.2 to 3 wt. % C:18 fatty acids;

ii) 0 to 20 wt. % C:16 fatty acids, e.g., 2 to 20 wt. % C:16 fatty acids;

iii) 0 to 5 wt. % C:14 fatty acids, e.g., 0.2 to 5 wt. % C:14 fatty acids;

iv) 0 to 0.2 wt. % C:12 fatty acids; and/or v) 0 to 0.1 wt. % C:10 fatty acids.

In varying embodiments, the composition comprises:

| Component | amount |
|---|---|
| Lipid Composition | |
| Total polar lipids | ≥15 wt. % |
| Total phospholipids | ≥6 wt. % |
| Total glycolipids | ≥9 wt. % |

-continued

| Component | amount |
|---|---|
| Fatty Acid Profile | |
| Total omega-3 | ≥25 wt. % |
| C20:5ω3 (EPA) | ≥25 wt. % |
| EPA/Total omega-3 | >98% wt. % |
| C16:1ω7 (omega-7) | ≥8 wt. % |
| Phytonutrients | |
| Chlorophyll | ≥5 wt. % |
| Total Carotenoids | ≥750 mg/kg |

In varying embodiments, the composition comprises:

| Component | wt. % |
|---|---|
| Fatty Acids | |
| Capric (10:0) | 0.1-0.2 |
| Lauric (12:0) | 0.1-0.2 |
| Myristic (14:0) | 1.0 |
| Palmitic (16:0) | 5.3-6.5 |
| Palmitoleic (16:1) | 7.0-8.0 |
| Hexadecadienoic (16:2) | 0.2-0.3 |
| Stearic (18:0) | 0.2-0.3 |
| Oleic (18:1ω9) | 2.0 |
| Oleic (18:1ω7) | 0.3-0.4 |
| Linoleic (18:2ω6) | 1.2-2.0 |
| Alpha-Linolenic (ALA) (18:3ω3) | 0.2 |
| Arachidonic (20:4ω6) | 1.0-8.0 |
| Eicosapentaenoic (EPA) (20:5ω3) | 19-30 |
| Total Fatty Acid | 40-55 |
| Total Omega-3 | 20-30 |
| EPA/Omega-3 | >93 |
| Total Omega-6 | 2-10 |
| Phospholipids | |
| Phosphatidylcholine | 4.7-7.4 |
| Lyso-Phosphatidylcholine | 0.3-0.4 |
| Phosphatidylinositol | 0.8-1.3 |
| Phosphatidylethanolamine | 0.5-0.8 |
| Phosphatidylglycerol | 1.8-2.8 |
| Glycolipids | |
| Digalactosyldiacylglycerol | 10-17 |
| Monogalactosyldiacylglycerol | 3-5 |
| Phytonutrients | |
| Phytosterols | 1.5 |
| Chlorophyll | 4-5 |
| Total Phospholipids (PL) (wt %) | 9-14 |
| Total Glycolipids (GL) (wt %) | 13-21 |
| Total PoL (PL + GL) (wt %) | 22-35 |

In varying embodiments, the composition comprises chlorophyll a. In varying embodiments, the composition comprises less than about 10.0 wt. % arachidonic acid, e.g., less than about 9.5 wt. %, 9.0 wt. %, 8.5 wt. %, 8.0 wt. %, 7.5 wt. %, 7.0 wt. %, 6.5 wt. %, 6.0 wt. %, 5.5 wt. %, 5.0 wt. %, 4.5 wt. %, 4.0 wt. %, 3.5 wt. %, 3.0 wt. %, 2.5 wt. %, 2.0 wt. %, 1.5 wt. % or 1.0% arachidonic acid, or does not comprise arachidonic acid (i.e., 0 wt. %).

In varying embodiments, the composition does not comprise or is substantially free of intact cells, cellular components, polynucleotides, and polypeptides. In varying embodiments, the composition does not comprise fatty acids selected from the group consisting of octadecatetraenoic acid or stearidonic acid (SDA=C18:4ω3), eicosatrienoic acid (ETE=C20:3ω3), eicosatetraenoic acid (ETA=C20:4ω3), heneicosapentaenoic acid or uncosapentaenoic acid (HPA=C21:5ω3), and docapentaenoic acid (DPA=C22:5ω3). In varying embodiments, the composition does not comprise carotenoids selected from the group consisting of astaxanthin, cis-lutein, trans-lutein, cis-zeaxanthin, trans-alpha-cryptoxanthin, trans-alpha-carotene, cis-alpha-carotene, cis-lycopene, and trans-lycopene. In varying embodiments, the composition does not comprise chlorophyll c. In varying embodiments, the composition does not comprise one or more phospholipids selected from the group consisting of N-acyl-phosphatidylethanolamine, lyso-phosphatidylcholine, phosphatidylinositol and phosphatidylethanolamine. In some embodiments, the composition does not comprise sphingolipids.

The compositions may further comprise a pharmaceutically acceptable carrier and/or one or more pharmaceutically acceptable excipients. Generally the compositions are not biphasic (e.g., are monophasic), and comprise less than about 10% water, e.g., less than about 9%, 8%, 7%, 6%, 5%, 4%, 3%, 2%, 1% water, or no water.

Also contemplated are capsules, tablets, solutions, syrups, and suspensions suitable for human consumption comprising the EPA composition described above and herein. In varying embodiments, the capsule is a gelatin capsule or a soft capsule, including soft capsules from non-animal, vegetarian sources. Further contemplated are foods, beverages, energy bars, and nutritional supplements comprising the EPA compositions described herein.

3. Methods of Producing Highly Bioavailable EPA Formulations

The methods provide for the energy and cost efficient production of EPA formulations derived from microalgal oils (e.g., from *Nannochloropsis*) that maximize the amounts of EPA in its most bioavailable forms (e.g., as a free fatty acid or as a glycolipid or phospholipid conjugate). Schematics illustrating steps for preparing the EPA formulations described herein are provided in FIGS. 1 and 4.

In varying embodiments, the methods comprise the steps of:

a) providing an algal paste;

b) extracting lipids from the algal paste with an organic solvent, thereby substantially isolating a crude algae extract (CAE) comprising neutral lipids and polar lipids from the water-soluble components of the paste;

c) substantially removing the water-soluble components, thereby yielding a crude algae oil (CAO);

d) hydrolyzing a first portion of the CAO, thereby releasing free fatty acids in the portion of CAO;

e) fractionating the released free fatty acids according to chain length, thereby isolating C20 free fatty acids and yielding a concentrated EPA free fatty acid fraction; and f) combining the concentrated EPA free fatty acid fraction produced in step e) and a second portion of the CAO produced in step c).

In varying embodiments, the methods comprise the steps of:

a) providing an algal paste;

b) extracting lipids from the algal paste with an organic solvent, thereby substantially isolating a crude algae extract (CAE) comprising neutral lipids and polar lipids from the water-soluble components of the paste;

c) substantially removing the water-soluble components, thereby yielding a crude algae oil (CAO);

d) contacting the CAO with supercritical CO2, wherein the supercritical CO2 selectively extracts the neutral lipids, thereby splitting the CAO into a neutral lipid fraction comprising free fatty acids and a polar lipid fraction comprising glycolipids and phospholipids;

e) isolating C20 free fatty acids from the neutral lipid fraction, thereby yielding a concentrated EPA free fatty acid fraction; and f) combining the concentrated EPA free fatty acid fraction produced in step e) and the polar lipid fraction produced in step d).

Generally, the methods do not comprise the steps of disrupting algal cells, subjecting algal cells to mechanical cracking, thermal pretreatment, alkaline treatment and/or acid treatment. In addition, the steps specifically avoid esterifying the fatty acids, including without limitation the conversion to methyl esters or ethyl esters.

The methods can be used to produce highly bioavailable EPA compositions from any biomass source of EPA. Preferably, the biomass source produces oils having EPA at a concentration in the range of about 30 wt. % to about 70 wt. %. For example, EPA is naturally produced in a variety of non-oleaginous and oleaginous microorganisms, including the heterotrophic diatoms *Cyclotella* sp. and *Nitzschia* sp. (U.S. Pat. No. 5,244,921), *Pseudomonas, Alteromonas* and *Shewanella* species (U.S. Pat. No. 5,246,841), filamentous fungi of the genus *Pythium* (U.S. Pat. No. 5,246,842), *Mortierella elongata, M. exigua*, and *M. hygrophila* (U.S. Pat. No. 5,401,646), and eustigmatophycean alga of the genus *Nannochloropsis* (Krienitz, L. and M. Wirth, Limnologica, 36:204-210 (2006)). Moreover, several types of yeast have been recombinantly engineered to produce EPA. See for example, work in the non-oleaginous yeast *Saccharomyces cerevisiae* (U.S. Pat. No. 7,736,884) and the oleaginous yeast, *Yarrowia lipolytica* (U.S. Pat. No. 7,238,482; U.S. Pat. No. 7,932,077; U.S. Pat. Appl. Pub. No. 2009-0093543-A1; U.S. Pat. Appl. Pub. No. 2010-0317072-A1). In varying embodiments, the biomass source can be fish or krill oil.

a. Providing an Algal Paste

In one step, algal cells are harvested and concentrated to form a paste. In various embodiments, a paste of the algal cell source material is provided.

In varying embodiments, the EPA formulations are derived from algal cells and do not contain any docosahexaenoic acid (DHA). In varying embodiments, the source biomass for the EPA compositions is from a microalgae of the genus *Nannochloropsis*. In varying embodiments the source biomass is from a *Nannochloropsis* selected from the group consisting of *Nannochloropsis gaditana, Nannochloropsis granulate, Nannochloropsis limnetica, Nannochloropsis maritime, Nannochloropsis oceanica, Nannochloropsis oculata, Nannochloropsis salina*, and *Nannochloropsis* sp. (e.g., 10S010, AN1/12-10, AN1/12-5, AN1/12-7, AN2/29-2, AN2/29-6, AS4-1, BR2, C95, CCAP211/46, CCAP211/78, CCMP1779, CCNM 1032, CCNM 1034, CSIRO P74, HSY-2011, JL11-8, JL2/4-1, KMMCC EUS-02, KMMCC EUS-05, KMMCC EUS-06, KMMCC EUS-08, KMMCC EUS-09, KMMCC EUS-11, KMMCC EUS-12, CCMP2195, KMMCC EUS-13, KMMCC EUS-14, KMMCC EUS-15, KMMCC EUS-16, KMMCC EUS-17, KMMCC EUS-18, KMMCC EUS-19, CCMP533, KMMCC EUS-20, KMMCC EUS-21, LL-2012, MA-2012, UTEX2164, MBTD-CMFRI-S006, MBTD-CMFRI-S007, MBTD-CMFRI-S012, MBTD-CMFRI-S076, MBTD-CMFRI-S077, MBTD-CMFRI-S078, CCMP525, MDL11-16, MDL3-4, NANNO-IOLR, RCC438, CCAP849/7, RCC504, SC-2012, strain IOLR, Tow 2/24 P-1w, UTEX2379, W2J3B, YJH-2012, YW0980). In varying embodiments, the source biomass is from a *Nannochloropsis* selected from the group consisting of *Nannochloropsis oceanica*, and *Nannochloropsis oculata.*

Microalgae, e.g., *Nannochloropsis* grows in relatively dilute culture that is typically in the range of 0.1 to 1.0 g/L of biomass and, more typically, in the range of 0.3 to 0.7 g/L. For a 0.5 g/L culture concentration, this implies that there is 0.5 g of dry weight equivalent biomass for every 1000 g of culture, a dilute concentration. Algae are further processed in a more concentrated state, typically in the range of 2 to 300 g/L. The microalgae are harvested from culture and concentrated into a paste using any method known in the art. In varying embodiments, dewatering, sedimentation, filtration, cross-flow filtration and/or centrifugation techniques that are known in the art can be employed. As appropriate, air sparging and flocculation techniques can be employed to facilitate concentration and harvesting of *Nannochloropsis* cells.

Methods for harvesting and concentrating *Nannochloropsis* cells are known in the art and find use. See, e.g., U.S. Patent Publ. Nos. 2013/0046105; 2012/0282651; 2012/0225472; 2012/0108793; and 2011/0081706 and Sirin, et al., *Bioresour Technol.* (2013) January 22; 132C:293-304; Farid, et al., *Bioresour Technol.* 2013 Jan. 23. doi:pii: S0960-8524(13)00081-3; and Wan, et al., *Bioresour Technol.* 2012 Oct. 16. doi:pii: S0960-8524(12)01506-4. The foregoing references are hereby incorporated herein in their entirety for all purposes.

In one embodiment, *Nannochloropsis* cells are harvested and concentrated by raising the pH of the culture fluid, e.g., to about pH 10.0, exposing the cells to a flocculant and/or coagulant, thereby concentrating the cellular biomass from about 0.5 g/L to about 10-20 g/L biomass. The coagulated/flocculated cells are allowed to settle, e.g., in a settling tank, the aqueous supernatant above the settled cellular biomass is decanted and the remaining fluid containing the settled cellular biomass is further dewatered by centrifugation, thereby forming an algal paste.

b. Extracting Lipids from Algal Paste with an Organic Solvent Lipids

Lipids can be extracted from the algal paste in either the wet or dry state using any method known in the art. In the wet state, the moisture content is between 400 and 1000% (w/w) dried biomass (25 to 10 wt % solids). In the dry state, the moisture content is less than 15% (w/w) of the dried biomass. Lipids can be extracted from the algal biomass using an organic solvent. In varying embodiments, about 1× to about 20×, e.g., about 2× to about 7×, the mass of organic solvent is mixed with the biomass to form a biomass, solvent, and extract slurry. The algal paste can be exposed to, contacted with and/or submerged in the solvent without pretreatment steps.

Surprisingly, we have found that biomass extraction to obtain the crude algae extract requires no mechanical cracking (such as a bead mill), thermal pretreatment, or cellular wall digestion, e.g., via acid or base. In some embodiments, the lipids are extracted from wet state algal paste. For wet extraction of biomass, a pure solvent or solvent mixture that is at least partially miscible with water is used. We have unexpectedly discovered that the extract from wet algal paste leads to between 1.5 and 3.5 times more fatty acid recovery from the biomass versus the extraction of the same biomass after drying. Even with no particular effort to disrupt the cell membrane via mechanical, thermal, or pH disruption (e.g., alkaline or acid treatment), the wet paste has a higher extraction yield than the same biomass after drying.

Solvents useful for extraction of lipids from the algal paste include a broad selection of solvents types, including ethers, ketones, and alcohols. Solvents and solvent mixtures of use have the ability to extract hydrophobic, non-polar lipid components such as triglycerides and hydrophilic, polar lipid components such as phospholipids and glycolipids from the algal paste. Illustrative solvent systems include ethanol, isopropyl alcohol, acetone and ethanol, dimethyl ether, dimethyl ether and ethanol. In varying embodiments, the solvent system is either an ether and alcohol mixture or a ketone and alcohol mixture. Illustrative solvent combinations of use include absolute ethanol, 190 proof (95 v/v %) ethanol (EtOH), denatured 190 proof ethanol, special denatured alcohols (SDA), acetone and ethanol, isopropyl alcohol, acetone and methanol, methyl ethyl ketone (MEK) and methanol, MEK and ethanol, dimethyl ether, dimethyl ether and methanol, dimethyl ether and ethanol. In varying embodiments, lipids are extracted from the algal paste using a solvent mixture that is 50 wt. % (v/v) acetone and 50 wt. % (v/v) 190 proof ethanol (EtOH). Other solvent mixtures of use include pure dimethyl ether (DME), DME mixed with methanol, or solely 190 proof EtOH. EtOH may be non-denatured or one of the Special Denatured Alcohol (SDA) grades (1-1, 1-2, 2B-2, 2B-3, 3A, 3C, 23A, 23H, 29, 30, 35A) proof denatured ethanol, where the major composition of the SDAs is given in Table 5.

Extraction can be performed by any method known in the art, including batchwise and continuous flow methods (e.g., countercurrent columns, crossflow filtration). Solvent percolation through the biomass paste can be facilitated by mixing paste with a filtration aid (e.g., diatomaceous earth) or by vigorous mixing with solvent coupled with crossflow filtration. The extracted lipid-rich solution can be separated from the biomass using any method known in the art, e.g., filtration or centrifugation, where filtration or, in some embodiments, cross-flow filtration is employed for removing solid from the solution. For nearly complete lipid extraction, multiple stages of extraction are performed, e.g., 2, 3, 4, 5, 6, 7, 8, 9, 10 or more stages, as appropriate. Extraction of lipid components from the algal paste using an organic solvent creates a crude algae extract (CAE). Crude algae extract (CAE) can contain between 10 and 80% of constituents that are not lipids. CAE generally comprises neutral lipids, polar lipids, chlorophyll, sterols, carotenoids, manitol, and glycerol.

c. Removing Water-Soluble Components from the CAE to Produce Crude Algal Oil (CAO)

The CAE contains a significant proportion of non-lipid organic material ("matter-organic non-lipid" or "MONL"). MONL is material not otherwise accounted for in the total fatty acids (TFA), phospholipids, glycolipids, and phytonutrients. MONL contains water-soluble components, e.g., water-soluble carbohydrates and proteins. Varying embodiments of the methods perform the step of substantially removing water-soluble components from the CAE to produce a crude algal oil (CAO). Water-soluble components can be substantially removed from CAE, thereby yielding CAO, through any method known in the art, e.g., through organic solvent and water partitioning. This approach separates the highly polar water-soluble constituents from the non-polar (e.g. neutral lipids) and mixed polarity (e.g., PL and GL) constituents. In varying embodiments, CAE recovered from solvent extraction can be solubilized in another solvent and then added to a liquid-liquid partitioning system to substantially remove water-soluble components.

In varying embodiments, MONL refinement may include a partition of the water-soluble components comprising excess water and organic solvent to CAE, bringing the water, organic solvent, and CAE into intimate contact with a high shear mixer, and separation of the water and organic phase via either settling or centrifugation. After agitation to assume intimate contact between the feed, the water and organic phase are separated by either a settling tank or centrifugation (i.e. through enhanced gravity). The material splits into an upper organic layer and lower aqueous layer. The neutral and polar lipids, sterols, and cholesterol have a much higher distribution coefficient for the organic layer and predominantly remain in the organic layer. Water-soluble constituents, including carbohydrates (especially mannitol), water-soluble proteins, and glycerol predominantly, go into solution within the aqueous layer. The organic phase is the CAO which contains a lipid rich mixture of polar lipids (PoL) and neutral lipids (NL).

Alternatively, CAE can be extracted in series with a solvent more suitable for neutral lipids followed by further extraction by a solvent suitable for polar lipids. Illustrative solvents suitable for extraction of neutral lipids include hexane, chloroform, cyclohexane, methylene chloride, carbon dioxide or combinations thereof. Illustrative solvents suitable for extraction of polar lipids include acetone, methanol, ethanol or combination thereof. A further useful solvent combination includes heptane (Hep), ethyl acetate (EtAc), methanol (MeOH), and water ($H_2O$), e.g., in a volume ratio of 1:1:1:1. A further useful solvent combination includes propane, EtAC, ethanol (EtOH), and water ($H_2O$), e.g., in a volume ratio of 1:1:1:1. A further useful solvent combination includes butane, EtAc, EtOH, and water ($H_2O$), e.g., in a volume ratio of 1:1:1:1.

In varying embodiments liquid-liquid partitioning can employ alternate environmentally friendly organic solvents. Illustrative environmentally friendly solvents include without limitation water, acetone, ethanol, 2 propanol, 1-propanol, ethyl acetate, isopropyl acetate, methanol, methyl ethyl ketone (MEK), 1-butanol, and t-butanol. Other solvents of use for liquid-liquid partitioning include liquid of cyclohexane, heptane, toluene, propane, butane, pentane, methylcylcohexane, methyl t-butyl ether, isooctane, acetonitrile, 2-methyltetrahydrofuran, tetrahydrofuran (THF), xylenes, dimethyl sulfoxide (DMSO), acetic acid, and ethylene glycol.

In varying embodiments, the solution partitions and the NL-rich upper phase is collected. A NL-rich extract is recovered by evaporating the solvent. The bottom phase, now rich in both PoL and MONL, is extracted with a PoL suitable solvent system. A PoL-rich extract is recovered by separating the hydrophobic layer from the hydrophilic layer and evaporating off the solvents. CAO results when the NL-rich and PoL-rich extracts are combined. Substantial removal of water-soluble components to effect the conversion from CAE to CAO results in between 30% and 50% reduction in mass. CAO is one of the constituents of the EPA standardized EPA/Polar Lipid blend. In varying embodiments, a portion of the CAE is included in the standardized EPA blend.

In varying embodiments, at least about 90% of the water-soluble components, e.g. at least about 91%, 92%, 93%, 94%, 95%, 96%, 97%, 98%, 99%, or more of the water-soluble components are removed from or separated from the crude algae extract to yield the crude algae oil.

d. Optionally Extracting Neutral Lipids from Crude Algal Oil with Supercritical $CO_2$ In varying embodiments, the CAO can be converted into a neutral lipid (NL)-rich stream that contains no polar lipid (PoL) mixture with high pressure/high temperature (HP/HT) supercritical carbon dioxide (SCCO2). Extraction can be performed by any method known in the art, including batchwise and continuous flow methods (e.g., countercurrent columns). We have found that SCCO2 extracts neutral lipids completely with essentially zero polar lipids in either the form of phospholipids or glycolipids. SCCO2 in the range from 100 to 1000 bar, e.g., 300 to 1000 bar, e.g., 100, 200, 300, 400, 500, 600, 700, 800, 900 or 1000 bar, and temperatures between 35 and 110° C., e.g., 60 and 110° C., e.g., 35, 40, 45, 50, 55, 60, 65, 70, 75, 80, 90, 95, 100, 110° C., has a high distribution coefficient for neutral lipids and, essentially, a zero distribution coefficient for polar lipids. In varying embodiments, the CAO is contacted with SCCO2 at pressures in the range of about 340 bar to about 700 bar and at temperatures in the range of about 40° C. to about 110° C. In varying embodiments, the CAO is contacted with SCCO2 at pressures in the range of about 350 bar to about 690 bar and at temperatures in the range of about 60° C. to about 90° C. At 350 bar and 60° C., the density of SCCO2 is 0.863 g/mL. At 700 bar/100° C., SCCO2 has a density of 0.9 g/mL. Process conditions in the pressure range between 340 bar and 700 bar that yield a density of 0.83 to 0.9 g/mL are suitable. High P/T SCCO2 produces a NL fraction with zero PoL. It extracts a proportion of the chlorophyll and almost all the sterols from the CAO. The NL fraction is comprised of free fatty acids (FFA), triglycerides (TG), diglycerides (DG), chlorophyll, and sterols. The residual material from high P/T SCCO2 extraction is concentrated polar lipids (Conc PoL), including phosopholipids and glycolipids. The Conc PoL is the second component in the EPA-standardized blend. This stream and the COA provide the polar lipids for the EPA standardized EPA/Polar Lipid blend.

In varying embodiments, either CAE or CAO can be combined with ethanol and water and extracted with propane or butane. This preferentially extracts the neutral lipids from polar lipids, forming a concentrated EPA fraction comprised of FFA, TG, and DG. The presence of water and ethanol result in a stronger distribution coefficient for the polar lipids, retaining them in the water/ethanol phase. In some embodiments, ethanol may be replaced by methanol, n-propanol, isopropanol, or a C4 alcohol such as n-butanol or tert-butanol. Volume ratios can be about 1:1 alcohol: water.

In varying embodiments, CAE can be split into an NL rich fraction and PoL rich fraction using HP/HT SCCO2 followed by extraction with dimethyl ether (DME).

e. Isolating C20 Free Fatty Acids from the Neutral Lipid Fraction

The NL-rich fraction of the CAO, a portion of the total CAO or a portion of the CAE is hydrolyzed to form free fatty acid (FFA) and then subject to SCCO2 fractionation to create a concentrate of EPA FFA. In varying embodiments, a first portion of the CAE, e.g., 30-80% of the total CAE, e.g., 30%, 35%, 40%, 45%, 50%, 55%. 60%, 65%, 70%, 75%, or 80% of the CAE is directly subject to hydrolysis. The second portion of the CAE can be reserved to include in the final blended EPA formulation.

Hydrolysis to release free fatty acids can be done by a variety of routes that are familiar to those in the art. The most common methods are saponification followed by acidification and direct acidification. In terms of product yield, saponification is a useful route because the first step in the reaction irreversibly forms a fatty acid salt. In varying embodiments, the neutral lipid mixture can be combined with a hydroxyl salt, e.g., KOH or NaOH, in the presence of an excess of the water. The oxyl bond between the fatty acid and the glycerol backbone is broken and the respective cationic interaction, e.g., $K^+$ or $Na^+$ cationic interaction, formed. This reaction can be completed under reflux at temperature conditions ranging between 50° C. and 90° C. Triglyceride (TG) and diglyceride (DG) constituents are converted to a salt and free glycerol. Free glycerol is highly polar. The salt solution is treated with an acid, such as phosphoric, sulfuric, hydrochloric, or formic acid. This removes the salt's cation and forms the corresponding free fatty acid (FFA). The solution partitions into two phases: an organic and aqueous phase. In the direct acidification method, the reaction has fewer steps but is reversible. Hence, the yield to FFA may not be as great as the saponification route. Under acidification, neutral lipid is combined with water and strong acid, such as sulfuric, hydrochloric, phosphoric, or formic. Water in excess of stoichiometry, e.g., on the order of at least about 5×, e.g., about 6×, 7×, 8×, 9×, 10×, or more, is added to the neutral lipid. Acid is added to lower the pH to approximately 2. The mixture is heated under reflux at a temperature between 60 and 100° C. This reaction, while single step, is reversible. An excess of water is required to drive the equilibrium in the direction of FFA. The mixture of biomass can then be solvent extracted, e.g., with hexanes. After evaporating the solvent, a partially hydrolyzed algae oil is recovered comprised of predominantly fatty acids of which nearly half are free fatty acids.

Once the neutral lipid has been hydrolyzed to form FFA, the EPA fraction within this mixture can be further concentrated and isolated from shorter chain length fatty acids. Under the previous processing step, all the triglycerides and diglycerides have been converted to FFA. This is known as high acid oil, a mixture of different fatty acid (FA) compounds that are predominantly in free fatty acid form. While is it known from the literature that SCCO2 can concentrate Omega-3 from methyl esters and, by extension, ethyl esters (Nilsson, et. al., "Supercritical Fluid CO2 Fractionation of Fish Oil Esters" in Advances in Seafood Biochemistry, 1992), it was not previously known that SCCO2 could fractionate mixtures of non-esterified FFA (FFA FA). FFA FA are polar moieties. Conventional thought in SCCO2 solubility is that these compounds would be insoluble in SCCO2 and, thus, not be amenable to tunable dissolving characteristics of SCCO2. Surprisingly, we have found that SCCO2 is capable of fractionating FFA FA by molecular weight. The FFA FA can be fractionated by applying a pressure or temperature gradient.

In varying embodiments, the FFA FA feedstock is fractionated under a pressure gradient of SCCO2. Without being bound by any particular theory, the non-polar effect of long carboxylic acid chain from 8 to 20 carbon molecules long overwhelms the polar characteristics of the carbonyl group. Thus, in the presence of isothermal conditions, increasing SCCO2 pressure from about 100 bar results in increasingly greater solubility for higher molecular weight carboxylic acids. Lower pressure SCCO2 at pressures above 100 bar, e.g., a stepwise or continuous gradient over pressures in the range of about 150 bar to about 350 bar, under isothermal conditions, e.g., at a temperature in the range of about 40° C. to about 60° C., can be used to remove the lower molecular weight free fatty acids from the higher molecular weight free fatty acids. This enables concentrating the C20 components, including EPA and ARA, while reducing or eliminating the C8, C10, C12, C14, C18 constituents. In varying embodiments, the EPA concentration is at least doubled. After concentration, this is the EPA-Concentrated FFA steam (Conc EPA) and is the third constituent in the mixture to create an EPA-standardized formulation.

f. Combining the C20 Free Fatty Acid Fraction and the Polar Lipid Fraction

Three components are blended to form a standardized combination of EPA and polar lipids: CAO, Conc PoL, and Conc EPA are used to create a standardized product that controls both the EPA and the polar lipid content in the blend.

g. Alternative Production Method

In varying embodiments, provided are methods for producing a composition comprising EPA and polar lipids, comprising:

a) providing an algal paste;

b) extracting the algal paste with concentrated ethanol, wherein the concentration of the ethanol is at least 70 vol. %, e.g., at least 75 vol. %, 80 vol. %, 85 vol. %, 90 vol. % or 95 vol. %;

c) substantially removing the ethanol from the algal paste, thereby yielding a crude algae extract (CAE) comprising neutral lipids and polar lipids;

d) extracting the CAE with a C3-C7 alkane solvent;

e) substantially removing the alkane solvent, thereby yielding a crude algae oil (CAO) enriched in polar lipids and fatty acids;

f) enriching for polar lipids in a first portion of the CAO, comprising:

- i) contacting the first portion of CAO with a first silica gel sorbent;
- ii) eluting neutral lipids by contacting the first silica gel sorbent with a C3-C7 alkane; and
- iii) eluting polar lipids by contacting the first silica gel sorbent with a C1-C4 alcohol; thereby yielding concentrated polar lipids (CPL);

g) enriching for free fatty acids in a second portion of the CAO, comprising:

- i) subjecting the second portion of the CAO and the neutral lipids eluted in step f) ii) to hydrolysis;
- ii) contacting the hydrolyzed CAO with a second silica gel sorbent;
- iii) eluting free fatty acids by contacting the second silica gel sorbent with a C3-C7 alkane; and
- iv) concentrating the EPA from the free fatty acids eluted in step g) iii), thereby yielding concentrated EPA; and h) combining the CPL obtained in step f) iii) and the concentrated EPA obtained in step g) iv), thereby producing a composition comprising EPA and polar lipids. In varying embodiments, the concentration of ethanol used in step b) is less than 96% (e.g., less than azeotrope forming concentration). In varying embodiments, the methods further comprise the step of extracting the CAE with ethyl acetate in step d). In varying embodiments, the methods further comprise after step f) ii), eluting polar lipids by contacting the first silica gel sorbent with acetone. In some embodiments, the EPA is concentrated from the free fatty acids by urea crystallization. In some embodiments, the EPA is concentrated from the free fatty acids by supercritical carbon dioxide fractionation. In some embodiments, the EPA is concentrated using a pressure gradient of supercritical $CO_2$. In some embodiments, the pressure gradient of supercritical $CO_2$ is from about 172 bar to about 345 bar. In some embodiments, the pressure gradient of supercritical $CO_2$ is isothermal. In some embodiments, the pressure gradient of supercritical $CO_2$ is maintained at a constant temperature of between about 50° C. and about 70° C.

This alternative methodology makes the production process much more immune to variance in the fatty acid composition. Ethanol (at least about 70 vol %, e.g., at least about 75 vol. %, 80 vol. %, 85 vol. %, 90 vol. % or 95 vol. % in water) is used to extract the biomass. The concentration of ethanol is less than about 96% or less than the concentration at which an azeotrope forms. It is not necessary to disrupt the algae. The ethanolic extract, after substantial removal and separation (e.g., via evaporation) of the bulk of the ethanolic solvent, is called wet Crude Algae Extract (Wet CAE). Wet CAE is transferred to a countercurrent column where it is extracted with a C3-C7 alkane solvent e.g., of at least about 95 wt. % purity. Illustrative C3-C7 alkane solvents of use include without limitation n-propane, n-butane, isobutane, pentane, hexane, isohexane, heptane, and mixtures thereof. Also of use is a mixture of n-propane, n-butane, and isobutene. In varying embodiments, the mixed alkane can be about 40-82 mol % n-butane, 18-60 mol % isobutane, less than 8 mol % n propane, and less than 0.5 mol % pentane. It is not necessary to have pure n-butane or isobutane. The addition of propane raises the vapor pressure of the mixture. The addition of pentane lowers the vapor pressure. This has no significant impact on extraction; however, it does effect the required pressure rating for process equipment. In varying embodiments a mixture comprising n-butane and n-propane is employed as alkane solvent to extract CAE. In some embodiments, butane or a mixture comprising n-butane and isobutane is employed as alkane solvent to extract CAE. In varying embodiments, the CAE is extracted with the C3-C7 alkane solvent in a countercurrent column. After substantial removal and separation (e.g., via evaporation) of the C3-C7 alkane solvent, Crude Algae Oil (CAO) results. CAO is a mixture enriched in polar lipids and fatty acids and more depleted in water soluble proteins and carbohydrates. Furthermore, ethyl acetate (EtAc) can be added to the Wet CAE feed mixture, facilitating the further shift of polar lipids into the alkane phase. This can enhance polar lipid recovery at the expense of secondary solvent removal to recover the EtAc from the CAO. In varying embodiments, the EtAc has at least about 95 wt % purity. In embodiments when EtAc is used, the EtAc is first added to the liquid mixture of CAE, ethanol, and water prior to contact with the C3-C7 alkane solvent. In varying embodiments, the ratio of EtAc:CAE is between 0:1 and 2:1, e.g., about 0.8:1, 1:1, 1.1:1, 1.2:1, 1.3:1, 1.4:1, 1.5:1 In varying embodiments, the ratio of C3-C7 alkane solvent: CAE is between about 0.5:1 to about 3.0:1, e.g., between about 0.8:1 to about 1.2:1.

CAO is the starting material for the components for the final blended EPA composition. It is converted into two forms: CPL (Concentrated Polar Lipids) and Super Concentrated EPA. CPL is a mixture component enhanced in polar lipids. The processing to CPL results in enrichment of the polar lipids through removal of and separation from neutral lipids (FFA, TG, and DG). Super Concentrated EPA consolidates the EPA from all the intermediate forms in a method that standardizes and enriches the EPA in its FFA form. In varying embodiments, the process to create Super Concentrated EPA involves hydrolysis, absorptive chromatography, and urea crystallization/winterization or supercritical carbon dioxide (SCCO2) fractionation.

CPL is created employing a silica gel sorbent. In varying embodiments, silica gel sorbent in a granulated form of either spherical or irregular shape with a pore diameter ranging from 40 angstroms to 2000 angstroms and a particle size from 5 to 2000 micron can be used. In some embodiments, the sorbent is free of any additional moiety bonded to the particle surface. In some embodiments, irregular granules with a pore size of about 60 angstroms and a particle size ranging from 60 to 200 micron is used. In varying embodiments, broad range normal silica in the range of 20 to 250 micron can be used. Suitable commercially available silica gel sorbents include without limitation Silicycle's SiliaFlash P60 and SiliaFlash GE60. The silica gel sorbent is use as an absorbent to separate gross classes of molecules by polarity (e.g., normal phase chromatography). The CAO is transferred onto a silica column using methods familiar to those in the art. In varying embodiments, the loaded silica is desorbed with a C3-C7 alkane solvent to remove a first fraction (F1) of the least polar components comprised of neutral lipids, chlorophyll, and carotenoids. For elution of this first fraction (F1), illustrative suitable C3-C7 alkane solvents include without limitation n-propane, n-butane, isobutane, pentane, hexane, isohexane, heptane, and mixtures thereof. In varying embodiments, the alkane solvent to elute F1 is butane. In varying embodiments, the column is subsequently desorbed with acetone (Ace) for elution of the second fraction (F2). Finally, a third wash with a C1-C4 alcohol is used to elute a third fraction (F3). Illustrative C1-C4 alcohols of use include without limitation ethanol (EtOH), ethanol and water (EtOH/H2O), methanol (MeOH), isopropyl alcohol (IPA), n-butanol (nBuOH), isobutanol (iBuOH), and mixtures thereof. In varying embodiments, EtOH/H2O is used because it is a FDA GRAS (Generally Regarded As Safe) solvent. Between 2 and 6 bed volumes of solvent are used for elution of a particular fraction. In certain embodiments, the process of creating CPL can be simplified by eliminating the F2 acetone wash and removing all constituents that would be desorbed by the combination of the acetone and alcohol washes (F2 and F3) solely with the alcohol wash (F3). Digalactosyldiacylglycerol (DGDG) is concentrated in F2. Phospholipids, other than the relatively non-polar phosphatidylinositol (PI), are concentrated in F3. F3 also contains the bulk of monogalactosyldiacylglycerol (MGDG). Generally, higher concentrations of EPA is eluted in F2 than in F3. The combination of F2 and F3 elutes total polar lipid concentrations that are in the range of from about 35 to about 50 wt %, which is useful for blending.

Depending on the growth history of the algae, F1, eluted from CAO using a C3-C7 alkane solvent in normal phase chromatography described above, contains neutral lipids that may or may not have a significant concentration of EPA. F1 contains mostly neutral lipids, including FFA, TG, and DG. It may contain PI. F1 can contain between 50 and 75% of the EPA present in the CAO. Accordingly, in varying embodiments, F1 is further processed by mixing it with unprocessed CAO and converting the CAO/F1 mixture to Super Concentrated EPA.

Super Concentrated EPA is created using a feedstock comprising CAO or a mixture of CAO and F1. In varying embodiments, Super Concentrated EPA can be manufactured in three steps:

1) Hydrolysis
2) Absorptive chromatography
3) Urea crystallization or SCCO2 fractionation For the hydrolysis step, the CAO or mixture of CAO and F1 can be subjected to the following illustrated process:

1) Add water to CAO. In varying embodiments, the water is filtered and deionized. In varying embodiments about 91 g of CAO or CAO/F1 mixture is combined with about 500 mL water.
2) Raise the temperature to at least about 60° C., e.g., for at least about 10 minutes.
3) Add base to raise the pH to 12.5. In varying embodiments, the base is sodium hydroxide (NaOH) is added in solid form at a concentration of about 22 g for every 500 mL water. In varying embodiments, the final concentration is in the range of about 0.5 wt % to about 5.0 wt % NaOH (0.125 M to 1.25 M NaOH), e.g., about 1.5 wt % (0.375 M NaOH). In varying embodiments, sodium hydroxide is added in solid form at a concentration of about 22 g for every 500 mL water.
4) Raise the temperature to at least about 80° C., e.g., for at least about 2 hours.
5) Cool the solution to ambient temperature (e.g., in the range of about 22° C. to about 30° C., e.g., about 25° C.).
6) Add acid to lower the pH to 1.5. In varying embodiments, the acid is sulfuric acid ($H_2SO_4$). In varying embodiments, about 12 mL of concentrated $H_2SO_4$ is added. The final concentration of $H_2SO_4$ is in the range of 1 to 12 wt % (0.102 M to 1.22 M $H_2SO_4$), with a typical value being 4.4 wt % (0.45 M $H_2SO_4$).
7) Add alkane solvent. In varying embodiments, the alkane solvent is a C3-C7 alkane solvent, e.g., n-propane, n-butane, isobutane, pentane, hexane, isohexane, heptane, and mixtures thereof. In some embodiments, the alkane solvent is hexane. In some embodiments, the alkane solvent is a butane, e.g., n-butane, isobutane and mixtures thereof. In varying embodiments, the alkane solvent is added to a concentration of 1:1. In varying embodiments, about 500 mL alkane solvent is added for every 500 mL water used in the first step of the hydrolysis process
8) Transfer the mixture to a suitable size separatory funnel.
9) Decant the lower, aqueous phase from the upper, darker, organic phase. Discard the aqueous phase.
10) Separate and recover the alkane solvent. In varying embodiments, the alkane solvent is removed via evaporation. The solvent-free mixture is predominately FFA and termed concentrated EPA.

In varying embodiments, the concentrated FFA from step 10 is in the range of from about 13 wt. % to about 15 wt. % EPA and from about 35 wt. % to about 40 wt. % total fatty acid (TFA). The remainder of the material in the mixture is non-fatty acid components, including carotenoids, chlorophyll, and other polar lipid components. In some embodiments, nBut, iBut, or But extraction, evaporation, and extract recovery is substituted for steps 7 through 10.

For the absorptive chromatography step, concentrated EPA is loaded onto a normal phase silica column using methods known to those in the art. Any normal phase silica with a broad particle range from 20 to 400 micron is suitable. An illustrative silica gel sorbent of use is Siliaflash P60. The FFA extract is eluted from the column using a C3-C7 alkane solvent for the first fraction (F1 FFA). The majority of the non-polar components are removed from the column using a C1-C4 alcohol solvent (F2 FFA). Any lower alcohol, including methanol (MeOH), ethanol (EtOH), EtOH/$H_2O$, isopropyl alcohol (IPA), n-butanol (nBuOH), isobutanol (iBuOH), and mixtures thereof, can be used to desorb polar constituents of the concentrated EPA feed. F1 FFA has a greatly enhanced TFA concentration that is typically in the range of 75 wt. % to 85 wt. %. Eluted EPA levels range from 28 wt. % to 40 wt. %. A typical F1 CAO would be in the range of from about 13 wt. % to about 15 wt. % EPA and the resultant eluted F1 FFA would be at least about 25 wt. % EPA, e.g., at least about 26 wt. %, 27 wt. %, 28 wt. % or 29 wt. %. Further concentration of the EPA from the F1 FFA elution fraction is desirable before blending with the concentrated polar lipid (CPL) fraction.

Two alternatives can be used for the further and final concentration step of EPA: (1) urea crystallization and winterization (UREA) or (2) supercritical carbon dioxide fractionation (SCCO2). In the former case, reagent grade urea (e.g., VWR Ultrapure grade urea (Catalog number: 97061-920)) is combined with the concentrated EPA eluted in the F1 FFA fraction above. Equal weights urea and concentrated EPA are mixed into acetone (e.g., 20 g urea and 20 g EPA are mixed in 80 g of acetone), heated and stirred at a temperature of at least about 50° C. for at least about 1 hour, and cooled to room temperature. The solution is subsequently cooled to about −30° C. for 4 hours. In varying embodiments, cooling can be accomplished in a cryogenic chiller. The urea complexes with saturated fatty acids (e.g. mostly palmitic acid (C16:0)) and mono-unsaturated fatty acids (e.g. mostly palmitoleic acid (C16:1)). These complexes precipitate from the urea solution when chilled. The urea solution is rapidly cold filtered to remove the precipitated material, retaining the filtrate. The filtrate (clear solution), after recovery of acetone (e.g., via evaporation), is enriched in EPA due to the removal of the saturated and mono-unsaturated fatty acids. The supernatant contains in the range of about 35 wt. % to about 55 wt. % EPA. This super concentrated EPA is suitable for blending to with the concentrated polar lipid (CPL) fraction to create the final EPA/polar lipid composition.

In some embodiments, SCCO2 is used to fractionate the concentrated EPA into superconcentrated EPA. This can be transferred to an SCCO2 extraction system with either internal reflux or external reflux. Lower pressure and temperature conditions (e.g., equal to or below about 2175 psi (150 bar) and 60° C.) are used to remove the lower molecular weight FFA components (C16:0 and C16:1). Higher pressure conditions (e.g., equal to and above about 4350 psi (300 bar) and 70° C.) are used to separate out the higher molecular weight components of the concentrated EPA (namely, arachidonic acid (C20:4n6) and EPA (C20:5n3)). In varying embodiments, such fractionation can start with a starting concentration of about 28-29 wt. % EPA and increase it to between 45 wt. % and 55 wt. % EPA. This super concentrated EPA is suitable for blending to with the concentrated polar lipid (CPL) fraction to create the final EPA/polar lipid composition.

Finally, the standardized blended EPA-polar lipid mixture is created through combining of concentrated polar lipid (CPL) fraction and superconcentrated EPA. The EPA level of both constituents are measured, and the appropriate blending ratio calculated to assure the final mixture is at least about 25 wt. % EPA. In varying embodiments, a rule of mixtures calculation is employed that is based on the weighted average of the concentrations of CPL and superconcentrated EPA.

4. Methods of Preventing and Treating Conditions Mitigated by EPA

Eicosapentaenoic acid (EPA, C20:5, n-3) is an important fatty acid in the omega-3 family based on its medically established therapeutic capabilities against numerous disease conditions and disorders, including without limitation psychiatric disorders (e.g., depression (including major depression, depressed mood and/or post-partum depression), bipolar disorder, anxiety, panic and social phobic disorders, mood disorders, schizophrenia, Obsessive Compulsive Disorder (OCD), borderline personality disorder, attention deficit hyperactivity disorder and related disorders, anorexia nervosa), cardiovascular diseases, osteopathic disorders (e.g., osteoarthritis, osteoporosis), cancers, and neurodegenerative disorders (e.g., Alzheimer's disease, Parkinson's disease, dementia, Huntington's disease, amyotrophic lateral sclerosis or any other "triplet repeat" disease, stroke, multi-infarct or other form of dementia, multiple sclerosis, chronic fatigue and epilepsy). See, e.g., Hegarty, et al., *Curr Opin Psychiatry*. (2013) 26(1):33-40; Parker, et al., *Am J Psychiatry*. (2006) 163(6):969-78; Martins, *J Am Coll Nutr*. (2009) 28(5):525-42; Stahl, et al., *Curr Opin Investig Drugs*. (2008) 9(1):57-64; Simopoulos, *Am. J. Clin. Nutr*. (1999) 70:560S-569S; and Ursin. *J. Nutr*. (2003) 133:4271-4274). The EPA formulations described herein find use in the prevention, amelioration, mitigation, delay of progression of, and/or treatment of any disease condition found to be prevented, ameliorated, mitigated, delayed and/or treated by EPA.

a. Subjects Who May Benefit

Subjects/patients amenable to prevention, amelioration, mitigation, delay of progression of, and/or treatment by administration of an effective amount of the EPA compositions described herein include individuals at risk of disease but not showing symptoms, as well as subjects presently showing symptoms. In certain embodiments, an effective amount of the EPA formulations are administered to individuals who do have a known genetic risk of the disease condition, whether they are asymptomatic or showing symptoms of disease. Such individuals include those having relatives who have experienced or been diagnosed with the disease condition (e.g., a parent, a grandparent, a sibling), and those whose risk is determined by analysis of genetic or biochemical markers. In some embodiments, the subject is asymptomatic but has familial and/or genetic risk factors for developing the disease condition. In some embodiments, the subject is exhibiting symptoms of disease or has been diagnosed as having the disease condition.

b. Conditions Amenable to Treatment

The EPA formulations described herein can be used for the prevention, amelioration, mitigation, delay of progression of, and/or treatment of a wide range of diseases and disorders including without limitation: any psychiatric, neurological or other central or peripheral nervous system disease—in particular depression, schizophrenia, bipolar disorder, anorexia nervosa and degenerative disorders of the brain including Alzheimer's disease and other dementias and Parkinson's disease; asthma and other respiratory diseases; inflammatory disease affecting any system; any form of inflammatory disease including any form of arthritis, any form of inflammatory skin disease including psoriasis and eczema, any form of inflammatory gastrointestinal disease including ulcerative colitis, Crohn's disease, inflammatory bowel diseases, irritable bowel syndrome, and any inflammatory conditions of any other organs including the eyes and brain; any form of cardiovascular or cerebrovascular disease; any form of metabolic disease including diabetes, syndrome X, and any disturbance of calcium metabolism including osteoporosis, unolithiase, or urinary tract stone formation; any form of renal or urinary tract disease; any form of disease or disorder of the reproductive system or menstrual cycle; kidney or urinary tract diseases; liver diseases; disease of the male or female reproductive organs such as the breast or the prostate gland; cancer and/or cancer cachexia; diseases of the head and neck, including disease of the mouth and teeth, of the eyes or of the ears; infection with viruses, bacteria, fungi, protozoa or other organisms.

Illustrative disease conditions that can be prevented, ameliorated, mitigated, delayed and/or treated by administration of an effective amount of the EPA compositions described herein include without limitation psychiatric disorders (e.g., depression (including unipolar depression, major depression, depressed mood and/or post-partum depression), bipolar disorder, mood disorders, schizophrenia, schizoaffective disorders, schizotypy, borderline personality disorder, attention deficit hyperactivity disorder and related disorders. anorexia nervosa), osteopathic disorders (e.g., osteoarthritis, osteoporosis), cardiovascular diseases (e.g., hypertension, coronary artery disease, hypercholesterolemia, dyslipidaemia, high blood pressure, and peripheral vascular system disease), cancers, cancer cachexia, neurodegenerative disorders (e.g., Alzheimer's disease, Parkinson's disease, dementia, Huntington's disease, amyotrophic lateral sclerosis or any other "triplet repeat" disease, stroke, multi-infarct or other form of dementia, multiple sclerosis, chronic fatigue and epilepsy), asthma and other respiratory diseases, liver diseases (e.g., chronic hepatitis; steatosis; liver fibrosis; cirrhosis), alcoholism; malnutrition; chronic parenteral nutrition; phospholipid deficiency; lipid peroxidation; disarrhythmia of cell regeneration; destabilization of cell membranes; menopausal or post-menopausal conditions; aging; benign prostatic hyperplasia; kidney disease; edema; skin diseases; gastrointestinal diseases (e.g., inflammatory bowel diseases and irritable bowel syndrome); and pregnancy toxemia. In varying embodiments, the EPA formulations can be taken as a general nutritional supplement.

Accordingly, methods of preventing, ameliorating, mitigating, delaying of progression of, and/or treating any of the aforesaid diseases or conditions, in particular neurological and psychiatric disorders, e.g., schizophrenia, schizoaffective disorders, schizotypy, depression (including major depression, depressed mood and/or post-partum depression), bipolar disorder, mood disorders, schizophrenia, borderline personality disorder, attention deficit hyperactivity disorder and related disorders by administration of an effective amount of the EPA compositions described herein are provided.

Furthermore, methods of preventing, ameliorating, mitigating, delaying of progression of, and/or treating any disease selected from: asthma and other respiratory diseases; degenerative disorders of the brain including Alzheimer's disease and other dementias and Parkinson's disease; diseases of the gastrointestinal tract including inflammatory bowel diseases and irritable bowel syndrome; inflammatory disease affecting any system; cardiovascular disease; any form of dyslipidaemia, any form of diabetes or any form of metabolic diseases; any form of dermatological diseases; any form of kidney or urinary tract disease; any form of liver disease; any form of disease of the male or female reproductive system or related secondary sexual organs such as the breast or prostate gland; any form of cancer or for cancer cachexia; any disease of the head and neck including diseases of the mouth and teeth, of the eyes or of the ears; and any form of infection with viruses, bacteria, fungi, protozoa or other organisms by administration of an effective amount of the EPA compositions described herein are also provided.

c. Formulation and Administration

In one embodiment, the EPA compositions are orally deliverable. The terms "orally deliverable" or "oral administration" herein include any form of delivery of a therapeutic agent or a composition thereof to a subject wherein the agent or composition is placed in the mouth of the subject, whether or not the agent or composition is swallowed. Thus "oral administration" includes buccal and sublingual as well as esophageal administration.

In some embodiments, the EPA compositions are in the form of solid dosage forms. Non-limiting examples of suitable solid dosage forms include tablets (e.g. suspension tablets, bite suspension tablets, rapid dispersion tablets, chewable tablets, melt tablets, effervescent tablets, bilayer tablets, etc), caplets, capsules (e.g. a soft or a hard gelatin capsule from animal gelatin or from a vegetarian source filled with solid and/or liquids), powder (e.g. a packaged powder, a dispensable powder or an effervescent powder), lozenges, sachets, cachets, troches, pellets, granules, microgranules, encapsulated microgranules, powder aerosol formulations, or any other solid dosage form reasonably adapted for oral administration.

In varying embodiments, the present EPA compositions can be formulated in single or separate dosage units. The terms "dose unit" and "dosage unit" herein refer to a portion of a pharmaceutical composition that contains an amount of a therapeutic agent suitable for a single administration to provide a therapeutic effect. Such dosage units may be administered one to a plurality (i.e. 1 to about 10, 1 to 8, 1 to 6, 1 to 4 or 1 to 2) of times per day, or as many times as needed to elicit a preventative, mitigating and/or therapeutic response.

In another embodiment, the EPA composition(s) can be in the form of liquid dosage forms or dose units to be imbibed directly or they can be mixed with food or beverage prior to ingestion. Non-limiting examples of suitable liquid dosage forms include solutions, suspension, elixirs, syrups, liquid aerosol formulations, etc. Generally, the liquid forms are not biphasic and contain less than about 10 wt. % $H_2O$, e.g., less than about 9 wt. %, 8 wt. %, 7 wt. %, 6 wt. %, 5 wt. %, 4 wt. %, 3 wt. %, 2 wt. %, or 1 wt. %, $H_2O$.

In varying embodiments, the EPA compositions are formulated for administration of EPA at a daily dose of less than or equal to 2 grams, e.g., less than 1 gram, less than 100 mg, less than 10 mg, less than 1 mg, e.g., about 1 mg to about 10 mg, e.g., about 10 mg to about 100 mg, e.g., about 10 mg to about 2 g, e.g., about 100 mg to about 2 g. In varying embodiments, the EPA compositions are formulated for administration of EPA at a total dosage in the range of 250 mg to 2 g per day. For example, the EPA compositions may be formulated for administration of EPA at a dose of 60 to 100 mg in a 300 mg capsule, e.g., 90 to 170 mg in a 500 mg capsule, e.g., 180 to 340 mg in a 1000 mg capsule. Without being bound to theory, the presence of glycolipids in the present EPA compositions allows for bioavailability of EPA to target tissues at levels that are equivalent or greater than EPA bioavailability to the same target tissues from krill oil or fish oil. The present EPA formulations can deliver EPA to target tissues with equal or greater bioavailability while containing less than half the concentration of polar lipids, allowing for reduced EPA dosing and reduced capsule size. Whereas krill oil or fish oil can contain at least about 35 wt. % polar lipids, e.g., at least about 39 wt. % polar lipids, and contains no glycolipids, the present EPA formulations contain glycolipids and in the range of about 10 wt. % to about 35 wt. % total polar lipids. Accordingly, in varying embodiments, the EPA compositions are formulated for administration of EPA at a daily dose that is 90%, 85%, 80%, 75%, 70%, or less, than the EPA doses set forth above or in comparison to EPA doses provided in krill oil or fish oil. In varying embodiments, capsule sizes for administration of the present EPA formulations can be about 30%, 40%, 50%, 60% or 70% the size of capsules currently used to achieve an equivalent bioavailability of EPA in a target tissue of interest (e.g., blood (plasma), liver, brain, skin).

In some embodiments, the EPA compositions further comprise a stabilizing agent that suppresses, prevents, hinders, or otherwise attenuates the decomposition of the active ingredient(s) during storage. For example, oxidative decomposition of EPA in compositions may be prevented or attenuated by the presence of antioxidants. Non-limiting examples of suitable antioxidants include tocopherol, Origanox™ (available from Frutarom Ltd.), lecithin, citric acid and/or ascorbic acid. One or more antioxidants, if desired, are typically present in a composition in an amount of about 0.001% to about 5%, about 0.005% to about 2.5%, or about 0.01% to about 1%, by weight.

Excipients

The EPA compositions optionally can comprise one or more pharmaceutically acceptable excipients. The term "pharmaceutically acceptable excipient" herein means any substance, not itself a therapeutic agent, used as a carrier or vehicle for delivery of a therapeutic agent to a subject or added to a pharmaceutical composition to improve its handling or storage properties or to permit or facilitate formation of a unit dose of the composition, and that does not produce unacceptable toxicity or interaction with other components in the composition.

The EPA compositions optionally can comprise one or more pharmaceutically acceptable diluents as excipients. Suitable diluents illustratively include, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of α- and amorphous cellulose (e.g., Rexcel™) and powdered cellulose; calcium carbonate; glycine; bentonite; polyvinylpyrrolidone; and the like. Such diluents, if present, can constitute in total about 5% to about 99%, about 10% to about 85%, or about 20% to about 80%, of the total weight of the composition.

The EPA compositions optionally can comprise one or more pharmaceutically acceptable disintegrants as excipients. Suitable disintegrants include, either individually or in combination, starches, including sodium starch glycolate (e.g., Explotab™ of PenWest) and pregelatinized corn starches (e.g., National™ 1551, National™ 1550, and Colocorn™ 1500), clays (e.g., Veegum™ HV), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, xanthan, locust bean, karaya, pectin and tragacanth gums. Such disintegrants, if present, typically comprise in total about 0.2% to about 30%, about 0.2% to about 10%, or about 0.2% to about 5%, of the total weight of the composition.

The EPA compositions optionally can comprise one or more antioxidants. Illustrative antioxidants include sodium ascorbate, Origanox™, and vitamin E (tocopherol). One or more antioxidants, if present, are typically present in the EPA composition in an amount of about 0.001% to about 5%, about 0.005% to about 2.5%, or about 0.01% to about 1%, by weight.

The EPA compositions optionally can comprise one or more pharmaceutically acceptable binding agents or adhesives as excipients. Such binding agents and adhesives can impart sufficient cohesion to a powder being tableted to allow for normal processing operations such as sizing, lubrication, compression and packaging, but still allow the tablet to disintegrate and the composition to be absorbed upon ingestion. Suitable binding agents and adhesives include, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™); and ethylcellulose (e.g., Ethocel™). Such binding agents and/or adhesives, if present, constitute in total about 0.5% to about 25%, about 0.75% to about 15%, or about 1% to about 10%, of the total weight of the composition.

The EPA compositions optionally can comprise one or more pharmaceutically acceptable wetting agents as excipients. Non-limiting examples of surfactants that can be used as wetting agents in the EPA compositions include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefosse), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefosse), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, about 0.4% to about 10%, or about 0.5% to about 5%, of the total weight of the composition.

The EPA compositions optionally can comprise one or more pharmaceutically acceptable lubricants (including anti-adherents and/or glidants) as excipients. Suitable lubricants include, either individually or in combination, glyceryl behapate (e.g., Compritol™ 888); stearic acid and salts thereof, including magnesium (magnesium stearate), calcium and sodium stearates; hydrogenated vegetable oils (e.g., Sterotex™); colloidal silica; talc; waxes; boric acid; sodium benzoate; sodium acetate; sodium fumarate; sodium chloride; DL-leucine; PEG (e.g., Carbowax™ 4000 and Carbowax™ 6000); sodium oleate; sodium lauryl sulfate; and magnesium lauryl sulfate. Such lubricants, if present, constitute in total about 0.1% to about 10%, about 0.2% to about 8%, or about 0.25% to about 5%, of the total weight of the composition.

Suitable anti-adherents include talc, cornstarch, DL-leucine, sodium lauryl sulfate and metallic stearates. Talc is an anti-adherent or glidant used, for example, to reduce formulation sticking to equipment surfaces and also to reduce static in the blend. Talc, if present, constitutes about 0.1% to about 10%, about 0.25% to about 5%, or about 0.5% to about 2%, of the total weight of the composition. Glidants can be used to promote powder flow of a solid formulation. Suitable glidants include colloidal silicon dioxide, starch, talc, tribasic calcium phosphate, powdered cellulose and magnesium trisilicate.

Compositions of the present invention optionally comprise one or more flavoring agents, sweetening agents, and/or colorants. Flavoring agents useful in the present invention include, without limitation, acacia syrup, alitame, anise, apple, aspartame, banana, Bavarian cream, berry, black currant, butter, butter pecan, butterscotch, calcium citrate, camphor, caramel, cherry, cherry cream, chocolate, cinnamon, citrus, citrus punch, citrus cream, cocoa, coffee, cola, cool cherry, cool citrus, cyclamate, cylamate, dextrose, *eucalyptus*, eugenol, fructose, fruit punch, ginger, glycyrrhetinate, *glycyrrhiza* (licorice) syrup, grape, grapefruit, honey, isomalt, lemon, lime, lemon cream, MagnaSweet®, maltol, mannitol, maple, menthol, mint, mint cream, mixed berry, nut, orange, peanut butter, pear, peppermint, peppermint cream, Prosweet® Powder, raspberry, root beer, rum, saccharin, safrole, sorbitol, spearmint, spearmint cream, strawberry, strawberry cream, *stevia*, sucralose, sucrose, Swiss cream, tagatose, tangerine, thaumatin, tutti fruitti, vanilla, walnut, watermelon, wild cherry, wintergreen, xylitol, and combinations thereof, for example, anise-menthol, cherry-anise, cinnamon-orange, cherry-cinnamon, chocolate-mint, honey-lemon, lemon-lime, lemon-mint, menthol-*eucalyptus*, orange-cream, vanilla-mint, etc.

Sweetening agents that can be used in the present invention include, for example, acesulfame potassium (acesulfame K), alitame, aspartame, cyclamate, cylamate, dextrose, isomalt, MagnaSweet®, maltitol, mannitol, neohesperidine DC, neotame, Prosweet® Powder, saccharin, sorbitol, *stevia*, sucralose, sucrose, tagatose, thaumatin, xylitol, and the like.

Flavoring agents, sweetening agents, and/or colorants can be present in the EPA compositions in any suitable amount, for example about 0.01% to about 10%, about 0.1% to about 8%, or about 1% to about 5%, by weight.

The EPA compositions optionally can comprise a suspending agent. Non-limiting illustrative examples of suitable suspending agents include silicon dioxide, bentonite, hydrated aluminum silicate (e.g. kaolin) and mixtures thereof. One or more suspending agents are optionally present in the EPA compositions in a total amount of about 0.01% to about 3.0%, about 0.1% to about 2.0%, or about 0.25% to about 1.0%, by weight The foregoing excipients can have multiple roles as is known in the art. For example, starch can serve as a filler as well as a disintegrant. The classification of excipients above is not to be construed as limiting in any manner. Excipients categorized in any manner may also operate under various different categories of excipients as will be readily appreciated by one of ordinary skill in the art.

When the EPA compositions are formulated as nutraceuticals, they can be in the form of foods, beverages, energy bars, sports drinks, supplements or other forms all as are known in the art.

Combination Therapies

In varying embodiments, the EPA formulations can be co-administered with an antidepressant, an antihypertensive agent and/or a cholesterol reducing agent, astaxanthin, vitamin E, phospholipids, coenzyme Q9 (CoQ9), and/or coenzyme Q10 (CoQ10). Co-administration with the herein described EPA formulations can allow for administration of the antidepressant, antihypertensive agent and/or cholesterol reducing agent at a subtherapeutic dose.

Illustrative antidepressants that can be co-administered with the present EPA formulations include without limitation, selective serotonin reuptake inhibitors, SSRIs (e.g., citalopram, escitalopram, paroxetine, fluoxetine, fluvoxamine, sertraline); selective norepinephrine reuptake inhibitors (NRIs) (e.g., atomoxetine, reboxetine, viloxazine); noradrenergic and specific serotonergic antidepressants (NaSSA) (e.g., mianserin, mirtazapine); serotonin-norepinephrine reuptake inhibitors (SNRIs) (e.g., desvenlafaxine, duloxetine, milnacipran, venlafaxine); serotonin antagonist and reuptake inhibitors (SARIs) (e.g., etoperidone, nefazodone, trazodone); norepinephrine-dopamine reuptake inhibitors (e.g., bupropion); selective serotonin reuptake enhancers (e.g., tianeptine, amineptine); norepinephrine-dopamine disinhibitors (NDDIs) (e.g., agomelatine); tricyclic antidepressants (e.g., amitriptyline, clomipramine, doxepin, imipramine, trimipramine, desipramine, nortriptyline, protriptyline); monoamine oxidase inhibitors (MAOIs) (e.g., isocarboxazid, moclobemide, phenelzine, pirlindole, selegiline, tranylcypromine).

Illustrative antihypertensive agents that can be co-administered with the present EPA formulations include without limitation, loop diuretics (e.g., bumetanide, ethacrynic acid, furosemide, torsemide); thiazide diuretics (e.g., epitizide, hydrochlorothiazide, chlorothiazide, bendroflumethiazide); thiazide-like diuretics (e.g., indapamide, chlorthalidone, metolazone); potassium-sparing diuretics (e.g., amiloride, triamterene, spironolactone); beta adrenergic receptor blockers (e.g., atenolol, metoprolol, nadolol, nebivolol, oxprenolol, pindolol, propranolol, timolol); alpha adrenergic receptor blockers (e.g., doxazosin, phentolamine, indoramin, phenoxybenzamine, prazosin, terazosin, tolazoline); mixed alpha+beta blockers (e.g., bucindolol, carvedilol, labetalol); calcium channel blockers (e.g., amlodipine, felodipine, isradipine, lercanidipine, nicardipine, nifedipine, nimodipine, nitrendipine, diltiazem, verapamil); renin inhibitors (e.g., aliskiren); angiotensin-converting enzyme (ACE) inhibitors (e.g., captopril, enalapril, fosinopril, lisinopril, perindopril, quinapril, ramipril, trandolapril, benazepril); angiotensin II receptor antagonists (e.g., candesartan, eprosartan, irbesartan, losartan, olmesartan, telmisartan, valsartan); aldosterone receptor antagonists (e.g., eplerenone, spironolactone); vasodilators (e.g., sodium nitroprusside, hydralazine); alpha-2 agonists (e.g., clonidine, guanabenz, methyldopa, moxonidine) and adrenergic neuron blockers (e.g., guanethidine, reserpine).

Illustrative hypolipidemic agents (a.k.a., antihyperlipidemic agents or lipid lowering drugs) that can be co-administered with the present EPA formulations include without limitation, statins or HMG-CoA reductase inhibitors (e.g., atorvastatin, cerivastatin, fluvastatin, lovastatin, mevastatin, pitavastatin, pravastatin, rosuvastatin, simvastatin), fibrates (e.g., bezafibrate, ciprofibrate, clofibrate, gemfibrozil, fenofibrate), niacin, bile acid sequestrants (resins) (e.g., cholestyramine, colesevelam, colestipol, colestipid), ezetimibe, lomitapide, phytosterols (e.g., β-sitosterol, campesterol, stigmasterol), and orlistat.

The EPA formulations can be co-administered with a therapeutically effective amount or a sub-therapeutic amount of one or more of an antidepressant, antihypertensive agent and/or antihyperlipidemic agent. The dosage of the specific compounds depends on many factors that are well known to those skilled in the art. They include for example, the route of administration and the potency of the particular compound. Dosing and scheduling of antidepressants, antihypertensive agents and/or antihyperlipidemic agents are known in the art, and can be found, e.g., in the published literature and in reference texts, e.g., the Physicians' Desk Reference, 67th Ed., 2013, Thomson Healthcare or Brunton, et al., Goodman & Gilman's The Pharmacological Basis of Therapeutics, 12th edition, 2010, McGraw-Hill Professional). Because of the cooperative action between the EPA formulations and the antidepressants, antihypertensive agents and/or antihyperlipidemic agents, one or both of the co-administered agents can be administered at a sub-therapeutic dose.

Determination of an effective amount is well within the capability of those skilled in the art, especially in light of the detailed disclosure provided herein. Generally, an efficacious or effective amount of a combination of one or more polypeptides of the present invention is determined by first administering a low dose or small amount of a polypeptide or composition and then incrementally increasing the administered dose or dosages, adding a second or third medication as needed, until a desired effect of is observed in the treated subject with minimal or no toxic side effects. Applicable methods for determining an appropriate dose and dosing schedule for administration of a combination of the present invention are described, for example, in *Goodman and Gilman's The Pharmacological Basis of Therapeutics,* 12th Edition, 2010, supra; in a Physicians' Desk Reference (PDR), $67^{th}$ Edition, 2013; in *Remington: The Science and Practice of Pharmacy,* $21^{st}$ Ed., 2005, supra; and in *Martindale: The Complete Drug Reference*, Sweetman, 2005, London: Pharmaceutical Press., and in Martindale, *Martindale: The Extra Pharmacopoeia,* 31st Edition., 1996, Amer Pharmaceutical Assn, each of which are hereby incorporated herein by reference.

EXAMPLES

The following examples are offered to illustrate, but not to limit the claimed invention.

Example 1

EPA Formulations with Improved Bioavailability

This Standardized Omega 3 and Polar Lipid Formulation derives from two strains of the microalgae *Nannochloropsis oculata*, hereafter referred to as S12 and S14. *N. Oculata* is a marine algal strain and, thus, must be grown in either seawater or brackish water. Brackish water has between one fifth and one times the dissolved solids that are present in seawater. Neither S12 nor S14 have been genetically modified. The strains are a result of selective breeding program. The S12 strain is, nominally, adapted for lower ambient temperature conditions, while the S14 can grow in warm temperature conditions. There is a natural variance in the composition of the algae due to variety of factors that include but are not limited to strain, media content, diurnal temperature variation, illumination, culture concentration.

In addition, the extract composition is a function of the handling of the algal biomass upon its removal from the growth system. Nominally, the algae grows in relatively dilute culture on a system that is typically on the range of 0.1 to 1.0 g/L of biomass and, more typically, in the range of 0.4 to 0.7 g/L. For a 0.5 g/L culture concentration, this implies that there is 0.5 g of dry weight equivalent biomass for every 1000 g of culture, a dilute concentration. Algae is further processed in a more concentrated state, typically in the range of 2 to 300 g/L, so a significant amount of water needs to be removed. Water, in this case, is understood to be saltwater, water with dissolved solids.

Omega-3 in S12 and S14 *N. Oculata* refers to the eicosapentanoic acid (EPA) (C20:5ω3) and alpha-linolenic acid (ALA) (C18:3ω3), nominally where the EPA represented the substantial fraction of the total Omega-3. Polar lipids include both phospholipids (PL) and glycolipids (GL). The PL fraction is comprised of four PL components: phosphatidylcholine (PC), phosphatidylglycerol (PG), phosphatidylethanolamine (PE), and phosphatidylinositol (PI). The glycolipids in the mixture are predominantly digalactosyldiacylglycerol (DGDG) and monogalactosyldiacylglycerol (MGDG). Omega-7 is nominally represented by palmitoleic acid (C16:1ω7). The fatty acids (FA) in the mixture are associated with four major lipid types: PL, GL, free fatty acids (FFA), and triglycerides (TG). There are also minor components of diglycerides (DG) present. Neutral lipids (LP) are comprised of FFA, TG, and DG. Polar lipids (PoL) are comprised of PL and GL.

Figure 4:
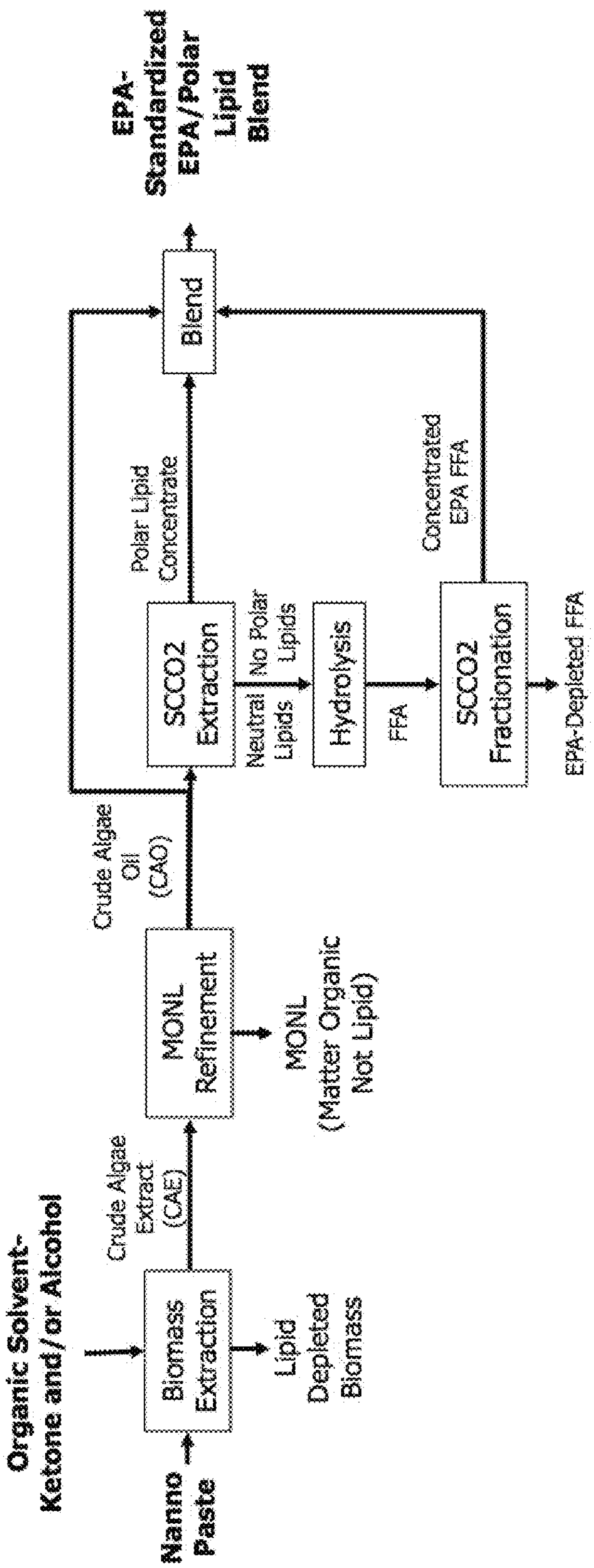
FIG. 4 illustrates an embodiment of extraction and refinement process to convert *Nannochloropsis* paste to a standardized EPA and polar lipid mixture.
Figure 5:
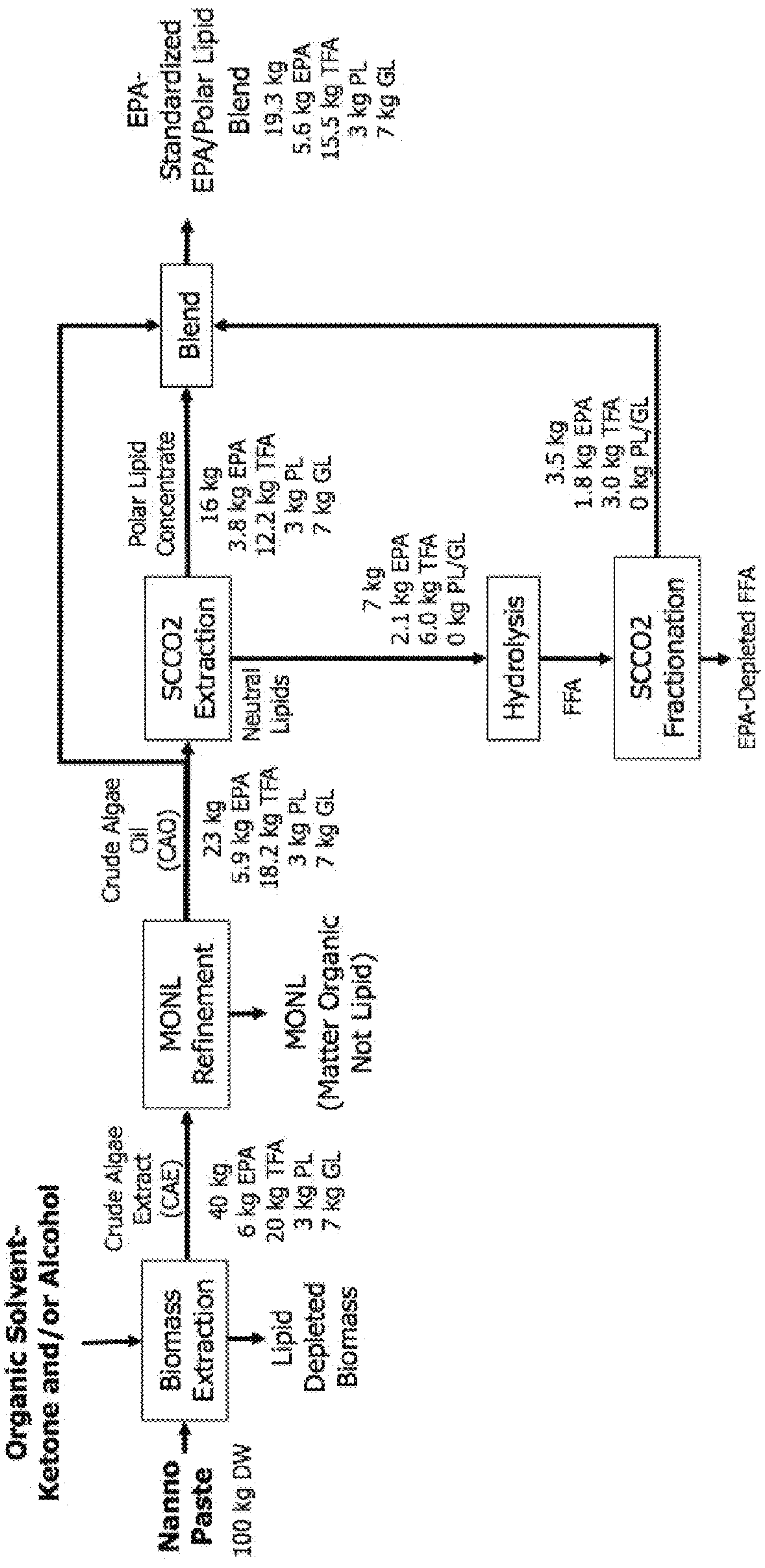
FIG. 5 illustrates an example of typical mass split of major mixture constituents during *Nannochloropsis* oil refining.

A specific embodiment of the process to create the standardized formulation is shown in FIG. 4. This differs from FIG. 1 in the details for Neutral and Polar Lipid Separation (NL/PoL Separation), Neutral Lipid Harmonization, and Lipid Fractionation. There are several variants on Biomass Extraction and then specific embodiments for NL/PoL Separation using supercritical carbon dioxide (SCCO2), Hydrolysis for Neutral Lipid Harmonization, and Lipid Fractionation via SCCO2 Fractionation. The Biomass Extraction method is nominally directed to maximize the recovery of NL and PoL. Because *Nannochloropsis Oculata* is a phototrophic single cell organism, the photosynthesis mechanisms and the lipid storage means are located within the same cell. CAE from the biomass has a high chlorophyll content and can vary from 2 wt % of the mixture up to 20 wt %, with a typical value being in the range of 5 to 8 wt %. Similarly, sterol content is on the order of 1 wt %. Carotenoids are between 2,500 and 10,000 ppm (0.25 to 1 wt %).

The Nanno Paste may be extracted in either the wet or dry state. In the wet state, the moisture content is between 400 and 1000% (w/w) dried biomass (25 to 10 wt % solids). In the dry state, the moisture content is less than 15% (w/w) of the dried biomass. CAE can contain between 10 and 80% of constituents that are not lipids. The components other than lipids and phytonutrients are termed MONL for Matter Organic-Not Lipid. The composition of this material is not fully known; however, it is known that the constituents that need to be eliminated are water-soluble components. The resultant output of MONL refinement is crude algae oil (CAO) that is in excess of 50 wt % total lipids and, in some embodiments, in excess of 60 or 70 wt % total lipids.

The benchmark technique for determining fatty acid content in algal biomass is the fat by acid hydrolysis (FAH) method. This involve treatment of the biomass with a strong acid to digest the cell member, followed by an extraction, conversion to fatty acid methyl esters (FAME), and analysis via AOCS (American Oil Chemist Society) Method Ce 1b 89 "Fatty Acid Composition of Marine Oils by GLC" and AOCS Method Ca 5b 71 "Crude Fatty Acids". The former method determines the relative amount of each fatty acid constituent in the total collection of fatty acids. The latter method determines the total saponifiable fat in a sample. The relative amount of each fatty acid normalized by the total saponifiable fat determines the sample basis amount of each fatty acid. New Jersey Feed Laboratory, Inc. (NJFL) in Trenton, N.J., USA has particular proprietary extensions of the acid digestion, extraction, and FAME conversion. Except as otherwise noted, all FAH profiles are measured by this method and organization. Furthermore, where the fatty acid profile (FAP) of a mixture derived via a different extraction method, AOCS Methods Ca 5b 71 and Ce 1b 89 are used. Except where otherwise noted, all FAP data is from NJFL.

The extraction of the lipids and phytonutrients from the remainder of the protein, carbohydrate, minerals, and fiber comprising the alga cells produces CAE. Biomass extraction results in the lipids being isolated from the biomass while removing a minimal carbohydrates, proteins, and minerals. The residual biomass is substantially depleted of lipids and, thus, termed lipid extracted algae (LEA). Surprisingly and unlike many other algae species, we have found that *N. Oculata* can be extracted without requiring disruption by either mechanical, thermal, or chemical means to disrupt the cellular membrane. This is illustrated by comparative extractions of replicate samples (N=3 or 4) S12 and S14 biomass in Tables 2 and 3, respectively. All algal biomass was dried in a low humidity environment at 60° C. until the solid was less than 10 wt % moisture. For the fatty acid profiles reported in Tables 2 and 3, the biomass was processed in a conventional or automated Soxhlet extractor (on the internet at en.wikipedia.org/wiki/Soxhlet_extractor). This is data reflective of CAE and, thus, has other components other than fats in the extract. The S12 extract has a lower TFA than the S14 extracts, indicating that there are non-lipid components in this extract. These tables illustrate that extraction of dry biomass via FAH and 70/30 v/v % hexane (Hex) and methanol (MeOH) (70/30 Hex/MeOH) solvent extraction that the extracted EPA on a biomass basis is essentially the same. The total fatty acid (TFA) is sufficiently the same that 70/30 Hex/MeOH can be applied as a representative and non-proprietary extraction technique. Surprisingly, in S12, the FAH method created an extract higher in TFA than 70/30 Hex/MeOH while in S14, the 70/30 Hex/MeOH results in the higher TFA in the extract. Nonetheless, when the amounts are normalized by the total extract from the biomass, leading to the fatty acid in dry solid, the two methods are produce the nearly the same amount of EPA for both strains. This is the first of several indications that extraction behavior of a biomass is very much a function of several variables that include the species, the growth history of the biomass, the harvest and handling conditions between the time of harvest and the time of extraction, and solvent system.

The comparison between the fatty acid profile between S12 and S14 is made in Table 4. This shows dried S12 and S14 processed both by FAH and 70/30 Hex/MeOH extraction. In all cases, the saturated FAs are about 25% of the fatty acid profile (FAP), the monosaturated FAs about 30%, and the polyunsaturated FAs about 35%. The EPA Omega-3 represents greater than 98% of the total Omega-3 with both S12 and S14. Thus, the EPA in the FAP is about 30% and is similar to the Omega-3 in the FAP. S12 has a characteristic ratio of EPA to ARA of 700 to 900% (i.e. seven to nine times the EPA than the ARA). S14 has lower EPA to ARA ratio of greater the range of 500 to 600%.

TABLE 2

S12 Extraction of Dry Biomass via Fat by Acid Hydrolysis and 70/30 Hex/MeOH

| | | Fat by Acid Hydrolysis | | | 70/30 (v/v %) Hexane/Methanol | | |
|---|---|---|---|---|---|---|---|
| | | Average Extract from Biomass % | | | | | |
| | | 20.88 | | | 36.29 | | |
| | | Standard Deviation % | | | | | |
| | | 1.66 | | | 4.60 | | |
| Fatty Acid | C#: Dbl. Bond | Normalized FA % | FA in Extract % | FA in Dry Solid % | Normalized FA % | FA in Extract % | FA in Dry Solid % |
| Caprylic | 8:0 | 0.17 | 0.11 | 0.02 | 0.24 | 0.11 | 0.04 |
| Capric | 10:0 | 0.26 | 0.17 | 0.04 | 0.95 | 0.43 | 0.16 |
| Lauric | 12:0 | 0.45 | 0.30 | 0.06 | 0.38 | 0.16 | 0.06 |
| Myristic | 14:0 | 6.66 | 4.38 | 0.92 | 6.00 | 2.62 | 0.95 |
| Myristoleic | 14:1 | 0.67 | 0.44 | 0.09 | 0.09 | 0.04 | 0.01 |
| Pentadecanoic | 15:0 | 0.43 | 0.28 | 0.06 | 0.41 | 0.18 | 0.06 |
| Palmitic | 16:0 | 17.93 | 11.79 | 2.46 | 17.17 | 7.51 | 2.73 |
| Palmitoleic | 16:1 | 20.83 | 13.70 | 2.86 | 20.55 | 8.99 | 3.26 |
| Hexadecadienoic | 16:2 | 0.20 | 0.13 | 0.03 | 0.19 | 0.08 | 0.03 |
| Hexadecatrienoic | 16:3 | 0.00 | 0.00 | 0.00 | 0.00 | 0.00 | 0.00 |
| Hexadecatetraenoic | 16:4 | 0.08 | 0.05 | 0.01 | 0.07 | 0.03 | 0.01 |
| Heptadecanoic | 17:0 | 0.19 | 0.13 | 0.03 | 0.18 | 0.08 | 0.03 |
| Stearic | 18:0 | 0.32 | 0.21 | 0.04 | 0.33 | 0.15 | 0.05 |
| Oleic | 18:1ω9 | 5.51 | 3.62 | 0.76 | 5.23 | 2.29 | 0.83 |
| Oleic | 18:1ω7 | 0.37 | 0.24 | 0.05 | 0.22 | 0.10 | 0.03 |
| Linoleic | 18:2ω6 | 4.34 | 2.85 | 0.60 | 4.31 | 1.88 | 0.68 |
| Gamma-Linolenic | 18:3ω6 | 0.00 | 0.00 | 0.00 | 0.20 | 0.09 | 0.03 |
| Alpha-Linolenic (ALA) | 18:3ω3 | 0.19 | 0.13 | 0.03 | 0.17 | 0.07 | 0.03 |
| Eicosadienoic | 20:2ω6 | 0.08 | 0.05 | 0.01 | 0.13 | 0.06 | 0.02 |
| Eicosatrienoic | 20:3ω6 | 0.29 | 0.19 | 0.04 | 0.21 | 0.09 | 0.03 |

TABLE 2-continued

S12 Extraction of Dry Biomass via Fat by Acid Hydrolysis and 70/30 Hex/MeOH

| | | Fat by Acid Hydrolysis | | | 70/30 (v/v %) Hexane/Methanol | | |
|---|---|---|---|---|---|---|---|
| | | Average Extract from Biomass % | | | | | |
| | | 20.88 | | | 36.29 | | |
| | | Standard Deviation % | | | | | |
| | | 1.66 | | | 4.60 | | |
| Fatty Acid | C#: Dbl. Bond | Normalized FA % | FA in Extract % | FA in Dry Solid % | Normalized FA % | FA in Extract % | FA in Dry Solid % |
| Arachidonic | 20:4ω6 | 3.92 | 2.58 | 0.54 | 3.48 | 1.52 | 0.55 |
| Eicosapentaenoic (EPA) | 20:5ω3 | 29.25 | 19.24 | 4.02 | 27.22 | 11.90 | 4.32 |
| Other | n/a | 7.86 | 5.17 | 1.08 | 12.28 | 5.38 | 1.95 |
| Total Fatty Acid | | 100.00 | 65.79 | 13.74 | 100.00 | 43.76 | 15.88 |
| Total Omega-3 | | 29.44 | 19.36 | 4.04 | 27.64 | 16.40 | 2.89 |
| Total Omega-6 | | 8.63 | 5.67 | 1.18 | 9.08 | 5.39 | 0.95 |

TABLE 3

S14 Extraction of Dry Biomass via Fat by Acid Hydrolysis and 70/30 Hex/MeOH

| | | Fat by Acid Hydrolysis | | | 70/30 (v/v %) Hexane/Methanol | | |
|---|---|---|---|---|---|---|---|
| | | Average Extract from Biomass % | | | | | |
| | | 17.64 | | | 16.78 | | |
| | | Standard Deviation % | | | | | |
| | | 0.56 | | | 1.36 | | |
| Fatty Acid | C#: Dbl. Bond | Normalized FA % | FA in Extract % | FA in Dry Solid % | Normalized FA % | FA in Extract % | FA in Dry Solid % |
| Caprylic | 8:0 | 0.23 | 0.13 | 0.02 | 0.30 | 0.23 | 0.04 |
| Capric | 10:0 | 0.20 | 0.12 | 0.02 | 0.58 | 0.44 | 0.07 |
| Lauric | 12:0 | 0.49 | 0.29 | 0.05 | 0.35 | 0.27 | 0.05 |
| Myristic | 14:0 | 4.39 | 2.61 | 0.46 | 3.58 | 2.74 | 0.46 |
| Myristoleic | 14:1 | 1.06 | 0.63 | 0.11 | 0.12 | 0.10 | 0.02 |
| Pentadecanoic | 15:0 | 0.34 | 0.20 | 0.04 | 0.34 | 0.26 | 0.04 |
| Palmitic | 16:0 | 18.29 | 10.86 | 1.92 | 15.91 | 12.18 | 2.04 |
| Palmitoleic | 16:1 | 21.41 | 12.70 | 2.24 | 19.19 | 14.69 | 2.47 |
| Hexadecadienoic | 16:2 | 0.17 | 0.10 | 0.02 | 0.17 | 0.13 | 0.02 |
| Hexadecatrienoic | 16:3 | 0.04 | 0.02 | 0.00 | 0.18 | 0.13 | 0.02 |
| Hexadecatetraenoic | 16:4 | 0.15 | 0.09 | 0.02 | 0.16 | 0.12 | 0.02 |
| Heptadecanoic | 17:0 | 0.26 | 0.16 | 0.03 | 0.27 | 0.21 | 0.04 |
| Stearic | 18:0 | 0.47 | 0.28 | 0.05 | 0.33 | 0.25 | 0.04 |
| Oleic | 18:1ω9 | 4.81 | 2.86 | 0.50 | 4.26 | 3.27 | 0.55 |
| Oleic | 18:1ω7 | 1.25 | 0.74 | 0.13 | 1.10 | 0.85 | 0.14 |
| Linoleic | 18:2ω6 | 3.80 | 2.26 | 0.40 | 3.55 | 2.73 | 0.46 |
| Gamma-Linolenic | 18:3ω6 | 0.40 | 0.24 | 0.04 | 0.25 | 0.19 | 0.03 |
| Alpha-Linolenic (ALA) | 18:3ω3 | 0.39 | 0.24 | 0.04 | 0.41 | 0.31 | 0.05 |
| Eicosadienoic | 20:2ω6 | 0.00 | 0.00 | 0.00 | 0.00 | 0.00 | 0.00 |
| Eicosatrienoic | 20:3ω6 | 0.04 | 0.02 | 0.00 | 0.04 | 0.03 | 0.01 |
| Arachidonic | 20:4ω6 | 4.84 | 2.87 | 0.51 | 4.08 | 3.13 | 0.52 |
| Eicosapentaenoic (EPA) | 20:5ω3 | 27.25 | 16.17 | 2.85 | 23.47 | 17.97 | 3.01 |
| Other | n/a | 9.71 | 5.80 | 1.02 | 21.37 | 16.51 | 2.77 |
| Total Fatty Acid | | 100.00 | 59.39 | 10.48 | 100.00 | 76.74 | 12.88 |
| Total Omega-3 | | 27.64 | 16.40 | 2.89 | 27.64 | 16.40 | 2.89 |
| Total Omega-6 | | 9.08 | 5.39 | 0.95 | 9.08 | 5.39 | 0.95 |

TABLE 4

Fatty Acid Classes in S12 and S14 Dried Biomass by FAH and 70/30 MeOH Extraction

| Fatty Acid Metric | S12- FAH Normalized FA % | S12- FAH FA in Extract % | S12- 70/30 Hex/MeOH Normalized FA % | S12- 70/30 Hex/MeOH FA in Extract % | S14- FAH Normalized FA % | S14- FAH FA in Extract % | S14- 70/30 Hex/MeOH Normalized FA % | S14- 70/30 Hex/MeOH FA in Extract % |
|---|---|---|---|---|---|---|---|---|
| Total Fatty Acid (TFA) | 100.00 | 65.79 | 100.00 | 43.76 | 100.00 | 59.39 | 100.00 | 76.74 |
| Total Saturates | 26.42 | 17.38 | 25.66 | 11.24 | 24.67 | 14.65 | 21.66 | 16.58 |
| Total Monounsaturates | 27.37 | 18.01 | 26.09 | 11.41 | 28.53 | 16.93 | 24.67 | 18.91 |
| Total Polyunsaturates | 38.35 | 25.22 | 35.97 | 15.73 | 37.08 | 22.01 | 32.30 | 24.74 |
| Total Omega-3 | 29.44 | 19.36 | 27.39 | 11.98 | 27.64 | 16.40 | 23.87 | 18.28 |
| Total Omega-6 | 8.63 | 5.67 | 8.33 | 3.64 | 9.08 | 5.39 | 7.92 | 6.08 |
| Total C16 | 39.04 | 25.68 | 37.97 | 16.61 | 40.06 | 23.77 | 35.60 | 27.26 |
| ARA (20:4ω6) | 3.92 | 2.58 | 3.48 | 1.52 | 4.84 | 2.87 | 4.08 | 3.13 |
| EPA (20:5ω3) | 29.25 | 19.24 | 27.22 | 11.90 | 27.25 | 16.17 | 23.47 | 17.97 |
| Saturates/TFA (%) | | 26.4 | | 25.7 | | 24.7 | | 21.6 |
| Monounsaturates/TFA (%) | | 27.4 | | 26.1 | | 28.5 | | 24.6 |
| Polyunsaturates/TFA (%) | | 38.3 | | 36.0 | | 37.1 | | 32.2 |
| Omega-3/TFA (%) | | 29.4 | | 27.4 | | 27.6 | | 23.8 |
| EPA/TFA (%) | | 29.2 | | 27.2 | | 27.2 | | 23.4 |
| EPA/Total Omega3 (%) | | 99.4 | | 99.4 | | 98.6 | | 98.3 |
| EPA/ARA (%) | | 746 | | 781 | | 563 | | 575 |

When the wet or dried Nanno Paste is extracted, cellular membrane disruption is not required to remove the lipids from the biomass. Wet extraction of biomass requires a pure solvent or solvent mixture that is at least partially miscible with water. This includes a broad selection of solvents types, including ethers, ketones, and alcohols. Some example solvents systems are ethanol, isopropyl alcohol, acetone and ethanol, dimethyl ether, dimethyl ether and ethanol. These techniques can be systematically compared using a common feedstock of wet paste (~15-25 wt %). Furthermore, surprisingly, we have found that biomass extraction requires no mechanical cracking (such as a bead mill), thermal pretreatment, or cellular wall digestion via acid or base. The extraction method acts on wet Nanno Paste (~15-25 wt %), does not utilize any mechanical cracking, thermal pretreatment, or alkaline or acid treatment. In varying embodiments, the solvent system is either an ether and alcohol mixture or a ketone and alcohol mixture. Solvent percolation through the biomass paste can be problematic. This can be alleviated by mixing paste with a filtration aid such as Celite® (diatomaceous earth) or Cellu-Flo™ or by vigorous mixing with solvent coupled with crossflow filtration. Example solvent combinations are absolute ethanol, 190 proof (95 v/v %) ethanol (EtOH), denatured 190 proof ethanol, special denatured alcohols (SDA), acetone and ethanol, isopropyl alcohol, acetone and methanol, methyl ethyl ketone (MEK) and methanol, MEK and ethanol, dimethyl ether, dimethyl ether and methanol, dimethyl ether and ethanol. The common characteristic of the solvent mixture is an ability to extract hydrophobic, non-polar lipid components such as triglycerides and hydrophilic, polar lipid components such as phospholipids and glycolipids.

In varying embodiments, the solvent mixture is 50% (v/v) acetone and 50% (v/v) 190 proof ethanol (EtOH). Other example mixtures are pure dimethyl ether (DME), DME mixed with methanol, or solely 190 proof EtOH. EtOH may be non-denatured or one of the Special Denatured Alcohol (SDA) grades (1-1, 1-2, 2B-2, 2B-3, 3A, 3C, 23A, 23H, 29, 30, 35A) proof denatured ethanol, where the major composition of the SDAs is given in Table 5. In varying embodiments, the ethanol is SDA 1-1, 3A, 3C, 23A, or 35A, where the major distinguishing characteristics are availability and price rather than any particular technical advantage for extraction.

TABLE 5

Major Constituents of Special Denatured Alcohols (SDA)

| Special Denature Grade | Ethanol 190 proof % (v/v) | Denaturants |
|---|---|---|
| SDA 1-1/ 190 proof | 96.15 | Methanol- 3.85% (v/v) |
| SDA 1-2/ 190 proof | 95.24 | Methanol- 3.81% (v/v), Methyl Isobutyl Ketone (MIBK) - 0.95% (v/v) |
| SDA 2B-2/ 190 proof | 99.50 | Rubber Solvent- 0.50% (v/v) |
| SDA 2B-3/ 190 proof | 99.50 | Toluene- 0.50% (v/v) |
| SDA 3A | 95.24 | Methanol- 4.78% (v/v) |
| SDA 3C | 95.24 | Isopropanol- 4.76% (v/v) |
| SDA 23A | 92.59 | Acetone- 7.41% (v/v) |
| SDA 23H | 91.32 | Acetone- 7.31% (v/v), MIBK- 1.37% (v/v) |
| SDA 29 | 99.01 | Ethyl acetate- 0.99% (v/v) |
| SDA 30 | 90.90 | Methanol- 9.10% (v/v) |
| SDA 35A | 95.92 | Ethyl acetate- 4.08% (v/v) |

Both S12 and S14 biomass are substantially depleted of lipid by the use of a six stage solvent system. In each stage, two times the mass of acetone/EtOH mixtures is mixed with the biomass to form a biomass, solvent, and extract slurry. The extract solution is separated from the biomass by either filtration or centrifugation, where filtration or, in some embodiments, cross-flow filtration is employed for removing solid from the solution. For nearly complete lipid extraction, a total of six stages must be completed. This method creates crude algae extract (CAE).

A comparison of different extraction techniques on dried biomass is given in Table 6. In all cases, the cellular material was not mechanically disrupted, thermally pretreated or otherwise subject to alkali or acidic digestion. The biomass was S12 algae grown in northern Israel. Wet algae concentrated was pooled from multiple harvests over the summer period, the concentrated wet biomass homogenized, and the resultant biomass solids suspension subjected to spray drying with hot air temperatures of approximately 120° C. The resulting dried algal powder had a moisture content of less than 10 wt % and, thus, represents algal biomass with the majority of extracellular and intracellular water removed.

This dried biomass was extracted in five different ways: FAH by NJFL, 70/30 (v/v %) Hex/MeOH by NJFL, 50/50 (v/v %) acetone and 190 proof denatured alcohol, and DME methods. The first DME method involved pretreatment of spray dried biomass to rewet the algae with a 75/25 (v/v %) mixture of water and methanol (MeOH). The test examined if the biomass could be rehydrated prior to extraction with DME, a solvent that is partially miscible with water in the absence of alcohol or ketone co-solvents (about 6 wt % solubility of water in neat DME). DME is miscible with a 25 wt % concentration of MeOH in water. The "Wet DME" test involved a light water spray of the dried biomass followed by extract of water-saturated neat DME. In this way, the water acts as a co-solvent for DME.

TABLE 6

Extraction of Spray Dried S12, northern Israel

| | | Fat by Acid Hydrolysis | | | 70/30 (v/v %) Hex/MeOH Test | | | 50/50 v/v % acetone/EtOH | |
|---|---|---|---|---|---|---|---|---|---|
| | | NJFL FAH, 1112-0307 | | | NJFL Hex/MeOH, 1112-0307 | | | QLTS-20 | |
| | | Percent Extract from Dry Biomass | | | | | | | |
| | | 13.0 | | | 24.7 | | | 30.4 | |
| Fatty Acid | C#: Dbl. Bond | Norm. FA % | FA in Extract % | FA in Dry Solid % | Norm. FA % | FA in Extract % | FA in Dry Solid % | Norm. FA % | FA in Extract % |
| Caprylic | 8:0 | 0.29 | 0.16 | 0.02 | 0.42 | 0.15 | 0.04 | 0.38 | 0.07 |
| Capric | 10:0 | 0.34 | 0.19 | 0.03 | 0.45 | 0.16 | 0.04 | 0.36 | 0.07 |
| Lauric | 12:0 | 0.98 | 0.55 | 0.07 | 0.59 | 0.21 | 0.05 | 0.70 | 0.14 |
| Myristic | 14:0 | 4.17 | 2.35 | 0.31 | 3.03 | 1.07 | 0.26 | 3.58 | 0.71 |
| Myristoleic | 14:1 | 0.74 | 0.42 | 0.05 | 0.00 | 0.00 | 0.00 | 4.26 | 0.84 |
| Pentadecanoic | 15:0 | 0.31 | 0.17 | 0.02 | 0.39 | 0.14 | 0.03 | 0.22 | 0.04 |
| Palmitic | 16:0 | 14.95 | 8.43 | 1.10 | 12.23 | 4.31 | 1.06 | 13.12 | 2.59 |
| Palmitoleic | 16:1 | 17.67 | 9.96 | 1.29 | 14.93 | 5.26 | 1.30 | 16.51 | 3.26 |
| Hexadecadienoic | 16:2 | 0.42 | 0.24 | 0.03 | 0.38 | 0.13 | 0.03 | 0.34 | 0.07 |
| Hexadecatrienoic | 16:3 | 0.00 | 0.00 | 0.00 | 0.00 | 0.00 | 0.00 | 0.00 | 0.00 |
| Hexadecatetraenoic | 16:4 | 0.00 | 0.00 | 0.00 | 0.28 | 0.10 | 0.02 | 0.00 | 0.00 |
| Heptadecanoic | 17:0 | 0.00 | 0.00 | 0.00 | 0.00 | 0.00 | 0.00 | 0.00 | 0.00 |
| Stearic | 18:0 | 0.47 | 0.27 | 0.03 | 0.59 | 0.21 | 0.05 | 0.25 | 0.05 |
| Oleic | 18:1ω9 | 2.95 | 1.66 | 0.22 | 2.21 | 0.78 | 0.19 | 2.77 | 0.55 |
| Oleic | 18:1ω7 | 1.09 | 0.62 | 0.08 | 0.92 | 0.32 | 0.08 | 0.88 | 0.17 |
| Linoleic | 18:2ω6 | 4.48 | 2.52 | 0.33 | 3.38 | 1.19 | 0.29 | 4.04 | 0.80 |
| Linoleic | 18:2ω4 | 0.09 | 0.05 | 0.01 | 0.00 | 0.00 | 0.00 | 0.00 | 0.00 |
| Gamma-Linolenic | 18:3ω6 | 0.20 | 0.11 | 0.01 | 0.00 | 0.00 | 0.00 | 0.25 | 0.05 |
| Alpha-Linolenic (ALA) | 18:3ω3 | 0.37 | 0.21 | 0.03 | 0.16 | 0.06 | 0.01 | 0.36 | 0.07 |
| Eicosadienoic | 20:2ω6 | 0.00 | 0.00 | 0.00 | 0.00 | 0.00 | 0.00 | 0.00 | 0.00 |
| Eicosatrienoic | 20:3ω6 | 0.00 | 0.00 | 0.00 | 0.00 | 0.00 | 0.00 | 0.13 | 0.02 |
| Arachidonic | 20:4ω6 | 4.50 | 2.54 | 0.33 | 4.12 | 1.45 | 0.36 | 3.97 | 0.78 |
| Eicosapentaenoic (EPA) | 20:5ω3 | 35.64 | 20.09 | 2.61 | 35.51 | 12.52 | 3.09 | 35.62 | 7.03 |
| Other | n/a | 10.32 | 5.82 | 0.76 | 20.40 | 7.19 | 1.78 | 12.27 | 2.42 |
| Total Fatty Acid | | 100.00 | 56.36 | 7.33 | 100.00 | 35.25 | 8.71 | 100.00 | 19.73 |
| Total Omega-3 | | 36.01 | 20.29 | 2.64 | 35.67 | 12.57 | 3.11 | 35.97 | 7.10 |
| Total Omega-6 | | 9.19 | 5.18 | 0.67 | 7.50 | 2.64 | 0.65 | 8.39 | 1.66 |

| | | 50/50 v/v % acetone/EtOH | $H_2O$/MeOH Pretreat, DME Test | | | Wet DME | | |
|---|---|---|---|---|---|---|---|---|
| | | QLTS-20 | QLTS-19 | | | QLTS-18 | | |
| | | Percent Extract from Dry Biomass | | | | | | |
| | | 30.4 | 19.2 | | | 46.0 | | |
| Fatty Acid | C#: Dbl. Bond | FA in Dry Solid % | Norm. FA % | FA in Extract % | FA in Dry Solid % | Norm. FA % | FA in Extract % | FA in Dry Solid % |
| Caprylic | 8:0 | 0.02 | 0.44 | 0.14 | 0.03 | 0.38 | 0.06 | 0.03 |
| Capric | 10:0 | 0.02 | 0.32 | 0.10 | 0.02 | 0.83 | 0.12 | 0.06 |
| Lauric | 12:0 | 0.04 | 0.88 | 0.28 | 0.06 | 0.88 | 0.13 | 0.06 |
| Myristic | 14:0 | 0.21 | 3.06 | 0.96 | 0.20 | 3.52 | 0.52 | 0.26 |
| Myristoleic | 14:1 | 0.26 | 0.08 | 0.02 | 0.00 | 0.00 | 0.00 | 0.00 |
| Pentadecanoic | 15:0 | 0.01 | 0.17 | 0.05 | 0.01 | 0.19 | 0.03 | 0.01 |
| Palmitic | 16:0 | 0.79 | 10.94 | 3.45 | 0.72 | 12.71 | 1.86 | 0.93 |
| Palmitoleic | 16:1 | 0.99 | 14.24 | 4.49 | 0.94 | 15.57 | 2.28 | 1.14 |
| Hexadecadienoic | 16:2 | 0.02 | 0.33 | 0.10 | 0.02 | 0.45 | 0.07 | 0.03 |
| Hexadecatrienoic | 16:3 | 0.00 | 0.00 | 0.00 | 0.00 | 0.00 | 0.00 | 0.00 |
| Hexadecatetraenoic | 16:4 | 0.00 | 0.00 | 0.00 | 0.00 | 0.32 | 0.05 | 0.02 |
| Heptadecanoic | 17:0 | 0.00 | 0.23 | 0.07 | 0.01 | 0.00 | 0.00 | 0.00 |

TABLE 6-continued

| Extraction of Spray Dried S12, northern Israel | | | | | | | | |
|---|---|---|---|---|---|---|---|---|
| Stearic | 18:0 | 0.02 | 0.33 | 0.10 | 0.02 | 0.47 | 0.07 | 0.03 |
| Oleic | 18:1ω9 | 0.17 | 2.03 | 0.64 | 0.13 | 2.46 | 0.36 | 0.18 |
| Oleic | 18:1ω7 | 0.05 | 0.71 | 0.22 | 0.05 | 1.03 | 0.15 | 0.08 |
| Linoleic | 18:2ω6 | 0.24 | 3.36 | 1.06 | 0.22 | 3.89 | 0.57 | 0.28 |
| Linoleic | 18:2ω4 | 0.00 | 0.00 | 0.00 | 0.00 | 0.00 | 0.00 | 0.00 |
| Gamma-Linolenic | 18:3ω6 | 0.02 | 0.24 | 0.08 | 0.02 | 0.00 | 0.00 | 0.00 |
| Alpha-Linolenic (ALA) | 18:3ω3 | 0.02 | 0.68 | 0.21 | 0.04 | 0.41 | 0.06 | 0.03 |
| Eicosadienoic | 20:2ω6 | 0.00 | 0.00 | 0.00 | 0.00 | 0.00 | 0.00 | 0.00 |
| Eicosatrienoic | 20:3ω6 | 0.01 | 0.14 | 0.04 | 0.01 | 0.00 | 0.00 | 0.00 |
| Arachidonic | 20:4ω6 | 0.24 | 4.36 | 1.37 | 0.29 | 4.14 | 0.61 | 0.30 |
| Eicosapentaenoic (EPA) | 20:5ω3 | 2.14 | 37.14 | 11.70 | 2.44 | 35.39 | 5.18 | 2.59 |
| Other | n/a | 0.74 | 20.34 | 6.41 | 1.34 | 17.36 | 2.54 | 1.27 |
| Total Fatty Acid | | 6.00 | 100.00 | 31.50 | 6.57 | 100.00 | 14.65 | 7.32 |
| Total Omega-3 | | 2.16 | 37.82 | 11.91 | 2.49 | 35.80 | 5.24 | 2.62 |
| Total Omega-6 | | 0.50 | 8.10 | 2.55 | 0.53 | 8.03 | 1.18 | 0.59 |

As shown in Table 6, the Hex/MeOH results in the greatest amount both of TFA and Omega 3 of all these methods, as shown by the 8.71% and 3.11% of the biomass respectively. For the Hex/MeOH sample, the EPA/Total EPA ratio was greater than 99.5% reflective of a very pure S12 sample. Conversely, the FAH method makes the extract most highly concentrated in fat, at over 56% versus 35.2, 19.7, 31.5, and 14.6 for the other techniques. Hex/MeOH results in more recovery of fat and EPA from the dried biomass at the expense of extracting other, non-lipid constituents that result in more dilute fatty acid mixture. The two DME methods yield about the same amount of fat at 6.57 and 7.32 wt % of biomass and similar amounts of EPA at 2.44 and 2.59 wt % of biomass. The $H_2O$/MeOH version of DME results in a more highly concentrated extract. This method has a slightly lower yield of EPA from the biomass but yields an extract that is more than twice as concentrated in fatty acid, Omega-3, and EPA. The acetone/EtOH method results in lower recovery of fats, Omega3 and EPA versus the other methods. From the standpoint of dried biomass, it is the inferior solvent system and, thus, one could conclude that it is not a suitable method. This would fail to account for the behavior of this solvent system, though, in the presence of a greater quantity of intracellular and extracellular water.

A good leading indication of the superior benefit of wet extraction over dry extraction can be observed in Table 7. The biomass was nominally of the same strain and lot, taken from S12 harvests grown in northern Israel. The spray dried material was collected over many days while wet slurry reflected a single day's harvest. The wet slurry had a solids content of 11.9 wt % or a 98.1 wt % moisture content. The spray dried was 8 wt % moisture. To put this in perspective, a 100 g of spray dried material was equivalent to 773 g of slurry. This implies that wet extraction, while perhaps more effective in fat and Omega 3 recovery, requires the handling of a significantly higher mass and volume of biomass. In the case of wet extraction, the TFA, Omega 3, and EPA recovery on a biomass basis were 18.46, 6.45, and 6.38 wt %, respectively. The same values for the spray dried S12 biomass grown at the same time were 7.32, 2.62, and 2.59 wt %. Wet extraction yielded 250% times the TFA and EPA versus spray dried material. While day-to-day variance could perhaps account for a 20 to 50% variance in the TFA and EPA extracted, it was at first implausible to us that the difference would be this great. Without being bound by any particular theory, the presence of intracellular water enables EPA and lipids to be extracted that would otherwise be bound with the dried biomass and, thus, not removed in the dry state. Wet extraction, also leads to improved concentration of fatty acid and EPA in the CAE, with the 30.8 wt % TFA and 10.6 wt % EPA in the CAE versus 14.6 wt % TFA and 5.18 wt % EPA in the CAE of the spray dried material.

A comparison of different extraction techniques on dried S14 biomass is given in Table 8. In all cases, the cellular material was not mechanically disrupted, thermally pretreated or otherwise subject to alkali or acidic digestion. The S14 biomass was grown in northern Israel and subsequently spray dried. All tests were taken from the same lot of dried biomass. As with the S12, the spray drying was completed with a hot air temperature of approximately 120° C. The resulting dried algal powder had a moisture content of less than 15 wt %, representing nearly complete removal of extracellular and intracellular water. This dried biomass was extracted in five different ways: 70/30 (v/v %) Hex/MeOH by NJFL, 67/33 (w/w %) Hex/MeOH, acetone, 190 proof (95/5 (v/v %) denatured EtOH, and dry DME. In the case of the 67/33 Hex/MeOH, acetone and 190 proof EtOH, the extraction was performed at room temperature with six contact stages, where each stage used two times by weight solvent per unit biomass. Dry DME did not add any water back to the system either by wetting the biomass or by saturating the DME with water. The 70/30 v/v % Hex/MeOH by NJFL used this solvent solution at elevated temperature just below the boiling point of the mixture (approximately 60° C.).

TABLE 7

DME Extraction of Dry versus Wet S12

| Fatty Acid | C#: Dbl. Bond | Spray Dried S12- Wet DME (Test) QLTS-18, Percent Extract from Dry Biomass 46.0 Norm. FA % | FA in Extract % | FA in Dry Solid % | Wet S12 Slurry- Dry DME (Test) QLTS-17, Percent Extract from Dry Biomass 60.0 Norm. FA % | FA in Extract % | FA in Dry Solid % |
|---|---|---|---|---|---|---|---|
| Caprylic | 8:0 | 0.38 | 0.06 | 0.03 | 0.38 | 0.12 | 0.07 |
| Capric | 10:0 | 0.83 | 0.12 | 0.06 | 1.29 | 0.40 | 0.24 |
| Lauric | 12:0 | 0.88 | 0.13 | 0.06 | 0.41 | 0.13 | 0.08 |
| Myristic | 14:0 | 3.52 | 0.52 | 0.26 | 3.18 | 0.98 | 0.59 |
| Myristoleic | 14:1 | 0.00 | 0.00 | 0.00 | 0.00 | 0.00 | 0.00 |
| Pentadecanoic | 15:0 | 0.19 | 0.03 | 0.01 | 0.17 | 0.05 | 0.03 |
| Palmitic | 16:0 | 12.71 | 1.86 | 0.93 | 10.61 | 3.26 | 1.96 |
| Palmitoleic | 16:1 | 15.57 | 2.28 | 1.14 | 12.28 | 3.78 | 2.27 |
| Hexadecadienoic | 16:2 | 0.45 | 0.07 | 0.03 | 0.65 | 0.20 | 0.12 |
| Hexadecatrienoic | 16:3 | 0.00 | 0.00 | 0.00 | 0.00 | 0.00 | 0.00 |
| Hexadecatetraenoic | 16:4 | 0.32 | 0.05 | 0.02 | 0.00 | 0.00 | 0.00 |
| Heptadecanoic | 17:0 | 0.00 | 0.00 | 0.00 | 0.00 | 0.00 | 0.00 |
| Stearic | 18:0 | 0.47 | 0.07 | 0.03 | 0.83 | 0.25 | 0.15 |
| Oleic | 18:1ω9 | 2.46 | 0.36 | 0.18 | 3.05 | 0.94 | 0.56 |
| Oleic | 18:1ω7 | 1.03 | 0.15 | 0.08 | 0.97 | 0.30 | 0.18 |
| Linoleic | 18:2ω6 | 3.89 | 0.57 | 0.28 | 3.10 | 0.95 | 0.57 |
| Linoleic | 18:2ω4 | 0.00 | 0.00 | 0.00 | 0.00 | 0.00 | 0.00 |
| Gamma-Linolenic | 18:3ω6 | 0.00 | 0.00 | 0.00 | 0.16 | 0.05 | 0.03 |
| Alpha-Linolenic (ALA) | 18:3ω3 | 0.41 | 0.06 | 0.03 | 0.37 | 0.11 | 0.07 |
| Eicosadienoic | 20:2ω6 | 0.00 | 0.00 | 0.00 | 0.00 | 0.00 | 0.00 |
| Eicosatrienoic | 20:3ω6 | 0.00 | 0.00 | 0.00 | 0.00 | 0.00 | 0.00 |
| Arachidonic | 20:4ω6 | 4.14 | 0.61 | 0.30 | 4.17 | 1.28 | 0.77 |
| Eicosapentaenoic (EPA) | 20:5ω3 | 35.39 | 5.18 | 2.59 | 34.55 | 10.63 | 6.38 |
| Other | n/a | 17.36 | 2.54 | 1.27 | 23.83 | 7.33 | 4.40 |
| Total Fatty Acid | | 100.00 | 14.65 | 7.32 | 100.00 | 30.77 | 18.46 |
| Total Omega-3 | | 35.80 | 5.24 | 2.62 | 34.91 | 10.74 | 6.45 |
| Total Omega-6 | | 8.03 | 1.18 | 0.59 | 7.43 | 2.29 | 1.37 |

TABLE 8

Spray Dried S14 Extracted by Various Methods

| Fatty Acid | C#: Dbl. Bond | 70/30 (v/v %) Hex/MeOH (Test) NJFL Hex/MeOH, 1112-2005, Percent Extract from Dry Biomass 34.7 Norm. FA % | FA in Extract % | FA in Dry Solid % | 67/33 w/w Hex/MeOH (Test) QLTS-10, Percent Extract from Dry Biomass 11.0 Norm. FA % | FA in Extract % | FA in Dry Solid % | Acetone (Test) QLTS-11, Percent Extract from Dry Biomass 2.7 Norm. FA % | FA in Extract % |
|---|---|---|---|---|---|---|---|---|---|
| Caprylic | 8:0 | 0.19 | 0.08 | 0.027 | 0.33 | 0.10 | 0.011 | 0.57 | 0.25 |
| Capric | 10:0 | 0.12 | 0.05 | 0.018 | 0.25 | 0.08 | 0.009 | 0.31 | 0.14 |
| Lauric | 12:0 | 0.39 | 0.16 | 0.056 | 0.53 | 0.17 | 0.018 | 0.76 | 0.34 |
| Myristic | 14:0 | 4.13 | 1.73 | 0.599 | 4.56 | 1.43 | 0.158 | 4.17 | 1.86 |
| Myristoleic | 14:1 | 0.08 | 0.03 | 0.011 | 0.57 | 0.18 | 0.020 | 0.00 | 0.00 |
| Pentadecanoic | 15:0 | 0.25 | 0.10 | 0.036 | 0.34 | 0.11 | 0.012 | 0.19 | 0.08 |
| Palmitic | 16:0 | 22.32 | 9.33 | 3.236 | 21.67 | 6.79 | 0.749 | 14.44 | 6.45 |
| Palmitoleic | 16:1 | 24.72 | 10.34 | 3.585 | 19.53 | 6.12 | 0.675 | 22.77 | 10.17 |
| Hexadecadienoic | 16:2 | 0.22 | 0.09 | 0.032 | 0.00 | 0.00 | 0.000 | 0.00 | 0.00 |
| Hexadecatrienoic | 16:3 | 0.11 | 0.05 | 0.016 | 0.11 | 0.03 | 0.004 | 0.00 | 0.00 |
| Heptadecanoic | 17:0 | 0.34 | 0.14 | 0.050 | 0.31 | 0.10 | 0.011 | 0.19 | 0.08 |
| Stearic | 18:0 | 0.79 | 0.33 | 0.115 | 0.84 | 0.26 | 0.029 | 0.57 | 0.25 |
| Oleic | 18:1ω9 | 3.12 | 1.30 | 0.452 | 5.56 | 1.74 | 0.192 | 5.55 | 2.48 |
| Oleic | 18:1ω7 | 0.42 | 0.18 | 0.061 | 1.60 | 0.50 | 0.055 | 1.16 | 0.52 |
| Linoleic | 18:2ω6 | 2.93 | 1.23 | 0.425 | 4.07 | 1.27 | 0.141 | 4.36 | 1.95 |

TABLE 8-continued

Spray Dried S14 Extracted by Various Methods

| | | | | | | | | | |
|---|---|---|---|---|---|---|---|---|---|
| Linoleic | 18:2ω4 | 0.00 | 0.00 | 0.000 | 0.00 | 0.00 | 0.000 | 0.00 | 0.00 |
| Gamma-Linolenic | 18:3ω6 | 0.95 | 0.40 | 0.137 | 0.25 | 0.08 | 0.009 | 0.00 | 0.00 |
| Alpha-Linolenic (ALA) | 18:3ω3 | 0.88 | 0.37 | 0.128 | 0.57 | 0.18 | 0.020 | 0.43 | 0.19 |
| Eicosadienoic | 20:2ω6 | 0.00 | 0.00 | 0.000 | 0.00 | 0.00 | 0.000 | 0.00 | 0.00 |
| Eicosatrienoic | 20:3ω6 | 0.33 | 0.14 | 0.047 | 0.00 | 0.00 | 0.000 | 0.00 | 0.00 |
| Arachidonic | 20:4ω6 | 6.05 | 2.53 | 0.878 | 3.23 | 1.01 | 0.112 | 4.15 | 1.85 |
| Eicosapentaenoic (EPA) | 20:5ω3 | 21.33 | 8.92 | 3.092 | 17.32 | 5.43 | 0.599 | 23.41 | 10.45 |
| Other | n/a | 10.34 | 4.32 | 1.499 | 18.38 | 5.76 | 0.635 | 16.77 | 7.49 |
| Total Fatty Acid | | 100.00 | 41.81 | 14.50 | 100.00 | 31.33 | 3.46 | 99.81 | 44.56 |
| Total Omega-3 | | 22.21 | 9.29 | 3.22 | 17.90 | 5.61 | 0.62 | 23.84 | 10.64 |
| Total Omega-6 | | 10.26 | 4.29 | 1.49 | 7.54 | 2.36 | 0.26 | 8.52 | 3.80 |

| | | Acetone | 95/5 (v/v %) EtOH Test | | | DME | | |
|---|---|---|---|---|---|---|---|---|
| | | QLTS-11 | QLTS-12 Percent Extract from Dry Biomass | | | QLTS-8 | | |
| | | 2.7 | 23.2 | | | 10.5 | | |
| Fatty Acid | C#: Dbl. Bond | FA in Dry Solid % | Norm. FA % | FA in Extract % | FA in Dry Solid % | Norm. FA % | FA in Extract % | FA in Dry Solid % |
| Caprylic | 8:0 | 0.007 | 0.30 | 0.05 | 0.013 | 0.45 | 0.22 | 0.023 |
| Capric | 10:0 | 0.004 | 0.18 | 0.03 | 0.008 | 0.89 | 0.44 | 0.046 |
| Lauric | 12:0 | 0.009 | 0.60 | 0.11 | 0.025 | 0.68 | 0.33 | 0.035 |
| Myristic | 14:0 | 0.050 | 4.79 | 0.87 | 0.201 | 5.04 | 2.46 | 0.258 |
| Myristoleic | 14:1 | 0.000 | 0.24 | 0.04 | 0.010 | 0.08 | 0.04 | 0.004 |
| Pentadecanoic | 15:0 | 0.002 | 0.30 | 0.05 | 0.013 | 0.29 | 0.14 | 0.015 |
| Palmitic | 16:0 | 0.174 | 22.42 | 4.05 | 0.942 | 20.84 | 10.19 | 1.065 |
| Palmitoleic | 16:1 | 0.274 | 21.03 | 3.80 | 0.883 | 18.40 | 8.99 | 0.940 |
| Hexadecadienoic | 16:2 | 0.000 | 0.14 | 0.03 | 0.006 | 0.28 | 0.14 | 0.014 |
| Hexadecatrienoic | 16:3 | 0.000 | 0.00 | 0.00 | 0.000 | 0.14 | 0.07 | 0.007 |
| Heptadecanoic | 17:0 | 0.002 | 0.00 | 0.00 | 0.000 | 0.31 | 0.15 | 0.016 |
| Stearic | 18:0 | 0.007 | 0.48 | 0.09 | 0.020 | 1.10 | 0.54 | 0.056 |
| Oleic | 18:1ω9 | 0.067 | 5.50 | 0.99 | 0.231 | 4.83 | 2.36 | 0.247 |
| Oleic | 18:1ω7 | 0.014 | 1.57 | 0.28 | 0.066 | 1.24 | 0.61 | 0.063 |
| Linoleic | 18:2ω6 | 0.053 | 4.77 | 0.86 | 0.200 | 3.18 | 1.56 | 0.163 |
| Linoleic | 18:2ω4 | 0.000 | 0.00 | 0.00 | 0.000 | 0.00 | 0.00 | 0.000 |
| Gamma-Linolenic | 18:3ω6 | 0.000 | 0.24 | 0.04 | 0.010 | 0.24 | 0.12 | 0.012 |
| Alpha-Linolenic (ALA) | 18:3ω3 | 0.005 | 0.40 | 0.07 | 0.017 | 0.36 | 0.18 | 0.019 |
| Eicosadienoic | 20:2ω6 | 0.000 | 0.00 | 0.00 | 0.000 | 0.00 | 0.00 | 0.000 |
| Eicosatrienoic | 20:3ω6 | 0.000 | 0.00 | 0.00 | 0.000 | 0.00 | 0.00 | 0.000 |
| Arachidonic | 20:4ω6 | 0.050 | 3.42 | 0.62 | 0.143 | 3.27 | 1.60 | 0.167 |
| Eicosapentaenoic (EPA) | 20:5ω3 | 0.282 | 19.78 | 3.58 | 0.831 | 19.08 | 9.33 | 0.975 |
| Other | n/a | 0.202 | 13.86 | 2.51 | 0.582 | 19.29 | 9.43 | 0.986 |
| Total Fatty Acid | | 1.20 | 100.00 | 18.07 | 4.20 | 100.00 | 48.89 | 5.11 |
| Total Omega-3 | | 0.29 | 20.18 | 3.65 | 0.85 | 19.44 | 9.51 | 0.99 |
| Total Omega-6 | | 0.10 | 8.42 | 1.52 | 0.35 | 6.69 | 3.27 | 0.34 |

The data shows that warm Hex/MeOH is more effective at extracting fatty acids and Omega 3 from the biomass than any of the room temperature extraction techniques. Dry DME is next most effective extraction method (5.11 wt % TFA versus 14.5 wt % TFA for 70/30 Hex/MeOH). Drying and room temperature extraction significantly inhibits the extraction of fatty acids.

With respect to the room temperature DME extraction, there was a possibility that the material could be either rehydrated or that the presence of water could assist in the extraction, perhaps as acting as a co-solvent with the DME. Two additional variants on DME were, thus, executed. This used the same biomass lot as in Table 8. This data is presented in Table 9. The "Wet DME" method involved a light application of water to the spray dried biomass. This amounted to the addition of less than 10% by weight of water to the dried biomass. The intent was to rehydrate the surface of the dried algae cells. This material was allowed to sit for an hour before processing. During processing, the DME was passed through a water bath prior to making contact with the biomass. This saturated the DME with water, as neat DME at room temperature has approximately a 6 wt % solubility for water. The "$H_2O$/MeOH-DME" method involved saturating the spray dried S14 with a 75/25 w/w % mixture of $H_2O$/MeOH. The biomass and liquid was allowed to soak overnight. This approach was intended to rehydrate the material with a mixture that enable efficient DME extraction. 75/25 w/w % $H_2O$/MeOH is miscible with DME and, thus, is enabling for a much smaller amount of DME to extract this water mixture and the lipids. The data in table 9 show that Wet DME may have a slight improvement over Dry DME. The extraction yielded 6.96 wt % TFA and 1.27 wt % EPA from the biomass with Wet DME versus 5.11 wt % TFA and 0.975 wt % EPA for Dry DME. This was inferior to 70/30 Hex/MeOH done at Soxhlet like conditions.

TABLE 9

| DME Extraction Variants with Spray Dried S14 | | | | | | | | | | | | | |
|---|---|---|---|---|---|---|---|---|---|---|---|---|---|
| | | Test | | | | | | | | | | | |
| | | 70/30 (v/v %) Hex/MeOH | | | Dry DME | | | Wet DME | | | $H_2O$/MeOH- Dry DME | | |
| | | NJFL Hex/MeOH, 1112-2005 | | | QLTS-8 | | | QLTS-13 | | | QLTS-14 | | |
| | | Percent Extract from Dry Biomass | | | | | | | | | | | |
| | | 34.7 | | | 11.0 | | | 40.5 | | | 15.1 | | |
| Fatty Acid | C#: Dbl. Bond | Norm FA % | FA in Extract % | FA in Dry Solid % | Norm FA % | FA in Extract % | FA in Dry Solid % | Norm FA % | FA in Extract % | FA in Dry Solid % | Norm FA % | FA in Extract % | FA in Dry Solid % |
| Caprylic | 8:0 | 0.19 | 0.08 | 0.027 | 0.45 | 0.22 | 0.023 | 0.34 | 0.06 | 0.02 | 0.31 | 0.10 | 0.015 |
| Capric | 10:0 | 0.12 | 0.05 | 0.018 | 0.89 | 0.44 | 0.046 | 1.65 | 0.28 | 0.11 | 0.31 | 0.10 | 0.015 |
| Lauric | 12:0 | 0.39 | 0.16 | 0.056 | 0.68 | 0.33 | 0.035 | 0.70 | 0.12 | 0.05 | 0.53 | 0.17 | 0.025 |
| Myristic | 14:0 | 4.13 | 1.73 | 0.599 | 5.04 | 2.46 | 0.258 | 4.47 | 0.77 | 0.31 | 4.79 | 1.50 | 0.227 |
| Myristoleic | 14:1 | 0.08 | 0.03 | 0.011 | 0.08 | 0.04 | 0.004 | 0.00 | 0.00 | 0.00 | 0.14 | 0.04 | 0.007 |
| Pentadecanoic | 15:0 | 0.25 | 0.10 | 0.036 | 0.29 | 0.14 | 0.015 | 0.34 | 0.06 | 0.02 | 0.38 | 0.12 | 0.018 |
| Palmitic | 16:0 | 22.32 | 9.33 | 3.236 | 20.84 | 10.19 | 1.065 | 21.76 | 3.75 | 1.52 | 22.81 | 7.13 | 1.080 |
| Palmitoleic | 16:1 | 24.72 | 10.34 | 3.585 | 18.40 | 8.99 | 0.940 | 18.60 | 3.20 | 1.30 | 20.12 | 6.29 | 0.952 |
| Hexadecadienoic | 16:2 | 0.22 | 0.09 | 0.032 | 0.28 | 0.14 | 0.014 | 0.79 | 0.14 | 0.06 | 0.00 | 0.00 | 0.000 |
| Hexadecatrienoic | 16:3 | 0.11 | 0.05 | 0.016 | 0.14 | 0.07 | 0.007 | 0.00 | 0.00 | 0.00 | 0.00 | 0.00 | 0.000 |
| Heptadecanoic | 17:0 | 0.34 | 0.14 | 0.050 | 0.31 | 0.15 | 0.016 | 0.44 | 0.07 | 0.03 | 0.30 | 0.09 | 0.014 |
| Stearic | 18:0 | 0.79 | 0.33 | 0.115 | 1.10 | 0.54 | 0.056 | 1.19 | 0.21 | 0.08 | 0.72 | 0.22 | 0.034 |
| Oleic | 18:1ω9 | 3.12 | 1.30 | 0.452 | 4.83 | 2.36 | 0.247 | 4.96 | 0.85 | 0.35 | 5.29 | 1.65 | 0.250 |
| Oleic | 18:1ω7 | 0.42 | 0.18 | 0.061 | 1.24 | 0.61 | 0.063 | 1.44 | 0.25 | 0.10 | 1.20 | 0.38 | 0.057 |
| Linoleic | 18:2ω6 | 2.93 | 1.23 | 0.425 | 3.18 | 1.56 | 0.163 | 3.48 | 0.60 | 0.24 | 4.38 | 1.37 | 0.207 |
| Linoleic | 18:2ω4 | 0.00 | 0.00 | 0.000 | 0.00 | 0.00 | 0.000 | 0.00 | 0.00 | 0.00 | 0.00 | 0.00 | 0.000 |
| Gamma-Linolenic | 18:3ω6 | 0.95 | 0.40 | 0.137 | 0.24 | 0.12 | 0.012 | 0.25 | 0.04 | 0.02 | 0.20 | 0.06 | 0.010 |
| Alpha-Linolenic (ALA) | 18:3ω3 | 0.88 | 0.37 | 0.128 | 0.36 | 0.18 | 0.019 | 0.53 | 0.09 | 0.04 | 0.42 | 0.13 | 0.020 |
| Eicosadienoic | 20:2ω6 | 0.00 | 0.00 | 0.000 | 0.00 | 0.00 | 0.000 | 0.00 | 0.00 | 0.00 | 0.00 | 0.00 | 0.000 |
| Eicosatrienoic | 20:3ω6 | 0.33 | 0.14 | 0.047 | 0.00 | 0.00 | 0.000 | 0.00 | 0.00 | 0.00 | 0.00 | 0.00 | 0.000 |
| Arachidonic | 20:4ω6 | 6.05 | 2.53 | 0.878 | 3.27 | 1.60 | 0.167 | 3.16 | 0.54 | 0.22 | 3.16 | 0.99 | 0.150 |
| Eicosapentaenoic (EPA) | 20:5ω3 | 21.33 | 8.92 | 3.092 | 19.08 | 9.33 | 0.975 | 18.24 | 3.14 | 1.27 | 19.01 | 5.94 | 0.900 |
| Other | n/a | 10.34 | 4.32 | 1.499 | 19.29 | 9.43 | 0.986 | 17.48 | 3.01 | 1.22 | 15.93 | 4.98 | 0.754 |
| Total Fatty Acid | | 100.00 | 41.81 | 14.50 | 100.00 | 48.89 | 5.11 | 99.81 | 17.18 | 6.96 | 100.00 | 31.26 | 4.73 |
| Total Omega-3 | | 22.21 | 9.29 | 3.22 | 19.44 | 9.51 | 0.99 | 18.77 | 3.23 | 1.31 | 19.43 | 6.07 | 0.92 |
| Total Omega-6 | | 10.26 | 4.29 | 1.49 | 6.69 | 3.27 | 0.34 | 6.89 | 1.19 | 0.48 | 7.74 | 2.42 | 0.37 |

Table 10 compares drying technique with spray dried S14 versus freeze dried S14. Biomass was extracted with Dry DME with the method associated with the data in Tables 8 and 9. The biomass was harvested in northern Israel. The biomass was taken from two different harvest days; however, the harvest is reflective of normal culture during this season of the year. The freeze dried biomass had an exceptionally low moisture content of 2.1 wt %. The TFA on a biomass basis was 4.73 wt % for spray dried versus 3.22 wt % for freeze dried. The lower extraction yield could be a result of the exceptionally low moisture content. For purposes of maximizing the recovery of EPA from the biomass, freeze dried material appears to be at a disadvantage to spray drying.

Table 11 contains the most direct comparison of S14 extraction in a dry versus wet state. The S14 was grown in New Mexico and harvested on a single day. The paste was 30.8 wt % solid. The wet biomass was combined with diatomaceous earth (DE) in a 1:1 w:w ratio prior to being loaded into the DME extraction. The dry biomass was created by room temperature freeze drying. The wet paste was subject to a vacuum of 50 mbar for 48 hour period. This results in an 89.2 wt % solid. This material, too, was combined with DE in 1:1 w:w prior to extraction. In both cases, dry DME was used to extract the material. As shown in Table 11, the wet paste yielded 16.8 wt % TFA and 3.32 wt % EPA from the biomass versus 6.12 wt % TFA and 1.10 wt % EPA with dried biomass. The same biomass yielded more than 2.5 times the lipid and over 3 times the EPA in the wet state versus the dry state. The CAE was also more highly concentrated from the wet paste versus the dried biomass as reflected in the TFA of 50 wt % and 38 wt % and the EPA content of 9.87 wt % and 6.90 wt %. Thus, there is a dramatic advantage to extracting biomass in the wet state versus the dry state. Without being bound by a particular theory, presence of intracellular and extracellular water is enabling for maintaining the cell membrane porosity to the DME solvent, better enabling lipid extraction.

On the basis of data shown in Table 11 for S14 and in Table 7 for S12, we have surprisingly found that the extract from wet Nanno Paste leads to between 1.5 and 3.5 times more fatty acid recovery from the biomass versus the extraction of the same biomass after drying. In spite of no particular effort to disrupt the cell membrane via mechanical, thermal, or pH disruption, the wet paste has a higher extraction yield than the same biomass after drying.

TABLE 10

DME Extraction Comparing Spray Dried S14 and Freeze Dried S14

| | | Test | | | | | |
|---|---|---|---|---|---|---|---|
| | | Dry DME- Spray Dried S14 | | | Dry DME- Freeze Dried S14 | | |
| | | Percent Extract from Dry Biomass | | | | | |
| | | QLTS-8 | | | QLTS-9 | | |
| | | 11.0 | | | 7.3 | | |
| Fatty Acid | C#: Dbl. Bond | Norm. FA % | FA in Extract % | FA in Dry Solid % | Norm. FA % | FA in Extract % | FA in Dry Solid % |
| Caprylic | 8:0 | 0.45 | 0.22 | 0.023 | 0.47 | 0.20 | 0.015 |
| Capric | 10:0 | 0.89 | 0.44 | 0.046 | 1.11 | 0.49 | 0.036 |
| Lauric | 12:0 | 0.68 | 0.33 | 0.035 | 0.52 | 0.23 | 0.017 |
| Myristic | 14:0 | 5.04 | 2.46 | 0.258 | 3.95 | 1.74 | 0.127 |
| Myristoleic | 14:1 | 0.08 | 0.04 | 0.004 | 0.07 | 0.03 | 0.002 |
| Pentadecanoic | 15:0 | 0.29 | 0.14 | 0.015 | 0.20 | 0.09 | 0.006 |
| Palmitic | 16:0 | 20.84 | 10.19 | 1.065 | 15.73 | 6.92 | 0.506 |
| Palmitoleic | 16:1 | 18.40 | 8.99 | 0.940 | 15.05 | 6.62 | 0.485 |
| Hexadecadienoic | 16:2 | 0.28 | 0.14 | 0.014 | 0.42 | 0.19 | 0.014 |
| Hexadecatrienoic | 16:3 | 0.14 | 0.07 | 0.007 | 0.00 | 0.00 | 0.000 |
| Heptadecanoic | 17:0 | 0.31 | 0.15 | 0.016 | 0.31 | 0.14 | 0.010 |
| Stearic | 18:0 | 1.10 | 0.54 | 0.056 | 0.68 | 0.30 | 0.022 |
| Oleic | 18:1ω9 | 4.83 | 2.36 | 0.247 | 2.92 | 1.28 | 0.094 |
| Oleic | 18:1ω7 | 1.24 | 0.61 | 0.063 | 0.85 | 0.37 | 0.027 |
| Linoleic | 18:2ω6 | 3.18 | 1.56 | 0.163 | 2.48 | 1.09 | 0.080 |
| Linoleic | 18:2ω4 | 0.00 | 0.00 | 0.000 | 0.00 | 0.00 | 0.000 |
| Gamma-Linolenic | 18:3ω6 | 0.24 | 0.12 | 0.012 | 0.28 | 0.12 | 0.009 |
| Alpha-Linolenic (ALA) | 18:3ω3 | 0.36 | 0.18 | 0.019 | 1.27 | 0.56 | 0.041 |
| Eicosadienoic | 20:2ω6 | 0.00 | 0.00 | 0.000 | 0.08 | 0.04 | 0.003 |
| Eicosatrienoic | 20:3ω6 | 0.00 | 0.00 | 0.000 | 0.25 | 0.11 | 0.008 |
| Arachidonic | 20:4ω6 | 3.27 | 1.60 | 0.167 | 4.46 | 1.96 | 0.144 |
| Eicosapentaenoic (EPA) | 20:5ω3 | 19.08 | 9.33 | 0.975 | 25.77 | 11.34 | 0.830 |
| Other | n/a | 19.29 | 9.43 | 0.986 | 23.12 | 10.17 | 0.745 |
| Total Fatty Acid | | 100.00 | 48.89 | 5.11 | 100.00 | 43.99 | 3.22 |
| Total Omega-3 | | 19.44 | 9.51 | 0.99 | 27.04 | 11.90 | 0.87 |
| Total Omega-6 | | 6.69 | 3.27 | 0.34 | 7.56 | 3.33 | 0.24 |

TABLE 11

DME Extraction Comparing Dry versus Wet S14

| | | Test | | | | | |
|---|---|---|---|---|---|---|---|
| | | Dry S14- Dry DME | | | S14 Paste- Dry DME | | |
| | | Percent Extract from Dry Biomass | | | | | |
| | | QLTS-1 | | | QLTS-2 | | |
| | | 16.0 | | | 33.7 | | |
| Fatty Acid | C#: Dbl. Bond | Norm. FA % | FA in Extract % | FA in Dry Solid % | Norm. FA % | FA in Extract % | FA in Dry Solid % |
| Caprylic | 8:0 | 0.17 | 0.07 | 0.01 | 0.15 | 0.07 | 0.02 |
| Capric | 10:0 | 1.17 | 0.45 | 0.07 | 1.52 | 0.76 | 0.26 |
| Lauric | 12:0 | 0.45 | 0.17 | 0.03 | 0.41 | 0.21 | 0.07 |
| Myristic | 14:0 | 4.83 | 1.85 | 0.30 | 4.54 | 2.27 | 0.76 |
| Myristoleic | 14:1 | 0.13 | 0.05 | 0.01 | 0.09 | 0.05 | 0.02 |
| Pentadecanoic | 15:0 | 0.42 | 0.16 | 0.03 | 0.36 | 0.18 | 0.06 |
| Palmitic | 16:0 | 22.52 | 8.62 | 1.38 | 23.48 | 11.75 | 3.95 |
| Palmitoleic | 16:1 | 24.37 | 9.33 | 1.49 | 24.32 | 12.17 | 4.09 |
| Hexadecadienoic | 16:2 | 0.45 | 0.17 | 0.03 | 0.25 | 0.13 | 0.04 |
| Hexadecatrienoic | 16:3 | 0.00 | 0.00 | 0.00 | 0.00 | 0.00 | 0.00 |
| Heptadecanoic | 17:0 | 0.41 | 0.16 | 0.02 | 0.31 | 0.15 | 0.05 |
| Stearic | 18:0 | 1.20 | 0.46 | 0.07 | 1.04 | 0.52 | 0.18 |
| Oleic | 18:1ω9 | 2.63 | 1.01 | 0.16 | 2.99 | 1.50 | 0.50 |
| Oleic | 18:1ω7 | 0.44 | 0.17 | 0.03 | 0.45 | 0.23 | 0.08 |
| Linoleic | 18:2ω6 | 1.99 | 0.76 | 0.12 | 2.40 | 1.20 | 0.40 |
| Linoleic | 18:2ω4 | 0.00 | 0.00 | 0.00 | 0.00 | 0.00 | 0.00 |

TABLE 11-continued

DME Extraction Comparing Dry versus Wet S14

| Fatty Acid | C#: Dbl. Bond | Dry S14- Dry DME Test QLTS-1 Percent Extract from Dry Biomass 16.0 Norm. FA % | FA in Extract % | FA in Dry Solid % | S14 Paste- Dry DME QLTS-2 33.7 Norm. FA % | FA in Extract % | FA in Dry Solid % |
|---|---|---|---|---|---|---|---|
| Gamma-Linolenic | 18:3ω6 | 0.27 | 0.10 | 0.02 | 0.48 | 0.24 | 0.08 |
| Alpha-Linolenic (ALA) | 18:3ω3 | 0.97 | 0.37 | 0.06 | 0.84 | 0.42 | 0.14 |
| Eicosadienoic | 20:2ω6 | 0.00 | 0.00 | 0.00 | 0.00 | 0.00 | 0.00 |
| Eicosatrienoic | 20:3ω6 | 0.28 | 0.11 | 0.02 | 0.31 | 0.15 | 0.05 |
| Arachidonic | 20:4ω6 | 4.50 | 1.72 | 0.28 | 4.79 | 2.40 | 0.81 |
| Eicosapentaenoic (EPA) | 20:5ω3 | 18.02 | 6.90 | 1.10 | 19.73 | 9.87 | 3.32 |
| Other | n/a | 14.77 | 5.65 | 0.90 | 11.54 | 5.78 | 1.94 |
| Total Fatty Acid | | 100.00 | 38.27 | 6.12 | 100.00 | 50.04 | 16.84 |
| Total Omega-3 | | 18.99 | 7.27 | 1.16 | 20.57 | 10.29 | 3.46 |
| Total Omega-6 | | 7.04 | 2.69 | 0.43 | 7.98 | 3.99 | 1.34 |

The same S14 biomass lot employed to generate the data in Table 11 was extracted by a number of different solvent systems in the wet state. As shown in Table 12, this included DME, 50/50 w/w % acetone/EtOH, 90/10 w/w % Acetone/MeOH, and 95/5 v/v % (190 proof) denatured EtOH. The TFA yield based on biomass for the different techniques was 16.84, 13.96, 8.95, and 16.12 wt %. We have observed variance in extraction performance on the order of 15%. Thus, the DME, 50/50 w/w % and 95/5 v/v % EtOH all give about the same TFA yield. From the standpoint of EPA extracted from the biomass, the trend is similar with 3.32, 2.79, 1.71, and 3.41 wt %. In terms of other components extracted with fatty acid, the EPA content in the extract was 9.9, 6.6, 6.4, and 7.1 wt %. The DME and 95/5 v/v % EtOH provided the best results.

In addition to the fatty acid profile, the polar lipids and other phytonutrients was determined by Spectral Service GmbH (Cologne, Germany) using a combination of $^{31}$P NMR (31P NMR), $^{1}$H-NMR (1H NMR), and $^{13}$C-NMR (13C NMR). All spectra were acquired using a Bruker Avance III 600 MHz NMR spectrometer (Bruker, Karlsruhe, Germany) with automated sample changer and QNP cryo probe. Qualitative 31P NMR was according to method SAA MET002 02. 1H NMR/13C NMR analysis was according to method SAA MET001-02. Bruker TopSpin was used for acquisition and data processing. For 31P NMR, the internal standard was triphenyl phosphate (TPP) (Alrich Chemia AG, Buchs, Czech Republic). For the 1H NMR and 13C NMR, the internal standards were TPP and D Sorbitol (C6H14O6, Sigma Aldrich, Steinheim, Germany). 31P NMR was used to quantify the phospholipid distribution in the samples. 1H NMR was used to quantify the digalactosyldiacylglycerol (DGDG), monogalactosyldiacylglyercol (MGDG), cholesterol, chlorophyll. DGDG and MGDG are glycolipids (GL). Polar lipids (PoL) are comprised of phospholipids and glycolipids. The Cholesterol was a marker, in general, for phytosterols and is, hereafter, referred to as phytosterols, total sterols, or sterols. 13C NMR was used to quantify mannitol and glycerol. Mannitol is a linear C6 carbohydrate. This constituent has not been previously identified in *Nannochloropsis oculata* extract.

TABLE 12

Wet S14 Paste Extracted with DME and Various Solvent Mixtures

| Fatty Acid | C#: Dbl. Bond | DME Test QLTS-2 Percent Extract from Dry Biomass 33.7 Norm. FA % | FA in Extract % | FA in Dry Solid % | 50/50 w/w % Acetone/EtOH QLTS-6 42.2 Norm. FA % | FA in Extract % | FA in Dry Solid % | 90/10 w/w % Acetone/MeOH QLTS-3 26.6 Norm. FA % | FA in Extract % | FA in Dry Solid % | 95/5 v/v % EtOH QLTS-7 48.4 Norm. FA % | FA in Extract % | FA in Dry Solid % |
|---|---|---|---|---|---|---|---|---|---|---|---|---|---|
| Caprylic | 8:0 | 0.15 | 0.07 | 0.025 | 0.16 | 0.05 | 0.022 | 0.10 | 0.03 | 0.009 | 0.17 | 0.06 | 0.028 |
| Capric | 10:0 | 1.52 | 0.76 | 0.256 | 0.91 | 0.30 | 0.128 | 1.72 | 0.58 | 0.154 | 0.98 | 0.33 | 0.158 |
| Lauric | 12:0 | 0.41 | 0.21 | 0.070 | 0.44 | 0.14 | 0.061 | 0.45 | 0.15 | 0.041 | 0.44 | 0.15 | 0.071 |
| Myristic | 14:0 | 4.54 | 2.27 | 0.764 | 4.62 | 1.53 | 0.645 | 4.68 | 1.57 | 0.418 | 4.50 | 1.50 | 0.726 |
| Myristoleic | 14:1 | 0.09 | 0.05 | 0.016 | 0.15 | 0.05 | 0.021 | 0.10 | 0.03 | 0.009 | 0.10 | 0.03 | 0.016 |
| Pentadecanoic | 15:0 | 0.36 | 0.18 | 0.061 | 0.34 | 0.11 | 0.047 | 0.33 | 0.11 | 0.029 | 0.38 | 0.13 | 0.061 |

TABLE 12-continued

Wet S14 Paste Extracted with DME and Various Solvent Mixtures

| | Test | DME | | | 50/50 w/w % Acetone/EtOH | | | 90/10 w/w % Acetone/MeOH | | | 95/5 v/v % EtOH | | |
|---|---|---|---|---|---|---|---|---|---|---|---|---|---|
| | | QLTS-2 | | | QLTS-6 | | | QLTS-3 | | | QLTS-7 | | |
| | Percent Extract from Dry Biomass | 33.7 | | | 42.2 | | | 26.6 | | | 48.4 | | |
| Fatty Acid | C#: Dbl. Bond | Norm. FA % | FA in Extract % | FA in Dry Solid % | Norm. FA % | FA in Extract % | FA in Dry Solid % | Norm. FA % | FA in Extract % | FA in Dry Solid % | Norm. FA % | FA in Extract % | FA in Dry Solid % |
| Palmitic | 16:0 | 23.48 | 11.75 | 3.953 | 22.59 | 7.47 | 3.155 | 23.72 | 7.98 | 2.122 | 23.00 | 7.66 | 3.707 |
| Palmitoleic | 16:1 | 24.32 | 12.17 | 4.095 | 24.69 | 8.17 | 3.448 | 25.59 | 8.62 | 2.289 | 24.99 | 8.32 | 4.029 |
| Hexadecadienoic | 16:2 | 0.25 | 0.13 | 0.043 | 0.22 | 0.07 | 0.031 | 0.11 | 0.04 | 0.010 | 0.24 | 0.08 | 0.038 |
| Hexadecatrienoic | 16:3 | 0.00 | 0.00 | 0.000 | 0.13 | 0.04 | 0.018 | 0.00 | 0.00 | 0.000 | 0.01 | 0.00 | 0.002 |
| Heptadecanoic | 17:0 | 0.31 | 0.15 | 0.052 | 0.37 | 0.12 | 0.051 | 0.39 | 0.13 | 0.034 | 0.41 | 0.14 | 0.066 |
| Stearic | 18:0 | 1.04 | 0.52 | 0.175 | 0.69 | 0.23 | 0.097 | 1.00 | 0.34 | 0.090 | 0.66 | 0.22 | 0.106 |
| Oleic | 18:1ω9 | 2.99 | 1.50 | 0.503 | 3.09 | 1.02 | 0.431 | 2.92 | 0.98 | 0.262 | 3.28 | 1.09 | 0.528 |
| Oleic | 18:1ω7 | 0.45 | 0.23 | 0.076 | 0.52 | 0.17 | 0.072 | 0.58 | 0.19 | 0.052 | 0.47 | 0.16 | 0.075 |
| Linoleic | 18:2ω6 | 2.40 | 1.20 | 0.405 | 2.73 | 0.90 | 0.381 | 2.43 | 0.82 | 0.217 | 2.74 | 0.91 | 0.441 |
| Linoleic | 18:2ω4 | 0.00 | 0.00 | 0.000 | 0.05 | 0.02 | 0.006 | 0.00 | 0.00 | 0.000 | 0.00 | 0.00 | 0.000 |
| Gamma-Linolenic | 18:3ω6 | 0.48 | 0.24 | 0.081 | 0.61 | 0.20 | 0.085 | 0.47 | 0.16 | 0.042 | 0.70 | 0.23 | 0.113 |
| Alpha-Linolenic (ALA) | 18:3ω3 | 0.84 | 0.42 | 0.142 | 1.06 | 0.35 | 0.148 | 0.91 | 0.30 | 0.081 | 0.99 | 0.33 | 0.160 |
| Eicosadienoic | 20:2ω6 | 0.17 | 0.09 | 0.029 | 0.13 | 0.04 | 0.018 | 0.10 | 0.03 | 0.009 | 0.07 | 0.02 | 0.012 |
| Eicosatrienoic | 20:3ω6 | 0.31 | 0.15 | 0.052 | 0.36 | 0.12 | 0.051 | 0.34 | 0.12 | 0.031 | 0.27 | 0.09 | 0.044 |
| Arachidonic | 20:4ω6 | 4.79 | 2.40 | 0.807 | 4.82 | 1.60 | 0.674 | 4.87 | 1.64 | 0.436 | 5.39 | 1.79 | 0.869 |
| Eicosapentaenoic (EPA) | 20:5ω3 | 19.73 | 9.87 | 3.322 | 19.96 | 6.60 | 2.787 | 19.08 | 6.43 | 1.707 | 21.18 | 7.05 | 3.414 |
| Other | n/a | 11.37 | 5.69 | 1.915 | 11.36 | 3.76 | 1.587 | 10.12 | 3.41 | 0.905 | 9.03 | 3.01 | 1.455 |
| Total Fatty Acid | | 100.00 | 50.04 | 16.84 | 100.00 | 33.07 | 13.96 | 100.00 | 33.67 | 8.95 | 100.00 | 33.30 | 16.12 |
| Total Omega-3 | | 20.57 | 10.29 | 3.46 | 21.02 | 6.95 | 2.93 | 19.99 | 6.73 | 1.79 | 22.17 | 7.38 | 3.57 |
| Total Omega-6 | | 8.15 | 4.08 | 1.37 | 8.66 | 2.86 | 1.21 | 8.21 | 2.76 | 0.73 | 9.17 | 3.05 | 1.48 |

TABLE 13

Polar Lipids of S12 and S14 Compared with Krill Oil

| | | *Nannochloropsis Oculata* | | | | Fish Oil | Refined EPA | Krill Oil |
|---|---|---|---|---|---|---|---|---|
| Lipid Class Component Name | Code | Wet S12 | Dry S12 | Wet S14 | Dry S14 | Ethyl Ester | Plus EPA | NOW NKO |
| Phospholipid | | | | | | | | |
| Phosphatidylcholine | PC | 3.09 | 2.33 | 8.55 | 4.46 | 0.00 | 0.00 | 27.73 |
| Lyso-Phosphatidylcholine | 1-LPC | 0.00 | 0.00 | 0.00 | 0.00 | 0.00 | 0.00 | 0.39 |
| Lyso-Phosphatidylcholine | 2-LPC | 0.00 | 0.00 | 0.41 | 0.36 | 0.00 | 0.00 | 3.45 |
| Phosphatidylinositol | PI | 1.35 | 0.00 | 1.95 | 1.26 | 0.00 | 0.00 | 0.27 |
| Lyso-Phosphatidylinositol | LPI | 0.00 | 0.00 | 0.00 | 0.00 | 0.00 | 0.00 | 0.00 |
| Phosphatidylserine | PS-Na | 0.00 | 0.00 | 0.00 | 0.00 | 0.00 | 0.00 | 0.00 |
| Lyso-Phosphatidylserine | LPS | 0.00 | 0.00 | 0.00 | 0.00 | 0.00 | 0.00 | 0.00 |
| Sphingomyelin | SPH | 0.00 | 0.00 | 0.00 | 0.00 | 0.00 | 0.00 | 0.00 |
| Phosphatidylethanolamine | PE | 0.66 | 0.00 | 2.28 | 0.50 | 0.00 | 0.00 | 2.72 |
| Lyso-Phosphatidylethanolamine | LPE | 0.00 | 0.00 | 0.00 | 0.00 | 0.00 | 0.00 | 0.40 |
| N-Acyl-Phosphatidylethanolamine | APE | 0.00 | 0.00 | 0.00 | 0.00 | 0.00 | 0.00 | 1.26 |
| Phosphatidylglycerol | PG | 2.63 | 2.30 | 4.91 | 2.31 | 0.00 | 0.00 | 0.00 |
| Diphosphatidylglycerol | DPG | 0.00 | 0.00 | 0.00 | 0.00 | 0.00 | 0.00 | 0.00 |
| Phosphatidic Acid | PA | 0.00 | 0.00 | 0.00 | 0.00 | 0.00 | 0.00 | 0.00 |
| Lyso-Phosphatidic Acid | LPA | 0.00 | 0.00 | 0.00 | 0.00 | 0.00 | 0.00 | 0.00 |
| | Other | 1.11 | 1.77 | 1.25 | 1.08 | 0.00 | 0.00 | 0.28 |
| Glycolipid | | | | | | | | |
| Digalactosyldiacylglycerol | DGDG | 17.25 | 7.61 | 18.35 | 16.36 | 0.00 | 0.00 | 0.00 |
| Monogalactosyldiacylglycerol | MGDG | 5.40 | 2.61 | 6.18 | 4.28 | 0.00 | 0.00 | 0.00 |
| Total Phospholipids (PL) (wt %) | | 8.84 | 6.39 | 19.34 | 9.96 | 0.00 | 0.00 | 36.50 |
| Total Glycolipids (GL) (wt %) | | 22.65 | 10.22 | 24.53 | 20.64 | 0.00 | 0.00 | 0.00 |
| Total PoL (PL + GL) (wt %) | | 31.49 | 16.61 | 43.86 | 30.60 | 0.00 | 0.00 | 36.50 |

Table 13 shows the polar lipid composition of semi-refined DME extracts of S12 and S14 biomass versus krill oil. The semi-refined material involves a water partition that removes approximately half of the water soluble, non-lipid constituents in the crude algae extract (CAE). By far, the largest difference between krill oil and *Nannochloropsis oculata* extract is that krill oil contains no GL. Krill lack the biosynthetic pathways to produce GLs. Furthermore, *N. oculata* produces less phospholipid than krill oil. *N. oculata* produces more GL than PL, in a range between 20% and 300% more GL than PL. The table shows the effect of spray drying versus wet paste. Wet paste enables between 50 and 100% more polar lipids to be extracted as reflected by the Total PoL contents of Wet S12 and Dry S12 of 31.5 and 16.6 and of Wet S14 and Dry S14 of 43.9 and 30.6 wt %. All S12 and S14 extract contains phosphatidylcholine (PC), phosphatidylglycerol (PG), and other phospholipid components. Except for Dry S12, S12 and S14 also have phosphatidylinositol (PI) and phosphatidylethanolamine (PE). S12 and S14 is devoid of 1 Lyso-Phosphatidylcholine (1 LPC), Lyso-Phosphatidylethanolamine (LPE), and N Acyl Phosphatidylethanolamine (APE) that are found in krill oil.

Table 14 shows the polar lipid content of dried versus wet S14 algae. This is the polar and phytonutrient analysis of QLTS 1 and QLTS 2. This extract is Crude Algae Extract (CAE) per the earlier definition. The FAP from extractions is reported in Table 11. For exactly the same lot of biomass, extraction via DME in the wet state yielded 4.34 wt % PL and 5.50 wt % GL on a biomass basis versus extraction via DME In the dry state which yielded 0.61 wt % PL and 0.81 wt % GL on a biomass basis. Wet state extract was more than 7 times more effective in extracting PL and over 6 times more effective in extracting GL. Phytosterols and chlorophyll are extracted 2 times more effectively in the wet state versus the dry state. The CAE from wet extraction has 12.89 wt % PL and 13.35 wt % GL. For dry extraction, the PL is 3.81 wt % and 5.06 wt %. CAE is over three times more concentrated in PL and more than 2.5 times more concentrated in GL. From this result, we conclude that there is a significant advantage of wet extraction versus dry extraction.

TABLE 14

Polar Lipids and Phytonutrients from Dry and Wet S14 Extracted with DME

| | | Dry S14- Dry DME Test | | S14 Paste- Dry DME | |
|---|---|---|---|---|---|
| | | QLTS-1 Percent Extract from Dry Biomass | | QLTS-2 | |
| | | 16.0 | | 33.7 | |
| Class<br>Component Name | Code | Extract Basis % | Biomass Basis % | Extract Basis % | Biomass Basis % |
| Phospholipid | | | | | |
| Phosphatidylcholine | PC | 1.43 | 0.23 | 5.70 | 1.92 |
| Lyso-Phosphatidylcholine | 1-LPC | 0.00 | 0.00 | 0.00 | 0.00 |
| Lyso-Phosphatidylcholine | 2-LPC | 0.00 | 0.00 | 0.27 | 0.09 |
| Phosphatidylinositol | PI | 0.54 | 0.09 | 1.30 | 0.44 |
| Lyso-Phosphatidylinositol | LPI | 0.00 | 0.00 | 0.00 | 0.00 |
| Phosphatidylserine | PS-Na | 0.00 | 0.00 | 0.00 | 0.00 |
| Lyso-Phosphatidylserine | LPS | 0.00 | 0.00 | 0.00 | 0.00 |
| Sphingomyelin | SPH | 0.00 | 0.00 | 0.00 | 0.00 |
| Phosphatidylethanolamine | PE | 0.53 | 0.08 | 1.52 | 0.51 |
| Lyso-Phosphatidylethanolamine | LPE | 0.00 | 0.00 | 0.00 | 0.00 |
| N-Acyl-Phosphatidylethanolamine | APE | 0.00 | 0.00 | 0.00 | 0.00 |
| Phosphatidylglycerol | PG | 0.96 | 0.15 | 3.27 | 1.10 |
| Diphosphatidylglycerol | DPG | 0.00 | 0.00 | 0.00 | 0.00 |
| Phosphatidic Acid | PA | 0.00 | 0.00 | 0.00 | 0.00 |
| Lyso-Phosphatidic Acid | LPA | 0.00 | 0.00 | 0.00 | 0.00 |
| | Other | 0.35 | 0.06 | 0.83 | 0.28 |
| Glycolipid | | | | | |
| Digalactosyldiacylglycerol | DGDG | 3.91 | 0.63 | 12.23 | 4.12 |
| Monogalactosyldiacylglycerol | MGDG | 1.15 | 0.18 | 4.12 | 1.39 |
| Phytonutrients | | | | | |
| Phytosterols | | 2.23 | 0.36 | 2.43 | 0.82 |
| Chlorophyll | | 6.73 | 1.08 | 6.54 | 2.20 |
| Total Phospholipids (PL) (wt %) | | 3.81 | 0.61 | 12.89 | 4.34 |
| Total Glycolipids (GL) (wt %) | | 5.06 | 0.81 | 16.35 | 5.50 |
| Total PoL (PL + GL) (wt %) | | 8.87 | 1.42 | 29.24 | 9.84 |

Table 15 compares different solvent systems in the extraction yield of polar lipids and phytonutrients from S14 algae paste. The FAP from extractions is reported in Table 12. The solvent systems were DME, 50/50 w/w % acetone/EtOH (Ace/EtOH), 90/10 w/w % Acetone/MeOH (Ace/MeOH), and 95/5 v/v % (190 proof) denatured EtOH (190 proof EtOH). On a biomass basis, the PL content was 4.34, 3.83, 1.53, and 4.79 and the GL content was 5.50, 3.88, 1.62, and 4.76 for DME, Ace/EtOH, Ace/MeOH, and 190 proof EtOH. The extraction yields were approximately the same for DME and 190 proof EtOH. Ace/EtOH could be lower due to sample to sample variance. In terms of the CAE, DME was the best at 29.24 wt % Total PoL, while Ace/EtOH and 190 proof EtOH were 18.26 and 19.73 wt %, respectively. We know from later work, that the liquid solvents have a greater amount of water-soluble non-lipid components than the DME extract. This water-soluble component is removed during the conversion of CAE to CAO. Note that all the liquid solvents on wet paste still produce better yield of PoL from the biomass and higher concentrations of PoL in the extract than the dry biomass extracted with DME (See, Table 14).

Table 16 shows the polar lipid content of dried versus wet S12 algae. This is the polar and phytonutrient analysis of QLTS 18 and QLTS 17. The FAP from these extractions is reported in Table 7. For biomass harvested in the same time period and for DME extraction results on a biomass basis, the wet state S12 yielded 3.53 wt % PL and 9.06 wt % GL on a biomass basis versus the dry state yielding 2.13 wt % PL and 3.41 wt % GL on a biomass basis. Wet state extract is more than 1.5 times more effective in extracting PL and more than 2.5 times more effective in extracting GL. The CAE from wet extraction has 5.89 wt % PL and 15.10 wt % GL. For dry extraction, the PL is 4.26 wt % and 6.81 wt %. CAE is over 33% more concentrated in PL and nearly 2.5 more concentrated in GL. This result further reinforces that there is a significant advantage of wet extraction over dry extraction.

TABLE 15

Polar Lipids and Phytonutrients from Wet S14 Paste Extracted with DME and Other Solvent Systems

| | | DME | | 50/50 w/w % Ace/EtOH | | 90/10 w/w % Ace/MeOH | | 95/5 v/v % EtOH | |
|---|---|---|---|---|---|---|---|---|---|
| | | Test | | | | | | | |
| | | QLTS-2 | | QLTS-6 | | QLTS-3 | | QLTS-7 | |
| | | Percent Extract from Dry Biomass | | | | | | | |
| | | 33.7 | | 42.2 | | 26.6 | | 48.4 | |
| Class<br>Component Name | Code | Extract Basis % | Biomass Basis % | Extract Basis % | Biomass Basis % | Extract Basis % | Biomass Basis % | Extract Basis % | Biomass Basis % |
| Phospholipid | | | | | | | | | |
| Phosphatidylcholine | PC | 5.70 | 1.92 | 4.16 | 1.76 | 2.93 | 0.78 | 3.81 | 1.84 |
| Lyso-Phosphatidylcholine | 1-LPC | 0.00 | 0.00 | 0.00 | 0.00 | 0.00 | 0.00 | 0.00 | 0.00 |
| Lyso-Phosphatidylcholine | 2-LPC | 0.27 | 0.09 | 0.19 | 0.08 | 0.13 | 0.03 | 0.29 | 0.14 |
| Phosphatidylinositol | PI | 1.30 | 0.44 | 0.60 | 0.25 | 0.28 | 0.07 | 0.91 | 0.44 |
| Lyso-Phosphatidylinositol | LPI | 0.00 | 0.00 | 0.00 | 0.00 | 0.00 | 0.00 | 0.00 | 0.00 |
| Phosphatidylserine | PS-Na | 0.00 | 0.00 | 0.00 | 0.00 | 0.00 | 0.00 | 0.00 | 0.00 |
| Lyso-Phosphatidylserine | LPS | 0.00 | 0.00 | 0.00 | 0.00 | 0.00 | 0.00 | 0.00 | 0.00 |
| Sphingomyelin | SPH | 0.00 | 0.00 | 0.00 | 0.00 | 0.00 | 0.00 | 0.00 | 0.00 |
| Phosphatidylethanolamine | PE | 1.52 | 0.51 | 1.12 | 0.47 | 0.47 | 0.13 | 1.26 | 0.61 |
| Lyso-Phosphatidylethanolamine | LPE | 0.00 | 0.00 | 0.00 | 0.00 | 0.00 | 0.00 | 0.00 | 0.00 |
| N-Acyl-Phosphatidylethanolamine | APE | 0.00 | 0.00 | 0.00 | 0.00 | 0.00 | 0.00 | 0.00 | 0.00 |
| Phosphatidylglycerol | PG | 3.27 | 1.10 | 2.56 | 1.08 | 1.65 | 0.44 | 2.84 | 1.38 |
| Diphosphatidylglycerol | DPG | 0.00 | 0.00 | 0.00 | 0.00 | 0.00 | 0.00 | 0.00 | 0.00 |
| Phosphatidic Acid | PA | 0.00 | 0.00 | 0.00 | 0.00 | 0.00 | 0.00 | 0.00 | 0.00 |
| Lyso-Phosphatidic Acid | LPA | 0.00 | 0.00 | 0.00 | 0.00 | 0.00 | 0.00 | 0.00 | 0.00 |
| | Other | 0.83 | 0.28 | 0.42 | 0.18 | 0.29 | 0.08 | 0.78 | 0.38 |
| Glycolipid | | | | | | | | | |
| Digalactosyldiacylglycerol | DGDG | 12.23 | 4.12 | 6.37 | 2.69 | 4.19 | 1.11 | 6.71 | 3.25 |
| Monogalactosyldiacylglycerol | MGDG | 4.12 | 1.39 | 2.83 | 1.19 | 1.90 | 0.51 | 3.12 | 1.51 |
| Phytonutrients | | | | | | | | | |
| Phytosterols | | 2.43 | 0.82 | 1.55 | 0.65 | 2.08 | 0.55 | 1.42 | 0.69 |
| Chlorophyll | | 6.54 | 2.20 | 4.78 | 2.02 | 3.65 | 0.97 | 4.61 | 2.23 |
| Total Phospholipids (PL) (wt %) | | 12.89 | 4.34 | 9.06 | 3.83 | 5.75 | 1.53 | 9.90 | 4.79 |
| Total Glycolipids (GL) (wt %) | | 16.35 | 5.50 | 9.20 | 3.88 | 6.09 | 1.62 | 9.83 | 4.76 |
| Total PoL (PL + GL) (wt %) | | 29.24 | 9.84 | 18.26 | 7.71 | 11.85 | 3.15 | 19.73 | 9.55 |

TABLE 16

Polar Lipids and Phytonutrients from DME Extracted Dry and Wet S12

| Class / Component Name | Code | Spray Dried S12- Wet DME Test; QLTS-18; Percent Extract from Dry Biomass 46.0: Extract Basis % | Biomass Basis % | Wet S12 Slurry- Dry DME; QLTS-17; 60.0: Extract Basis % | Biomass Basis % |
|---|---|---|---|---|---|
| Phospholipid | | | | | |
| Phosphatidylcholine | PC | 1.55 | 0.78 | 2.06 | 1.24 |
| Lyso-Phosphatidylcholine | 1-LPC | 0.00 | 0.00 | 0.00 | 0.00 |
| Lyso-Phosphatidylcholine | 2-LPC | 0.00 | 0.00 | 0.00 | 0.00 |
| Phosphatidylinositol | PI | 0.00 | 0.00 | 0.90 | 0.54 |
| Lyso-Phosphatidylinositol | LPI | 0.00 | 0.00 | 0.00 | 0.00 |
| Phosphatidylserine | PS-Na | 0.00 | 0.00 | 0.00 | 0.00 |
| Lyso-Phosphatidylserine | LPS | 0.00 | 0.00 | 0.00 | 0.00 |
| Sphingomyelin | SPH | 0.00 | 0.00 | 0.00 | 0.00 |
| Phosphatidylethanolamine | PE | 0.00 | 0.00 | 0.44 | 0.26 |
| Lyso-Phosphatidylethanolamine | LPE | 0.00 | 0.00 | 0.00 | 0.00 |
| N-Acyl-Phosphatidylethanolamine | APE | 0.00 | 0.00 | 0.00 | 0.00 |
| Phosphatidylglycerol | PG | 1.53 | 0.77 | 1.75 | 1.05 |
| Diphosphatidylglycerol | DPG | 0.00 | 0.00 | 0.00 | 0.00 |
| Phosphatidic Acid | PA | 0.00 | 0.00 | 0.00 | 0.00 |
| Lyso-Phosphatidic Acid | LPA | 0.00 | 0.00 | 0.00 | 0.00 |
| | Other | 1.18 | 0.59 | 0.74 | 0.44 |
| Glycolipid | | | | | |
| Digalactosyldiacylglycerol | DGDG | 5.07 | 2.54 | 11.50 | 6.90 |
| Monogalactosyldiacylglycerol | MGDG | 1.74 | 0.87 | 3.60 | 2.16 |
| Phytonutrients | | | | | |
| Phytosterols | | 0.57 | 0.29 | 1.20 | 0.72 |
| Chlorophyll | | 4.51 | 2.26 | 12.00 | 7.20 |
| Total Phospholipids (PL) (wt %) | | 4.26 | 2.13 | 5.89 | 3.53 |
| Total Glycolipids (GL) (wt %) | | 6.81 | 3.41 | 15.10 | 9.06 |
| Total PoL (PL + GL) (wt %) | | 11.07 | 5.54 | 20.99 | 12.59 |

In addition to the greater yield, wet extraction of S12 has another advantage in that the distribution of phospholipids differs from that from dry S12. Note that in QLTS-17, the phospholipid distribution includes Phosphatidylinositol (PI) and Phosphatidylethanolamine (PE). PI and PE contribute 0.90 and 0.44 wt %, respectively, of the total 5.89 wt % PL in the CAE. PI and PE represent 15.2% and 9.0% by mass of the total PL, nearly 25% of the mixture. The difference in the PL distribution is almost completely accounted for by these two missing constituents. With S12 *Nannochloropsis oculata*, it appears that the presence of intracellular water is essential for the extraction of these two PL constituents.

A CAE comprised of NL, PL, GL, chlorophyll, sterols, carotenoids, manitol, and glycerol results from these different drying approaches, pretreatment methods, and solvent extraction methods on S12 and S14. PL and GL together comprise the polar lipids. The phospholipids in S12 and S14 are PC (Phosphatidylcholine), PI (Phosphatidylinositol), PE (Phosphatidylethanolamine), PG (Phosphatidylglycerol), and other non-specific phospholipids. Based on Table 14, there are higher proportions of "other" phospholipids in S12 and S14 oil than in hill oil. This implies that there are a greater number of unique PL compounds in S12 and S14 oil than in krill oil. The following phospholipids are notably absent in S12 and S14 N. *Oculata* oil: LPI (Lyso-Phosphatidylinositol), PS (Phosphatidylserine), LPS (Lyso Phosphatidylserine), SPH (Sphingomyelin), LPE (Lyso Phosphatidylethanolamine), APE (N Acyl Phosphatidylethanolamine), PA (Phosphatidic Acid), and LPA (Lyso Phosphatidic Acid). The glycolipids are DGDG (Digalactosyldiacylglycerol) and MGDG (Monogalactosyldiacylglycerol). There is zero GL in krill oil.

Figure 6:
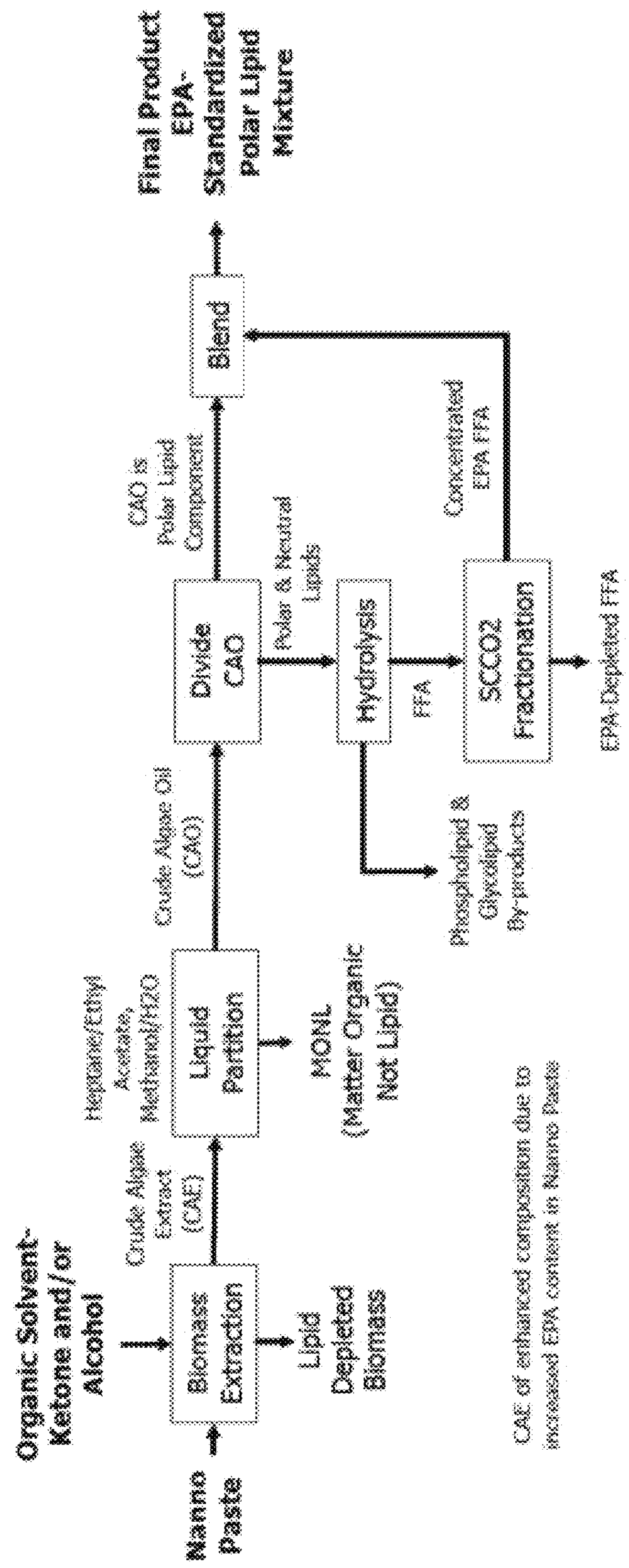
FIG. 6 illustrates an example of typical mass split of major mixture constituents during *Nannochloropsis* oil refining.

As shown in FIG. 6, the CAE contains a significant proportion of MONL. MONL is material not otherwise accounted for in the TFA, phospholipids, glycolipids, and phytonutrients. MONL is believed to be water-soluble carbohydrates and proteins; however, the composition of this fraction is currently unexplored. CAE can be converted to CAO through water partitioning. MONL refinement may include a partition of the water-soluble components comprising excess water to CAE, bringing the water and CAE into intimate contact with a high shear mixer, and separation of the water and organic phase via either settling or centrifugation. The organic phase is the CAO and is a lipid rich mixture of polar lipids (PoL) and neutral lipids (NL). Alternatively, CAE can be extracted in series with a solvent more suitable for neutral lipids, such as hexane, chloroform, cyclohexane, methylene chloride, or combinations thereof, followed by further extraction by a solvent suitable for PoL, such as acetone, methanol, ethanol or combination thereof. In the first step, the solution partitions and the NL rich upper phase is collected. A NL rich extract is recovered by evaporating the solvent. The bottom phase, now rich in both PoL and MONL, is extracted with a PoL suitable solvent system. After extraction, the PoL rich extract is recovered by evaporating the solvent. CAO results when the NL rich and PoL rich extracts are combined. The conversion from CAE to CAO results in between 30 and 50% reduction in mass. CAO is one of the constituents of the EPA standardized EPA/Polar Lipid blend.

Figure 7:
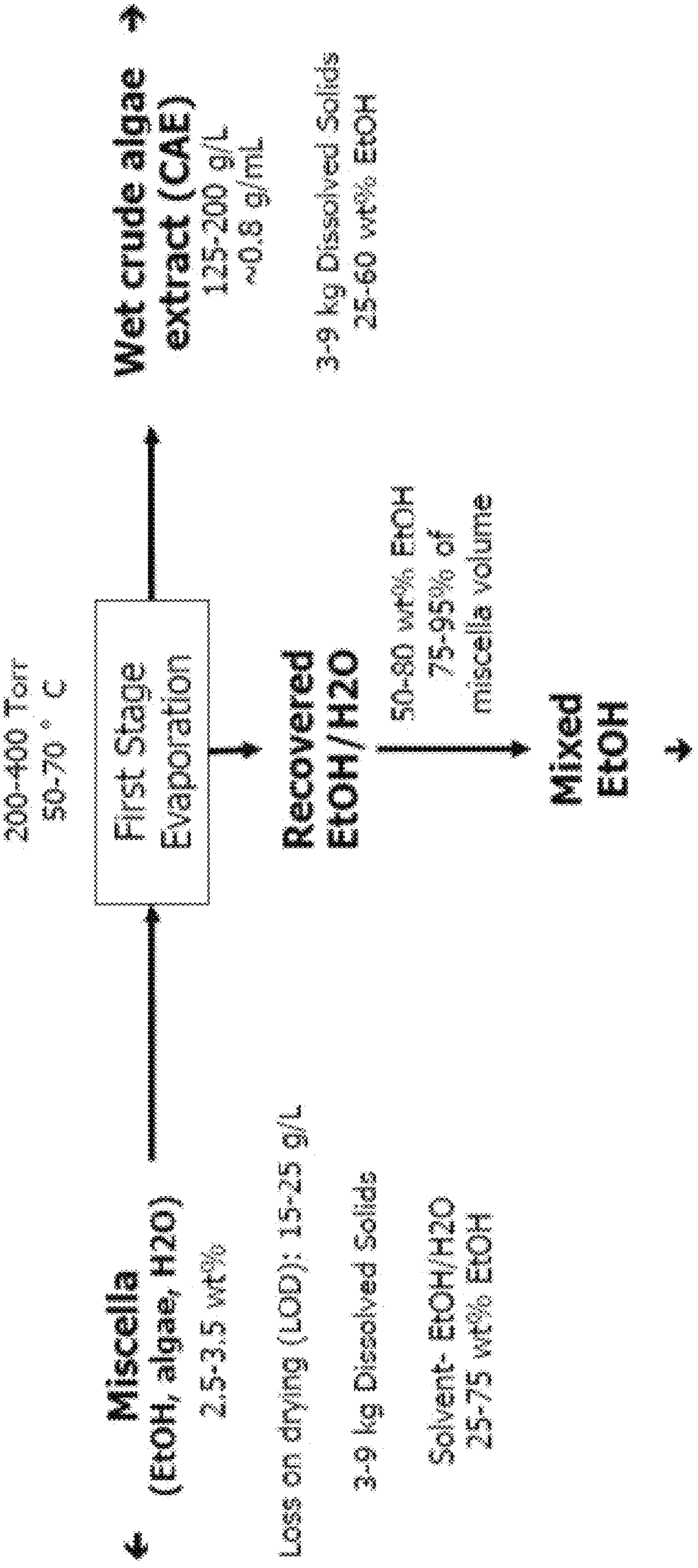
FIG. 7 illustrates a schematic of a process to concentrate the soluble components in solution, for enrichment of algae into a crude algae extract (CAE). A solvent mixture of EtOH and $H_2O$ is retained with the CAE to both facilitate subsequent process steps that require the presence of these solvents and to facilitate handling.
Figure 8:
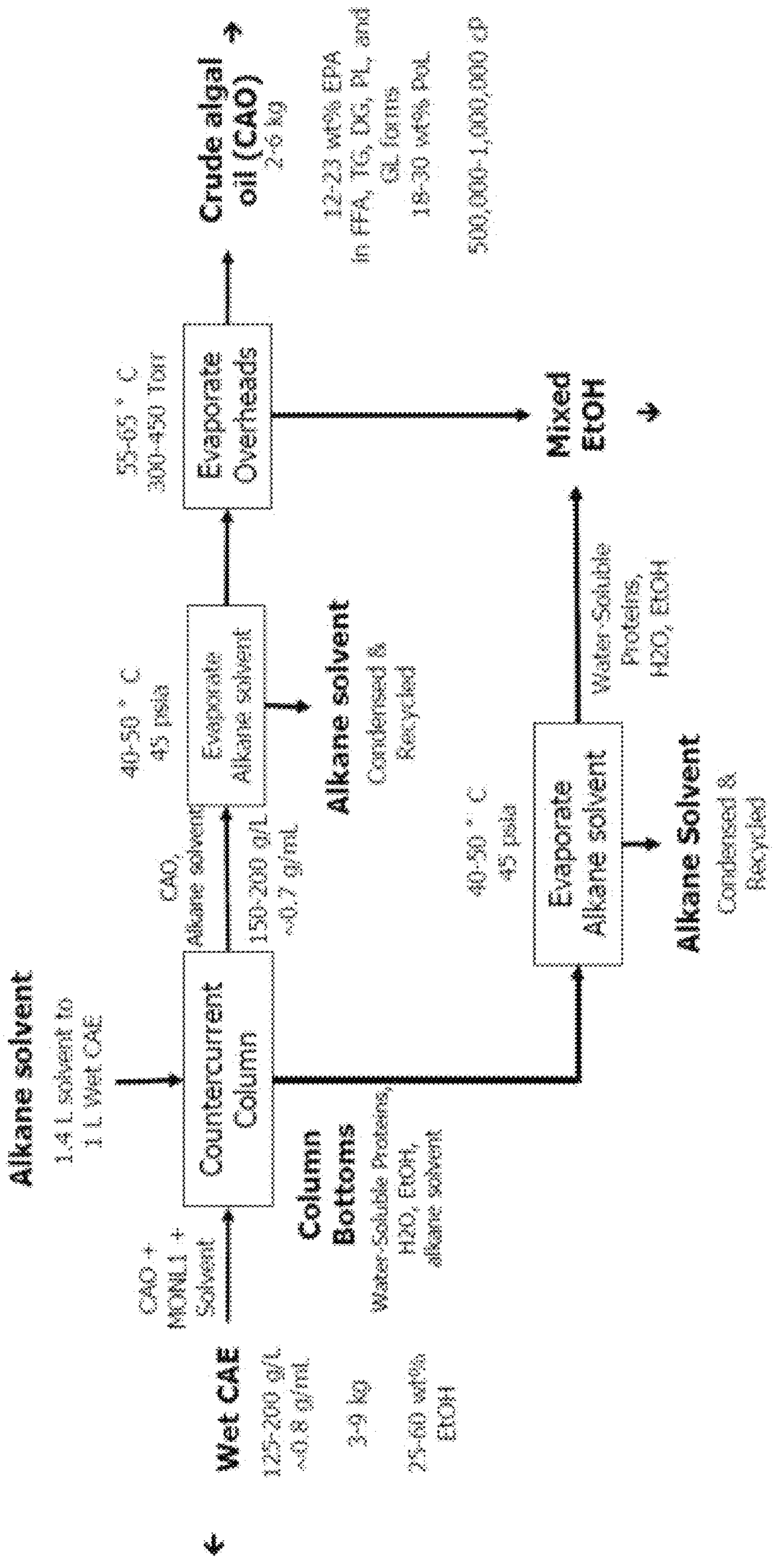
FIG. 8 illustrates a schematic of a process for enrichment of the CAE into crude algal oil (CAO). The alkane-soluble phase that becomes CAO contains the fatty acid and polar lipid constituents that are a major component of the final EPA composition.

The composition of CAE, CAO, and the distribution of FA among the different lipid classes for S12 *Nannochloropsis* are shown in FIGS. 6, 7, and 8, respectively. CAE of S12 contains between 35 and 45 wt % MONL. This MONL is substantially reduced in CAO. In CAO, MONL is between 4 and 10 wt % of the CAO. Fatty acid is distributed between NL other than FFA, FFA, PL, and GL. In S12, the FA is almost equally divided between NL and PoL. The TG/DG NLs are between 35 and 48% of the FA, and the FFA NL is between 3 and 12%, with 6% being typical. Exposure to elevated temperature in harvesting or in extraction can result in the conversion of FA with GL, PL, or TG/DG to FFA. This is a hydrolysis process. Care is taken to minimize elevated temperature and to reduce the time at any temperature above ambient. Of the PoL, the GL represents about ⅗ of the FA in PoL (29%), and the PL represents about ⅖ of the FA in the PoL (21%). These numbers could fluctuate by ±10% from their nominal values based on growth media and environmental conditions.

Figure 9:
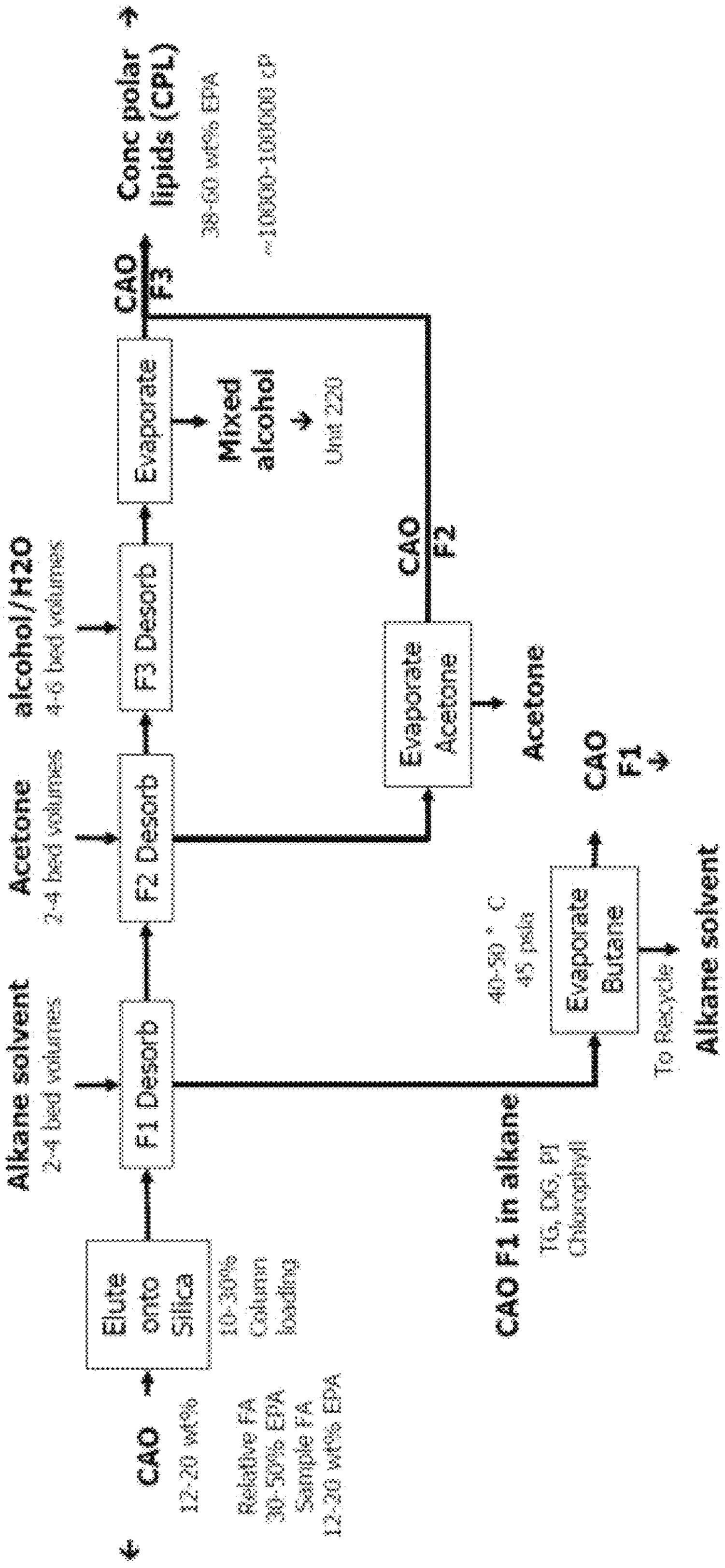
FIG. 9 illustrates a schematic of a process for enrichment of polar lipids in CAO to produce concentrated polar lipids (CPL). The CAO is transferred as a liquid solution onto silica and subsequently extracted with a C3-C7 alkane, acetone, and a C1-C4 alcohol/water. The alkane separates TG, DG, PI, and chlorophyll. The acetone yields glycolipids, in particular, DGDG. The alcohol/water yields the remaining polar lipids including most of the phospholipids and MGDG.
Figure 10:
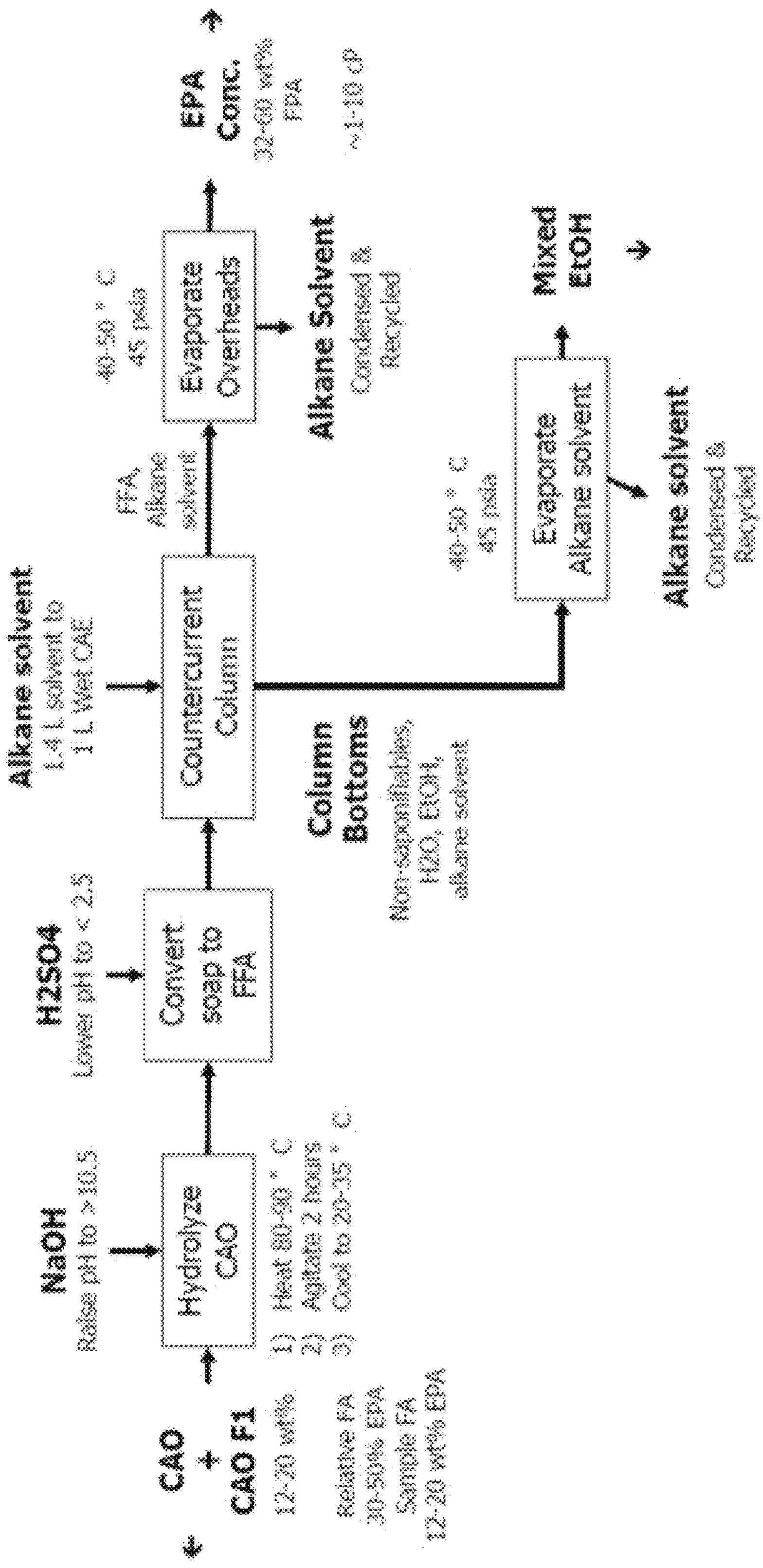
FIG. 10 illustrates a schematic of a process used for enrichment of the CAO. The alkane-soluble phase that becomes CAO contains the fatty acid and polar lipid constituents that are a major component of the product.
Figure 11:
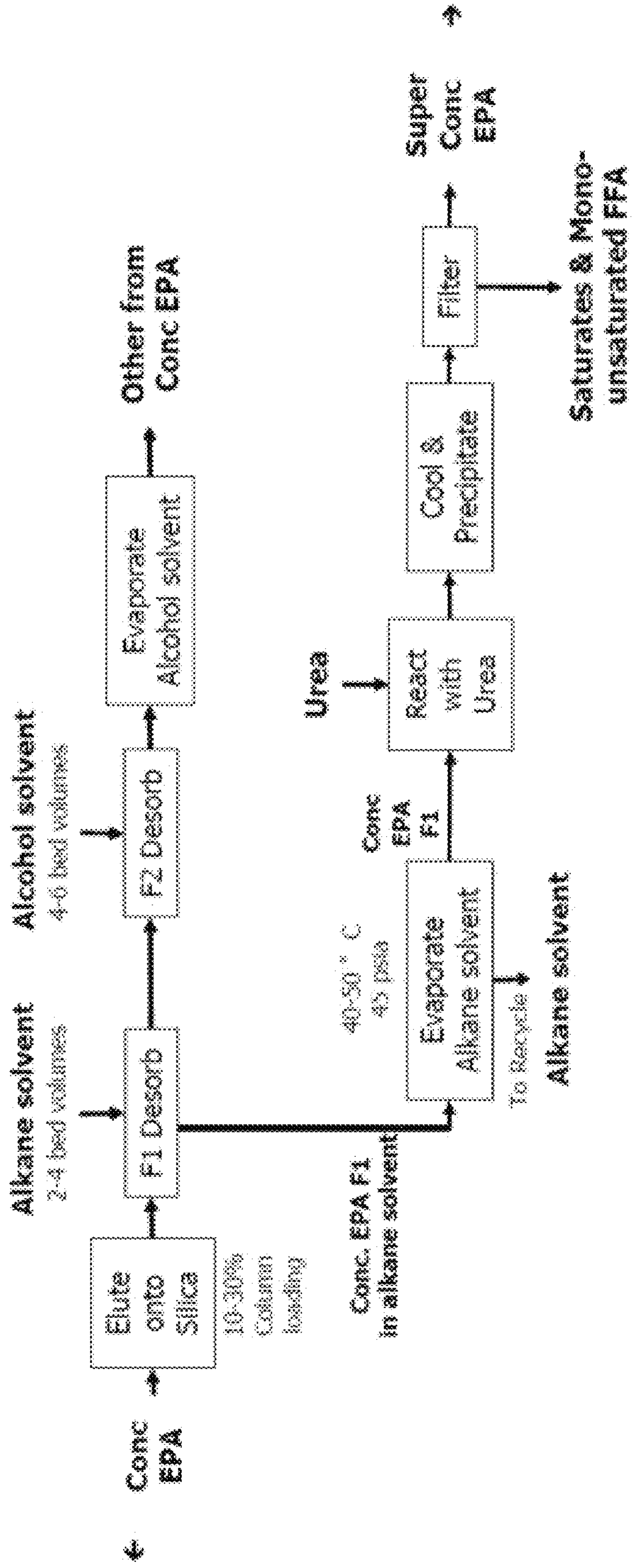
FIG. 11 illustrates a schematic of a process used for further enrichment further enrichment of EPA. The process employs a combination of chromatography, urea crystallization, and winterization to remove non-EPA components from the concentrated EPA. Chromatography removes enriches the free fatty acids by removing non-FA components of EPA. Urea crystallization forms complexes with the saturates (i.e. C16:0) and mono-unsaturated (i.e. C16:1). The winterization step cools the solution, causing the complexes to precipitate from solution, thereby enriching the EPA fraction.

The composition of CAE, CAO, and the distribution of FA among the different lipid classes for S14 *Nannochloropsis* are shown in FIGS. 9, 10, and 11, respectively. CAE of S14 contains between 40 and 60 wt % MONL. This MONL is substantially reduced in CAO. In CAO, MONL is between 5 and 15 wt % of the CAO. Fatty acid is distributed between NL other than FFA, FFA, PL, and GL. In S14, the FA is about 40% PoL and about 60% NL. The TG/DG NLs are between 40 and 50% of the FA, and the FFA NL is between 10 and 25%, with 17% being typical. As with S12, exposure to elevated temperature in harvesting or in extraction can result in the conversion of FA with GL, PL, or TG/DG to FFA. Of the PoL, the GL represents about half of the FA in PoL (17%), and the PL represents about half of the FA in the PoL (20%). These numbers could fluctuate by ±10% from their nominal values based on growth media and environmental conditions.

As shown in FIG. 4, CAO can be split into a NL-rich and zero PoL mixture with high pressure/high temperature (HP/HT) supercritical carbon dioxide (SCCO2). We have found that SCCO2 extracts neutral lipids completely and essentially zero polar lipids in either the form of phospholipids or glycolipids. SCCO2 in the range from 100 to 1000 bar and temperatures between 35 and 110° C. has a high distribution coefficient for neutral lipids and an essentially zero distribution coefficient for polar lipids. Typical values would, at a minimum, be 340 bar and 40° C. up to 700 bar and 110° C. In varying embodiments, pressure and temperature ranges are between 350 bar/60° C. and 690 bar/90° C. At 350 bar and 60 C, the density of SCCO2 is 0.863 g/mL. At 700 bar/100° C., SCCO2 has a density of 0.9 g/mL. Process conditions in the pressure range between 340 bar and 700 bar that yield a density of 0.83 to 0.9 g/mL are suitable. High P/T SCCO2 produces a NL fraction with zero PoL. It extracts a proportion of the chlorophyll and almost all the sterols from the CAO. The NL fraction is comprised of free fatty acids (FFA), triglycerides (TG), diglycerides (DG), chlorophyll, and sterols. The residual material from high P/T SCCO2 extraction is concentrated polar lipids (Conc PoL), including phosopholipids and glycolipids. The Conc PoL is the second component in the EPA-standardized blend. This stream and the COA provide all the polar lipids for the EPA standardized EPA/Polar Lipid blend.

As an alternative to the process in FIG. 4, CAE can be split into an NL rich fraction and PoL rich fraction using HP/HT SCCO2 followed by extraction with dimethyl ether (DME). An example of wet paste process by acetone/ethanol to produce CAE, the resultant HT/HP SCCO2 fraction, and DME fraction are presented in Table 17A, 17B, and 17C. Table 17A shows the fatty acid profile. The most notable characteristics is the relatively low TFA in the CAE. This is due to the presence of MONL. Table 17B shows the polar lipid and phytonutrient composition for the same samples. The most critical observation from Table 17B is that HP/HT SCCO2 does not extract any polar lipids (PoL). Neither PL nor GL are soluble in HP/HT SCCO2. SCCO2 extracts a large fraction of the NL. Table 17C shows the distribution of FA in the NL, PL, and GL classes and the fraction of NL, PL, and GL in the overall sample. In the CAE, the NL is nearly 75% of the FA and the balance of FA is split almost equally between PL and GL. In the HP/HT SCCO2 fraction, the NL is concentrated and there is zero PL and zero GL. The NL goes from being 23.5 wt % of the CAE to 69.3 wt % in the NL concentrate (HP/HT SCCO2). The MONL is almost completely removed in the NL concentrate. Finally, the DME or PoL concentrate fraction contains virtually all PoL from the CAE. The FA distribution in the PoL concentrate contains 40.4% NL, 28.0% PL, 31.6% GL. In the total DME sample, total lipids are 62.4 wt % comprised of 19.3 wt % NL, 18.9 wt % PL, and 24.3 wt % GL.

TABLE 17A

Fatty Acid Composition of S14 CAE, HP/HT SCCO2 Extract and DME Extract

| | | Control Sample | | High P/T SCCO2 Test | | DME after SCCO2 | |
|---|---|---|---|---|---|---|---|
| | | QLTS-B-4 Extract | | QLTS-B-5 F1 | | QLTS-B-5 F2 + F3 | |
| | | Percent of Control Material | | | | | |
| | | | | 24.8 | | 30.2 | |
| Fatty Acid | C#: Dbl. Bond | Norm. FA % | FA in Mixture % | Norm. FA % | FA in Fraction % | Norm. FA % | FA in Fraction % |
| Caprylic | 8:0 | 0.21 | 0.07 | 0.20 | 0.14 | 0.23 | 0.11 |
| Capric | 10:0 | 0.12 | 0.04 | 0.24 | 0.16 | 0.00 | 0.00 |
| Lauric | 12:0 | 0.44 | 0.14 | 0.59 | 0.41 | 0.26 | 0.12 |
| Myristic | 14:0 | 4.87 | 1.54 | 4.86 | 3.36 | 4.88 | 2.32 |
| Myristoleic | 14:1 | 0.11 | 0.03 | 0.16 | 0.11 | 0.05 | 0.02 |

TABLE 17A-continued

Fatty Acid Composition of S14 CAE, HP/HT SCCO2 Extract and DME Extract

| Fatty Acid | C#: Dbl. Bond | Control Sample<br>QLTS-B-4 Extract<br>Norm. FA % | Control Sample<br>QLTS-B-4 Extract<br>FA in Mixture % | High P/T SCCO2 Test<br>QLTS-B-5 F1<br>Percent of Control Material 24.8<br>Norm. FA % | High P/T SCCO2 Test<br>QLTS-B-5 F1<br>Percent of Control Material 24.8<br>FA in Fraction % | DME after SCCO2<br>QLTS-B-5 F2 + F3<br>Percent of Control Material 30.2<br>Norm. FA % | DME after SCCO2<br>QLTS-B-5 F2 + F3<br>Percent of Control Material 30.2<br>FA in Fraction % |
|---|---|---|---|---|---|---|---|
| Pentadecanoic | 15:0 | 0.28 | 0.09 | 0.38 | 0.26 | 0.16 | 0.08 |
| Palmitic | 16:0 | 22.70 | 7.15 | 25.63 | 17.75 | 19.12 | 9.11 |
| Palmitoleic | 16:1 | 25.05 | 7.89 | 32.94 | 22.81 | 15.58 | 7.42 |
| Hexadecadienoic | 16:2 | 0.21 | 0.07 | 0.26 | 0.18 | 0.15 | 0.07 |
| Hexadecatrienoic | 16:3 | 0.00 | 0.00 | 0.17 | 0.12 | 0.00 | 0.00 |
| Heptadecanoic | 17:0 | 0.43 | 0.13 | 0.62 | 0.43 | 0.20 | 0.09 |
| Stearic | 18:0 | 0.79 | 0.25 | 1.22 | 0.85 | 0.27 | 0.13 |
| Oleic | 18:1ω9 | 3.06 | 0.96 | 3.57 | 2.47 | 2.45 | 1.17 |
| Oleic | 18:1ω7 | 0.49 | 0.16 | 0.58 | 0.40 | 0.39 | 0.19 |
| Linoleic | 18:2ω6 | 2.29 | 0.72 | 1.82 | 1.26 | 2.84 | 1.35 |
| Linoleic | 18:2ω4 | 0.00 | 0.00 | 0.00 | 0.00 | 0.00 | 0.00 |
| Gamma-Linolenic | 18:3ω6 | 0.63 | 0.20 | 0.38 | 0.26 | 0.92 | 0.44 |
| Alpha-Linolenic (ALA) | 18:3ω3 | 0.77 | 0.24 | 0.80 | 0.55 | 0.74 | 0.35 |
| Arachidic | 20:0 | 0.16 | 0.05 | 0.37 | 0.25 | 0.00 | 0.00 |
| Eicosatrienoic | 20:3ω6 | 0.40 | 0.13 | 0.51 | 0.35 | 0.26 | 0.13 |
| Arachidonic | 20:4ω6 | 4.73 | 1.49 | 3.45 | 2.39 | 6.23 | 2.97 |
| Eicosapentaenoic (EPA) | 20:5ω3 | 20.72 | 6.53 | 9.92 | 6.87 | 33.49 | 15.96 |
| Other | n/a | 11.53 | 3.63 | 11.34 | 7.85 | 11.80 | 5.62 |
| Total Fatty Acid | | 100.00 | 31.50 | 100.00 | 69.25 | 100.00 | 47.65 |
| Total Omega-3 | | 21.50 | 6.77 | 10.72 | 7.43 | 34.23 | 16.31 |
| EPA/Total Omega-3 | | 96.41 | | 92.53 | | 97.85 | |
| Total Omega-6 | | 8.20 | 2.58 | 6.54 | 4.53 | 10.25 | 4.88 |

TABLE 17B

Polar Lipid and Phytonutrient Composition of S14 CAE, HP/HT SCCO2 Extract and DME Extract

| Class<br>Component Name | Code | Test<br>Control Sample QLTS-B-4 Extract<br>Relative Basis % | Test<br>Control Sample QLTS-B-4 Extract<br>Extract Basis % | Test<br>High P/T SCCO2 QLTS-B-5 F1<br>Relative Basis % | Test<br>High P/T SCCO2 QLTS-B-5 F1<br>Extract Basis % | Test<br>DME after SCCO2 QLTS-B-5 F2 + F3<br>Relative Basis % | Test<br>DME after SCCO2 QLTS-B-5 F2 + F3<br>Extract Basis % |
|---|---|---|---|---|---|---|---|
| Phospholipid | | | | | | | |
| Phosphatidylcholine | PC | 41.1 | 2.35 | | 0.00 | 40.9 | 7.73 |
| Lyso-Phosphatidylcholine | 1-LPC | 0.0 | 0.00 | | 0.00 | 0.0 | 0.00 |
| Lyso-Phosphatidylcholine | 2-LPC | 3.0 | 0.17 | | 0.00 | 1.8 | 0.34 |
| Phosphatidylinositol | PI | 10.4 | 0.59 | | 0.00 | 12.3 | 2.33 |
| Lyso-Phosphatidylinositol | LPI | 0.0 | 0.00 | | 0.00 | 0.0 | 0.00 |
| Phosphatidylserine | PS-Na | 0.0 | 0.00 | | 0.00 | 0.0 | 0.00 |
| Lyso-Phosphatidylserine | LPS | 0.0 | 0.00 | | 0.00 | 0.0 | 0.00 |
| Sphingomyelin | SPH | 0.0 | 0.00 | | 0.00 | 0.0 | 0.00 |
| Phosphatidylethanolamine | PE | 8.7 | 0.50 | | 0.00 | 9.7 | 1.83 |
| Lyso-Phosphatidylethanolamine | LPE | 0.0 | 0.00 | | 0.00 | 0.0 | 0.00 |
| N-Acyl-Phosphatidylethanolamine | APE | 0.0 | 0.00 | | 0.00 | 0.0 | 0.00 |
| Phosphatidylglycerol | PG | 25.6 | 1.47 | | 0.00 | 25.9 | 4.90 |
| Diphosphatidylglycerol | DPG | 0.0 | 0.00 | | 0.00 | 0.0 | 0.00 |
| Phosphatidic Acid | PA | 0.0 | 0.00 | | 0.00 | 0.0 | 0.00 |
| Lyso-Phosphatidic Acid | LPA | 0.0 | 0.00 | | 0.00 | 0.0 | 0.00 |
| | Other | 11.2 | 0.64 | | 0.00 | 9.3 | 1.76 |
| Glycolipid | | | | | | | |
| Digalactosyldiacylglycerol | DGDG | 74.2 | 4.71 | | 0.00 | 72.9 | 17.68 |
| Monogalactosyldiacylglycerol | MGDG | 25.8 | 1.64 | | 0.00 | 27.1 | 6.57 |

TABLE 17B-continued

Polar Lipid and Phytonutrient Composition of S14 CAE, HP/HT SCCO2 Extract and DME Extract

| Class<br>Component Name | Code | Control Sample QLTS-B-4 Extract<br>Relative Basis % | <br>Extract Basis % | High P/T SCCO2 QLTS-B-5 F1<br>Relative Basis % | <br>Extract Basis % | DME after SCCO2 QLTS-B-5 F2 + F3<br>Relative Basis % | <br>Extract Basis % |
|---|---|---|---|---|---|---|---|
| Phytonutrients | | | | | | | |
| Phytosterols | | | 1.45 | | 4.98 | | 0.38 |
| Chlorophyll | | | 4.33 | | 3.44 | | 9.93 |
| Total Phospholipids (PL) (wt %) | | | 5.73 | | 0.00 | | 18.90 |
| Total Glycolipids (GL) (wt %) | | | 6.35 | | 0.00 | | 24.24 |
| Total PoL (PL + GL) (wt %) | | | 12.08 | | 0.00 | | 43.14 |

TABLE 17C

Fatty Acid Distribution and NL, PL, GL distribution of S14 CAE, HP/HT SCCO2 Extract and DME Extract

| Compound Class | Control Sample QLTS-B-4 Extract<br>Wt % Oil | <br>% of FA | High P/T SCCO2 QLTS-B-5 F1<br>wt % in Fraction | <br>% of FA | DME after SCCO2 QLTS-B-5 F2 + F3<br>wt % in Fraction | <br>% of FA |
|---|---|---|---|---|---|---|
| Fatty Acid as Neutral Lipids (NL) | 23.5 | 74.7 | 69.3 | 100.0 | 19.3 | 40.4 |
| Fatty Acid as Phospholipids (PL) | 4.0 | 12.8 | 0.0 | 0.0 | 13.3 | 28.0 |
| Fatty Acid as Glycolipids (GL) | 3.9 | 12.5 | 0.0 | 0.0 | 15.1 | 31.6 |
| Total Fatty Acid (TFA) | 31.5 | 100.0 | 69.3 | 100.0 | 47.7 | 100.0 |
| Total NL | 23.5 | | 69.3 | | 19.3 | |
| Total PL | 5.7 | | 0.0 | | 18.9 | |
| Total GL | 6.4 | | 0.0 | | 24.3 | |
| Total Lipids = NL + PL + GL | 35.6 | | 69.3 | | 62.4 | |

To create the controlled concentration of EPA in the mixture, the NL fraction must be further concentrated in EPA. As shown in FIG. 1, the NL fraction lipids must be homogenized. This means that any fatty acids associated with a glycerol backbone must be separated from this backbone. Little concentration of the EPA fatty acid is possible while the EPA is conjugated with the glycerol backbone. Suitable methods for FA homogenization include transesterification to form methyl or ethyl esters or hydrolysis to create FFA. The preferred method is hydrolysis to create FFA. Transesterification to form methyl or ethyl esters requires additional process steps and the consumption of methanol or ethanol during the transesterification. Hydrolysis can be achieved through saponification and acidification or direct pressurized steam hydrolysis. Once the fatty acids are freed of the covalent bond to the glycerol backbone, they can be reorganized according to a combination of their molecular weight and degree of unsaturation (i.e., number of double bonds). Many methods can be used to concentrate EPA. For example, urea crystallization can be used to remove the majority of saturated and monounsaturated FA from the mixture. Furthermore, the fatty acid mixture can be dissolved in solvent and complexed with silver nitrate or silver functionalized silica. This has the net effect of removing the highly polyunsaturated material from the balance of the mixture. Another alternative is to use pressure profiling with SCCO2 to selectively remove the lower molecular weight components (i.e., C12-C18) from the higher molecular weight constituents (i.e. C20).

FIG. 4 shows the combination of hydrolysis and SCCO2 fractionation to create a concentrate of EPA FFA. The NL fraction is first hydrolyzed to form FFA. This can be done by a variety of routes that are familiar to lipid chemists. The most common methods are saponification followed by acidification and direct acidification. In terms of product yield, saponification is a useful route because the first step in the reaction irreversibly forms a fatty acid salt. In this case, the neutral lipid mixture is combined with KOH or NaOH in the presence of an excess of the water. The oxyl bond between the fatty acid and the glycerol backbone is broken and the respective K or Na salt formed. This reaction is completed under reflux at temperature conditions between 50 and 90° C. TG and DG constituents are converted to a salt and free glycerol. Free glycerol is highly polar. The salt solution is treated with an acid, such as phosphoric, sulfuric, or hydrochloric acid. This removes the salt's cation and forms the corresponding free fatty acid (FFA). The solution partitions into two phases: an organic and aqueous phase. In the direct acidification method, the reaction has fewer steps but is reversible. Hence, the yield to FFA may not be as great as the saponification route. Under acidification, neutral lipid is combined with water and strong acid, such as sulfuric, hydrochloric, phosphoric, or formic. Water in excess of stoichiometry, on the order of 6 times, is added to the neutral lipid. Acid is added to lower the pH to approximately 2. The mixture is heated under reflux at a temperature between 60 and 100° C. This reaction, while single step, is reversible. An excess of water is required to drive the equilibrium in the direction of FFA.

Once the neutral lipid has been hydrolyzed to form FFA, the EPA fraction within this mixture can be further concentrated. Under the previous processing step, all the triglycerides and diglycerides have been converted to FFA. This is known as high acid oil, a mixture of different FA compounds that are predominantly in free fatty acid form. While is it known from the literature that SCCO2 can concentrate Omega-3 from methyl esters and, by extension, ethyl esters (Nilsson, et. al., "Supercritical Fluid CO2 Fractionation of Fish Oil Esters" in Advances in Seafood Biochemistry, 1992), it was not previously known that SCCO2 could fractionate mixtures of FFA. FFAs are polar moieties. Conventional thought in SCCO2 solubility is that these compounds would be insoluble in SCCO2 and, thus, not be amenable to tunable dissolving characteristics of SCCO2. Surprisingly, we have found that SCCO2 is capable of fractionating FFAs by molecular weight. Without being bound by any particular theory, the non-polar effect of long carboxylic acid chain from 8 to 20 carbon molecules long overwhelms the polar characteristics of the carbonyl group. Thus, in the presence of isothermal conditions, increasing SCCO2 pressure about 100 bar results in increasingly greater solubility for higher molecular weight carboxylic acids. Using lower pressure SCCO2 at a pressure above 100 bar and 40 C can be used to remove the lower molecular weight free fatty acids from the higher molecular weight free fatty acids. This enables concentrating the C20 components, including EPA and ARA, while reducing or eliminating the C8, C10, C12, C14, C18 constituents. This enables at least doubling of the EPA concentration. After concentration, this is the EPA-Concentrated FFA stream (Conc EPA) and is the third constituent in the mixture to create an EPA-standardized formulation.

Surprisingly, we have found that a high FFA feedstock can be fractionated by pressure gradient SCCO2. As an example, a feedstock was derived from S14 biomass via a hydrolyzing extraction method. The biomass was treated with sulfuric acid and heated to 70° C. The mixture of biomass was then extracted with hexanes. After evaporating the hexanes, a partially hydrolyzed algae oil was recovered. This mixture was approximately 44.7% FFA with a 80.03 wt % TFA. The composition of the feedstock is shown in Table 18. Under 60° C. isothermal conditions, this oil was extracted with a pressure profile, starting at 2500 psi (172 bar) for the first fraction (F1) and increasing 100 psi (6.9 bar) with each subsequent fraction (i.e. 2600 psi (179 bar) for the second fraction (F2), 2700 psi (186 bar) for the third fraction (F3), etc.). The final pressure was for fraction F12 was 5000 psi (345 bar). This fully extracted the feedstock material.

Figure 12:
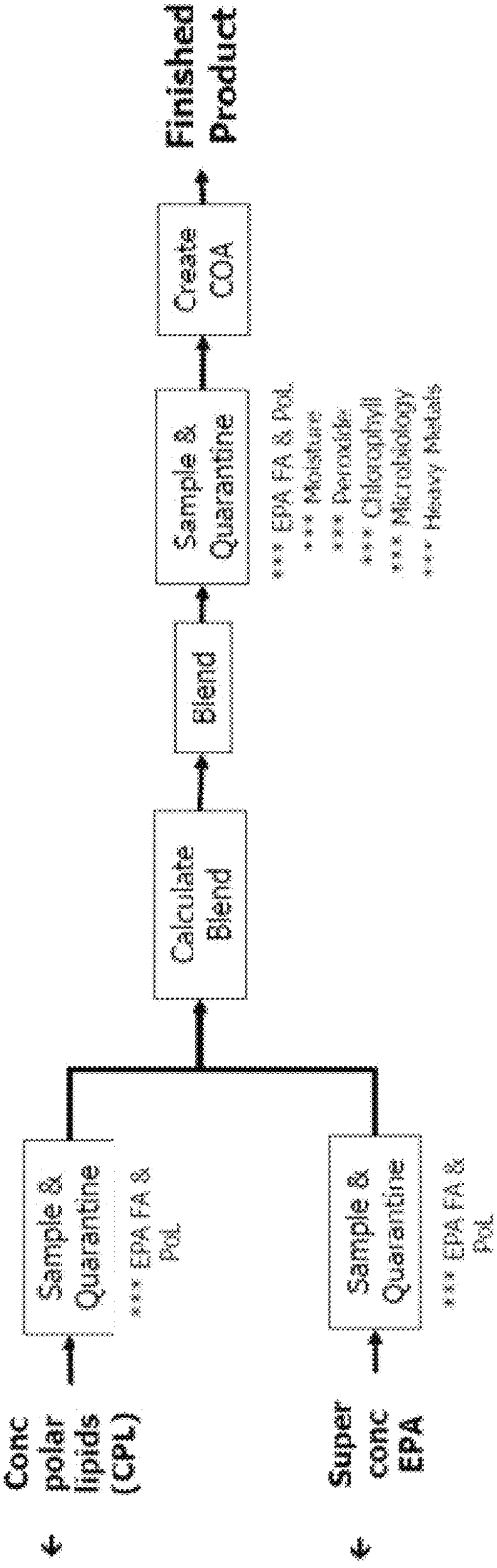
FIG. 12 illustrates a schematic of a process for standardizing the final EPA composition so that it contains desired minimum concentrations of EPA and Polar Lipids. The CAO contains both EPA and Polar Lipids. The super-concentrated EPA contains concentrated Omega-3 fatty acids (including EPA) and may or may not contain polar lipids. The CPL and super-concentrated EPA components are blended according to a calculation procedure to create the final EPA composition. The final EPA composition is fully characterized to assure that it meets product quality and product specifications.
Figure 13:
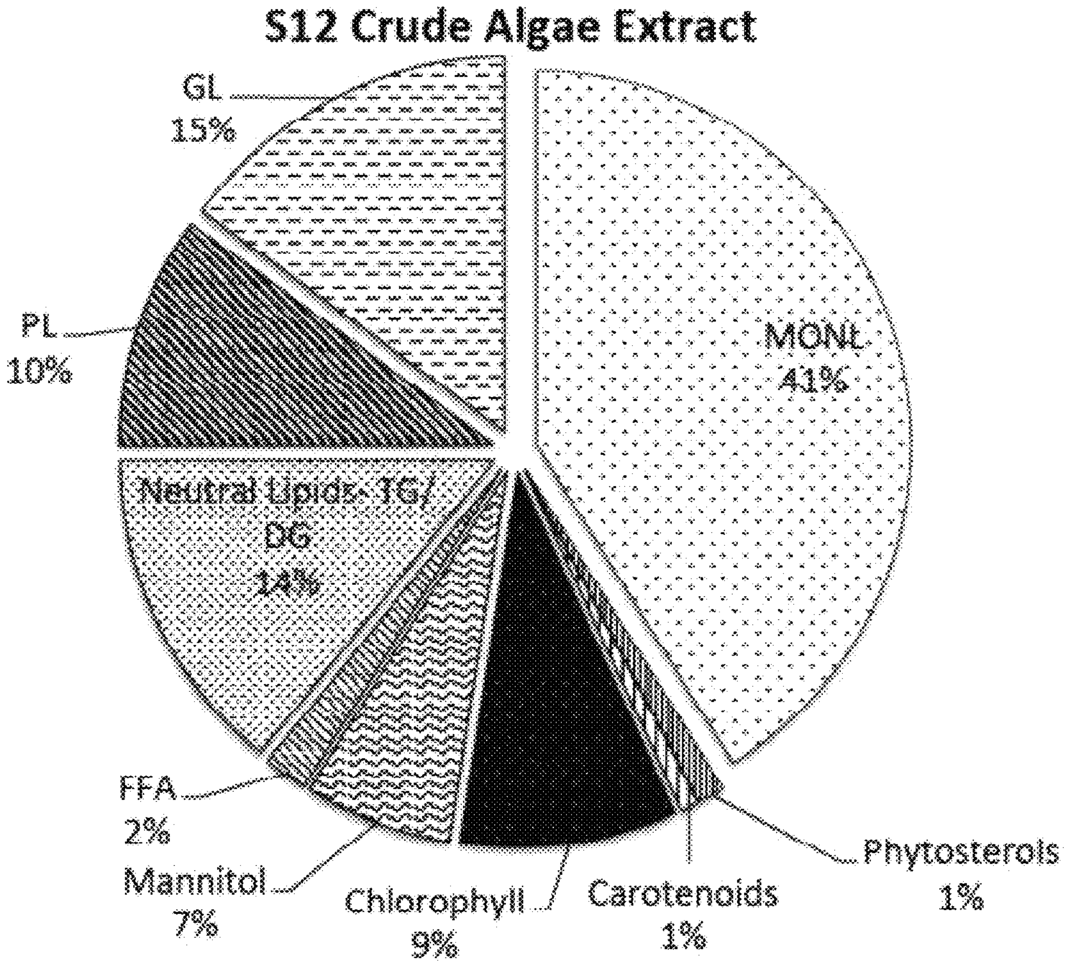
FIG. 13 illustrates a typical composition of S12 crude algae extract.

The FFA level and the percentage of the feed for each fraction is shown in Table 19. The FFA levels are shown in the plot in FIG. 12. Both the table and the figure show high FFA levels in fractions F1 through F6. In fractions F7 through F12, the non-hydrolyzed triglycerides exist. Table 20 shows the FA compositions of fractions F1 through F7 and the percentage of the feedstock mass that was recovered in each of these fractions. Surprisingly, the lower molecular weight compounds were concentrated in fractions F1 through F3. The higher molecular weight compounds were concentrated in fractions F4 through F6. F7 is a combination of EPA FFA and lower molecular weight TGs based on the FFA measurement of 23.1% versus 68.5% for F6. F7 has significant EPA within it, so this is included with the higher MW fraction despite the presence of lower MW TGs. Collectively, this data implies that if a FFA feedstock were extracted with process conditions similar to F3, the resultant extract was concentrated in lower molecular weight FA while the higher molecular weight FA would be the residue. This can be accomplished in a countercurrent column extractor. The extract is the concentrate of the lower molecular weight compounds. The raffinate (column bottom) is the concentrate of the higher molecular weight compounds, including EPA. Based on the ratio of the recovered mass in each molecular weight class, an effective mass fraction can be defined by molecular weight range, as is given in Table 21. This table shows that 85 wt % of the EPA in the hydrolyzed feedstock can be recovered in the EPA concentrated fraction (raffinate). FIG. 13 shows the distribution of several characteristic molecular weight components and the FFA level associated with each fraction.

TABLE 18

Fatty Acid Distribution of Hydrolyzed S14 Algae Oil Feedstock

| Fatty Acid | C#: Dbl. Bond | Control Sample Test QLTS-B-8 Control Norm. FA % | FA in Mixture % |
|---|---|---|---|
| Caprylic | 8:0 | 0.15 | 0.12 |
| Capric | 10:0 | 0.13 | 0.10 |
| Lauric | 12:0 | 0.39 | 0.31 |
| Myristic | 14:0 | 4.74 | 3.79 |
| Myristoleic | 14:1 | 0.35 | 0.28 |
| Pentadecanoic | 15:0 | 0.40 | 0.32 |
| Palmitic | 16:0 | 29.04 | 23.24 |
| Palmitoleic | 16:1 | 25.45 | 20.37 |
| Hexadecadienoic | 16:2 | 0.29 | 0.23 |
| Hexadecatrienoic | 16:3 | 0.23 | 0.18 |
| Heptadecanoic | 17:0 | 0.31 | 0.25 |
| Stearic | 18:0 | 0.86 | 0.69 |
| Oleic | 18:1ω9 | 3.80 | 3.04 |
| Oleic | 18:1ω7 | 0.74 | 0.59 |
| Linoleic | 18:2ω6 | 3.02 | 2.42 |
| Linoleic | 18:2ω4 | 0.00 | 0.00 |
| Gamma-Linolenic | 18:3ω6 | 0.46 | 0.37 |
| Alpha-Linolenic (ALA) | 18:3ω3 | 1.09 | 0.87 |
| Arachidic | 20:0 | 0.24 | 0.19 |
| Eicosadienoic | 20:2ω6 | 0.21 | 0.17 |
| Eicosatrienoic | 20:3ω6 | 0.25 | 0.20 |
| Arachidonic | 20:4ω6 | 4.10 | 3.28 |
| Eicosapentaenoic (EPA) | 20:5ω3 | 15.66 | 12.53 |
| Other | n/a | 8.10 | 6.49 |
| Total Fatty Acid | | 100.00 | 80.03 |
| Total Omega-3 | | 16.75 | 13.40 |
| Total Omega-6 | | 8.04 | 6.44 |

TABLE 19

FFA and Mass fraction of Pressure Gradient Fractions of a High-FFA S14 Oil Feedstock

| Fraction | Sample ID | FFA Level wt % | Recovered Mass % |
|---|---|---|---|
| Control | QLTS-B-8 Control | 44.70 | |
| F1 | QLTS-B-8 F1 | 72.00 | 4.7 |
| F2 | QLTS-B-8 F2 | 94.90 | 8.3 |
| F3 | QLTS-B-8 F3 | 94.90 | 12.0 |
| F4 | QLTS-B-8 F4 | 95.50 | 7.6 |
| F5 | QLTS-B-8 F5 | 85.50 | 8.0 |
| F6 | QLTS-B-8 F6 | 68.50 | 5.8 |
| F7 | QLTS-B-8 F7 | 23.10 | 4.7 |
| F8 | QLTS-B-8 F8 | 19.70 | 10.1 |

TABLE 19-continued

FFA and Mass fraction of Pressure Gradient Fractions of a High-FFA S14 Oil Feedstock

| Fraction | Sample ID | FFA Level wt % | Recovered Mass % |
|---|---|---|---|
| F9 | QLTS-B-8 F9 | 3.60 | 8.0 |
| F10 | QLTS-B-8 F10 | 2.00 | 7.6 |
| F11 | QLTS-B-8 F11 | 4.70 | 13.4 |
| F12 | QLTS-B-8 F12 | 18.40 | 4.7 |
| Recovered Mass, F1-F7, (% of Feed) | | | 51.09 |
| Recovered Mass, F8-F12, (% of Feed) | | | 43.84 |
| Mass Balance (Total % of Feed Recovered) | | | 94.93 |

TABLE 20

Fatty Acid Profile of Pressure Gradient Fractions F1 through F7

| | | Fraction | | | | | | | |
|---|---|---|---|---|---|---|---|---|---|
| | | Test | | | | | | | |
| | | F1 | | F2 | | F3 | | F4 | |
| | | QLTS-B-8 F1 | | QLTS-B-8 F2 | | QLTS-B-8 F3 | | QLTS-B-8 F4 | |
| Fatty Acid | C#: Dbl. Bond | Norm. FA % | % FA in Fract | Norm. FA % | % FA in Fract | Norm. FA % | % FA in Fract | Norm. FA % | % FA in Fract |
| Caprylic | 8:0 | 1.44 | 1.24 | 0.13 | 0.12 | 0.00 | 0.00 | 0.00 | 0.00 |
| Capric | 10:0 | 0.78 | 0.67 | 0.14 | 0.13 | 0.00 | 0.00 | 0.00 | 0.00 |
| Lauric | 12:0 | 1.51 | 1.30 | 0.82 | 0.78 | 0.12 | 0.11 | 0.00 | 0.00 |
| Myristic | 14:0 | 10.17 | 8.74 | 11.57 | 10.94 | 4.35 | 4.16 | 0.90 | 0.85 |
| Myristoleic | 14:1 | 5.20 | 4.47 | 0.78 | 0.73 | 0.35 | 0.33 | 0.06 | 0.05 |
| Pentadecanoic | 15:0 | 0.60 | 0.52 | 0.69 | 0.66 | 0.50 | 0.48 | 0.20 | 0.19 |
| Palmitic | 16:0 | 18.84 | 16.20 | 30.01 | 28.37 | 35.83 | 34.22 | 28.84 | 27.08 |
| Palmitoleic | 16:1 | 20.94 | 18.00 | 32.88 | 31.08 | 31.15 | 29.74 | 18.46 | 17.33 |
| Hexadecadienoic | 16:2 | 0.37 | 0.32 | 0.45 | 0.42 | 0.49 | 0.46 | 0.27 | 0.25 |
| Hexadecatrienoic | 16:3 | 0.34 | 0.29 | 0.43 | 0.41 | 0.35 | 0.33 | 0.18 | 0.16 |
| Heptadecanoic | 17:0 | 0.00 | 0.00 | 0.13 | 0.12 | 0.20 | 0.19 | 0.29 | 0.27 |
| Stearic | 18:0 | 0.14 | 0.12 | 0.13 | 0.12 | 0.23 | 0.22 | 0.60 | 0.56 |
| Oleic | 18:1ω9 | 1.11 | 0.96 | 1.62 | 1.53 | 3.14 | 3.00 | 6.13 | 5.76 |
| Oleic | 18:1ω7 | 0.30 | 0.26 | 0.36 | 0.34 | 0.64 | 0.61 | 1.29 | 1.21 |
| Linoleic | 18:2ω6 | 1.19 | 1.02 | 1.83 | 1.73 | 3.53 | 3.37 | 6.27 | 5.89 |
| Linoleic | 18:2ω4 | 0.00 | 0.00 | 0.00 | 0.00 | 0.00 | 0.00 | 0.00 | 0.00 |
| Gamma-Linolenic | 18:3ω6 | 0.22 | 0.19 | 0.35 | 0.33 | 0.61 | 0.59 | 0.88 | 0.82 |
| Alpha-Linolenic (ALA) | 18:3ω3 | 1.02 | 0.88 | 0.96 | 0.91 | 1.49 | 1.43 | 2.54 | 2.38 |
| Arachidic | 20:0 | 0.00 | 0.00 | 0.00 | 0.00 | 0.00 | 0.00 | 0.14 | 0.13 |
| Eicosadienoic | 20:2ω6 | 0.00 | 0.00 | 0.00 | 0.00 | 0.00 | 0.00 | 0.13 | 0.12 |
| Eicosatrienoic | 20:3ω6 | 0.00 | 0.00 | 0.00 | 0.00 | 0.00 | 0.00 | 0.16 | 0.15 |
| Arachidonic | 20:4ω6 | 0.79 | 0.68 | 0.83 | 0.79 | 1.99 | 1.90 | 5.85 | 5.49 |
| Eicosapentaenoic (EPA) | 20:5ω3 | 2.72 | 2.34 | 3.03 | 2.87 | 7.18 | 6.85 | 20.43 | 19.18 |
| Other | n/a | 32.32 | 27.78 | 12.83 | 12.13 | 7.86 | 7.51 | 6.39 | 6.00 |
| Total Fatty Acid | | 100.00 | 85.97 | 100.00 | 94.54 | 100.00 | 95.49 | 100.00 | 93.89 |
| Total Omega-3 | | 3.74 | 3.22 | 4.00 | 3.78 | 8.67 | 8.28 | 22.97 | 21.56 |
| Total Omega-6 | | 2.19 | 1.89 | 3.02 | 2.85 | 6.14 | 5.86 | 13.29 | 12.48 |

| | | Fraction | | | | | |
|---|---|---|---|---|---|---|---|
| | | Test | | | | | |
| | | F5 | | F6 | | F7 | |
| | | QLTS-B-8 F5 | | QLTS-B-8 F6 | | QLTS-B-8 F7 | |
| Fatty Acid | C#: Dbl. Bond | Norm. FA % | % FA in Fract | Norm. FA % | % FA in Fract | Norm. FA % | % FA in Fract |
| Caprylic | 8:0 | 0.00 | 0.00 | 0.00 | 0.00 | 0.13 | 0.07 |
| Capric | 10:0 | 0.00 | 0.00 | 0.05 | 0.04 | 0.19 | 0.09 |
| Lauric | 12:0 | 0.00 | 0.00 | 0.21 | 0.15 | 0.89 | 0.45 |
| Myristic | 14:0 | 0.29 | 0.24 | 1.01 | 0.72 | 6.21 | 3.12 |
| Myristoleic | 14:1 | 0.00 | 0.00 | 0.00 | 0.00 | 0.11 | 0.05 |
| Pentadecanoic | 15:0 | 0.00 | 0.00 | 0.10 | 0.07 | 0.40 | 0.20 |
| Palmitic | 16:0 | 11.38 | 9.66 | 7.76 | 5.55 | 27.13 | 13.63 |

TABLE 20-continued

Fatty Acid Profile of Pressure Gradient Fractions F1 through F7

| | | | | | | | |
|---|---|---|---|---|---|---|---|
| Palmitoleic | 16:1 | 6.08 | 5.16 | 5.30 | 3.79 | 25.13 | 12.63 |
| Hexadecadienoic | 16:2 | 0.07 | 0.06 | 0.00 | 0.00 | 0.20 | 0.10 |
| Hexadecatrienoic | 16:3 | 0.06 | 0.05 | 0.00 | 0.00 | 0.12 | 0.06 |
| Heptadecanoic | 17:0 | 0.20 | 0.17 | 0.12 | 0.09 | 0.15 | 0.07 |
| Stearic | 18:0 | 0.83 | 0.70 | 0.66 | 0.47 | 0.47 | 0.24 |
| Oleic | 18:1ω9 | 6.24 | 5.30 | 3.94 | 2.82 | 2.94 | 1.48 |
| Oleic | 18:1ω7 | 1.38 | 1.17 | 0.88 | 0.63 | 0.58 | 0.29 |
| Linoleic | 18:2ω6 | 5.89 | 5.00 | 3.47 | 2.48 | 2.40 | 1.20 |
| Linoleic | 18:2ω4 | 0.00 | 0.00 | 0.00 | 0.00 | 0.00 | 0.00 |
| Gamma-Linolenic | 18:3ω6 | 0.65 | 0.55 | 0.36 | 0.26 | 0.31 | 0.16 |
| Alpha-Linolenic (ALA) | 18:3ω3 | 2.51 | 2.13 | 1.63 | 1.17 | 1.20 | 0.60 |
| Arachidic | 20:0 | 0.66 | 0.56 | 1.28 | 0.92 | 0.53 | 0.26 |
| Eicosadienoic | 20:2ω6 | 0.00 | 0.00 | 0.00 | 0.00 | 0.00 | 0.00 |
| Eicosatrienoic | 20:3ω6 | 0.59 | 0.50 | 0.71 | 0.51 | 0.22 | 0.11 |
| Arachidonic | 20:4ω6 | 12.15 | 10.32 | 12.79 | 9.16 | 4.11 | 2.06 |
| Eicosapentaenoic (EPA) | 20:5ω3 | 43.96 | 37.33 | 48.85 | 34.97 | 18.68 | 9.39 |
| Other | n/a | 7.08 | 6.01 | 10.78 | 7.72 | 7.91 | 3.97 |
| Total Fatty Acid | | 100.00 | 84.92 | 99.90 | 71.51 | 100.00 | 50.24 |
| Total Omega-3 | | 46.47 | 39.46 | 50.48 | 36.13 | 19.88 | 9.99 |
| Total Omega-6 | | 19.27 | 16.36 | 17.33 | 12.41 | 7.03 | 3.53 |

TABLE 21

Mass Fraction of Major Fatty Acid Components, including EPA Concentration Factor

| | | Fraction F4-F7 | |
|---|---|---|---|
| Fatty Acid | C#: Dbl. Bond | Lower MW Extract Mass Fraction of Feed wt % | Higher MW Raffinate Mass Fraction of Feed wt % |
| Myristic | 14:0 | 86.98 | 13.02 |
| Palmitic | 16:0 | 65.55 | 34.45 |
| Palmitoleic | 16:1 | 73.32 | 26.68 |
| Oleic | 18:1ω9 | 32.70 | 67.30 |
| Oleic | 18:1ω7 | 32.52 | 67.48 |
| Linoleic | 18:2ω6 | 36.26 | 63.74 |
| Gamma-Linolenic | 18:3ω6 | 45.28 | 54.72 |
| Alpha-Linolenic (ALA) | 18:3ω3 | 39.16 | 60.84 |
| Arachidic | 20:0 | 14.82 | 85.18 |
| Eicosapentaenoic (EPA) | 20:5ω3 | 14.48 | 85.52 |
| Other | n/a | 68.98 | 31.02 |
| % of Feed | | 48.94 | 51.06 |

A typical example of EPA concentration is shown in Table 22. A feedstock derived from S12 algae was first fractionated with SCCO2 to remove the NL from other CAO constituents. This mixture was then hydrolyzed to form free fatty acids. The feed mixture was over 85% FFA. In the feed, the EPA constitutes 46% of the fatty acid and 28.7 wt % of the mixture. This mixture was concentrated with SCCO2 using the previously described method. In the concentrated EPA mixture, the EPA is 65.1% of the fatty acid and 48.1 wt % of the mixture. There was zero polar lipids in either the FFA feedstock or the EPA concentrate. The ratio of EPA to total Omega-3 as greater than 99% for both the feedstock material and the EPA concentrate, a typical value for S12 algae.

This high EPA faction is used to maintain a consistent EPA level in the standardized formulation. This FFA is in an FFA form, and, thus, facilitates more rapid bioabsorbance. The EPA to total Omega-3 ratio is greater than 99% in this example. This is used to maintain the high fraction of EPA to total Omega-3 in the standardized formulation. With respect to the this blend, the EPA to total EPA ratio is always greater than 94% and more typically 95%, 96%, 97%, or 98%.

TABLE 22

Composition of S12 Derived FFA and Concentrated EPA Mixture

| | | S12 FFA Feedstock | | EPA Concentrate | |
|---|---|---|---|---|---|
| Fatty Acid | C#: Dbl. Bond | Norm. FA % | FA in Extract % | Norm. FA % | FA in Extract % |
| Caprylic | 8:0 | 0.43 | 0.27 | 0.09 | 0.07 |
| Capric | 10:0 | 0.37 | 0.23 | 0.08 | 0.06 |
| Lauric | 12:0 | 1.49 | 0.93 | 0.32 | 0.24 |
| Myristic | 14:0 | 3.16 | 1.97 | 0.68 | 0.50 |
| Myristoleic | 14:1 | 0.46 | 0.29 | 0.10 | 0.07 |
| Pentadecanoic | 15:0 | 0.14 | 0.09 | 0.03 | 0.02 |
| Palmitic | 16:0 | 7.45 | 4.65 | 4.25 | 3.14 |
| Palmitoleic | 16:1 | 11.83 | 7.38 | 5.22 | 3.86 |
| Hexadecadienoic | 16:2 | 0.22 | 0.14 | 0.10 | 0.07 |
| Hexadecatrienoic | 16:3 | 0.32 | 0.20 | 0.14 | 0.11 |
| Stearic | 18:0 | 0.54 | 0.34 | 0.61 | 0.45 |
| Oleic | 18:1ω9 | 1.73 | 1.08 | 1.93 | 1.42 |
| Oleic | 18:1ω7 | 0.85 | 0.53 | 0.95 | 0.70 |
| Linoleic | 18:2ω6 | 2.74 | 1.71 | 2.89 | 2.13 |
| Linoleic | 18:2ω4 | 0.14 | 0.09 | 0.15 | 0.11 |
| Gamma-Linolenic | 18:3ω6 | 0.38 | 0.24 | 0.35 | 0.26 |
| Alpha-Linolenic (ALA) | 18:3ω3 | 0.26 | 0.16 | 0.26 | 0.19 |
| Eicosatrienoic | 20:3ω6 | 0.24 | 0.15 | 0.34 | 0.25 |
| Arachidonic | 20:4ω6 | 6.12 | 3.82 | 8.63 | 6.37 |
| Eicosapentaenoic (EPA) | 20:5ω3 | 46.02 | 28.71 | 65.13 | 48.09 |
| Other | n/a | 15.08 | 9.41 | 7.74 | 5.72 |
| Total Fatty Acid | | 100.00 | 62.39 | 100.00 | 73.83 |
| Total Omega-3 | | 46.27 | 28.87 | 65.39 | 48.28 |
| EPA/Omega-3 | | 99.4 | | 99.6 | |
| Total Omega-6 | | 9.49 | 5.92 | 12.21 | 9.01 |

Three components are blended to form a standardized combination of EPA and polar lipids: CAO, Conc PoL, and Conc EPA are used to create a standardized product that controls both the EPA and the polar lipid content in the blend. Nominally, the EPA is 25 wt %, the total polar lipids are greater than 15 wt % with more than 5 wt % being PL and more than 10 wt % being GL.

Tables 23 and 24 show the fatty acid profile and polar lipid profile, respectively, of a typical standardized formulation of polar lipids and EPA. In this example, CAO is not used in the mixture. The polar lipid contribution to the standardized formulation comes from the Conc PoL fraction. The PoL fraction is comprised of phospholipids and glycolipids. In the PoL, the TFA (total fatty acid) can vary between 25 and 45 wt. %, where a typical and measured value was about 35 wt. %. In this fatty acid, EPA can vary from a low of 5 wt. % to high of 25 wt. %. A typical value was about 10 wt. % (measured). In this particular measure, the EPA was about 29 wt. % of the fatty acid distribution.

The ratios of PL and GL can vary. We have purified a PL/GL fraction that completely removes the TG/DG/MG and FFA. Hence, the fraction has zero neutral lipid. In an example of polar lipid distribution, the PL was about 20 wt % and the GL was about 35 wt %. Thus, PL and GL were 37 wt % and 63 wt % of the polar lipids, respectively. Fatty acid was distributed between PL and GL as 39.5% and 60.5%, respectively. Given that the distribution of fatty acids between the lipid classes is nearly identical to the ratio of the two lipid classes, it is most likely that EPA is distributed uniformly by weight. Thus, a typical EPA distribution would be 39.5 wt % with the PL and 60.5% with the GL. A reasonable ratio of EPA distribution between PL and GL would be between 3:1 and 1:3. Thus, at the one extreme, EPA can be 64% with the PL and 36% with the GL. At the other extreme, EPA can be 16% with the PL and 83.6% with the GL. It is more likely that the EPA is biased toward the GL than the PL; however, depending on the metabolic and environmental history, the algae could produce it in either distribution.

The EPA level can be adjusted using the EPA-FFA from the Conc EPA. Note that the ratio of EPA to total Omega-3 is greater than 99%. The EPA constitutes greater than 25% of the mixture. A typical value is about 25%; however, with more refinement of the EPA concentrate, this value could be as much as about 50%. Values characteristic of the standardized formulation are 30%, 35%, 40%, 45%, and 50%. C16:0 and C16:1, collectively, represent 11% of the mixture. A typical range is 2 to 15 wt %. In any event, the total of the C16 fatty acids will be present in the mixture at an amount greater than 2 wt % and less than 20 wt %. Lower molecular weight compounds, such as C10:0, C12:0, C14:0, are relatively minor components in the mixture. All these constituents may be detectable. C14:0 fatty acids are present at greater than 0.2 wt % and less than 5 wt % of the standardized mixture. The C18 compounds represent a minor component of the standardize mixture and are typically less than 5% of the composition. The composition contains detectable quantities of C18:0, C18:1ω9, C18:1ω7, C18:2ω6, C18:3ω3 and all compounds in this list, other than C18:0, are present in the standardized mixture at a mass fractions greater than 0.2 wt % and less than 3 wt %.

TABLE 23

Fatty Acid Composition of Standardized Mixture derived from S12 PoL and EPA Concentrate

| | | S12 PoL Concentrate | | S12 EPA Concentrate wt % of Blend | | Standardized Mixture | |
|---|---|---|---|---|---|---|---|
| | | 64.7 | | 35.3 | | | |
| Fatty Acid | C#: Dbl. Bond | Norm. FA % | % FA in Mixture | Norm. FA % | % FA in Mixture | Norm. FA % | % FA in Mixture |
| Capric | 10:0 | 0.19 | 0.08 | 0.08 | 0.06 | 0.13 | 0.07 |
| Lauric | 12:0 | 0.33 | 0.13 | 0.33 | 0.24 | 0.33 | 0.17 |
| Myristic | 14:0 | 3.58 | 1.43 | 0.68 | 0.50 | 2.12 | 1.10 |
| Palmitic | 16:0 | 14.86 | 5.93 | 4.25 | 3.14 | 9.53 | 4.95 |
| Palmitoleic | 16:1 | 18.05 | 7.21 | 5.23 | 3.86 | 11.61 | 6.03 |
| Hexadecadienoic | 16:2 | 0.36 | 0.14 | 0.09 | 0.07 | 0.23 | 0.12 |
| Stearic | 18:0 | 0.16 | 0.06 | 0.61 | 0.45 | 0.39 | 0.20 |
| Oleic | 18:1ω9 | 2.66 | 1.06 | 1.92 | 1.42 | 2.29 | 1.19 |
| Oleic | 18:1ω7 | 0.84 | 0.33 | 0.95 | 0.70 | 0.89 | 0.46 |
| Linoleic | 18:2ω6 | 4.39 | 1.75 | 2.89 | 2.13 | 3.64 | 1.89 |
| Alpha-Linolenic (ALA) | 18:3ω3 | 0.38 | 0.15 | 0.35 | 0.26 | 0.36 | 0.19 |
| Arachidonic | 20:4ω6 | 3.44 | 1.37 | 8.63 | 6.37 | 6.04 | 3.14 |
| Eicosapentaenoic (EPA) | 20:5ω3 | 32.08 | 12.81 | 65.14 | 48.09 | 48.67 | 25.26 |
| Other | n/a | 18.68 | 7.46 | 8.86 | 6.54 | 13.75 | 7.14 |
| Total Fatty Acid | | 100.00 | 39.93 | 100.00 | 73.83 | 100.00 | 51.90 |
| Total Omega-3 | | 32.45 | 12.96 | 65.49 | 48.35 | 49.04 | 25.45 |
| EPA/Omega-3 | | 98.8 | | 99.5 | | 99.3 | |
| Total Omega-6 | | 7.83 | 3.13 | 11.51 | 8.50 | 9.68 | 5.02 |

TABLE 24

Polar Lipid and Phytonutrient Profile of Standardized Mixture derived from S12 PoL and EPA Concentrate

| | | S12 PoL Concentrate | | S12 EPA Concentrate | | Standardized Mixture | |
|---|---|---|---|---|---|---|---|
| Class Component Name | Code | Relative Basis % | Extract Basis % | Relative Basis % | Extract Basis % | Relative Basis % | Extract Basis % |
| Phospholipid | | | | | | | |
| Phosphatidylcholine | PC | 45.1 | 7.42 | | 0.00 | 45.1 | 4.80 |
| Lyso-Phosphatidylcholine | 2-LPC | 0.0 | 0.00 | | 0.00 | 0.0 | 0.00 |

TABLE 24-continued

| Polar Lipid and Phytonutrient Profile of Standardized Mixture derived from S12 PoL and EPA Concentrate | | | | | | | |
|---|---|---|---|---|---|---|---|
| | | S12 PoL Concentrate | | S12 EPA Concentrate | | Standardized Mixture | |
| Class<br>Component Name | Code | Relative Basis % | Extract Basis % | Relative Basis % | Extract Basis % | Relative Basis % | Extract Basis % |
| Phosphatidylinositol | PI | 0.0 | 0.00 | | 0.00 | 0.0 | 0.00 |
| Phosphatidylethanolamine | PE | 0.0 | 0.00 | | 0.00 | 0.0 | 0.00 |
| Phosphatidylglycerol | PG | 25.1 | 4.13 | | 0.00 | 25.1 | 2.67 |
| | Other | 29.8 | 4.90 | | 0.00 | 29.8 | 3.17 |
| Glycolipid | | | | | | | |
| Digalactosyldiacylglycerol | DGDG | 72.1 | 21.97 | | 0.00 | 72.1 | 14.22 |
| Monogalactosyldiacylglycerol | MGDG | 27.9 | 8.50 | | 0.00 | 27.9 | 5.50 |
| Phytonutrients | | | | | | | |
| Phytosterols | | | 0.35 | | 0.85 | | 0.53 |
| Chlorophyll | | | 16.50 | | 1.20 | | 11.10 |
| Other Constituents | | | | | | | |
| Mannitol | | | 2.97 | | 0.00 | | 1.92 |
| Free Glycerol | | | 0.20 | | 0.00 | | 0.13 |
| Total Phospholipids (PL) (wt %) | | | 16.45 | | 0.00 | | 10.64 |
| Total Glycolipids (GL) (wt %) | | | 30.47 | | 0.00 | | 19.72 |
| Total PoL (PL + GL) (wt %) | | | 46.92 | | 0.00 | | 30.36 |

In Table 24, the polar lipid and phytonutrient composition is shown. The PL and GL are associated with the PoL concentrate. There is zero PL and GL in the EPA concentrate. Phytosterols have a higher concentration in the EPA concentrate. This is characteristic of SCCO2 fractionated material, as carotenoids are highly soluble in SCCO2. The standardized mixture contains a total of 10.6 wt % total PL and 19.7 wt % total GL.

These are typical values. The PL constituents always contain PC and PG. Other PLs that can exist in the mixture are 2 LPC, PI, and PE. PC and PG is typically greater than 30 wt % and 15 wt %, respectively, of the PL constituents. The ratio of GL to PL can vary from 0.75 to 4.0, with typical values being in the range from 1.5 to 2.5. The GL always contains DGDG and MGDG. Typically, DGDG is greater than 50 wt % of the GL with more typical values of 50 wt %, 05 wt %, 60 wt %, 65 wt %, 70 wt %, 75 wt %, or 80 wt %. The standardized mixture contains at least 0.1 wt % phytosterols, with a typical range between 0.25 wt % and 0.75 wt %. Chlorophyll is present in larger quantities. A value of 11.1 wt % is typical. Chlorophyll levels are no less than 1 wt % of the standardized mixture and more typically 5 wt %, 6 wt %, 7 wt %, 8 wt %, 9 wt %, 10 wt %, 11 wt %, 12 wt %, 13 wt %, 14 wt %, or 15 wt % of the mixture. Furthermore, the chlorophyll would most commonly be in the range from 8 to 12 wt %. The amount of mannitol in the blend is between 0.1 wt % and 3.0 wt %. A typical value is around 2 wt % and more typically 0.5 wt %, 1.0 wt %, 1.5 wt %, or 2.0 wt %.

Figure 14:
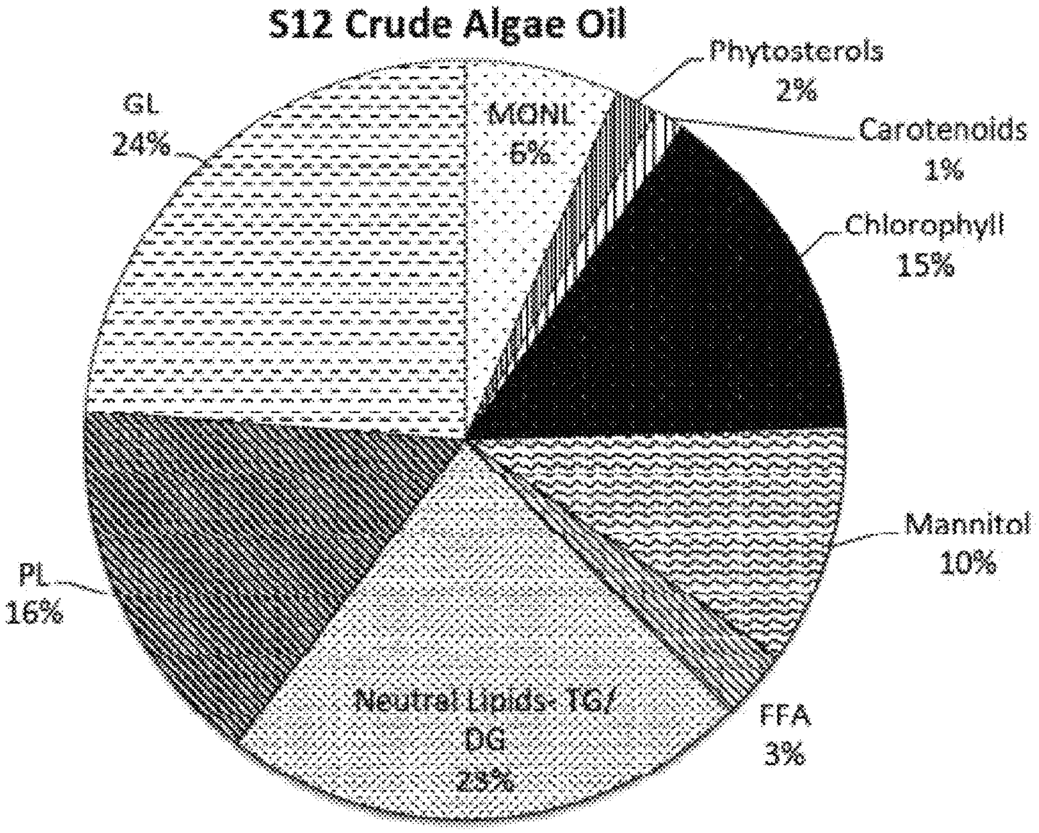
FIG. 14 illustrates a typical composition of S12 crude algae oil.
Figure 15:
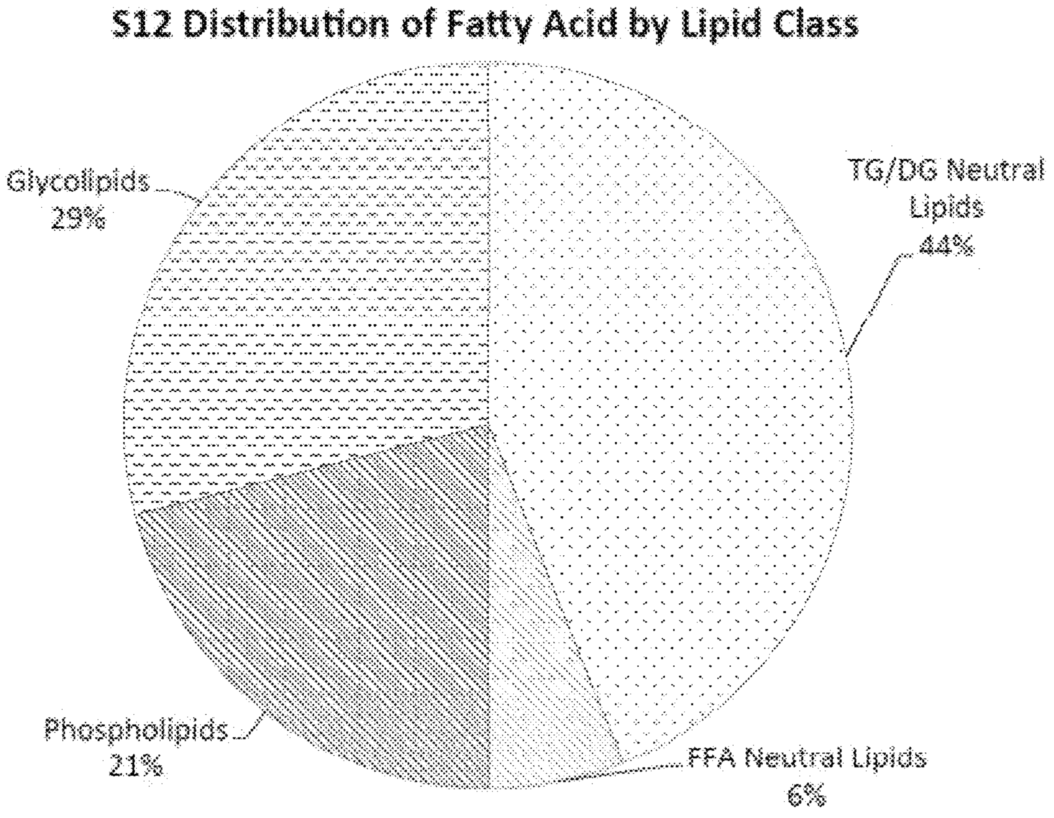
FIG. 15 illustrates a typical distribution of fatty acid by lipid class in S12 crude algae oil.
Figure 16:
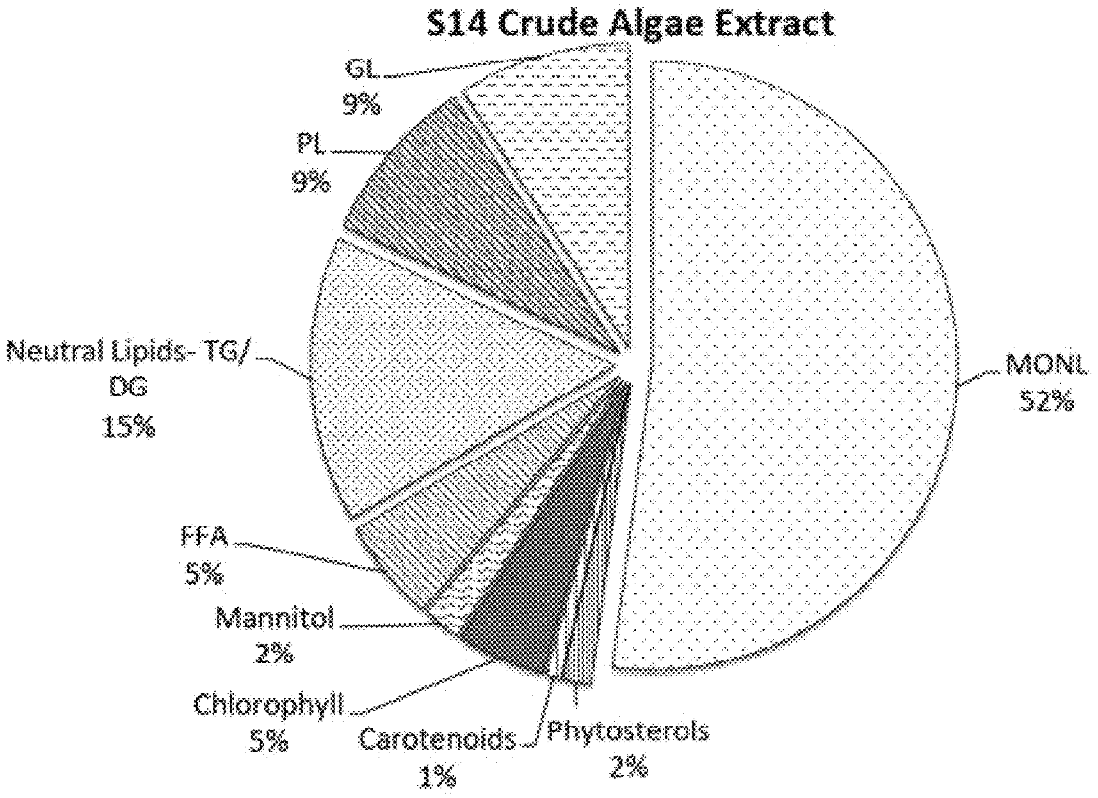
FIG. 16 illustrates a typical composition of S14 crude algae extract.

The constituents of a typical embodiment of the standardized mixture are shown in FIG. 14. The formulation includes PL, GL, NL as TG and DG, and NL as FFA. EPA is distributed between all of these lipid classes. The mixture contains minor components of phytonutrients, including chlorophyll, mannitol, phytosterols, and carotenoids. The distribution of fatty acids among the different lipid classes is shown in FIG. 15, with 53 wt % as FFA, 9 wt % as Neutral TG and DG, 16 wt % as PL, and 22 wt % as GL. The FFA fraction could be as low as 30 wt % and as high as 60 wt %, with more typical values being 40 wt %, 45 wt %, 50 wt %, and 55 wt %. Type NL as TG/DG fraction could be as low as 1 wt % and as high as 14%. Typical values are 5 wt %, 6 wt %, 7 wt %, 8 wt %, 9 wt %, and 10 wt %. PL could vary in the range from 5% to 30%, with typical values being 12 wt %, 14 wt %, 16 wt %, 18 wt %, and 20 wt %. GL could vary on the range from 10 wt % to 40 wt %, with typical values of 16 wt %, 18 wt %, 20 wt %, 22 wt %, 24 wt %, and 26 wt %.

Example 2

Streamlined Processing Method

This example summarizes a streamlined method for producing the present EPA formulations that takes advantage of the improvements in the cultivation of *Nannochloropsis* biomass that raises the EPA fraction in the fatty acid profile of the algal biomass to greater than 35 wt %. Under this scenario both the polar lipids and the neutral lipids have enhanced EPA content. A schematic of the methodology is depicted in FIG. 6. Generally, this process eliminates the step of subjecting the CAO to SCCO2 extraction to split the CAO into a neutral lipid fraction and a polar lipid fraction. Instead, a first portion of the CAO is subject to hydrolysis and free fatty acid fractionation and the second portion of the CAO is included directly in the final blended EPA formulation. Generally, the first portion and the second portion of the CAO are about equal, or have a volume ratio in the range of about 3:1 to about 1:3.

As described in Example 1, an organic solvent comprised from the genera of ketones and alcohols and mixtures thereof, is used to create CAE from the wet algal biomass. The solid content of this wet biomass is greater than 17 wt. %.

After recovery from the solvent, the resultant CAE can be solubilized in methanol and then added to a liquid-liquid partitioning system. A typical solvent combination would be heptane (Hep), ethyl acetate (EtAc), methanol (MeOH), and water ($H_2O$) in the volume ratio of 1:1:1:1. The mixture is agitated and allowed to settle. The material splits into an upper organic layer dominated by the Hep and EtAc and lower aqueous layer comprised of MeOH and $H_2O$. The neutral and polar lipids, sterols, and cholesterol have a much higher distribution coefficient for the organic layer and predominantly remain in the organic layer. Water-soluble carbohydrates including mannitol, water-soluble proteins, and glycerol predominantly go into solution within the aqueous layer.

In varying embodiments liquid-liquid partitioning can employ alternate environmentally friendly organic solvents for any one of the Hep, EtAc, MeOH, or $H_2O$ components. Illustrative environmentally friendly solvents include without limitation water, acetone, ethanol, 2-propanol, 1-propanol, ethyl acetate, isopropyl acetate, methanol, methyl ethyl ketone (MEK), 1-butanol, and t-butanol. Other solvents of use for liquid-liquid partitioning include liquid of cyclohexane, heptane, toluene, methylcylcohexane, methyl t-butyl ether, isooctane, acetonitrile, 2-methyltetrahydrofuran, tetrahydrofuran (THF), xylenes, dimethyl sulfoxide (DMSO), acetic acid, and ethylene glycol.

As a typical example of liquid partitioning, 11.9 g of CAE was dissolved in 33 mL of MeOH. This solution was then added to a mixture of 125 mL of EtAc and 125 mL of Hep. The combination was mixed well in a separation funnel. 125 mL of $H_2O$ was added to this mixture and further agitated. The system was allowed to settle into two phases: an upper organic layer and a lower aqueous layer.

The composition of the feed material was a typical CAE:

Moisture: 1.40 wt %
FFA=5 wt %
Total Fatty Acid (TFA): 36.4 wt %
EPA in mixture: 14.6 wt %
EPA in fatty acid (FA): 40.8%
Total PL: 9.1 wt %
Total GL: 14.9 wt %
Total Polar Lipids (PoL): 24.0 wt %
Cholesterol/phytosterols: 1.0 wt %
Chlorophyll: 11.8 wt %
Mannitol: 7.3 wt %
Glycerol 0.4 wt %

After recovery of the solvent, the organic phase contained the recovered CAO. This was 66.2 wt % of the feed materials. It had the following solvent-free constituents:

Moisture: less than 1.76 wt %
FFA=21.6 wt %
TFA: 51.6 wt %
EPA: 18.5 wt %
EPA in FA: 35.9%
Total PL: 14.3 wt %
Total GL: 21.9 wt %
Total PoL: 36.2 wt %
Phytosterols: 5.4 wt %
Chlorophyll: 5.4 wt %
Mannitol: 0.0 wt %
Glycerol 0.0 wt %

The recovery of the EPA in the organic layer was 95.9 wt %. The EPA content in this CAO is greater than 15 wt % and total PoL is greater than 25 wt %. Because the feed material has a high EPA content, this CAO can serve, without further processing, as concentrated PoL for forming the Standardized EPA blend.

After evaporation of solvent (including water), the aqueous layer (41.3% of feed) had the following constituents:

Moisture: greater than 1.03 wt %
FFA=32.0 wt %
TFA: 3.14 wt %
EPA: 1.27 wt %
EPA in FA: 40.6%
Total PL: 2.3 wt %
Total GL: 2.0 wt %
Total PoL: 4.3 wt %
Phytosterols: 0.02 wt %
Chlorophyll: 0.3 wt %
Mannitol: 5.8 wt %
Glycerol 2.2 wt %

There was 4.1% loss of EPA into the aqueous layer.

With this CAO, we have the option to either hydrolyze the CAO directly (as shown in FIG. 6) or to hydrolyze a portion of the CAE. In either case, all hydrolyzed lipid classes are converted into FFA. This FFA is then pressure profile fractionated to preferentially remove a high-EPA fraction. This is concentrated EPA FFA (or EPA-FFA). Knowing both composition of the CAO and the EPA-FFA, the mass ratios can be determined to create a standardized EPA formulation.

Example 3

Distribution of Lipid and Metabolites in Rat Tissues

The objective of the rat study was to examine the digestibility and distribution of lipids and metabolites in rat organs, including plasma, brain, liver, retroperitoneal adipose, and gonadal adipose tissue after a seven day feed trial supplemented with krill or EicoOil. In this study, two groups of Sprague Dawley male and female rats were subjected to gavage feeding with krill and EicoOil. Krill oil was NOW Food Supplements Krill Oil containing Neptune Krill Oil (NKO) by Neptune BioTech Ltd, Canada that was 23 wt % total Omega-3 with 13 wt % EPA and 7.5 wt % DHA and 39 wt % phospholipids. EicoOil is a polar and EPA formulation derived from *Nannochloropsis oculata* extract that has total Omega-3 of about 25 wt % EPA in a variety of lipid classes and about 15 wt % polar lipids comprised of a combination of glycolipids (about 10 wt %) and phospholipids (about 5 wt %), at about a 2:1 ratio. EicoOil has 0 wt % DHA.

In the study, equal numbers of rats were male and female. Typical body weight was in the range of 200-250 g at study initiation. The minimum and maximum weight of individual animals was within the range of ±20% of the group mean weight. The rats were acclimatized for the five days prior to the feeding trial. Animals were fed ad libitum a commercial rodent diet (Teklad Certified Global 18% Protein Diet (Cat #: 2018SC), Madison, Wis., USA), a diet containing 18.6% crude protein, 6.2% crude fat, 44.2% carbohydrate, 3.5% crude fiber, 14.7% neutral detergent fiber, and 5.3% ash. The commercial rodent diet contained 0.9 wt % saturated fatty acid, 1.3 wt % monounsaturated fatty acid, and 3.4 wt % polyunsaturated fatty acid. Major fatty acid components were 0.7 wt % palmitic (C16:0), 0.2 wt % stearic (C18:0), 1.2 wt % oleic (C18:1ω9), 3.1 wt % linoleic (C18:2ω6), and 0.3 wt % alpha-linolenic (C18:3ω3). Animals were given free access to acidified drinking water (pH between 2.5 and 3.5) obtained from the municipal water supply. Animals were housed in a climate controlled environment with a temperature range between 20-24° C. and a relative humidity of 30-70% with a 12 hour light and 12 hour dark cycle.

The animals were fed 5 mL of oil per kg body weight. Total EPA plus DHA concentration in krill oil is 230 mg/g. Total EPA plus DHA in EicoOil is 250 mg/g. The total amount of oil fed to each rat over seven days is 35 mL/kg body weight. For krill oil (density of 0.9 g/mL), this was 31.5 g oil and 7.245 g of total EPA+DHA, both on a per kg body weight basis. For EicoOil (density of 0.836 g/mL), this was 29.3 g oil and 7.315 g of total EPA+DHA, both on a per kg body weight basis. For both krill oil and EicoOil, the dosage was further diluted 1:1 with olive oil at 37° C.

Animals were divided into two groups (A and B), each with five female and five male rats. Prior to feeding with the Omega-3 supplemented diet, both groups were acclimatized for five days. Group A was gavage fed krill oil for days 0 through 6 of the study. Group B was gavage fed EicoOil for days 0 through 6 of the study. In all cases gavage feed was done in the morning hours (8:00-10:00 AM). On day 7, animals were sacrificed and blood collected through cardiac puncture. The brain, liver, gonadal adipose tissue, and retroperitoneal adipose tissue were also collected. Blood was centrifuged in EDTA-containing tubes for 15 minutes at 5000 RPM at 4° C. The upper layer (plasma) was separated via pipet and placed in a sample collection tube. Plasma and organs were stored at 80° C. until the time of analysis. Plasma and Organs were process via Folch extraction to recover the lipids and converted to methyl esters for fatty acid methyl ester (FAME) analysis via AOAC method 963.22. Results were expressed on an organ weight basis as μg fatty acid per 100 mg of tissue.

Figure 17:
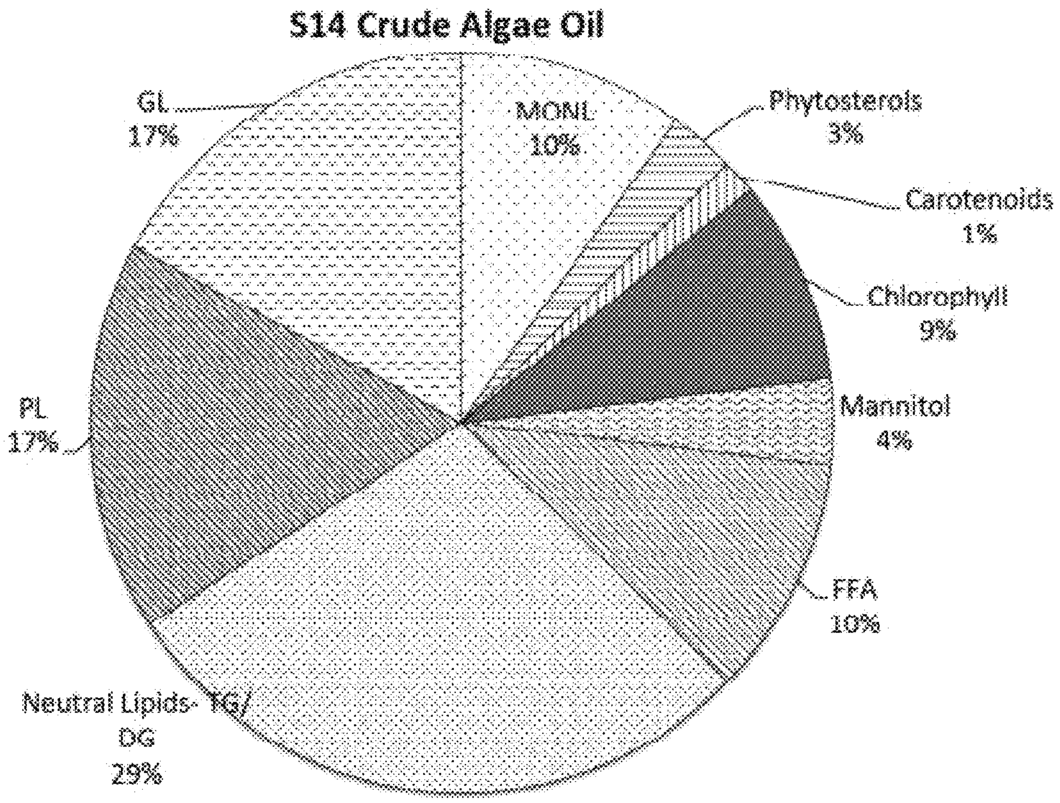
FIG. 17 illustrates a typical composition of S14 crude algae oil.

The results of the analysis are given in Tables 25-29 and depicted in FIG. 17 for fatty acid concentration in the blood plasma, brain, liver, gonadal adipose tissue, and retroperitoneal adipose tissue, respectively. One female rat in the krill oil group died from causes unrelated to the test prior to the conclusion of the feeding trial. Results are given as the sum of EPA and Docosapentaenoic acid (DPA) (C22:5ω3), designated as EPA*. DPA is directly synthesized from EPA in vivo. Total Omega-3 focuses on the content of EPA*+DHA in the organs. Results for male and female rats were combined. Data were analyzed using the SAS® version 9.1 (SAS Institute, Cary, N.C., USA) by MediStat Ltd. (Israel). The two sample T test and non-parametric Wilcoxon Mann Whitney Rank sum test for independent samples were applied for testing the statistical significance of the difference in all variables between Krill oil and EicoOil. All tests were two tailed, and a p-value of 0.05 or less was considered statistically significant.

The results show that there is no statistically significant difference between the update of EPA and DHA from EicoOil and NOW NKO krill oil. EicoOil has similar absorption coefficients into the tissue of rats as krill oil. Most importantly, the polar lipids in EicoOil, i.e. the combination of phospholipids and glycolipids, act in a similar way to the phospholipids in krill oil in transporting the fatty acids across the intestinal barrier and into the blood plasma and, subsequently, depositing the fatty acid in the various tissues examined. Moreover, since the amount of polar lipid in the EicoOil was 15% of the EicoOil versus 39% in the krill oil, it appears that the combination of glycolipid and phospholipids appears to enable a lower amount of combined polar lipid to enhance Omega-3 uptake in rat organs versus the phospholipid only in krill.

TABLE 25

Distribution of EPA* and DHA in Plasma

| Concentration (μg fatty acid PER 100 MG Tissue) | Krill N | Krill Mean | Krill Std | Krill Min | Krill Median | Krill Max | Krill Lower 95% CI | Krill Upper 95% CI | Algae N | Algae Mean | Algae Std |
|---|---|---|---|---|---|---|---|---|---|---|---|
| EPA | 8 | 5.22 | 1.59 | 3.53 | 4.87 | 7.24 | 3.89 | 6.55 | 8 | 9.80 | 4.23 |
| DPA | 8 | 1.24 | 1.71 | 0.00 | 0.84 | 5.06 | −0.19 | 2.67 | 8 | 0.86 | 1.01 |
| DHA | 8 | 3.48 | 1.23 | 1.86 | 3.74 | 5.38 | 2.46 | 4.51 | 8 | 1.31 | 0.60 |
| EPA + DPA | 8 | 6.46 | 1.82 | 3.71 | 6.75 | 8.93 | 4.94 | 7.99 | 8 | 10.66 | 4.95 |
| Total Omega-3 | 8 | 9.95 | 2.19 | 6.38 | 10.29 | 12.63 | 8.12 | 11.78 | 8 | 11.97 | 5.44 |

| Concentration (μg fatty acid PER 100 MG Tissue) | Algae Min | Algae Median | Algae Max | Algae Lower 95% CI | Algae Upper 95% CI | P-value from T-test * | P-value from Wilcoxon test * |
|---|---|---|---|---|---|---|---|
| EPA | 5.53 | 8.67 | 19.07 | 6.26 | 13.34 | 0.0188 | 0.0139 |
| DPA | 0.00 | 0.42 | 2.53 | 0.02 | 1.70 | 0.5953 | 0.8322 |
| DHA | 0.51 | 1.42 | 2.13 | 0.81 | 1.81 | 0.0005 | 0.0091 |
| EPA + DPA | 6.22 | 8.74 | 20.91 | 6.52 | 14.79 | 0.0514 | 0.0585 |
| Total Omega-3 | 6.94 | 9.87 | 23.04 | 7.42 | 16.51 | 0.3543 | 0.7183 |

TABLE 26

Distribution of EPA* and DHA in Brain

| Concentration (μg fatty acid PER 100 MG Tissue) | Krill N | Krill Mean | Krill Std | Krill Min | Krill Median | Krill Max | Krill Lower 95% CI | Krill Upper 95% CI | Algae N | Algae Mean | Algae Std |
|---|---|---|---|---|---|---|---|---|---|---|---|
| EPA | 9 | 2.14 | 1.01 | 0.99 | 2.26 | 4.03 | 1.37 | 2.92 | 9 | 3.17 | 1.4 |
| DPA | 9 | 10.08 | 9.29 | 3.39 | 5.53 | 26.54 | 2.94 | 17.23 | 9 | 7.93 | 2.19 |

TABLE 26-continued

Distribution of EPA* and DHA in Brain

| | | | | | | | | | | | |
|---|---|---|---|---|---|---|---|---|---|---|---|
| DHA | 9 | 202.8 | 79.56 | 120.1 | 172.7 | 371.4 | 141.6 | 263.9 | 9 | 210.2 | 62.88 |
| EPA + DPA | 9 | 12.23 | 9.59 | 4.38 | 9.56 | 29.32 | 4.86 | 19.6 | 9 | 11.1 | 2.96 |
| Total Omega-3 | 9 | 215 | 81.62 | 127.4 | 200.8 | 381.1 | 152.2 | 277.7 | 9 | 221.3 | 65.31 |

| Concentration (µg fatty acid PER 100 MG Tissue) | Algae Min | Median | Max | Lower 95% CI | Upper 95% CI | P-value from T-test * | P-value from Wilcoxon test * |
|---|---|---|---|---|---|---|---|
| EPA | 1.35 | 2.93 | 5.51 | 2.09 | 4.24 | 0.0951 | 0.1117 |
| DPA | 4.78 | 7.79 | 11.44 | 6.25 | 9.61 | 0.5166 | 0.5447 |
| DHA | 141.4 | 204.1 | 313.3 | 161.9 | 258.6 | 0.8275 | 0.6031 |
| EPA + DPA | 7.48 | 10.43 | 15.65 | 8.82 | 13.37 | 0.7433 | 0.3895 |
| Total Omega-3 | 148.8 | 217.4 | 329 | 171.1 | 271.5 | 0.8575 | 0.7283 |

TABLE 27

Distribution of EPA* and DHA in Liver

| Concentration (µg fatty acid PER 100 MG Tissue) | Krill N | Mean | Std | Min | Median | Max | Lower 95% CI | Upper 95% CI | Algae N | Mean | Std |
|---|---|---|---|---|---|---|---|---|---|---|---|
| EPA | 9 | 90.9 | 38.2 | 51.9 | 74.0 | 172.5 | 61.6 | 120.2 | 9 | 116.1 | 33.28 |
| DPA | 9 | 69.2 | 23.8 | 35.7 | 73.0 | 111.1 | 50.9 | 87.5 | 9 | 116.2 | 35.66 |
| DHA | 9 | 274.1 | 119.3 | 90.52 | 315.3 | 438.4 | 182.4 | 365.8 | 9 | 112.8 | 70.21 |
| EPA + DPA | 9 | 160.1 | 60.4 | 87.5 | 147.0 | 283.6 | 113.6 | 206.5 | 9 | 232.3 | 60.7 |
| Total Omega-3 | 9 | 434.2 | 170.2 | 178 | 469.3 | 671.9 | 303.3 | 565 | 9 | 345.1 | 113.5 |

| Concentration (µg fatty acid PER 100 MG Tissue) | Algae Min | Median | Max | Lower 95% CI | Upper 95% CI | P-value from T-test * | P-value from Wilcoxon test * |
|---|---|---|---|---|---|---|---|
| EPA | 70.6 | 128.1 | 157.7 | 90.53 | 141.7 | 0.1547 | 0.1517 |
| DPA | 74.52 | 105.7 | 175.5 | 88.79 | 143.6 | 0.0046 | 0.0140 |
| DHA | 51.61 | 80.24 | 241.3 | 58.8 | 166.7 | 0.0030 | 0.0140 |
| EPA + DPA | 155.2 | 202.6 | 319.9 | 185.7 | 279.0 | 0.0223 | 0.0243 |
| Total Omega-3 | 217.7 | 293.4 | 561.2 | 257.8 | 432.3 | 0.2100 | 0.2669 |

TABLE 28

Distribution of EPA* and DHA in Gonadal Adipose Tissue

| Concentration (µg fatty acid PER 100 MG Tissue) | Krill N | Mean | Std | Min | Median | Max | Lower 95% CI | Upper 95% CI | Algae N | Mean | Std |
|---|---|---|---|---|---|---|---|---|---|---|---|
| EPA | 9 | 45.3 | 24.3 | 21.7 | 37.8 | 96.6 | 26.6 | 63.99 | 9 | 74.08 | 45.16 |
| DPA | 9 | 23.2 | 10.1 | 10.6 | 21.5 | 40.3 | 15.4 | 30.9 | 9 | 29.66 | 19.18 |
| DHA | 9 | 52.1 | 21.7 | 26.2 | 53.7 | 89.4 | 35.4 | 68.7 | 9.0 | 21.8 | 12.6 |
| EPA + DPA | 9 | 68.5 | 33.8 | 34.4 | 58.9 | 136.9 | 42.5 | 94.4 | 9 | 103.7 | 64.1 |
| Total Omega-3 | 9 | 120.5 | 54.61 | 61.11 | 112.8 | 226.3 | 78.52 | 162.5 | 9 | 125.5 | 75.84 |

| Concentration (µg fatty acid PER 100 MG Tissue) | Algae Min | Median | Max | Lower 95% CI | Upper 95% CI | P-value from T-test * | P-value from Wilcoxon test * |
|---|---|---|---|---|---|---|---|
| EPA | 29.62 | 59.1 | 164.2 | 39.38 | 108.8 | 0.1115 | 0.1758 |
| DPA | 12.57 | 20.7 | 72.59 | 14.91 | 44.4 | 0.3818 | 0.7283 |
| DHA | 9.3 | 19.3 | 52.0 | 12.1 | 31.5 | 0.0023 | 0.0066 |

TABLE 28-continued

| Distribution of EPA* and DHA in Gonadal Adipose Tissue | | | | | | | |
|---|---|---|---|---|---|---|---|
| EPA + DPA | 42.2 | 79.8 | 236.8 | 54.4 | 153.0 | 0.1635 | 0.2669 |
| Total Omega-3 | 53.47 | 98.34 | 288.8 | 67.23 | 183.8 | 0.8738 | 0.9307 |

TABLE 29

Distribution of EPA* and DHA in Retroperitoneal Adipose Tissue

| Concentration (µg fatty acid PER 100 MG Tissue) | Krill N | Krill Mean | Krill Std | Krill Min | Krill Median | Krill Max | Krill Lower 95% CI | Krill Upper 95% CI | Algae N | Algae Mean | Algae Std |
|---|---|---|---|---|---|---|---|---|---|---|---|
| EPA | 9 | 116.5 | 114.6 | 35.6 | 45.4 | 346.1 | 28.4 | 204.5 | 9 | 387.1 | 203.1 |
| DPA | 9 | 48.9 | 47.7 | 11.9 | 18.1 | 129.2 | 12.2 | 85.5 | 9 | 111.7 | 41.41 |
| DHA | 9 | 145.0 | 163.5 | 30.0 | 43.0 | 459.5 | 19.3 | 270.7 | 9.0 | 56.6 | 22.1 |
| EPA + DPA | 9 | 165.3 | 161.7 | 50.2 | 61.0 | 475.3 | 41.0 | 289.7 | 9 | 498.8 | 242.7 |
| Total Omega-3 | 9 | 510.3 | 135.2 | 81.34 | 104 | 934.7 | 60.33 | 560.3 | 9 | 555.4 | 142.6 |

| Concentration (µg fatty acid PER 100 MG Tissue) | Algae Min | Algae Median | Algae Max | Algae Lower 95% CI | Algae Upper 95% CI | P-value from T-test * | P-value from Wilcoxon test * |
|---|---|---|---|---|---|---|---|
| EPA | 106.7 | 419.9 | 717.4 | 231 | 543.2 | 0.0031 | 0.0117 |
| DPA | 43.74 | 119.8 | 162.9 | 79.84 | 143.5 | 0.0088 | 0.0243 |
| DHA | 35.7 | 43.8 | 94.1 | 39.7 | 73.6 | 0.1454 | 1.0000 |
| EPA + DPA | 150.4 | 558.0 | 880.3 | 312.2 | 685.4 | 0.0034 | 0.0117 |
| Total Omega-3 | 186.1 | 643.1 | 924 | 368.9 | 741.9 | 0.0888 | 0.0953 |

Example 4

Human Subject Bioavailability Study

The human pilot trial was an open label, single dose, two way crossover study of two different Omega-3 fatty acid products from algal and krill sources to assess the bioavailability and disposition of Omega 3 fatty acids in healthy male volunteers. The study's objective was to evaluate the pharmacokinetic signal after a single dose of Omega-3 formulation (EicoOil) derived from algae compared to a single dose of an Omega-3 formulation (Krill) based on a krill source over the first 10 hours with respect to the concentrations of EPA and DHA in the plasma lipids. EicoOil is a polar and EPA formulation derived from *Nannochloropsis Oculata* extract that has total Omega-3 of about 25 wt % mostly in the EPA form and in a variety of lipid classes and about 15 wt % polar lipids comprised of a combination of glycolipids (about 10 wt %) and phospholipids (about 5 wt %), at about a 2:1 ratio. EicoOil has 0 wt % DHA. Krill oil was NOW Food Supplements Krill Oil containing Neptune Krill Oil (NKO) by Neptune Technologies and Bioresources Inc., Canada that was 23 wt % total Omega-3 with 13 wt % EPA and 7.5 wt % DHA and 39 wt % phospholipids.

Ten adult, healthy, non-smoking male volunteers were recruited for the study. Each volunteer was screened by the investigator for the study based on series of inclusion and exclusion criterion according to Tables 30 and 31. Prior to the test periods, patients were evaluated for medical history, concomitant medications, physical examination, height/weight/body mass index, vital signs, ECG, clinical laboratory analysis. The clinical laboratory analysis was administered prior to the test period with the tests listed in Table 32. Volunteers were required to not take over-the-counter (OTC) or herbal medications. Furthermore, medications known to influence Omega-3 fatty acid levels or to control inflammation were not allowed during the wash-out or dosing periods. All volunteers were given dietary instructions prior to the start of the test periods, including the avoidance of consumption of oily fish during a wash out period prior to each dosing date.

TABLE 30

| Inclusion Criteria |
|---|
| 1. Subject is male, 18-45 years of age, inclusive. |
| 2. Subject has a body mass index (BMI) of ≥20 and ≤32 $kg/m^2$ at screening. |
| 3. Subject is non-smoker. |
| 4. Subject is judged by the investigator to be in general good health on the basis of medical history, laboratory values, physical examination, vital signs and 12-lead electrocardiogram. |
| 5. Subject is willing to adhere to the study protocol |
| 6. Subject understands the study procedures and signs forms providing informed consent to participate in the study. |

TABLE 31

| Exclusion Criteria |
|---|
| 1. Clinical relevant abnormal laboratory test results at screening (at the discretion of the investigator). |
| 2. Subject has a history or presence of clinically important metabolic, endocrine, cardiovascular, hepatic, renal, hematologic, immunologic, neurologic, psychiatric or biliary disorders. |
| 3. Existing Diabetes (type 1 or type 2). |

TABLE 31-continued

| Exclusion Criteria |
|---|
| 4. Subject has a history or presence of clinically important chronic gastrointestinal disorders (e.g. inflammatory bowel disease (IBD), irritable bowel syndrome (IBS), celiac disease, cancer). |
| 5. Recent history of (within 12 months of screening) of strong potential for alcohol or substance abuse. Alcohol abuse is defined as >21 drinks per week for males (1 drink = 340 ml beer, 142 ml wine, or 4 cl distilled spirits). |
| 6. Subject is consuming more than one oily fish meal per week. |
| 7. Use of any prescription drug within 2 weeks before Day 1 and use of any OTC drug within 1 week before Day 1. |
| 8. Use of any medication within four weeks of Day 1 and throughout the study, with the potential to control inflammation. |
| 9. Use of any medication within four weeks of Day 1 and throughout the study, with the potential to alter lipid concentrations. |
| 10. Consumption of fish oil or other oil supplements within 3 weeks before Day 1 and throughout the study. |
| 11. Participation in another clinical trial 30 days prior to the Day 1. |
| 12. Known allergy or sensitivity to omega-3 fatty acids, fish, other seafood, or any ingredient in the study drugs. |
| 13. Individual has a condition the investigator believes would interfere with his or her ability to provide informed consent, comply with the study protocol, which might confound the interpretation of the study results, or put the subject at undue risk. |

TABLE 32

| Clinical Laboratory Analysis |
|---|
| Hematology: hemoglobin, hematocrit, RBC, WBC with differential leukocyte count (neutrophils, eosinophils, basophils, monocytes, lymphocytes) |
| Clinical Chemistry: AST, ALT, GGT, alkaline phosphatase, total bilirubin, total cholesterol, HDL, LDL, triglyceride, total protein, albumin, BUN, creatinine, sodium, potassium, chloride, calcium, phosphorous, LDH |
| Serology: HIV, HBsAG and HCVAB |
| Alcohol Breath Test |
| Urinalysis: dipstick with pH, specific gravity, protein, glucose, ketones, bilirubin, occult blood, nitrite, urobilinogen |
| Urine Drug Screening: barbiturates, opiates, amphetamines, cocaine, cannabis, and benzodiazepines. |

Throughout the study, volunteers were monitored for adverse events (AE), an untoward medical occurrence in a patient or clinical investigation subject administered a product or device and which does not necessarily have a causal relationship with this treatment. An AE could be any unfavorable or unintended sign (including an abnormal laboratory finding), symptom, or disease temporally associated with the use of a produce or device, whether or not related to the product or device. No AEs occurred during this pilot study.

The ten healthy male subjects were randomized (1:1) to one of two treatment sequences: 7 day wash out period, one dose of either Krill or EicoOil, a 7 day wash out period, and one dose of EicoOil or Krill. Over the sixteen day study period, each subject was administered both Krill and EicoOil. In both treatment A and B, the dose was 1.5 g total Omega-3 in the form of soft gel capsules. Possible bias in assignment of subjects to treatments was avoided by the randomized allocation of the subjects to the treatment sequence.

Prior to each single dose, the subjects arrived at the test location in a fasted state. After evaluation for concomitant medication, adverse events and vital signs, each subject was given a single oral dose of the investigational product during a standardized high fat breakfast comprised of toast with jam or marmalade (to provide carbohydrate) and a milkshake made from milkshake powder, double cream, oils, and water to provide fat and protein. The net composition is given in Table 33.

TABLE 33

| High Fat Breakfast Content | |
|---|---|
| Total fat (g) | 55.1 |
| Total carbohydrate (g)* | 130.0 |
| Total protein (g)* | 12.0 |
| Total energy (kJ) | 4.3 |
| **Major sources of fatty acids** | |
| Safflower oil (mL) | 8.8 |
| Double cream (mL) | 47.6 |
| Linseed oil (mL) | 1.8 |
| Olive oil (mL) | 6.9 |
| **Fatty Acid composition (%)** | |
| Lauric acid (C12:0) | 1.8 |
| Myristic acid (C14:0) | 6.3 |
| Palmitic acid (C16:0) | 21.5 |
| Palmitoleic acid (C16:1) | 1.5 |
| Stearic acid (C18:0) | 8.4 |
| Oleic acid (C18:1ω9) | 34.0 |
| Linoleic acid (C18:2ω6) | 22.1 |
| Alpha-linolenic acid (C18:3ω3) | 3.7 |

As part of the high-fat breakfast, each subject was administered 1.5 of Omega-3 fatty acids. Capsules were swallowed with 200 mL of water. A mouth check was carried out to ensure the product was swallowed. Subjects were permitted to drink water or tea but no other liquids until the last blood sample was collected. A standardized low fat snack was provided six hours after the breakfast.

On each dosing day, twelve blood samples of 7.5 mL each were taken from each volunteer for pharmacokinetic (PK) analysis. Blood samples were taken pre dose and 0.5, 1, 1.5, 2, 2.5, 3, 4, 5, 6, 8, and 10 hours after dosing. Each blood sample was collected into a lithium heparin tube. Samples were centrifuged at 1500 g at room temperature for 15 minutes. Plasma was pipetted into 4×0.5 mL aliquots and stored at −80° C. Samples were shipped on dry ice to the analytical laboratory.

Figure 18:
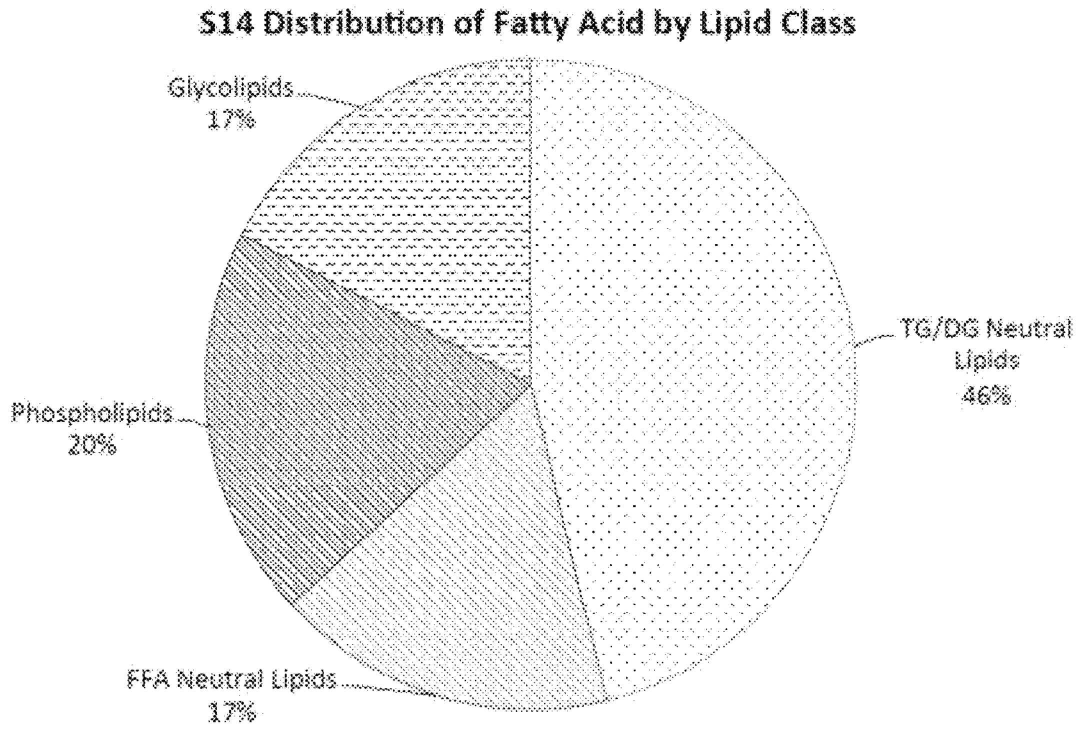
FIG. 18 illustrates a typical distribution of fatty acid by lipid class in S14 crude algae oil.
Figure 19:
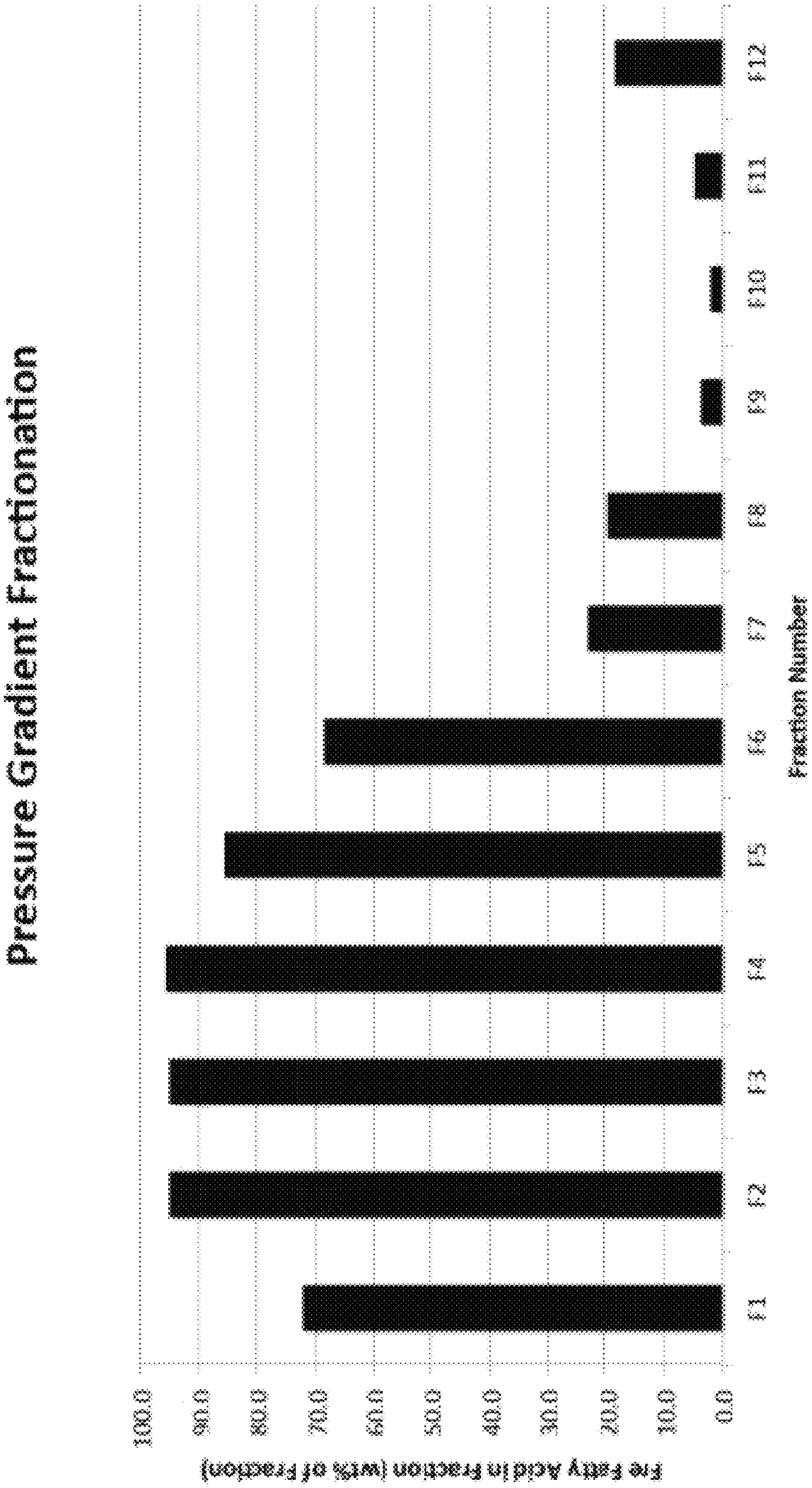
FIG. 19 illustrates free fatty acid (FFA) content of supercritical carbon dioxide fractionated partially hydrolyzed S14 neutral lipids.
Figure 20:
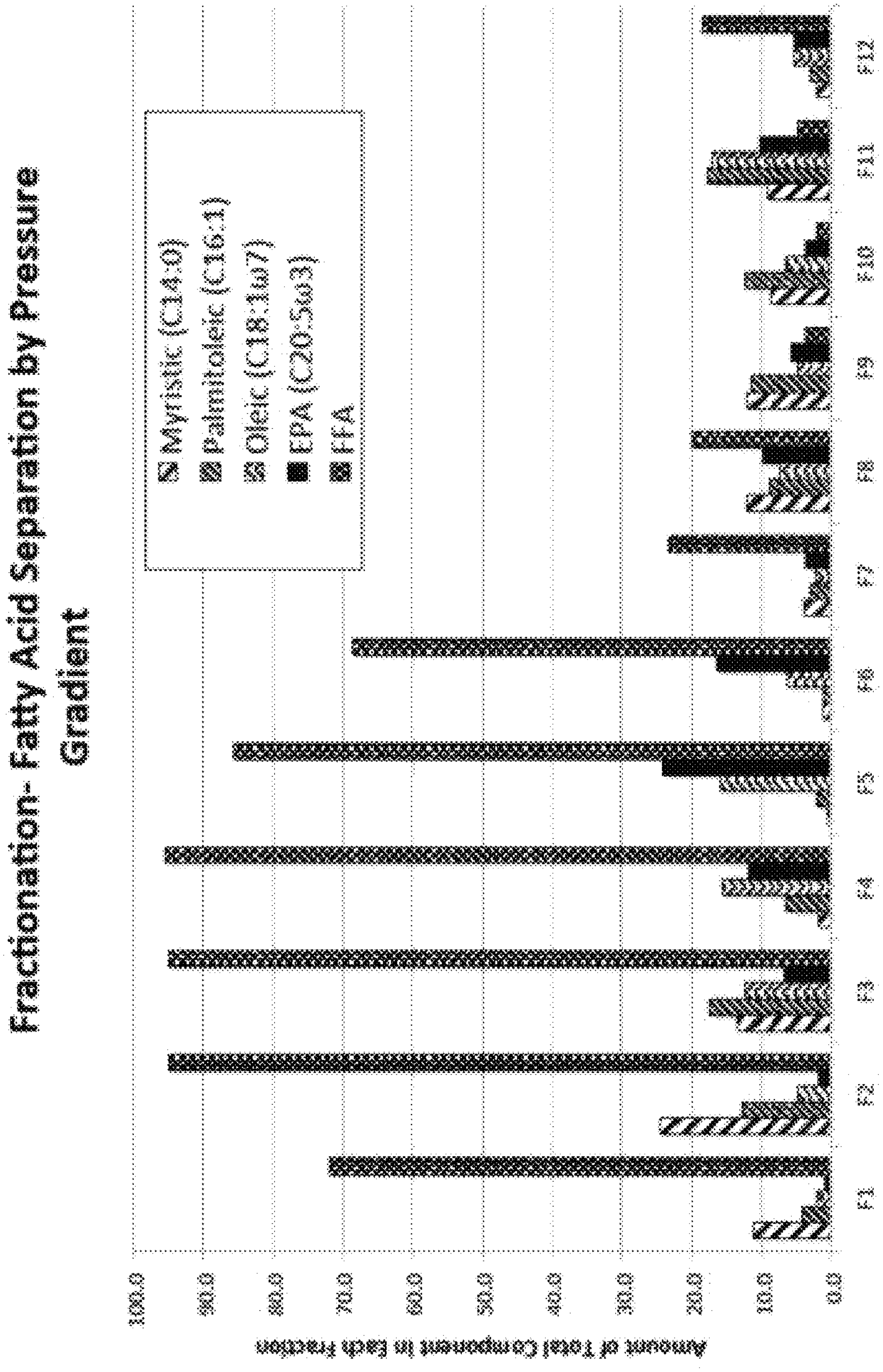
FIG. 20 illustrates a distribution of characteristics of fatty acid molecular weight chains and FFA as fractionated by supercritical carbon dioxide.
Figure 21:
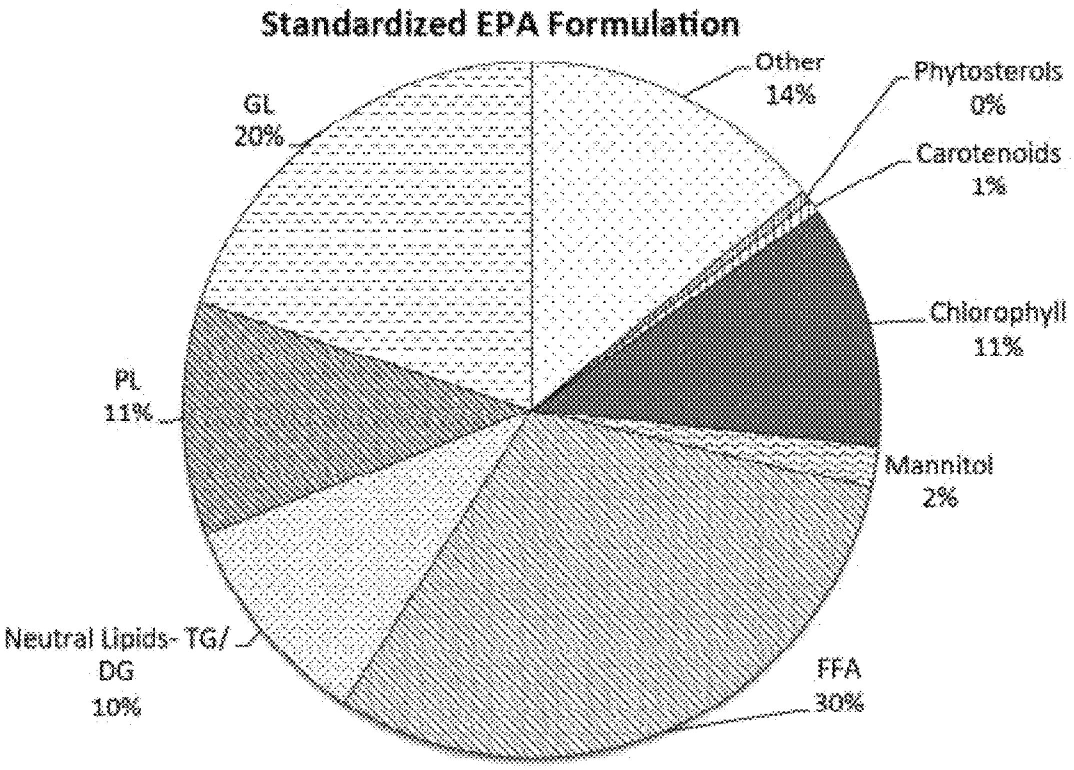
FIG. 21 illustrates a typical composition of standardized EPA formulation that includes glycolipids, phospholipids, neutral lipids at triglycerides and diglycerides, and free fatty acid.
Figure 22:
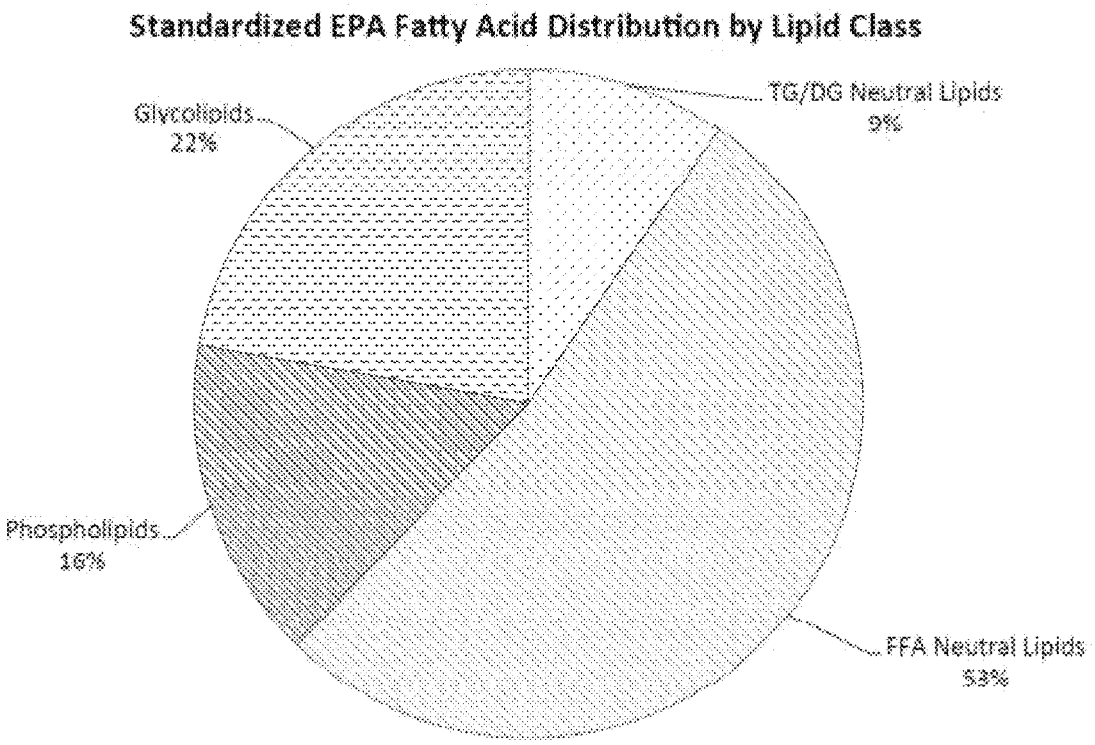
FIG. 22 illustrates a typical distribution of fatty acid acids by lipid class in the standardized EPA formulation.
Figure 23:
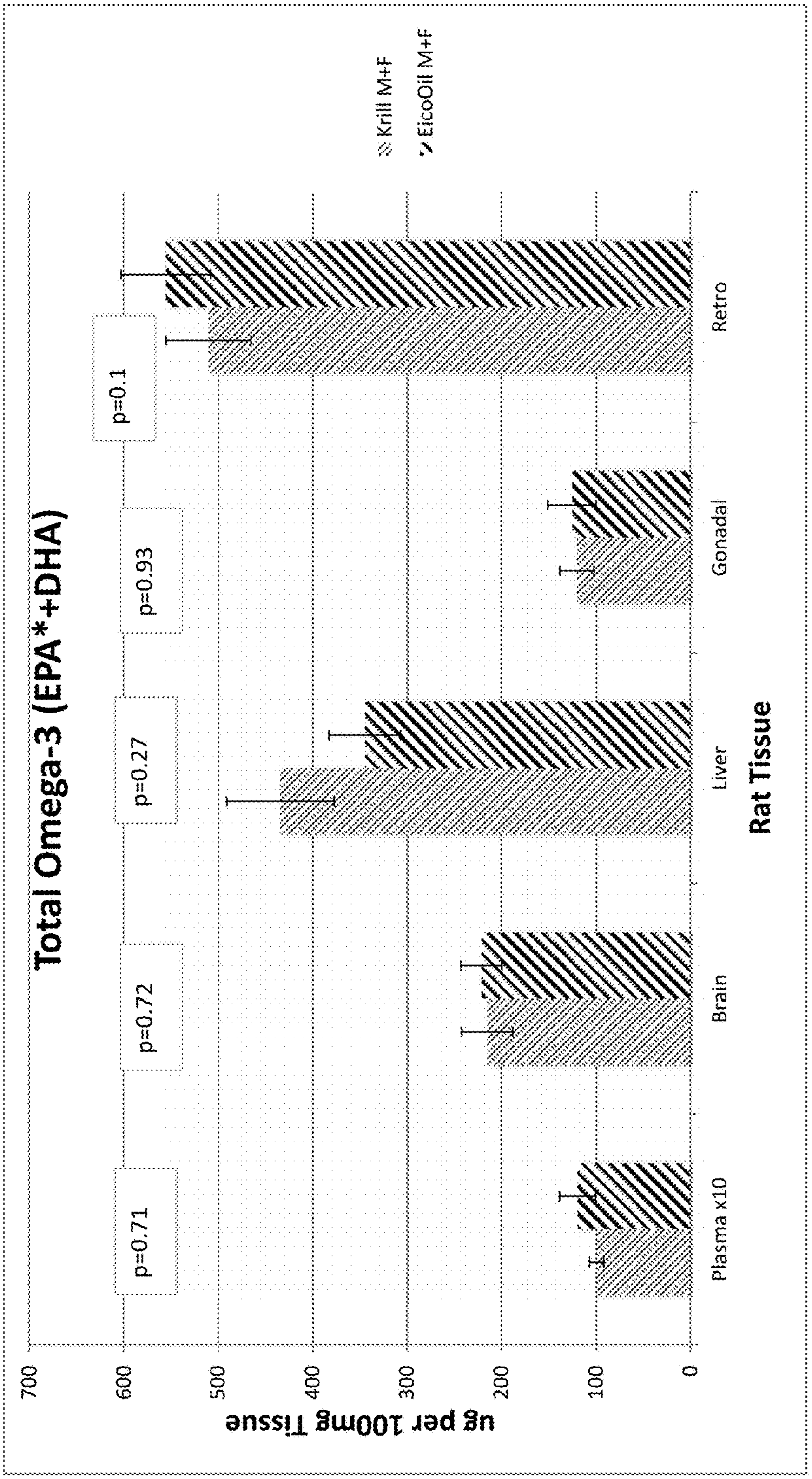
FIG. 23 illustrates a graphical comparison of tissue distribution of EPA and DHA in the tissues of male and female (M+F) rats administered either EicoOil or krill oil. EicoOil is a polar and EPA formulation derived from *Nannochloropsis oculata* extract that has total Omega-3 of about 25 wt % EPA in a variety of lipid classes and about 15 wt % polar lipids comprised of a combination of glycolipids (about 10 wt %) and phospholipids (about 5 wt %), at about a 2:1 ratio. EicoOil has 0 wt % DHA. The results show that there is no statistically significant difference between the tissue distribution of EPA and DHA from EicoOil and krill oil.
Figure 24:
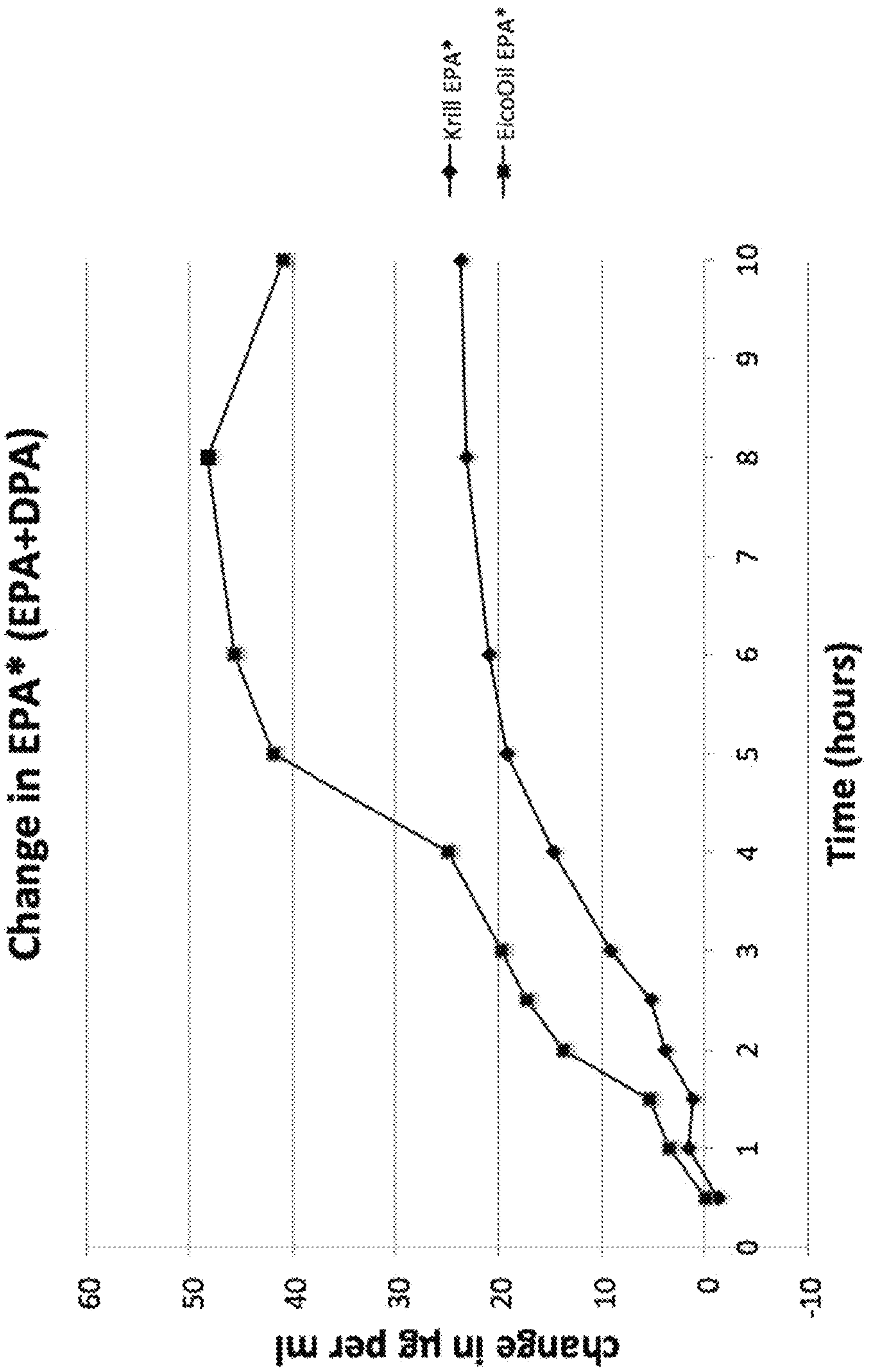
FIG. 24 illustrates the change in plasma concentrations of EPA+Docosapentaenoic acid (DPA) in human subjects receiving EicoOil or krill oil as a function of time.
Figure 25:
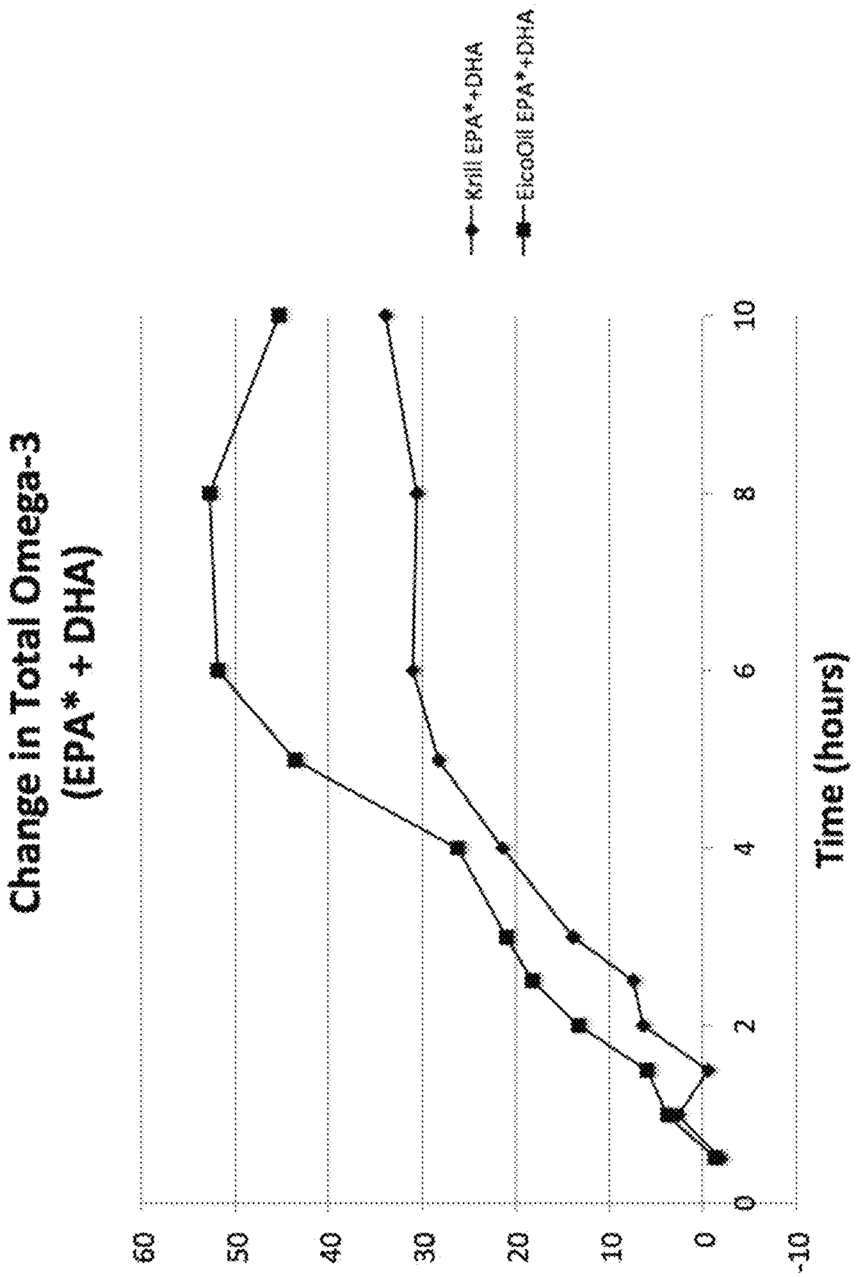
FIG. 25 illustrates the change in plasma concentrations of total Omega-3 in human subjects receiving EicoOil or krill oil as a function of time.

At the analytical laboratory, plasma samples were process via Folch extraction to recover the lipids and converted to methyl esters for fatty acid methyl ester (FAME) analysis via AOAC method 963.22. Results were expressed as a change μg fatty acid in the sample in Table 34. The predose sample was used as the baseline for all other samples. Results are given in terms of EPA*, the sum of EPA and DPA. Docosapentaenoic acid (DPA) (C22:5ω3) is directly synthesized from EPA in vivo. Total Omega-3 focuses on the content of EPA*+DHA. The change in Omega-3 as a function of time is given in FIG. 18 for EPA* and FIG. 19 for Total Omega-3. Data were analyzed using the SAS® version 9.1 (SAS Institute, Cary, N.C., USA) by MediStat Ltd. (Israel). The two sample T test and non-parametric Wilcoxon Mann Whitney Rank sum test for independent samples were applied for testing the statistical significance of the difference in all variables between Krill oil and EicoOil. All tests were two tailed, and a p-value of 0.05 or less was considered statistically significant.

TABLE 34

Summary Statistics of Changes in AUC (Area Under Curve) (μg) of Fatty Acid

| Changes in AUC (μg) | Krill N | Krill Mean | Krill SD | Krill Min | Krill Med | Krill Max | Krill Lower 95% CI | Krill Upper 95% CI | EicoOil N | EicoOil Mean | EicoOil SD | EicoOil Min |
|---|---|---|---|---|---|---|---|---|---|---|---|---|
| EPA | 10 | 137.4 | 39.26 | 72.83 | 142.7 | 199.0 | 109.3 | 165.4 | 10 | 277.3 | 135.2 | 164.9 |
| DPA | 10 | 25.37 | 12.19 | 10.17 | 25.84 | 52.33 | 16.64 | 34.09 | 10 | 39.55 | 26.64 | 12.38 |
| DHA | 10 | 70.44 | 38.75 | 30.63 | 62.66 | 131.1 | 42.72 | 98.17 | 10 | 64.49 | 45.07 | 18.77 |
| Omega-3 (EPA + DHA) | 10 | 202.4 | 71.81 | 108.9 | 191.5 | 325.1 | 151.0 | 253.8 | 10 | 314.2 | 174.1 | 142.3 |
| Total Omega-3 (EPA + DPA + DHA) | 10 | 215.9 | 85.14 | 102.1 | 206.3 | 349.8 | 155.0 | 276.8 | 10 | 347.7 | 202.8 | 146.9 |

| Changes in AUC (μg) | EicoOil Med | EicoOil Max | EicoOil Lower 95% CI | EicoOil Upper 95% CI | P-value from Wilcoxon test | P-value from T-test | P-value from Median test |
|---|---|---|---|---|---|---|---|
| EPA | 264.4 | 625.9 | 180.6 | 373.9 | 0.0033 | 0.0099 | 0.0005 |
| DPA | 32.08 | 84.67 | 20.49 | 58.61 | 0.3955 | 0.1505 | 1.0000 |
| DHA | 48.90 | 174.6 | 32.25 | 96.73 | 0.7375 | 0.7551 | 1.0000 |
| Omega-3 (EPA + DHA) | 265.0 | 719.7 | 189.7 | 438.7 | 0.1053 | 0.0850 | 0.3833 |
| Total Omega-3 (EPA + DPA + DHA) | 293.1 | 800.7 | 202.7 | 492.8 | 0.1568 | 0.0822 | 0.3833 |

P-value indicates the statistical significance of the differences between Krill and EicoOil The results show that there is the Omega-3 bioavailability of EicoOil is equal or even better than NOW NKO krill oil. Digestion of EicoOil is equal to or faster than NKO krill oil. Comparative doses of Algae Oil provide much higher level of EPA and EPA* than NKO krill oil. Most importantly, the polar lipids in EicoOil, i.e., the combination of phospholipids and glycolipids, act in a similar way to the phospholipids in krill oil in transporting the fatty acids across the intestinal barrier and into the blood plasma. Moreover, since the amount of polar lipid was about 15% of the EicoOil versus about 39% in the krill oil, it appears that the combination of glycolipid and phospholipids enable a lower amount of combined polar lipid to enhance Omega-3 uptake in male human blood plasma versus the phospholipid alone in krill.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of increasing EPA bioavailability in a subject, comprising administering to the subject and EPA composition comprising from about 15 wt. % to about 90 wt. % eicosapentaenoic acid (EPA) and about 10 wt. % to about 70 wt. % polar lipids, wherein:

the polar lipids comprise phospholipid conjugates and glycolipid conjugates;

about 3 wt. % to about 50 wt. % of the EPA in the composition is a phospholipid conjugate;

about 5 wt. % to about 50 wt. % of the EPA in the composition is a glycolipid conjugate;

about 0 wt. % to about 10 wt. % of the EPA is a triglyceride conjugate or a diglyceride conjugate; and the composition does not comprise docosahexaenoic acid (DHA) or methyl esters or ethyl esters, and wherein the composition is suitable for human consumption.

2. The method of claim 1, wherein the EPA composition is administered as a capsule, tablet, solution, syrup, suspension, food, beverage, energy bar, or nutritional supplement.

3. The method of claim 1, wherein about 15 wt. % to about 85 wt. % of the EPA in the composition is in free fatty acid form.

4. The method of claim 1, wherein the composition comprises from about 10 wt. % to about 35 wt. % polar lipids.

5. The method of claim 1, wherein the composition comprises at least about 13 wt. % polar lipids.

6. The method of claim 1, wherein the composition comprises at least about 13 wt. % polar lipids, less than 0.2 wt. % glyceride conjugates and at least about 30 wt. % free fatty acids.

7. The method of claim 1, wherein the polar lipids are comprised of phospholipid conjugates and glycolipid conjugates at a wt. % ratio in the range of about 3:1 to about 1:3.

8. The method of claim 1, wherein the glycolipid conjugates comprise one or more of digalactosyldiacylglycerol and monogalactosyldiacylglycerol.

9. The method of claim 1, wherein the EPA to total omega-3 fatty acids ratio is greater than 90%.

10. The method of claim 1, wherein the composition comprises about 15 wt. % to about 75 wt. % EPA.

11. The method of claim 1, wherein the composition comprises about 20 wt. % to about 50 wt. % EPA.

12. The method of claim 1, wherein the composition comprises less than about 1 wt. % phytosterols.

13. The method of claim 1, wherein the composition comprises less than about 2 wt. % carotenoids.

14. The method of claim 1, wherein the composition does not comprise fatty acids selected from the group consisting of octadecatetraenoic acid or stearidonic acid (SDA=C18:4ω3), eicosatrienoic acid (ETE=C20:3ω3), eicosatetraenoic acid (ETA=C20:4ω3), heneicosapentaenoic acid or uncosapentaenoic acid (HPA=C21:5ω3), and docapentaenoic acid (DPA=C22:5ω3).

15. The method of claim 1, wherein the composition comprises about 20 50 wt. % EPA, about 10-25 wt. % glycolipids, and about 5-25 wt. % phospholipids.

16. The method of claim 1, wherein the phospholipid conjugates comprise one or more of phosphatidylcholine, lyso-phosphatidylcholine, phosphatidylinositol, phosphatidylethanolamine and phosphatidylglycerol.

17. The method of claim 1, wherein the phospholipid conjugates comprise one or more of phosphatidylcholine and phosphatidylglycerol.

18. The method of claim 1, wherein the composition comprises:

i) 0 to 5 wt. % C:18 fatty acids;

ii) 0 to 20 wt. % C:16 fatty acids;

iii) 0 to 5 wt. % C:14 fatty acids;

iv) 0 to 0.5 wt. % C:12 fatty acids; and/or v) 0 to 0.5 wt. % C:10 fatty acids.

19. The method of claim 1, wherein the composition comprises chlorophyll a and does not comprise chlorophyll c.

20. The method of claim 1, wherein the composition comprises less than about 10.0 wt. % arachidonic acid.

* * * * *